(12) United States Patent
Behrens et al.

(10) Patent No.: US 9,695,226 B2
(45) Date of Patent: Jul. 4, 2017

(54) GROWTH HORMONES WITH PROLONGED IN-VIVO EFFICACY

(75) Inventors: Carsten Behrens, Koebenhavn N (DK); Nils Langeland Johansen, Koebenhavn Oe (DK); Henrik Sune Andersen, Holte (DK); Leif Noerskov-Lauritsen, Tappernoeje (DK); Jens Buchardt, Gentofte (DK)

(73) Assignee: Novo Nordisk HealthCare AG, Zurich (CH)

( * ) Notice: Subject to any disclaimer, the term of this patent is extended or adjusted under 35 U.S.C. 154(b) by 643 days.

(21) Appl. No.: 13/522,390

(22) PCT Filed: Jan. 24, 2011

(86) PCT No.: PCT/EP2011/050923
§ 371 (c)(1),
(2), (4) Date: Aug. 24, 2012

(87) PCT Pub. No.: WO2011/089255
PCT Pub. Date: Jul. 28, 2011

(65) Prior Publication Data
US 2012/0309944 A1 Dec. 6, 2012

Related U.S. Application Data

(60) Provisional application No. 61/297,305, filed on Jan. 22, 2010.

(30) Foreign Application Priority Data

Jan. 22, 2010 (EP) ..................... 10151405

(51) Int. Cl.
*A61K 38/00* (2006.01)
*C07K 14/61* (2006.01)
*A61K 47/48* (2006.01)

(52) U.S. Cl.
CPC ........ *C07K 14/61* (2013.01); *A61K 47/48023* (2013.01); *A61K 47/48038* (2013.01); *A61K 47/48061* (2013.01)

(58) Field of Classification Search
None
See application file for complete search history.

(56) References Cited

U.S. PATENT DOCUMENTS

| | | |
|---|---|---|
| 4,683,202 A | 7/1987 | Mullis |
| 5,045,312 A | 9/1991 | Aston et al. |
| 5,156,956 A | 10/1992 | Motoki et al. |
| 5,252,469 A | 10/1993 | Andou et al. |
| 5,438,040 A | 8/1995 | Ekwuribe |
| 5,545,618 A | 8/1996 | Buckley et al. |
| 5,646,272 A | 7/1997 | Kramer et al. |
| 5,731,183 A | 3/1998 | Kobayashi et al. |
| 5,736,356 A | 4/1998 | Sano et al. |
| 5,834,250 A | 11/1998 | Wells et al. |
| 5,849,535 A | 12/1998 | Cunningham et al. |
| 5,891,840 A | 4/1999 | Cady et al. |
| 5,951,972 A | 9/1999 | Daley et al. |
| 6,004,931 A | 12/1999 | Cunningham et al. |
| 6,057,292 A | 5/2000 | Cunningham et al. |
| 6,136,536 A | 10/2000 | Tomkinson et al. |
| 6,143,523 A | 11/2000 | Cunningham et al. |
| 6,268,343 B1 | 7/2001 | Knudsen et al. |
| 6,358,705 B1 | 3/2002 | Kjeldsen et al. |
| 6,528,486 B1 | 3/2003 | Larsen et al. |
| 6,608,183 B1 | 8/2003 | Cox, III |
| 7,132,269 B2 | 11/2006 | Lacoux |
| 7,153,930 B1 | 12/2006 | Morrison et al. |
| 8,513,192 B2 | 8/2013 | Olsen et al. |
| 8,779,109 B2 | 7/2014 | Behrens et al. |
| 8,841,249 B2 | 9/2014 | Johansen et al. |
| 8,865,868 B2 | 10/2014 | Behrens et al. |
| 9,211,342 B2 | 12/2015 | Demuth et al. |
| 2001/0011071 A1 | 8/2001 | Knudsen et al. |
| 2002/0142964 A1 | 10/2002 | Nissen et al. |
| 2003/0125232 A1 | 7/2003 | Griffin et al. |
| 2003/0162949 A1 | 8/2003 | Cox |
| 2003/0165996 A1 | 9/2003 | Halkier et al. |
| 2004/0001827 A1 | 1/2004 | Dennis |
| 2004/0053370 A1 | 3/2004 | Glaesner et al. |
| 2005/0170404 A1 | 8/2005 | Cho et al. |
| 2005/0260237 A1 | 11/2005 | Byun et al. |
| 2005/0266532 A1 | 12/2005 | Rosen et al. |
| 2006/0094655 A1 | 5/2006 | Guyon et al. |

(Continued)

FOREIGN PATENT DOCUMENTS

| | | |
|---|---|---|
| CN | 1269805 A | 10/2000 |
| CN | 1867360 A | 11/2006 |

(Continued)

OTHER PUBLICATIONS

Ghuman et al. J. Mol. Biol. (2005) 353, 38-52.*
Berge et al., Journal of Pharmaceutical Sciences, "Pharmaceutical Salts", 1977, vol. 66, No. 1, pp. 1-19.
Gregory J. Russel-Jones and David H. Alpers, Membrane Transporters as Drug Targets, 1999, Chapter 17, New York.
Alexander Deitrs, et al, Journal of the American Chemical Society, "Adding Amino Acids With Novel Reactivity to the Genetic Code of *Saccharomyces cerevisiae*", 2003, vol. 125, 39, pp. 11782-11783.
Altschul SF, Madden TL, Schäffer AA, Zhang J, Zhang Z, Miller W, Lipman DJ. Gapped BLAST and PSI-BLAST: A new generation of protein database search programs. Nucleic Acids Res. Sep. 1, 1997;25(17):3389-402.

(Continued)

*Primary Examiner* — Jeanette Lieb
(74) *Attorney, Agent, or Firm* — Jianjie Hu

(57) ABSTRACT

The invention relates to growth hormone compounds with a protracted profile. The effect is obtained by linking an albumin binding residue via a hydrophilic spacer to growth hormone variants. Further described are methods of preparing and using such compounds. These growth hormone compounds are based on there altered profile considered particular useful in therapy.

14 Claims, 2 Drawing Sheets

(56) References Cited

U.S. PATENT DOCUMENTS

Figure 1:
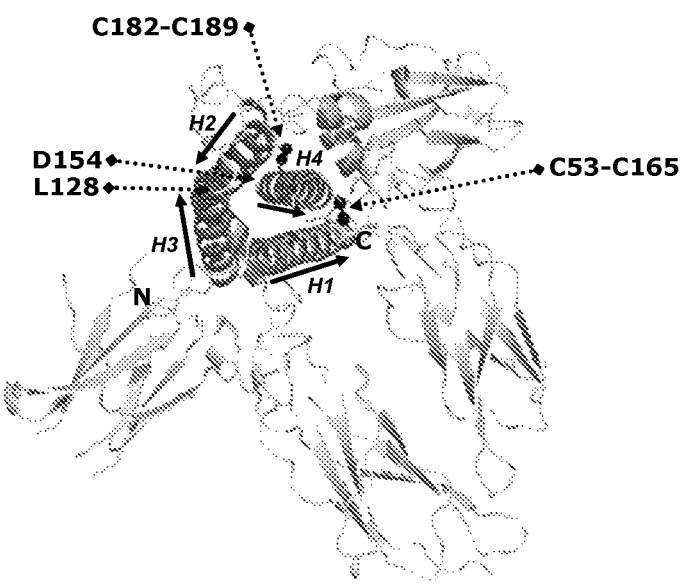

| | | | |
|---|---|---|---|
| 2006/0183197 A1* | 8/2006 | Andersen et al. | 435/69.4 |
| 2007/0105770 A1 | 5/2007 | Johansen et al. | |
| 2007/0203058 A1* | 8/2007 | Lau et al. | 514/12 |
| 2008/0095837 A1 | 4/2008 | Dinh et al. | |
| 2009/0156478 A1 | 6/2009 | Lau et al. | |
| 2011/0189124 A1 | 8/2011 | Rosendahl et al. | |
| 2011/0223151 A1 | 9/2011 | Behrens et al. | |
| 2012/0172303 A1 | 7/2012 | Johansen et al. | |
| 2013/0012684 A1 | 1/2013 | Buchardt | |
| 2014/0107324 A1 | 4/2014 | Behrens et al. | |
| 2014/0329750 A1 | 11/2014 | Andersen et al. | |
| 2016/0058879 A1 | 3/2016 | Nielsen et al. | |

FOREIGN PATENT DOCUMENTS

| | | |
|---|---|---|
| EA | 010626 B1 | 10/2008 |
| EP | 243929 A2 | 11/1987 |
| EP | 0458064 A2 | 11/1991 |
| EP | 534568 A2 | 3/1993 |
| EP | 555649 A2 | 8/1993 |
| EP | 785276 A1 | 7/1997 |
| EP | 950665 A1 | 10/1999 |
| EP | 1012184 A1 | 6/2000 |
| EP | 1329458 A2 | 7/2003 |
| EP | 05102171.5 | 3/2005 |
| EP | 1704165 A1 | 9/2006 |
| EP | 1941901 A1 | 7/2008 |
| JP | H07503600 A | 4/1995 |
| JP | H1156378 A | 3/1999 |
| JP | H1192499 A | 4/1999 |
| JP | 2000-500505 A | 1/2000 |
| JP | 2001510033 A | 7/2001 |
| JP | 2001521402 A | 11/2001 |
| JP | 2002-504527 A | 2/2002 |
| JP | 2002-508162 A | 3/2002 |
| JP | 2003-505347 | 2/2003 |
| JP | 2003-199569 A | 7/2003 |
| JP | 2004-528014 A | 9/2004 |
| JP | 2004-535442 A | 11/2004 |
| JP | 2005500831 A | 1/2005 |
| JP | 2009-523815 A | 6/2009 |
| JP | 2010-116407 A | 5/2010 |
| RU | 2073686 C1 | 2/1997 |
| RU | 2075509 C1 | 3/1997 |
| RU | 2006107600 A | 10/2007 |
| WO | 90/04788 A1 | 5/1990 |
| WO | 90/11296 | 10/1990 |
| WO | 91/11457 A1 | 8/1991 |
| WO | 92/05271 A1 | 4/1992 |
| WO | 92/09690 A2 | 6/1992 |
| WO | 94/03198 A1 | 2/1994 |
| WO | 94/10200 A1 | 5/1994 |
| WO | 96/06931 A1 | 3/1996 |
| WO | 96/12505 A1 | 5/1996 |
| WO | 96/22366 A1 | 7/1996 |
| WO | 96/29342 | 9/1996 |
| WO | 97/11178 A1 | 3/1997 |
| WO | 97/39768 A1 | 10/1997 |
| WO | 98/08871 | 3/1998 |
| WO | 99/43341 A1 | 3/1998 |
| WO | 98/38285 A2 | 9/1998 |
| WO | 99/03887 | 1/1999 |
| WO | 99/43341 | 9/1999 |
| WO | 99/43361 A1 | 9/1999 |
| WO | 99/43705 A1 | 9/1999 |
| WO | 99/43708 | 9/1999 |
| WO | 9943707 | 9/1999 |
| WO | 00/34331 | 6/2000 |
| WO | 00/69911 | 11/2000 |
| WO | 01/04156 | 1/2001 |
| WO | 01/09163 A2 | 2/2001 |
| WO | 01/12155 A1 | 2/2001 |
| WO | 0151071 | 7/2001 |
| WO | 01/58935 A2 | 8/2001 |
| WO | 0258725 | 1/2002 |
| WO | 02/46227 A2 | 6/2002 |
| WO | 02/055532 A2 | 7/2002 |
| WO | 02055532 A2 | 7/2002 |
| WO | WO02055532 A1 * | 7/2002 |
| WO | 02/087597 A1 | 11/2002 |
| WO | 02098446 A1 | 12/2002 |
| WO | 03/002136 | 1/2003 |
| WO | 03/013573 A1 | 2/2003 |
| WO | 03/040309 A2 | 5/2003 |
| WO | 03/042245 A2 | 5/2003 |
| WO | 03/044056 A2 | 5/2003 |
| WO | 03/087139 A2 | 10/2003 |
| WO | 03/093465 A1 | 11/2003 |
| WO | 2004/022593 A2 | 3/2004 |
| WO | 2004/065621 A1 | 8/2004 |
| WO | 2004/074315 A2 | 9/2004 |
| WO | 2004/099246 A2 | 11/2004 |
| WO | 2005/014035 A2 | 2/2005 |
| WO | 2005/014049 A2 | 2/2005 |
| WO | 2005/027978 A2 | 3/2005 |
| WO | 2005/028516 A2 | 3/2005 |
| WO | 2005/035553 A2 | 4/2005 |
| WO | 2005/058958 A2 | 6/2005 |
| WO | 2005/070468 A2 | 8/2005 |
| WO | 2005/105148 | 11/2005 |
| WO | 2006/005667 A2 | 1/2006 |
| WO | 2006/013202 A2 | 2/2006 |
| WO | 2006/037810 A2 | 4/2006 |
| WO | 2006/048777 A2 | 5/2006 |
| WO | 2006048777 A2 | 5/2006 |
| WO | 2006071840 A2 | 7/2006 |
| WO | 2006/097536 A2 | 9/2006 |
| WO | 2006/097537 A2 | 9/2006 |
| WO | 2006/097538 A1 | 9/2006 |
| WO | 2006/134148 A2 | 12/2006 |
| WO | 2006/134173 A2 | 12/2006 |
| WO | 2007/020290 A1 | 2/2007 |
| WO | 2007025988 A2 | 3/2007 |
| WO | 2007/093594 A1 | 8/2007 |
| WO | 2008/003750 A2 | 1/2008 |
| WO | 2008/14430 A1 | 1/2008 |
| WO | 2008/020075 A1 | 2/2008 |
| WO | 2008/027854 A2 | 3/2008 |
| WO | 2008/101240 A1 | 8/2008 |
| WO | 2009/030771 A1 | 3/2009 |
| WO | 2010/015668 A1 | 2/2010 |
| WO | 2010/029159 A1 | 3/2010 |
| WO | 2010029107 A1 | 3/2010 |
| WO | 2010/084173 A1 | 7/2010 |
| WO | 2010/102886 A1 | 9/2010 |
| WO | 2011015649 A1 | 2/2011 |
| WO | 2011/89250 A2 | 7/2011 |
| WO | 2011089255 A1 | 7/2011 |
| WO | 2011101261 A2 | 8/2011 |

OTHER PUBLICATIONS

Beaucage&CaruthersTetrahedron Lettersdeoxynucleoside Phosphoramidites—A New Class of Key Intermediates for Deoxypolynucleotide Synthesis198122201859-1862.

Cabrita,et al, Biotechnology Annual Reviewprotein Expression and Refolding—A Practical Guide to Getting the Most Out of Inclusion Bodies, 2004, vol. 10, pp. 31-50.

Chalasani et al, Journal of the Controlled Releasea Novel Vitamin B12-Nanosphere Conjugate Carrier System for Peroral Delivery of Insulin, 2007, vol. 117, pp. 421-429.

Chin et al, Science, An Expanded Eukaryotic Genetic Code, 2003, vol. 301,pp. 964-967.

Dombkowski A, Bioinformatics, Disulfide by Design:A Computational Method for the Rational Design of Disulfide Bonds in Proteins, 2003, vol. 19, No. 14, pp. 1852-1853.

Greene, et al Protective Groups in Organic Chemistry Synthesis Protective Groups in Organic Synthesis 2006 9-0-471.

Gumbleton.M, Advanced Drug Delivery Reviews, Caveolae as Potential Macromolecule Trafficking Compartments Within Alveolar Epithelium, 2001, vol. 49, No. 3, pp. 281-300.

H.Li & Z.M.Qian, Medicinal Research Reviews. Transferrin/Transferrin Receptor-Mediated Drug Delivery, 2002, vol. 22, No. 3, pp. 225-250.

(56) References Cited

OTHER PUBLICATIONS

Kondoh.et al, Molecular Pharmacology, A Novel Strategy for the Enhancement of Drug Absorption Using a Claudin Modulator, 2005 vol. 67, No. 3, pp. 749-756.
Lee et al, Biotechnology and Applied Biochemistry, Expression and Characterization of Human Growth Hormone-FC Fusion Proteins for Transcytosis Induction, 2007, vol. 46, pp. 211-217.
Lei Wang,et al, Science, Expanding the Genetic Code of *Escherichia coli*, 2001, vol. 292, pp. 498-500.
Leitner.V.M.et al European Journal of Pharmaceutics and Biopharmaceutics : Official Thiolated Ploymers: Evidence for the Formation of Disulphide Bonds With Mucus Glycoproteins 2003 56-207-214.
Leuben.H.L.et al International Journal of Pharmaceutics Mucoadhesive Polymers in Personal Peptide Drug Delivery.V.Effect of Poly(Acrylates)on the Enzymatic of Peptide Drugs by Intestinal Brush Border Membrane Vesicles 1996, vol. 141, Nos. 1-2, pp. 39-52.
Liang & Young, Biochemical and Biophysical Research Communications, Insulin-Cell Penetrating Peptide Hybrids With Improved Intestinal Absorption Efficiency, 2005, vol. 335, pp. 734-738.
Lueben.H.L.et al Pharmaceutical Research Mucoadhesive Polymers in Peroral Peptide Drug Delivery .VI.Carbomer and Chitosan Improve the Intestinal Absorption of the Peptide Drug Buserelin In Vivo, 1996, vol. 13, No. 11, pp. 1668-1672.
Masuda.N,et al Biochimica et Biophysica Acta Molecular Cloning of CDNA Encoding 2O KDA Variant Human Growth Hormone and the Alternative Splicing Mechanism 1988 949 1 125-131.
Matthes,et al EMBO Journal Simultaneous Rapid Chemical Synthesis of Over 100 Oligonucleotides on a Microscale 1984 3 4 801-805.
Palmberger.et al European Journal of Pharmaceutics and Biopharmaceutics : Official Thiolated Polymers: Evaluation of the Influenece of the Amount of Covalently Attached L-Cysteine to Poly(Acrylic Acid) 2007 66-405-412.
Partlow.K.C.et al Biomaterials Exploiting Lipid Raft Transport With Membrane Targeted Nanoparticles:A Strategy for Cytosolic Drug Delivery 2008 29-3367-3375.
Petersen,et al Protein Engineering Amino Acid Neighbours and Detailed Conformational Analysis of Cysteines in Proteins 1999 12 7 535-548.
S.Y.Chae,et al Bioconjugate Chemistry Preparation, Characterization and Application of Biotinylated and Biotin-Pegylated Glucagon-Like Peptide-1 Analogues for Enhanced Oral Delivery 2008 19-334-341.
Said, Hamid M; Mohammed, Zainab M. Current Opinion in Gastroenterology Intestinal Absorption of Watersoluble Vitamins: An Update 2006 22 2 140-146.
Saiki,et al Science Primer-Directed Enzymatic Amplification of DNA With a Thermostable DND Polymerase 1988 239 4839 487-491.
Takatsuka.et al European Journal of Pharmaceutics and Biopharmaceutics : Official Enhancement of Intestinal Absorption of Poorly Absorbed Hydrophilic Compounds by Simultaneous Use of Mucolytic Agent and Non-Ionic Surfacant 2006 62-52-58.
Zhiwen Zhang et al, Science, A New Strategy for the Synthesis of Glycoproteins, 2004 vol. 303, pp. 371-373.
Filikov et al, "Computational Stabilization of Human Growth Hormone," Protein Science, 2002, vol. 11, No. 6, pp. 1452-1461.
Szente et al., "Solubilization of Fatty Acids and Similar Lipids by Methylated Cyclodextrins," Proceedings of the International Symposium on Cyclodextrins, Jan. 1, 1992, pp. 340-344.
Szejtli, Jozsef, Cyclodextrin Technology (A book), Published by Springer, 1988, p. 271.
Pasut, G et al., Expert Opinion on Therapeutic Patents, "Protein, Peptide and Non-Peptide Drug Pegylation . . . " 2004, vol. 14, No. 6, pp. 859-894.
Bebernitz et al., Journal of Medicinal Chemistry, "Reduction in Glucose Levels in STZ Diabetic Rats by 4-(2,2-Dimethyl-1-Oxopropyl) Benzoic Acid: A Prodrug Approach for Targeting the Liver" 2001 vol. 44 pp. 512-523.
Beljaars et al., Journal of Drug Targeting, "Neoglyco-and Neopeptide Albumins for Cell-Specific Delivery of Drugs to Chronically Diseased Livers" 2001 vol. 115 pp. 189-240.
Biessen et al., Journal of Medicinal Chemistry, "Synthesis of Cluster Galactosides With High Affinity for the Hepatic Asialoglycoprotein Receptor" 1995 vol. 38 Part 9 pp. 1538-1546.
Hatori et al., Journal of the Controlled Release, "Controlled Biodistribution of Galactosylated Liposomes and Incorporated Probucol in Hepatocyte-Selective Drug Targeting" 2000 vol. 69 pp. 369-377.
Kim et al., Journal of Drug Targeting, "Evaluation of the Bile Acid Transporter in Enhancing Intestinal Permeability to Renininhibitory Peptides" 1993 vol. 1 pp. 347-359.
Kramer et al., Journal of Biological Chemistry, "Liver-Specific Drug Targeting by Coupling to Bile Acids", 1992 vol. 267 Part 26 pp. 18598-18604.
Kramer et al., Journal of the Controlled Release, "Modified Bile Acids as Carriers for Peptides and Drugs", 1997 vol. 46 Part 1-2 pp. 17-30.
Kramer et al., Journal of Biological Chemistry, "Intestinal Absorption of Peptides by Coupling to Bile Acids" 1994 vol. 269 Part 14 pp. 10621-10627.
Kullack-Ublick et al., Gastroenterology, "Chlorambucil-Taurocholate is Transported by Bile Acid Carriers Expressed in Human Hepatocellular Carcinomas" 1997, vol. 113 pp. 1295-1305.
Leeson et al., Journal of Medicinal Chemistry, "Selective Thyromimetics. Cardiac-Sparing Thyroid Hormone Analogues Containing 3'-Arylmet HYL Substituents" 1989 vol. 32 Part 2 pp. 320-326.
Nezasa et al., Drug Metabolism and Disposition, "Liver-Specific Distribution of Rosuvastatin in Rats: Comparison With Pravastatin and Simvastatin" 2002 vol. 30 Part 11 p. 1158-1163.
Pecher et al., Biophysical Chemistry, "The Effect of Additional Disulfide Bonds on the Stability and Folding of Ribonuclease" 2009 vol. 141 Part 1 pp. 21-28.
Starke et al., Bioorganic & Medicinal Chemistry Letters, "Bile Acid-Oldigodeoxynucleotide Conjugates: Synthesis and Liver Excretion in Rats", 2001 vol. 11 pp. 945-949.
Swaan, PW et al., Bioconjugate Chemistry, "Enhanced Transepithelial Transport of Peptides by" 1997 vol. 8 Part 4 pp. 520-525.
Wess et al., Tetrahedron Letters, "Modified Bile Acids: Preparation of 7A, 12A-Dihydroxy-3a-and 7A, L2A-Dihydroxy-3A-(2-Hydroxyethoxy)-SIJ-Cholanic Acid and Their Biological Activity" 1992, vol. 33 Part 2 pp. 195-198.
Inflammatory Bowel Disease from e-Medicine, pp. 1.24, Accessed Sep. 24, 2008.
Ngo JT et al., "Computational Complexity, Protein Structure Prediction, and the Levinthal Paradox," The Protein Folding Problem and Tertiary Structure Prediction, K. Mere Jr. and S. LeGrand Edition, 1994, pp. 433-495.
Residue definition from www.dictionary.com, pp. 1-6, Accessed May 5, 2009.
Green, Brian D. et al Biological Chemistry. Degradation, Receptor Binding, Insulin . . . 2004 385 2 169-177.
Greenwald Journal of the Controlled Release PEG Drugs: An Overview 2001 74-159-171.
Ji, J. et al. Biomaterials Stearyl Poly (Ethylene Oxide) Grafted Surfaces for Preferential Adsorption of Albumin. 2001 22-3015-3023.
Knudsen, L.B. Journal of Medicinal Chemistry Glucagon-Like Peptide-1 . . . 2004 47-4128-4134.
Simonovsky et al. Journal of Biomaterials Science, Polymer Edition Poly(Ether Urethane)S Incorporating Long Alkyl Side-Chains With Terminal Carboxyl Groups as Fatty Acid Mimics: Synthesis, Structural Characterization and Protein Adsorption 2005 16 12 1463-1483.
Soltero and Ekwurlbe Innovations in Pharmaceutical Technology the Oral Delivery of Protein and Peptide Drugs. 2001 1-106-110.

(56) References Cited

OTHER PUBLICATIONS

Still, J. Gordon, Diabetes/Metabolism Research Reviews, Development of Oral Insulin: Progress and Current Status, 2002, vol. 18, Suppl 1, pp. S29-S37.
Veronese F. M Biomaterials Peptide and Protein Pegylation: A Review of Porblems and Solutions 2001 22 5 405-417.
English abstract of JP 2004535442.
English abstract of RU 2006107600.
English abstract of JP 2010116407.
English abstract of JP 2004528014.
Berendsen, 1998, "A Glimpse of the Holy Grail?" Science 282:642-643.
Bradley et al., 2002, "Limits of Cooperativity in a Structually Modular Protein: Response of the Notch Ankyrin Domain to Analogous Alanine Substitutions in Each Repeat," Journal of Molecular Biology 324:373-386.
Chuang et al., 2002, "Pharmaceutical Strategies Utilizing Recombinant Human Serum Albumin," Pharmaceutical Research 19(5):569-577.
Han, 2002, "Targeted Prodrug Design to Optimize Drug Delivery," AAPS Pharmsci 2(1):1-11.
Hodgson et al., 2004, "The Synthesis of Peptides and Proteins Containing Non-Natural Amino Acids," Chemical Reviews 33(7):422-430.
Holz et al., 2003, "Glucagon-Like Peptide-1 Synthetic Analogs: New Therapeutic Agents for Use in the Treatment of Diabetes Mellitus," Current Medicinal Chemistry 10(22):2471-2483.
Kim et al., 2003, "Development and Characterization of a Glucagon-Like Peptide 1-Albumin Conjugate," Diabetes 52:751-759.
Makino et al., 2005, "Semisynthesis of Human Ghrelin: Condensation of a Boc-Protected Recombinant Peptide With a Synthetic O-Acylated Fragment," Biopolymers 79(5):238-247.
Okada, 2001, "Synthesis of Peptides by Solution Methods," Current Organic Chemistry 5(1):1-43.
Ostrovsky, 1975, "Comparative Characteristics of the Hydrophobic Nature of Certain Proteins by Their Interaction With 2-P Toluidino," Ukrayins'kyi Biokhimichnyi Zhurnal 47(6):701-707.
Picó, 1990, "Use of 1-Anilino-8-Naphthalene Sulfonate as a Reporter Molecule to Study the Bile Salts-Bovine Serum Albumin Binding," Studia Biophysica 136(1):21-26, Abstract XP-008039734.
Rudinger, 1976, "Characteristics of the Amino Acids as Components of a Peptide Hormone Sequence," Peptides Hormones, JA Parsons Edition, University Park Press, Jun. 1976, pp. 1-7.
Schinzel et al., 1991, "The Phosphate Recognition Site of *Escherichia coli* Maltodextrin Phosphorylase," Federation of European Biochemical Society Jul. 1991, 286(1, 2):125-128.
Sheffield, 2001, "Modification of Clearance of Therapeutic and Potentially Therapeutic Proteins," Current Drug Targets Cardiovascular & Haematological Disorders 1(1):1-22.
Sigma Genosys (Web Site), Designing Custom Peptides, pp. 1-2, Accessed Dec. 16, 2004.
Voet et al., 1995, Biochemistry 2nd ed., John Wiley & Sons, Inc., pp. 235-241.
Wallace, 1995, "Peptide Ligation and Semisynthesis," Current Opinion in Biotechnology 6(4):403-410.
Zobel et al., 2003, "Phosphate Ester Serum Albumin Affinity Tags Greatly Improve Peptide Half-Life In Vivo," Bioorganic & Medicinal Chemistry Letters 13:1513-1515.
Knudsen, L.B. et al., "Potent Derivatives of Glucagon-Like Peptide-1 With Pharmacokinetic Properperties Suitable for Once Daily Administration", Journal of Medicinal Chemistry, 2000 vol. 43, pp. 1664-1669.
Deacon, C.F. et al., "Dipeptidyl peptidase IV resistant analogues of glucagon-like peptide-1 which have extended metabolic stability and improved biological activity." 1998, Diabetologia, vol. 41, pp. 271-278.
Watanabe et al., "Structure-Activity Relationships of Glucagon-Like Peptide-1 (7-36) Amide: Insulinotropic Activities in Perfused Rat Pancreases, and Receptor Binding and Cyclic AMP Production in RINm5F Cells," Journal of Endocrinology, 1994, vol. 140, pp. 45-52.
Jung-Guk Kim et al. Diabetes Development and Characterization of a Glucagon-Like Peptide 1-Albumin Conjugate/ The Ability to Activate the Glucagon-Lile Peptide 1 Receptor In Vivo 2003 52-751-759.
Definition of Moiety, From http://dictionary.reference.com/browse/moiety, pp. 1-2. Accessed Aug. 26, 2010.
Small Bowel Syndrome from e-Medicine, pp. 1-12, Accessed Sep. 24, 2008.
Carey et al, The Liver: Biology and Pathobiology 2nd Edition, Raven Press Ltd, "Enterohepatic Circulation", 1988, vol. 33, pp. 573-616.
Lu, X et al. J. Nucl. Med. Antisense DNA delivery in vivo: liver targeting by receptor-mediated uptake. 1994. vol. 35(2). pp. 269-275.
Holzinger, F et al. Hepatology. "Fluorescent bile acid derivatives: Relationship between chemical structure and hepatic and intestinal transport in the rat." 1997. vol. 26. pp. 1263-1271.
Taniyama Y. et al. "Evidence for intramolecular disulfide bond shuffling in the folding of mutant human lysozyme." Journal of Biological Chemistry 1991, vol. 266 No. 10 pp. 6456-6461.
Sahin-Toth M et al. "Cysteine scanning mutagenesis of the N-terminal 32 amino acid residues in the lactose permease of *Escherichia coli*." Protein Science, 1994, vol. 3, p. 240-247.
Takahashi Y, Chihara K. "Short stature by mutant growth hormones", Growth Hormone & IGF Research, 1999,vol. 9: pp. 37-41.
V.M. Stepanov, "Molecular biology. Protein structure and function", Moscow, Nauka, 2005, pp. 61-62.
Ghuman J. et al., Structural basis of the drug-binding specificity of human serum albumin, Journal of Molecular Biology, 2005, vol. 353, No. 1, pp. 38-52.
Chou D. K. et al., Effects of Tween 20 (R) and Tween 80 (R) on the stability of albutropin during agitation, Journal of Pharmaceutical Sciences, American Pharmaceutical Association, Washington, US, 2005, vol. 94, No. 6, pp. 1368-1381.
Osborn B. L. et al., Albutropin: a growth hormone-albumin fusion with improved pharmacokinetics and pharmacodynamics in rats and monkeys, European Journal of Pharmacology, Elsevier Science, NL, 2002, vol. 456, No. 1-3, pp. 149-158.
Poznansky M. J. et al., Growth hormone-albumin conjugates Reduced renal toxicity and altered plasma clearance, FEBS Letters, Elsevier, Amsterdam, NL, 1988, vol. 239, No. 1, pp. 18-22.
Katakam M. et al., Use of Poloxamer Polymers to Stabilize Recombinant Human Growth Hormone Against Various Processing Stresses, Pharmaceutical Development and Technology, New York, NY, US, 1997, vol. 2, No. 2, pp. 143-149.
Bam N. B. et al.,Tween protects recombinant human growth hormone against agitation-induced damage via hydrophobic interactions, Journal of Pharmaceu Tical Sciences, American Pharmaceutical Association, Washington, 1998, US, vol. 87, No. 12, pp. 1554-1559.
Katakam M. et al., Effect of Surfactants on the Physical Stability of Recombinant Human Growth Hormone, Journal of Pharmaceutical Sciences, American Pharmaceutical Association, Washington, US, 1995, vol. 84, No. 6, pp. 713-716.
Urban J. Lewis et al "An interchain disulfide dimer of human growth hormone" Journal of Biological Chemistry, 1977, vol. 252, No. 11, pp. 3697-3702.
Frostell-Karlsson et al., Journal of Medicinal Chemistry, "Albumin Binding Property", 2000, vol. 43, No. 10, pp. 1986-1992.
Masters, "Applications of Spray Drying," in Spray-Drying Handbook (5.sup.th ed; Longman Scientific and Technical), pp. 491-676 (1991).
Altschul et al, -, "Blast Manual" downloaded Jan. 10, 2013.
Altschul et al., Journal of Molecular Biology., "BLASTP, BLASTN, and FASTA", 1990, vol. 215, No. -, pp. 403-410.
B. Lee and F.M. Richards, Journal of Molecular Biology, "The Interpretation of Protein Structures: Estimation of Static Accessibility", 1971, vol. 55, No. -, pp. 379-400.

(56) References Cited

OTHER PUBLICATIONS

B. Peschke et al., Bioorganic & Medicinal Chemistry, "C-Terminally Pegylated HGH Derivatives", 2007, vol. 15, No. -, pp. 4382-4395.
Broadhead et al., Drug Delivery, "The Spray Drying of Pharmaceuticals", 1992, vol. 18, No. 11 & 12, pp. 1169-1206.
C. A. Lipinski et al., Advanced Drug Delivery Reviews, "Experimental and Computational Approaches to Estimate Solubility and Permeability in Drug Discovery and Development Settings", 1997, vol. 23, pp. 3-25.
Carpenter and Crowe, Cryobiology, "Modes of Stabilization of a Protein by Organic Solutes During Dessication", 1988, vol. 25, No. -, pp. 459-470.
Dayhoff et al., A Model of Evolutionary Change in Protiens, "Atlas of Protein Sequence and Structure", 1978, vol. 5, No. 3, pp. 345-352.
G. T. Hermanson, -, "Bioconjugate Techniques, Elsevier", 2008, vol. 2, No. -, pp. -.
I. Moriguchi, S. Hirono, I. Nakagome, H. Hirano, Chemical & Pharmaceutical Bulletin, "Comparison of Reliability of LOGP Values for Drugs Calculated by Several Methods", 1994, vol. 42, No. -, pp. 976-978.
Kurtzhals, P et al., Biochemical Journal, "Albumin Binding of Insulins Acylated With Fatty Acides . . . ", 1995, vol. 312, No. -, pp. 725-731.
Kaempfer, Journal of General Microbiology, "Genus *Streptomyces*", 1991, vol. 137, No. -, pp. 1831-1892.
M. M. Kurfurst, Analytical Biochemistry, "-", 1992, vol. 200(2), No. -, pp. 244-248.
Mumenthaler et al. Pharmaceutical Research, "Feasibility Study on Spray-Drying Protein Pharmaceuticals: Recombinant Human Growth Hormone and Tissue-Type Plasminogen Activator", 1994, vol. 11, No. 1, pp. 41263.
Chene, N., "Growth hormones. II. Structure-function relationships," Reprod. Nutr. Dev., 1989. , 29 1-25.
Roser, Biopharmaceutical, "Trehalsoe Drying: A Novel Replacement for Freeze Drying", 1991, vol. 4, No. -, pp. 47-53.
Sato, H, Advanced Drug Delivery Reviews, "Enzymatic Procedure for Site-Specific Pegylation of Proteins", 2002, vol. 54, No. -, pp. 487-504.
T. Fujita; J. Iwasa and C. Hansch, Journal of the American Chemical Society, "A New Substituent Constant, PI, Derived From Partition Coefficients", 1964, vol. 86, No. -, pp. 5175-5180.
Wada, E et al., Biotechnology Letters, "Enzymatic Modification of . . . ", 2001, vol. 23, No. -, pp. 1367-1372.
Williams and Polli, Journal of Parenteral Science & Technology, "The Lyophilization of Pharmaceuticals: A Literature Review", 1984, vol. 38, No. 2, pp. 48-59.
Carillo,et al, Journal of Applied Mathametics "The Multiple Sequence Alignment Problem in Biology" 1988 vol. 48 Part 5 pp. 1073-1082.
De Vos, A.M.et al Science—Human Growth Hormone and Extracellular Domain of Its Receptor: Crystal Structure of the Complex—1992—vol. 255—pp. 306-312.
Devereux et alNucleic Acids Researcha Comprehensive Set of Sequence Analysis Programs for the VAX, 1984, vol. 12, No. 1, pp. 387-395.
M. Gribskov, J. Devereux, Sequence Analysis Primer, Stockton Press, NewYork and Macmillan, Basingstoke (1991), pp. 90-157.
Griffm,et al Humana Press, Totowa New Jersey "Methods in Molecular Biology, vol. 24: Computer Analysis of Sequence Data Part I" 1994.
Henikoff,et al Proceedings of the National Academy of Sciences of the USA Amino Acid Substitution Matrices Form Protein Blocks 1992, vol. 89, pp. 10915-10919.
Lesk.A.M—Oxford University Press—Computational Molecular Biology: Sources and Methods for Sequence Analysis—1988—pp. 247-255.
Needeleman,et al—Journal of Molecular Biology—A General Method Applicable to the Search for Similarities in the Amino Acid Sequence of Two Proteins—1970, 48—pp. 443-453.
Von Heijne.G—Academic Press—Sequence Analysis of Molecular Biology: Treasure Torve or Trivial Pursuit—1987—pp. 186-188.
Kasimova, MR et al., "NMR Studies of the Bacbone Flixibility and Structure of Human Growth Hormone: A Comparison of High and Low PH Conformations," Journal of Molecular Biology, 2002, vol. 318, pp. 679-695.
Dennis, MS et al., Journal of Biological Chemistry, "Albumin Binding as a General Strategy for Improving the Pharmacokinetics of Proteins", 2002, vol. 277, No. 28 pp. 35035-35043.
Kurtzhals, P, et al., "Albumin Binding of Insulins Acylated With Fatty Acids: Characterization of the Ligand-Protein Interaction and Correlation Between Binding Affinity and Timing of the Insulin Effect In Vivo," Biochem J, 1995, vol. 312, pp. 725-731.
Alam K S M et al, Journal of Biotechnology, "Expression and Purification of a Mutant Human Growth Hormone That is Resistant to Proteolytic Cleavage by Thrombin, Plasmin and Human Plasma In Vitro", 1998, vol. 65, No. 2-3, pp. 183-190.
Chantalet L et al, Protein and Peptide Letters, "The Crystal Structure of Wild-Type Growth Hormone at 2.5A Resolution", 1995, vol. 2, No. 2, pp. 333-340.
Devos A. M. et al, Science, "Human Growth Hormone and Extracelleular Domain of Its Receptor: Crystal Structure of the Complex", 1992, vol. 255, pp. 306-312.
Garcia-Barros,et al, Journal of Endocrinology, "Proteolytic Processing of Human Growth Hormone (GH)by Rat Tissues In Viitro: Influence of Sex and Age", 2000, vol. 23, pp. 748-754.
Lewis.U.J, Annual Review of Physiology, "Variants of Growth Hormone and Prolactin and Their Posttranslational Modifications", 1984, vol. 46, pp. 33-42.

\* cited by examiner

Figure 2

```
  1  FPTIP.....RIF .............. .............. .....IPKEQ KYSFLQNPQT SLCFSESIPT
              H1                                                    L1
 61  PSNREETQQK S............. ............. ...........NS LVYGAS....... .. .......
                      H2                                     L2           H3
121  ......LED GSPRTGQIFK QTYSKFDTNS HNDD....... ........... ...........
            L3                                        H4
181  ...VEGSCG F   (SEQ ID NO.1)
```

GROWTH HORMONES WITH PROLONGED IN-VIVO EFFICACY

CROSS-REFERENCE TO RELATED APPLICATIONS

This application is a 35 U.S.C. §371 national stage application of International Patent Application PCT/EP2011/050923 (published as WO 2011/089255 A1), filed Jan. 24, 2011, which claimed priority of European Patent Application 10151405.7, filed Jan. 22, 2010; this application further claims priority under 35 U.S.C. §119 of U.S. Provisional Application 61/297,305, filed Jan. 22, 2010.

FIELD OF THE INVENTION

The present invention relates to a growth hormone compound linked to an albumin binding residue via a hydrophilic spacer, and to methods of preparing and using such compounds. These growth hormone conjugates have increased resistance to proteolytic degradation in combination with a protracted profile of action and are useful in therapy.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jul. 10, 2012. The Sequence Listing is made up of 2,026 bytes, and the information contained in the attached "SEQUENCE LISTING" is identical to the information in the specification as originally filed. No new matter is added.

BACKGROUND OF THE INVENTION

Growth hormone is a polypeptide hormone secreted by the anterior pituitary in mammals. Dependent on species growth hormone is a protein composed of approximately 190 amino acid residues corresponding to a molecular weight of approximately 22 kDa. Growth hormone binds to and signals through cell surface receptors, the growth hormone receptors (GHR). Growth hormone plays a key role in promoting growth, maintaining normal body composition, anabolism and lipid metabolism. It also has direct effects on intermediate metabolism, such as decreased glucose uptake, increased lipolysis, increased amino acid uptake and protein synthesis. The hormone also exerts effects on other tissues including adipose tissue, liver, intestine, kidney, skeleton, connective tissue and muscle. Recombinant human growth hormone (hGH) has been produced and commercially available as, for ex: Genotropin™ (Pharmacia Upjohn), Nutropin™ and Protropin™ (Genentech), Humatrope™ (Eli Lilly), Serostim™ (Serono), Norditropin (Novo Nordisk), Omnitrope (Sandoz), Nutropin Depot (Genentech and Alkermes). Additionally, an analogue with an additional methionine residue at the N-terminal end is also marketed as, for ex: Somatonorm™ (Pharmacia Upjohn/Pfizer).

Growth hormone shares a common topology with the other members of the growth hormone family of proteins, Prolactin (PRL) and Placental Lactogen (PL). Growth hormone is classified as a four-helix bundle protein (FIG. 1) exhibiting an "up-up-down-down" topology with two conserved disulphide linkages. Specifically, wild-type human Growth hormone (hGH) is composed of 191 amino acid residues and has four cysteine residues at positions 53, 165, 182 and 189, which stabilizes the three dimensional structure of the protein by forming two intramolecular disulphide bonds connecting C53 with C165 and C182 with C189, respectively (FIG. 1). The structure of hGH has been experimentally determined by X-ray crystallography in the free form (Chantalet L. et al *Protein and Peptide Letters* 3, 333-340, (1995)) and in complex with its binding protein (the extra cellular domain of the human GHR (hGHR)) (Devos, A. M. et al *Science* 255, 306-312, (1992)). These structures have been deposited in the Protein Data Bank (PDB) and are publicly available (PDB accession codes 1 HGU and 1 HWG, respectively). Thus, from the published hGH structures residues important for hGH binding to hGHR can be identified. Furthermore, the dynamic properties of hGH has been studied by Nuclear Magnetic Resonance (NMR) spectroscopy (Kasimova M. R. et al. *J. Mol. Biol.* 318, 679-695, (2002)). In combination, the X-ray and NMR data can distinguish regions of hGH which are well structured and well defined from regions which are less structured and dynamic. Less structured and dynamic regions of hGH are expected to be particularly susceptible to proteolytic cleavage and proper stabilization of such regions would lead to improved proteolytic stability.

hGH has been subject to extensive mutagenesis in attempts to produce hGH analogues with desired chemical or biological properties. Specifically, cysteine mutants for several purposes have been described.

US 2003/0162949 disclose cysteine variants of members of the GH supergene family. A general method is provided for creating site-specific, biologically active conjugates of these proteins. The method involves adding cysteine residues to non-essential regions of the proteins or substituting cysteine residues for non-essential amino acids in the proteins using site-directed mutagenesis and then covalently coupling a cysteine-reactive polymer or other type of cysteine-reactive moiety to the proteins via the added cysteine residue WO 02/055532 describes genetically engineered hGH mutants having at least one non-polypeptide moiety covalently attached, particularly hGH mutants where a introduced cysteine residue was used for pegylation.

U.S. Pat. No. 5,951,972 describes physiologically active derivatized natural and recombinant mammalian and human proteins and polypeptides wherein at least one-naturally-occurring or incorporated cysteine residue within the protein is derivatized with various substituents.

The proteolytic cleavage of hGH has been studied in detail. The long loop composed of residues 128 to 154 has putative cleavage sites for several proteases, such as thrombin, plasmin, collagenase, subtilisin and chymotrypsin-like serine proteases. Accordingly, this part of hGH has been shown to be particularly susceptible to proteolytic cleavage (Lewis, U. J. *Ann. Rev. Physiol.* 46, 33-42, (1984)). Enzymes reported to degrade hGH include thrombin, plasmin, subtilisin, chymotrypsin-like serine proteinases and kallikreins.

The degradation of hGH in rat tissue has been investigated (Garcia-Barros et al. *J. Endocrinol. Invest.* 23, 748-754, (2000)).

In rat thyroid gland chymotrypsin-like proteases, favouring cleavage at bulky and lipophilic amino acid residues, were found initially to cleave the peptide bond between Y143 and S144 resulting in a two chain molecule, followed by cleavage between Y42 and S43, liberating the N-terminal peptide F1-Y42. The split loop in the two chain molecule is processed further by cleavage between F146 and D147 by chymotrypsin-like proteases and further by the action of carboxypeptidases.

Several methods to produce hGH analogues stabilized towards proteolytic degradation have been reported.

Alam et al., *J. Biotech.* 65, 183-190, (1998) designed hGH mutants resistant to thrombin and plasmin by specific point mutations. Thrombin cleaves hGH specifically between R134 and T135, and the double mutant R134D, T135P yielded a hGH variant resistant to cleavage by thrombin, and the triple mutant R134D, T135P, K140A resulted in resistance to plasmin. Furthermore, the latter hGH mutant was resistant to proteolysis by human plasma over a period of 7 days.

EP 534568 describes hGH mutants stabilized towards proteolytic degradation by mutating R134 to alanine, leucine, threonine, phenylalanine, proline or histidine.

WO 2004/022593/Nautilus describes general high through-put directed evolution methods to produce modified cytokines, including GH variants, with increased proteolytic stability.

WO 2006/048777/Nautilus specifically describes modified hGH analogues with improved proteolytic stability. The analogues contain one to five mutations at positions 1-55, 57, 58, 60-63, 67-87, 89-91, 93, 95-100, 102-128, 131-132, 135-139, 141, 142, 144, 148-182, 184, 185 and 187-191. Introduction of cysteine residues can potentially lead to the formation of undesired disulfide linked dimers and in WO 2006/048777 the substitution of amino acid residues by cysteine is specifically excluded from the scope; in WO 2006/048777 (p. 65) it is stated: "The replacement of amino acids by cysteine residues is explicitly avoided since this change would potentially lead to the formation of intermolecular disulfide bonds".

There is an obvious need to develop hGH compounds which are resistant to proteolytic degradation. Such stabilized compounds should exhibit increased stability towards proteolytic cleavage while retaining the desired biological properties of hGH. Such GH molecules would have increased stability, slower clearance and/or prolong in vivo half-life.

Furthermore it is well-known to modify the properties and characteristics of peptides by conjugating groups to the peptide which duly changes the properties of the peptide. Such conjugation generally requires some functional group in the peptide to react with another functional group in a conjugating group. Typically, amino groups, such as the N-terminal amino group or the ∈-amino group in lysines, have been used in combination with a suitable acylating reagent. Alternatively, polyethylene glycol (PEG) or derivatives thereof may be attached to proteins. For a review, see *Exp. Opion. Ther. Patent.* 14, 859-894, (2004). It has been shown that the attachment of PEG to growth hormone may have a positive effect on the plasma half-life of growth hormone, WO 03/044056.

The use of carboxypeptidases to modify the C-terminal of peptides has been described earlier. WO 92/05271 discloses the use of carboxypeptidases and nucleophilic compounds to amidate the C-terminal carboxy group, and WO 98/38285 discloses variants of carboxypeptidase Y particular suitable for this purpose.

EP 243 929 discloses the use of carboxypeptidase to incorporate polypeptides, reporter groups or cytotoxic agents into the C-terminal of proteins or polypeptides.

WO 2005/035553 describes methods for selective conjugation of peptides by enzymatically incorporating a functional group at the C-terminal of a peptide.

Activated halogen derivatives and maleimides represent some of the most common used functional groups when incorporateing conjugates to sulfhydryl groups in peptides (G. T. Hermanson in Bioconjugate Techniques 2. Ed. 2008, Elsevier).

Transglutaminase has previously been used to alter the properties of peptides. In the food industry and particular in the diary industry many techniques are available to e.g. cross-bind peptides using transglutaminases. Other documents disclose the use of transglutaminase to alter the properties of physiologically active peptides. EP 950665, EP 785276 and Sato, *Adv. Drug Delivery Rev.* 54, 487-504, (2002) disclose the direct reaction between peptides comprising at least one Gln and amine-functionalised PEG or similar ligands in the presence of transglutaminase, and Wada, *Biotech. Lett.* 23, 1367-1372, (2001) discloses the direct conjugation of β-lactoglobulin with fatty acids by means of transglutaminase. The international patent application published as WO 2005/070468 discloses the use of transglutaminase to incorporate a handle whereto conjugating groups can be attached.

Growth hormone is a key hormone involved in the regulation of not only somatic growth, but also in the regulation of metabolism of proteins, carbohydrates and lipids. The major effect of growth hormone is to promote growth. Human growth hormone is a 191 amino acid residue protein with the sequence:

(SEQ ID NO: 1)
FPTIPLSRLFDNAMLRAHRLHQLAFDTYQEFEEAYIPKEQKYSFLQNPQTSLCFSESIPTPSN

REETQQKSNLELLRISLLLIQSWLEPVQFLRSVFANSLVYGASDSNVYDLLKDLEEGIQTLMG

RLEDGSPRTGQIFKQTYSKFDTNSHNDDALLKNYGLLYCFRKDMDKVETFLRIVQCRSVEG

SCGF.

Administration of human growth hormone and closely related variants thereof is used to treat a variety of growth hormone deficiency related diseases. Being a polypeptide, growth hormone is administered parenterally, i.e., by means of a needle. Growth hormone is, furthermore, characterised by a relative short half-life, hence frequent administrations are required with the corresponding pain and inconvenience for the patient. Hence, there is still a need for the provision of growth hormone compounds with improved pharmacological properties, such as e.g. prolonged half-life.

The present invention provides novel growth hormone compound conjugates with improved pharmakinetic and pharmacological properties as well as methods for their production.

SUMMARY OF THE INVENTION

The bioavailability of a subcutaneously administered pharmaceutical compound may be related to the absorption rate. The ability of a compound to pass the tight junctions of the subcutaneous capillaries may in part be related to their physical and chemical properties as well as the molecular size or the hydrodynamic volume of the compound. A protein conjugate such as a pegylated hGH (PEG-hGH) with a 40 kDa PEG has an apparent molecular weight of 150-250 kDa. A hGH molecule with covalent bound albumin has a molecular weight of 87 kDa, whereas a hGH molecule with a non-covalent bound albumin will be dissociated from albumin part of the time and thus have a molecular weight of 22 kDa.

It is contemplated that the time spend in the dissociated state depends, at least partly, on the affinity of the albumin binding moiety. Thus the absorption rate of a hGH molecule with a non-covalent bound albumin may be faster than for a PEG-hGH. An increased rate of absorption may be obtained when using albumin binding moieties having lower affinity for albumin.

Additionally, the physical and chemical properties of the linker and/or the spacer providing the attachment of the albumin binding moiety to hGH will influence the functionalities of the compounds.

The present inventors have surprisingly found that growth hormone compounds (GH) with a single Cys mutation and/or an additional disulfide bridge may be selectively linked to an albumin binding residue—via a hydrophilic spacer that separates the GH and the albumin binding residue, typically with a chemical moiety having a mLog P<0—or a cLog P<0.5 to obtain GH conjugates with improved properties, such as high in vitro potency, or such as an increase in vivo half life, or such as increased resistant to proteolytic degradation possibly in combination with a protracted in vivo profile of action. By linking an albumin binding residue via a hydrophilic spacer to the single Cys mutation the biological activity may be retained and one or more of the above mention improvements may be obtained. Such improvements are also obtained when an albumin binding residue via a hydrophilic spacer is linked to the growth hormone having an additional disulfide bridge, such as to the N-terminal, position 40 or position 141 of hGH. The growth hormone compound may also comprise both a single Cys mutation and an additional disulfide bridge, in which aspect the albumin binding residue via a hydrophilic spacer is linked to the single Cys mutation.

In a broad aspect the present invention relates to a growth hormone conjugate which comprises a growth hormone compound (GH) having
  a) a single Cys mutation,
  b) an additional disulfide bridge, or
  c) a single Cys mutation and an additional disulfide bridge,
wherein an albumin binding residue via a hydrophilic spacer is linked to said GH, or a pharmaceutically acceptable salt thereof.

In one embodiment of the present invention the stable hGH compounds have additional disulphide bond(s). The disulphide bonds are formed between pairs of cysteines of which one or both are introduced by point mutations in the wild type hGH sequence.

In another embodiment of the present invention the stable hGH compounds have additional cysteines. The cysteines are introduced by point mutations in the wild type hGH sequence.

In a further embodiment of the present invention the stable hGH compounds have additional disulphide bond(s) and one or more additional cysteines. The additional disulphide bond(s) formed between pairs of additional cysteines and the additional cysteines are introduced by point mutations in the wild type hGH sequence.

Furthermore, the present invention is based on the observation that introducing an albumin binding residue via a hydrophilic spacer in human growth hormone (hGH) can be done selectively wherein a large proportion of the activity has been retained. Preferably, an albumin binding residue via a hydrophilic spacer is introduced at the position(s) corresponding to the introduced cystein(s) and/or in position glutamine 40 and/or in position glutamine 141 and/or the N-terminal in hGH having the sequence of SEQ ID NO: 1. The use of transglutaminase (TGase), and in particular TGase from *Streptoverticillium mobaraenae* or *Streptomyces lydicus* allows a selective introduction of an albumin binding residue via a hydrophilic spacer at position 40 or position 141, and the remaining 11 glutamine residues are left untouched despite the fact that glutamine is a substrate for transglutaminase.

Thus, in one embodiment of the present invention the growth hormone compound (GH) is linked to one albumin binding residue via a hydrophilic spacer. Typically, the albumin binding residue is attached to the N-terminal, or to position 18, 30, 40, 42, 62, 69, 88, 95, 98, 99, 100, 101, 102, 108, 135, 141 or 154 of hGH via a hydrophilic spacer. In further embodiments two albumin binding residues are attached to the single Cys mutation and any one of the above positions, such as the N-terminal, position 40 or position 141 of hGH via a hydrophilic spacer.

The growth hormone compound conjugates of the present invention have faster subcutaneous absorption compared to PEGylated hGH, and thus, provides less or no lipoathrophy. Furthermore, the albumin binding residue and the hydrophilic spacer are biodegradable in contrast to PEG.

It is a still further objective of the present invention to provide a method for improving the properties of a GH by conjugation said protein according to the methods of the present invention.

In further aspects the invention relates to isolated growth hormone compounds (GH) comprising a single cys mutation, an additional disulfide bond or growth hormone compounds comprising a single cys mutation and an additional disulfide bond. In a further object of the invention such compounds are soluble.

DEFINITIONS

In the present context, the term "growth hormone compound" as used herein means growth hormone of mammalian origin, such as human, bovine, or porcine growth hormone, and recombinant growth hormone, such as recombinant human, bovine, or porcine growth hormone, and variants as well as mutants of such growth hormones. As used herein "GH" and "growth hormone compound" are interchangeable. When GH is a variant of growth hormone of mammalian origin, such as hGH and recombinant hGH, said variant is understood to be the compound obtained by substituting one or more amino acid residues in the growth hormone, e.g. hGH, sequence with another natural or unnatural amino acid; and/or by adding one or more natural or unnatural amino acids to the growth hormone, e.g. hGH, sequence; and/or by deleting one or more amino acid residue from the growth hormone, e.g. hGH, sequence, wherein any of these steps may optionally be followed by further derivatization of one or more amino acid residues. Typically, the GH has at least 80% identity with hGH, and typically, at least 10% of the growth hormone activity of hGH as determined in assay (I) (Example 46) herein.

In the present context, the term "albumin binding residue" as used herein means a residue which binds noncovalently to human serum albumin. The albumin binding residue attached to the growth hormone compound (GH) typically has a binding affinity towards human serum albumin that is below about 10 μM or even below about 1 μM. A range of albumin binding residues are known among linear and branched lipohophillic moieties containing 12-40 carbon atoms, compounds with a cyclopentanophenanthrene skeleton, and/or peptides having 10-45 amino acid residues etc. Albumin binding properties can be measured by surface plasmon resonance as described in *J. Biol. Chem.* 277(38), 35035-35042, (2002).

The term "hydrophilic spacer" as used herein means a spacer that separates a growth hormone compound and an albumin binding residue with a chemical moiety which comprises at least 5 nonhydrogen atoms where 30-50% of these are either N or O.

In the present context, the term "transamination" and related terms are intended to indicate a reaction wherein the amide nitrogen in the side chain of glutamine is exchanged with nitrogen from another compound, in particular nitrogen from another nitrogen containing nucelophile.

Transglutaminase (E.C.2.3.2.13) is also known as protein-glutamine-γ-glutamyltransferase and catalyses the general reaction

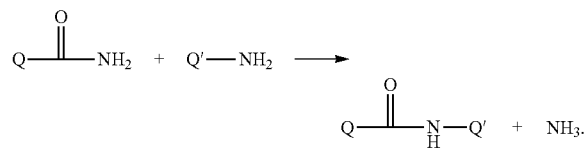

Q-C(O)—NH$_2$ (amine acceptor) may represent a glutamine residue containing peptide or protein and Q'—NH$_2$ (amine donor) represents an amine-containing nucleophile. Alternatively, QC(O)—NH$_2$ and Q'—NH$_2$ may represent an amine acceptor and a lysine-containing peptide or protein, respectively. In the present invention, however, Q-C(O)—NH$_2$ represents a glutamine residue containing growth hormone and Q'—NH$_2$ represents an amine-containing nucleophile as indicated above.

Examples of useful transglutaminases include microbial transglutaminases, such as e.g. those from *Streptomyces mobaraense*, *Streptomyces cinnamoneum* and *Streptomyces griseocarneum* (all disclosed in U.S. Pat. No. 5,156,956, which is incorporated herein by reference), and from *Streptomyces lavendulae* (disclosed in U.S. Pat. No. 5,252,469, which is incorporated herein by reference) and *Streptomyces ladakanum* (JP 2003/199569, which is incorporated herein by reference). It should be noted that members of the former genus *Streptoverticillium* are now included in the genus *Streptomyces* (Kaempfer, *J. Gen. Microbiol.* 137, 1831-1892, (1991)). Other useful microbial transglutaminases have been isolated from *Bacillus subtilis* (disclosed in U.S. Pat. No. 5,731,183, which is incorporated herein by reference) and from various Myxomycetes. Other examples of useful microbial transglutaminases are those disclosed in WO 96/06931 (e.g. transglutaminase from *Bacilus lydicus*) and WO 96/22366, both of which are incorporated herein by reference. Useful non-microbial transglutaminases include guinea-pig liver transglutaminase, and transglutaminases from various marine sources like the flat fish *Pagrus major* (disclosed in EP-0555649, which is incorporated herein by reference), and the Japanese oyster *Crassostrea gigas* (disclosed in U.S. Pat. No. 5,736,356, which is incorporated herein by reference).

In the present context, the term "not accessible" is intended to indicate that something is absent or de facto absent in the sense that it cannot be reached. When it is stated that functional groups are not accessible in a protein to be conjugated it is intended to indicate that said functional group is absent from the protein or, if present, in some way prevented from taking part in reactions. By way of example, said functional group could be buried deep in the structure of the protein so that it is shielded from participating in the reaction. It is recognised that whether or not a functional group is accessible depends on the reaction conditions. It may be envisaged that, e.g. in the presence of denaturing agents or at elevated temperatures the protein may unfold to expose otherwise not accessible functional groups. It is to be understood that "not accessible" means "not accessible at the reaction condition chosen for the particular reaction of interest".

The term "alkane" or "alkyl" is intended to indicate a saturated, linear, branched and/or cyclic hydrocarbon. Unless specified with another number of carbon atoms, the term is intended to indicate hydrocarbons with from 1 to 30 (both included) carbon atoms, such as 1 to 20 (both included), such as from 1 to 10 (both included), e.g. from 1 to 5 (both included). The terms alkyl and alkylene refer to the corresponding radical and bi-radical, respectively.

The term "$C_{1-6}$ alkyl" refers to a straight chained or branched saturated hydrocarbon having from one to six carbon atoms inclusive. Examples of such groups include, but are not limited to, methyl, 2-propyl, 1-butyl, 2-butyl, 2-methyl-2-propyl, 2-methyl-1-butyl and n-hexyl.

The term "$C_{3-10}$ cycloalkyl" typically refers to cyclopropyl, cyclobutyl, cyclopentyl, cyclohexyl, cycloheptyl, cyclooctyl, cyclononyl, and cyclodecanyl.

The term "alkene" is intended to indicate linear, branched and/or cyclic hydrocarbons comprising at least one carbon-carbon double bond. Unless specified with another number of carbon atoms, the term is intended to indicate hydrocarbons with from 2 to 30 (both included) carbon atoms, such as 2 to 20 (both included), such as from 2 to 10 (both included), e.g. from 2 to 5 (both included). The terms alkenyl and alkenylene refer to the corresponding radical and bi-radical, respectively.

The term "alkyne" is intended to indicate linear, branched and/or cyclic hydrocarbons comprising at least one carbon-carbon triple bond, and it may optionally comprise one or more carbon-carbon double bonds. Unless specified with another number of carbon atoms, the term is intended to indicate hydrocarbons with from 2 to 30 (both included) carbon atoms, such as 2 to 20 (both included), such as from 2 to 10 (both included), e.g. from 2 to 5 (both included). The terms alkynyl and alkynylene refer to the corresponding radical and bi-radical, respectively.

The term "homocyclic aromatic compound" is intended to indicate aromatic hydrocarbons, such as benzene and naphthalene.

The term "heterocyclic compound" is intended to indicate a cyclic compound comprising 5, 6 or 7 ring atoms from which 1, 2, 3 or 4 are hetero atoms selected from N, O and/or S. Examples include heterocyclic aromatic compounds, such as thiophene, furan, pyran, pyrrole, imidazole, pyrazole, isothiazole, isooxazole, pyridine, pyrazine, pyrimidine, pyridazine, as well as their partly or fully hydrogenated equivalents, such as piperidine, pirazolidine, pyrrolidine, pyrroline, imidazolidine, imidazoline, piperazine and morpholine.

The terms "hetero alkane", "hetero alkene" and "hetero alkyne" are intended to indicate alkanes, alkenes and alkynes as defined above, in which one or more hetero atom or group have been inserted into the structure of said moieties. Examples of hetero groups and atoms include —O—, —S—, —S(O)—, —S(O)$_2$—, —C(O)— —C(S)— and —N(R*)—, wherein R* represents hydrogen or C$_1$-C$_6$-alkyl. Examples of heteroalkanes include.

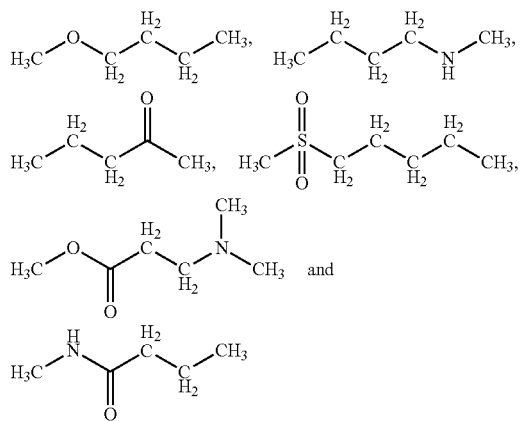

The term "radical" or "biradical" is intended to indicate a compound from which one or two, respectively, hydrogen atoms have been removed. When specifically stated, a radical may also indicate the moiety formed by the formal removal of a larger group of atoms, e.g. hydroxyl, from a compound.

The term "halogen" is intended to indicate members of the seventh main group of the periodic table, e.g. F, Cl, Br and I.

In the present context, the term "aryl" is intended to indicate a carbocyclic aromatic ring radical or a fused aromatic ring system radical wherein at least one of the rings are aromatic. Typical aryl groups include phenyl, biphenylyl, naphthyl, and the like.

The term "heteroaryl" or "hetaryl", as used herein, alone or in combination, refers to an aromatic ring radical with for instance 5 to 7 member atoms, or to a fused aromatic ring system radical with for instance from 7 to 18 member atoms, wherein at least one ring is aromatic, containing one or more heteroatoms as ring atoms selected from nitrogen, oxygen, or sulfur heteroatoms, wherein N-oxides and sulfur monoxides and sulfur dioxides are permissible heteroaromatic substitutions. Examples include furanyl, thienyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, and indazolyl, and the like.

The term "conjugate" as a noun is intended to indicate a modified protein, i.e. a protein with a moiety bonded to it in order to modify the properties of said protein. As a verb, the term is intended to indicate the process of bonding a moiety to a protein to modify the properties of said protein.

The term "single cys" or a "free cysteine" refers to a cysteine residue, which is not engaged in double bond. A protein, may thus include one or more single cys residues in addition to one or more additional disulfide bridge(s), as long as said single cys's do not lead to internal disulfide bridge(s).

As used herein, the term "prodrug" indicates biohydrolyzable amides and biohydrolyzable esters and also encompasses a) compounds in which the biohydrolyzable functionality in such a prodrug is encompassed in the compound according to the present invention, and b) compounds which may be oxidized or reduced biologically at a given functional group to yield drug substances according to the present invention. Examples of these functional groups include 1,4-dihydropyridine, N-alkylcarbonyl-1,4-dihydropyridine, 1,4-cyclohexadiene, tert-butyl, and the like.

As used herein, the term "biohydrolyzable ester" is an ester of a drug substance (in casu, a compound according to the invention) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is, for example increased solubility or that the biohydrolyzable ester is orally absorbed from the gut and is transformed to a compound according to the present invention in plasma. Many examples of such are known in the art and include by way of example lower alkyl esters (e.g., C$_1$-C$_4$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in casu, a compound according to the present invention) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is, for example increased solubility or that the biohydrolyzable amide is orally absorbed from the gut and is transformed to a compound according to the present invention in plasma. Many examples of such are known in the art and include by way of example lower alkyl amides, α-amino acid amides, alkoxyacyl amides, and alkylaminoalkylcarbonyl amides.

In the present context, the term "pharmaceutically acceptable salt" is intended to indicate salts which are not harmful to the patient. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, paminobenzoic, glutamic, benzenesulfonic, p-toluenesulfonic acids and the like. Further examples of pharmaceutically acceptable inorganic or organic acid addition salts include the pharmaceutically acceptable salts listed in *J. Pharm. Sci.* 66, 2, (1977) which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

A "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The patient to be treated is preferably a mammal; in particular a human being, but it may also include animals, such as dogs, cats, cows, sheep and pigs.

DESCRIPTION OF THE INVENTION

In a broad aspect the present invention relates to a stable growth hormone conjugate which comprises a growth hormone compound (GH) having a) a single Cys mutation,
b) an additional disulfide bridge, or
c) a single Cys mutation and an additional disulfide bridge, wherein an albumin binding residue via a hydrophilic spacer is linked to said GH, or a pharmaceutically acceptable salt thereof.

When a single Cys mutation is present, an albumin binding residue via a hydrophilic spacer is linked to the sulphur residue of the Cys. When an additional disulphide bridge is present (but no single Cys mutation) then an albumin binding residue via a hydrophilic spacer is linked to a position in the growth hormone compound, such as position 40, position 141 or the N-terminal of hGH, as described herein. When two or more albumin binding residues are linked to the growth hormone compound via a hydrophilic spacer, then such albumin binding residues are linked to a single Cys mutation if such mutation is present or if only an additional disulphide bridge is present then an albumin binding residue via a hydrophilic spacer is linked to a position in the growth hormone compound as described herein.

In one embodiment the growth hormone compound has one single Cys mutation.

In another embodiment the growth hormone compound has two single Cys mutations.

In a further embodiment the growth hormone compound has an additional disulfide bridge.

In a further embodiment the growth hormone compound has one single Cys mutation and one additional disulfide bridge.

In a further embodiment GH represents a growth hormone compound comprising an amino acid sequence having at least 90% identity to the amino acid sequence of human growth hormone (hGH) (SEQ ID NO: 1). In further embodiments, GH has at least 80%, such as at least 85%, such as at least 95% identity with hGH, such at at least 96%, such as at least 97%, such as at least 98% or such as at least 99% identity with SEQ ID NO: 1. In further embodiments, said identities to hGH is coupled to at least 10%, such as at least 20%, such as at least 40%, such as at least 60%, such as at least 80% of the growth hormone activity of hGH as determined in assay I herein. Any one of the sequence identity embodiments may be combined with any one of the activity embodiments, such as a GH having at least 80% identity with hGH and coupled to at least 60% of the growth hormone activity of hGH; a GH having at least 90% identity with hGH and coupled to at least 40% of the growth hormone activity of hGH; a GH having at least 95% identity with hGH and coupled to at least 80% of the growth hormone activity of hGH, and so forth. As described herein HG may be expressed as MetHG which indicates that the sequence comprise an additional N-terminal methionine.

In an embodiment GH is a growth hormone variant wherein a single Cys mutation is introduced. In further embodiments GH represents a growth hormone compound containing one to five mutations in addition to a single Cys mutation.

In a further embodiment the albumin binding residue via a hydrophilic spacer is linked to the single Cys mutation. In an embodiment the single Cys mutation is position in the N-terminal, H1, H2, L2 or H3 of GH. In further embodiments, the single Cys mutation is positioned in the N-terminal, the mutation being such as any one of T3C, P5C, S7C, or in H1 (corresponding to AA 9-35), the mutation being such as any one of D11C, $H_{18}C$, Q29C, E30C, E33C, A34C, Y35C, or in L1 (corresponding to AA36-71), the mutation being such as any one of K38C, E39C, Y42C, S43C, D47C, P48C, S55, S57C, P59C, S62C, E65C, Q69C or preferably any one of Y42C, S55C, S57C, S62C, Q69C or in H2, L2 or H3 (corresponding to AA 72-98, AA 99-106 and AA 107-127), the mutation being such as any one of E88C, Q91C, S95C, A98C, N99C, S100C, L101C, V102C, Y103C, D107C, S108C, D112C, Q122C and G126C of hGH (SEQ ID NO: 1) or in L3 or H4 (corresponding to AA128-154 and AA155-184) In L3 and H4 (128-154 and AA155-184) the mutation being such as any one of E129C, D130C, G131C, P133C, T135C, G136C, T142C, D147C, N149C, D154C, A155C, L156C, R178C, V180C or in the C-terminal the mutation being such as any one of E186C G187C G190C.

If the single Cys mutation is present in a hGH variant the mutation is located in corresponding amino acid residues.

In particular embodiment the GH the single Cys mutation has been introduced in a position equivalent to a parent GH that is equivalent to a position of hGH (SEQ ID NO: 1) selected from the group consisting of: T3, P5, S7, D11, H18, Q29, E30, E33, A34, Y35, K38, E39, Y42, S43, D47, P48, S55, S57, P59, S62, E65, Q69, E88, Q91, S95, A98, N99, S100, L101, V102, Y103, D107, S108, D112, Q122, G126, E129, D130, G131, P133, T135, G136, T142, D147, N149, D154, A155, L156, R178, E186, G187 and G190, such as the group consisting of: T3, P5, S7, D11, H18, Q29, E30, E33, A34, Y35, E88, Q91, S95, A98, N99, S100, L101, V102, Y103, D107, S108, D112, Q122 and G126 the GH conjugate further comprising an albumin binding moiety at the side chain of said single cysteine residue.

In further embodiments the single Cys mutation is located within AA 93-106 in hGH or corresponding residues in hGH variants. In further specified embodiments the single Cys mutation is located within L2, such as within AA 99-106 or AA 99-103 or corresponding residues.

When a single Cys mutation is present in the growth hormone compound conjugate of the present invention, a typical single Cys mutation is E30C. A further typical single Cys mutation is Y42C. A further typical single Cys mutation is S55C. A further typical single Cys mutation is S57C. A further typical single Cys mutation is S62C. A further typical single Cys mutation is Q69C. A further typical single Cys mutation is S95C. A further typical single Cys mutation is A98C. A further typical single Cys mutation is N99C. A further typical single Cys mutation is S100C. A further typical single Cys mutation is L101C. A further typical single Cys mutation is V102C. A further typical single Cys mutation is S108C.

According to the crystal structure of the rhGH/receptor complex (PDB: 3HHR) the bundle consists of four major helices: first helix (A) from residue 9 to 34, second helix (B) from residue 72 to 92 and from residue 94 to 100, third helix (C) from residue 106 to 128, and fourth helix (D) from residue 155 to 184 (M. R. Kasimova et. al. *J. Mol. Biol.* 318, 679-695, (2002)). The four main helices are referred to as the core of the protein. Residues that are not part of the helical regions are defined as loop residues, and may be part of flexible regions, loops, β-turns, hairpins and coils. A slightly different localization of helix's is obtained when hGH is in complex with its binding protein (PDB: 1 HWG), which is the helix definition referred to above.

Moreover, the invention relates to a GH conjugate comprising at least one introduced cysteine residue which residue has been introduced in a position equivalent to a position in a helix or loop region of hGH. In particular the amino acid residues may be introduced in a surface exposed position in a helix or loop region that has more than 25% of its side chain exposed at the surface, preferably more than 50% of its side chain exposed at the surface, e.g. in a model structure of hGH alone or in a model structure of hGH complexed to its two receptor molecules. In a preferred embodiment, the position in the helix or the loop is equivalent to a position outside a receptor binding site of hGH. Surface exposed residues may be identified using computational chemistry algorithms. For example, relative surface accessibilities can be calculated with the computer program Quanta 2005 from Accelrys Inc. using the atomic coordinates from the publicly available structures (PDB accession codes 1 HGU and 1 HWG structure) and default parameter settings. A description of the underlying principle behind the algorithm can be found in B. Lee and F. M. Richards, "The Interpretation of Protein Structures: Estimation of Static Accessibility" *J. Mol. Biol.* 55, 379-400, (1971).

In a further embodiment the albumin binding residue via a hydrophilic spacer is linked to the GH having an additional disulfide bridge. Typically, the albumin binding residue via a hydrophilic spacer is linked to the N-terminal, position 40 or position 141 of hGH.

In a further embodiment the GH comprises additional disulfide bonds between a loop segment and a helical segment or within loop segment or between loop segments or between helical segments.

In a further embodiment the GH comprises an additional disulfide bond wherein at least one of the cysteines is present in a loop segment, such from amino acid residues 128-154 (L3).

In a further embodiment the GH comprises an additional disulfide bond wherein the additional disulfide bond connects a loop segment with a helical segment.

In a further embodiment the GH comprises an additional disulfide bond wherein the additional disulfide bond connects a loop segment with helix B or helix 2 (corresponding to AA 72-98).

In a further embodiment the GH comprises and additional disulfide bond linking helix 2 (corresponding to AA 72-98) with loop 3 (corresponding to AA 128-154).

In a further embodiment the GH comprise an addition disulfide bond between one of the amino acid pairs in positions corresponding to R16C/L117C, A17C/E174C, H21C/M170C, D26C/V102C, D26C/Y103C, N47C/T50C, Q49C/G161C, F54C/Y143C, F54C/S144C, F54C/F146C, S55C/Y143C, S57C/Y143C, I58C/Q141C, I58C/Y143C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C, F92C/T148C, R94C/D107C, V102C/A105C, L156C/F146C, L156C/T148C and/or V185C/S188C in SEQ ID NO: 1.

In a further embodiment the additional disulfide bridge of GH is between at least one of the amino acid pairs in the positions corresponding to R16C/L117C, A17C/E174C, $H_{18}$C/Y143C, H21C/M170C, N47C/T50C, Q49C/G161C, F54C/S144C, F54C/F146C, I58C/Q141C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, S85C/Y143C, P89C/F146C, F92C/F146C, F92C/T148C, R94C/D107C, V102C/A105C, L156C/F146C, L156C/T148C and/or V185C/S188C in hGH (SEQ ID NO: 1).

In a further embodiment the additional disulfide bond is between one of the amino acid pairs in positions corresponding to A17C/E174C, H21C/M170C, D26C/V102C, D26C/Y103C, F54C/Y143C, F54C/S144C, F54C/F146C, S55C/Y143C, S57C/Y143C, I58C/Q141C, I58C/Y143C, I58C/S144C, P59C/Q137C, S71C/S132C, L81C/Y143C, Q84C/Y143C, S85C/Y143C, S85C/S144C, F92C/T148C and/or R94C/D107C in SEQ ID NO: 1.

In a further embodiment the additional disulfide bond is between one of the amino acid pairs in positions corresponding to D26C/V102C, D26C/Y103C, S57C/Y143C, I58C/S144C, P59C/Q137C, S71C/S132C, Q84C/Y143C, S85C/Y143C, S85C/S144C, F92C/T148C and/or R94C/D107C in SEQ ID NO: 1.

In a further embodiment the additional disulfide bond is between one of the amino acid pairs in positions corresponding to H21C/M170C, D26C/V102C, D26C/Y103C, F54C/Y143C, F54C/S144C, S55C/Y143C, S57C/Y143C, I58C/Q141C, I58C/Y143C, I58C/S144C, P59C/Q137C, S71C/S132C, L81C/Y143C, Q84C/Y143C, S85C/Y143C and/or S85C/S144C in SEQ ID NO: 1.

In a further embodiment the additional disulfide bond is between one of the amino acid pairs in positions corresponding to S57C/Y143C, Q84C/Y143C, S85C/Y143C and/or S85C/S144C in SEQ ID NO: 1. Typically, the additional disulfide bridge is Q84C/Y143C.

In a further embodiment the albumin binding residue via a hydrophilic spacer is linked to the GH having a single Cys mutation and an additional disulfide bridge. Typically, the albumin binding residue via a hydrophilic spacer is linked to the single Cys mutation. In a particular embodiment the GH has an additional disulfide bridge Q84C/Y143C and a single Cys mutation L101C where to the albumin binding residue via a hydrophilic spacer is linked.

In further embodiments the GH has an additional disulfide bond and a single Cys mutation selected from any one of:

T3C, P5C, S7C, D11C, H$_{18}$C, Q29C, E30C, E33C, A34C, Y35C, K38C, E39C, Y42C, S43C, D47C, P48C, S55C, S57C, P59C, S62, E65C, Q69C, E88C, Q91C, S95C, A98C, N99C, S100C, L101C, V102C, Y103C, D107C, S108C, D112C, Q122C, G126C, E129C, D130C, G131C, P133C, T135C, G136C, T142C, D147C, N149C, D154C, A155C, L156C, R178C, E186C, G187C and G190C, such as any one of: T3C, P5C, S7C, D11C, H$_{18}$C, Q29C, E30C, E33C, A34C, Y35C, E88C, Q91C, S95C, A98C, N99C, S100C, L101C, V102C, Y103C, D107C, S108C, D112C, Q122C and G126C of hGH (SEQ ID NO:1) or corresponding residues in a hGH variant.

In a particular embodiment the GH has an additional disulfide bond and a single Cys mutation, and said single Cys mutation has been introduced in a position equivalent to a parent GH that is equivalent to a position of hGH (SEQ ID NO: 1) selected from the group consisting of: T3, P5, S7, D11, H18, Q29, E30, E33, A34, Y35, K38, E39, Y42, S43, D47, P48, S55, S57, P59, S62, E65, Q69, E88, Q91, S95, A98, N99, S100, L101, V102, Y103, D107, S108, D112, Q122, G126, E129, D130, G131, P133, T135, G136, T142, D147, N149, D154, A155, L156, R178, E186, G187 and G190, preferably the group: T3, P5, S7, D11, H18, Q29, E30, E33, A34, Y35, E88, Q91, S95, A98, N99, S100, L101, V102, Y103, D107, S108, D112, Q122 and G126. The GH conjugate further comprise an albumin binding moiety at the side chain of said single cysteine residue.

In a further embodiment the GH comprises a single cys mutation and additional disulfide bonds between a loop segment and a helical segment or within loop segment or between loop segments or between helical segments.

In a further embodiment the GH comprises a single cys mutation and an additional disulfide bond wherein at least one of the cysteines is present in a loop segment, such from amino acid residues 128-154 (L3).

In a further embodiment the GH comprises a single cys mutation and an additional disulfide bond wherein the additional disulfide bond which connects a loop segment, such from amino acid residues 128-154, with a helical segment, such as helix B or helix 2 (corresponding to AA 72-98).

In a further embodiment the GH comprises a single cys mutation and additional disulfide bond linking helix 2 (corresponding to AA 72-98) with loop 3 (corresponding to AA 128-154).

In a further embodiment the GH comprises a single cys mutation and an addition disulfide bond between one of the amino acid pairs in positions corresponding to R16C/L117C, A17C/E174C, H21C/M170C, D26C/V102C, D26C/Y103C, N47C/T50C, Q49C/G161C, F54C/Y143C, F54C/S144C, F54C/F146C, S55C/Y143C, S57C/Y143C, I58C/Q141C, I58C/Y143C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C, F92C/T148C, R94C/D107C, V102C/A105C, L156C/F146C, L156C/T148C and/or V185C/S188C in SEQ ID NO: 1.

In a further embodiment the GH comprises a single cys mutation and an additional disulfide bridge between at least one of the amino acid pairs in the positions corresponding to R16C/L117C, A17C/E174C, H$_{18}$C/Y143C, H21C/M170C, N47C/T50C, Q49C/G161C, F54C/S144C, F54C/F146C, I58C/Q141C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, S85C/Y143C, P89C/F146C, F92C/F146C, F92C/T148C, R94C/D107C, V102C/A105C, L156C/F146C, L156C/T148C and/or V185C/S188C in hGH (SEQ ID NO: 1).

In a further embodiment the GH comprises a single cys mutation and an additional disulfide bond between one of the amino acid pairs in positions corresponding to A17C/E174C, H21C/M170C, D26C/V102C, D26C/Y103C, F54C/Y143C, F54C/S144C, F54C/F146C, S55C/Y143C, S57C/Y143C, I58C/Q141C, I58C/Y143C, I58C/S144C, P59C/Q137C, S71C/S132C, L81C/Y143C, Q84C/Y143C, S85C/Y143C, S85C/S144C, F92C/T148C and/or R94C/D107C in SEQ ID NO: 1.

In a further embodiment the additional disulfide bond is between one of the amino acid pairs in positions corresponding to D26C/V102C, D26C/Y103C, S57C/Y143C, I58C/S144C, P59C/Q137C, S71C/S132C, Q84C/Y143C, S85C/Y143C, S85C/S144C, F92C/T148C and/or R94C/D107C in SEQ ID NO: 1.

In a further embodiment the GH comprises a single cys mutation and an additional disulfide bond between one of the amino acid pairs in positions corresponding to H21C/M170C, D26C/V102C, D26C/Y103C, F54C/Y143C, F54C/S144C, S55C/Y143C, S57C/Y143C, I58C/Q141C, I58C/Y143C, I58C/S144C, P59C/Q137C, S71C/S132C, L81C/Y143C, Q84C/Y143C, S85C/Y143C and/or S85C/S144C in SEQ ID NO: 1.

In a further embodiment the GH comprises a single cys mutation and an additional disulfide bond between one of the amino acid pairs in positions corresponding to S57C/Y143C, Q84C/Y143C, S85C/Y143C and/or S85C/S144C in SEQ ID NO: 1.

Solubility of a hydrophilic spacer (B) can be described by its log P value. Log P, also known as the partition coefficient, is the logarithm of the ratio of concentrations of a compound in the two phases of a mixture of two immiscible solvents at equilibrium. Typically one of the solvents is water while the second is selected from octan-1-ol, chloroform, cyclohexane and propylene glycol dipelargonate (PGDP). Log P values measured in these different solvents show differences principally due to hydrogen bonding effects. Octanol can donate and accept hydrogen bonds whereas cyclohexane is inert. Chloroform can donate hydrogen bonds whereas PGDP can only accept them. Log P values may be measured by standard methods know in the art.

In one embodiment of the invention, the hydrophilic spacer has a Log P below 0, such as below 0.5 in either octan-1-ol, chloroform, cyclohexane and propylene glycol dipelargonate (PGDP).

In a further embodiment, the hydrophilic spacer has a log P below −1 in either octan-1-01, chloroform, cyclohexane and propylene glycol dipelargonate (PGDP).

Alternatively, the Log P value can be calculated as mLog P and/or cLog P for the albumin binder part or hydrophilic spacer part using published algorithms (T. Fujita; J. Iwasa and C. Hansch, *J. Am. Chem. Soc.* 86, 5175-5180, (1964) "A New Substituent Constant, Pi, Derived from Partition Coefficients", C. A. Lipinski et al. *Advanced Drug Delivery Reviews*, 23, 3-25, (1997) "Experimental and Computational Approaches to Estimate Solubility and Permeability in Drug Discovery and Development Settings" and I. Moriguchi, S. Hirono, I. Nakagome, H. Hirano, *Chem. Pharm. Bull.* 42, 976-978, (1994) "Comparison of Reliability of log P Values for Drugs Calculated by Several Methods").

In one embodiment of the present invention the hydrophilic spacer (B) has a mLog P<0.

In a further embodiment the growth hormone compound (GH) is linked to one albumin binding residue via a hydrophilic spacer (B).

In a further embodiment the growth hormone compound (GH) is linked to an albumin binding residue via a hydrophilic spacer (B) coupled to a free cysteine in the growth hormone compound (GH).

In another embodiment the growth hormone compound (GH) is linked to two albumin binding residues via one or two hydrophilic spacer(s). Thus, in one example one albumin binding residue is linked via one hydrophilic spacer (B) to the single Cys mutation and the other albumin binding residue is linked via one hydrophilic spacer (B') to glutamine in position 40 or position 141; or alternatively two albumin binding residues are linked via one hydrophilic spacer (B) to the single Cys mutation or to glutamine in position 40, position 141 or the N-terminal. In still another embodiment the growth hormone compound (GH) is linked to three albumin binding residues via one or more hydrophilic spacer(s).

In an embodiment the hydrophilic spacer comprise at least one OEG motif, the radical 8-amino-3,6-dioxaoctanic acid, i.e. —NH—$(CH_2)_2$—O—$(CH_2)_2$—O—$CH_2$—C(O)—. In a further specified embodiment the hydrophilic spacer comprise at least two OEG motifs. The orientation of such OEG motif(s) is in one embodiment so that the —C(O)— is closest to the growth hormone compound but not connecting the growth hormone compound and the albumin binder linker and the —NH— is closest to the albumin binding residue. In additional embodiments comprising two OEG motifs the two motifs have identical orientation or different orientation. In an embodiment two such OEG motifs are located adjactant to each other whereas in alternative embodiments such OEG mofifs are sperated by one or more covalently linked atoms.

In an embodiment the hydrophilic spacer comprise at least one glutamic acid residue. The amino acid glutamic acid comprises two carboxylic acid groups. Its gamma-carboxy group may be used for forming an amide bond with the epsilon-amino group of lysine, or with an amino group of an OEG molecule, if present, or with the amino group of another Glu residue, if present. The alfa-carboxy group may alternatively be used for forming a similar amide bond with the epsilon-amino group of lysine, or with an amino group of an OEG molecule, if present, or with the amino group of another Glu residue, if present. The amino group of Glu may in turn form an amide bond with the carboxy group of the albumin binding residue, or with the carboxy group of an OEG motif, if present, or with the gamma-carboxy group or alfa carboxy group of another Glu, if present. The linkage of the amino group of one Glu to a gamma-carboxy group of a second Glu may be referred to as a "gamma-Glu" motif.

In an embodiment the hydrophilic spacer comprise at least one combined OEG-Glu motif (—NH—$(CH_2)_2$—O—$(CH_2)_2$—O—$CH_2$—C(O)NH—CH(C(O)OH)—$(CH_2)_2$—C(O)—) or at least one combined Glu-OEG motif (—NH—CH(C(O)OH)—$(CH_2)_2$—C(O)NH—$(CH_2)_2$—O—$(CH_2)_2$—O—$CH_2$—C(O)—) or combinations here of, where in such Glu-OEG and OEG-Glu motifs may be separated by one or more covalently likned atoms or directly bond to each other by an amide bond of the Glu's forming a gammal-Glu.

In a further aspect the present invention relates to a growth hormone conjugate wherein the growth hormone conjugate has the formula (I):

A-W—B-GH    (I)

Wherein
GH represents a growth hormone compound having a single Cys mutation,
B represents a hydrophilic spacer linked to the sulphur residue of the Cys mutation,
W is a chemical group linking A and B, and
A represent an albumin binding residue; and
pharmaceutically acceptable salts thereof.

In a further embodiment GH represents a growth hormone compound comprising an amino acid sequence having at least 90% identity to the amino acid sequence of human growth hormone (hGH) (SEQ ID NO:1). In further embodiments, GH has at least 80%, such as at least 85%, such as at least 95%, such as at least 96%, such as at least 97%, such as at least 98% or such as at least 99% identity with hGH (SEQ ID NO: 1). In further embodiments, said identities to hGH are coupled to at least 10%, such as at least 20%, such as at least 40%, such as at least 60%, such as at least 80% of the growth hormone activity of hGH as determined in assay I herein. Any one of the sequence identity embodiments may be combined with any one of the activity embodiments, such as a GH having at least 80% identity with hGH and coupled to at least 60% of the growth hormone activity of hGH; a GH having at least 90% identity with hGH and coupled to at least 40% of the growth hormone activity of hGH; a GH having at least 95% identity with hGH and coupled to at least 80% of the growth hormone activity of hGH, and so forth.

In further embodiments the GH of the conjugate has a single Cys mutation selected from any one of a single Cys mutation in the N-terminal, H1, H2, L2 or H3 regions of GH. In further such embodiments, the single Cys mutation is positioned in the N-terminal, the mutation being such as any one of T3C, P5C, S7C, or in H1 (corresponding to AA 9-35), the mutation being such as any one of D11C, $H_{18}C$, Q29C, E30C, E33C, A34C, Y35C, or in L1 (corresponding to AA36-71), the mutation being such as any one of K38C, E39C, Y42C, S43C, D47C, P48C, S55, S57C, P59C, S62C, E65C, Q69C or preferably any one of Y42C, S55C, S57C, S62C, Q69C or in H2, L2 or H3 (corresponding to AA 72-98, AA 99-106 and AA 107-127), the mutation being such as any one of E88C, Q91C, S95C, A98C, N99C, S100C, L101C, V102C, Y103C, D107C, S108C, D112C, Q122C and G126C of hGH (SEQ ID NO: 1) or in L3 or H4 (corresponding to AA128-154 and AA155-184) In L3 and H4 (128-154 and AA155-184) the mutation being such as any one of E129C, D130C, G131C, P133C, T135C, G136C, T142C, D147C, N149C, D154C, A155C, L156C, R178C, V180C or in the C-terminal the mutation being such as any one of E186C G187C G190.

If the single Cys mutation is present in a hGH variant the mutation is located in corresponding amino acid residues.

Further embodiments includes GH conjugates wherein the single cys mutation in GH is selected from any one of: T3C, P5C, S7C, D11C, $H_{18}C$, Q29C, E30C, E33C, A34C, Y35C, K38C, E39C, Y42C, S43C, D47C, P48C, S55C, S57C, P59C, S62, E65C, Q69C, E88C, Q91C, S95C, A98C, N99C, S100C, L101C, V102C, Y103C, D107C, S108C, D112C, Q122C, G126C, E129C, D130C, G131C, P133C, T135C, G136C, T142C, D147C, N149C, D154C, A155C, L156C, R178C, E186C, G187C and G190C, such as any one of; T3C, P5C, S7C, D11C, $H_{18}C$, Q29C, E30C, E33C, A34C, Y35C, E88C, Q91C, S95C, A98C, N99C, S100C, L101C, V102C, Y103C, D107C, S108C, D112C, Q122C and G126C of hGH (SEQ ID NO: 1).

In even further embodiments the single Cys mutation is located within AA 93-106 in hGH or corresponding residues in hGH variants. In further specified embodiments the single Cys mutation is located within L2, such as within AA 99-106 or AA 99-103 or corresponding residues.

In a further embodiment A is selected from

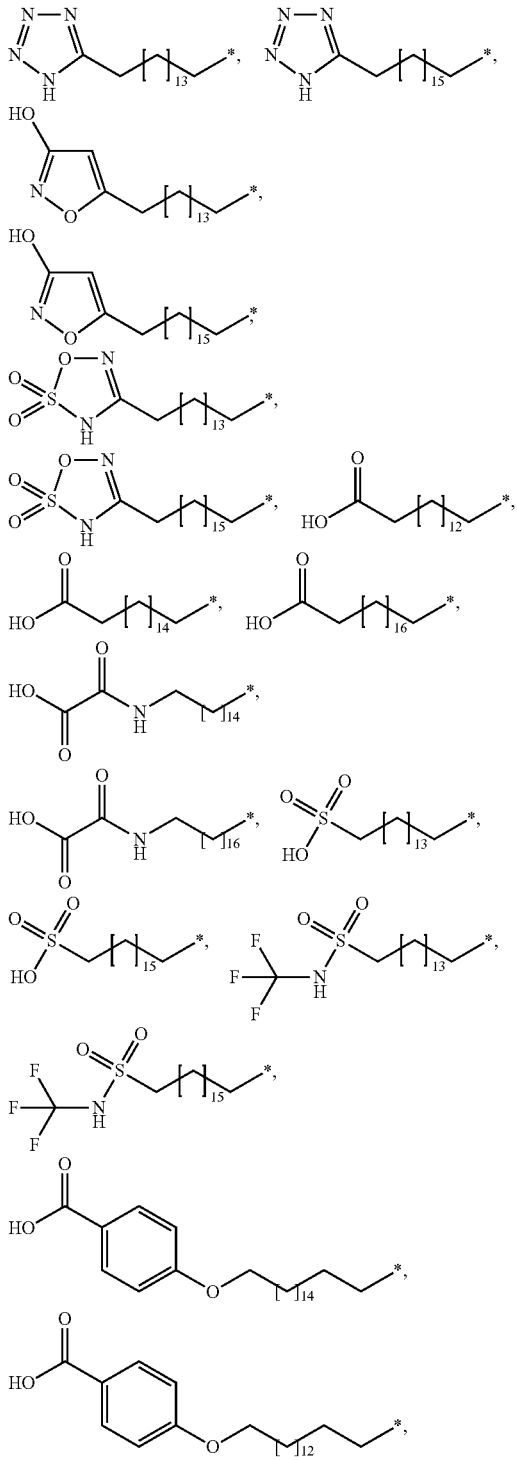

wherein * denotes the attachment to B through W.

In a further embodiment W has the formula

—$W_7$—$Y$—, wherein $Y$ is —$(CH_2)_{l7}$—$C_{3-10}$-cycloalkyl-$W_8$— or a valence bond, l7 is 0-6, $W_7$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s3}$—, —C(O)—, —C(O)O—, —OC(O)—, or a valence bond; wherein s3 is 0 or 1, $W_8$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s4}$—, —C(O)—, —C(O)O—, —OC(O)—, or a valence bond; wherein s4 is 0 or 1.

In further embodiments B comprise or consist of one or more OEG, and/or gamma-Glu motiv as described above.

In a further embodiment B has the formula

—$X_1$—$X_2$—$X_3$—$X_4$— wherein $X_1$ is —$W_1$—[(CHR$^1$)$_{l1}$—$W_2$]$_{m1}$—{[(CH$_2$)$_{n1}$E1]$_{m2}$—[(CHR$^2$)$_{l2}$—$W_3$]$_{m3}$}$_{n2}$—, $X_2$ is —[(CHR$^3$)$_{l3}$—$W_4$]$_{m4}$—{[(CH$_2$)$_{n3}$E2]$_{m5}$—[(CHR$^4$)$_{l4}$—$W_5$]$_{m6}$}$_{n4}$—, $X_3$ is —[(CHR$^5$)$_{l5}$—$W_6$]$_{m7}$—, $X_4$ is F-D1-(CH$_2$)$_{l6}$-D2-, l1, l2, l3, l4, l5 and l6 independently are selected from 0-16, m1, m3, m4, m6 and m7 independently are selected from 0-10, m2 and m5 independently are selected from 0-25, n1, n2, n3 and n4 independently are selected from 0-16, F is aryl, hetaryl, pyrrolidine-2,5-dione or a valence bond, wherein the aryl and hetaryl groups are optionally substituted with halogen, —CN, —OH, —C(O)OH, —C(O)NH$_2$, —S(O)$_2$OH or C$_{1-6}$-alkyl, R$^1$, R$^2$, R$^3$, R$^4$ and R$^5$ independently are selected from hydrogen, —C(O)OH, —C(O)NH$_2$, —S(O)OH, —S(O)$_2$OH, —NH—C(=NH)—NH$_2$, C$_{1-6}$-alkyl, aryl or hetaryl; wherein the alkyl, aryl and hetaryl groups optionally are substituted with halogen, —C(O)OH, —C(O)NH$_2$, —S(O)OH, —S(O)$_2$OH, —CN or —OH, D1, D2, E1 and E2 independently are selected from —O—, —N(R$^6$)—, —N(C(O)R$^7$)— or a valence bond; wherein R$^6$ and R$^7$ independently represent hydrogen or C$_{1-6}$-alkyl, $W_1$ to $W_5$ independently are selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s2}$—, —C(O)—, —C(O)O—, —OC(O)—, or a valence bond; wherein s2 is 0 or 1, $W_6$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s1}$—, —C(O)—, —C(O)O—, —OC(O)—, —NHC(O)C$_{1-6}$-alkyl, —C(O)NHC$_{1-6}$-alkyl or a valence bond; wherein s1 is 0 or 1 and the C$_{1-6}$-alkyl group is optionally substituted with oxo, pyrrolidine-2,5-dione, —NHC(O)CH*CH$_2$COOH or —NHC(O)CH₂CH*COOH; wherein (*) indicates the attachment point from the carbon atom of CH to $X_4$.

In a further embodiment l1, l2, l3, l4, l5 and l6 independently are 0-6.

In a further embodiment m1, m3, m4, m6 and m7 independently are 0-6.

In a further embodiment m2 and m5 independently are 0-10.

In a further embodiment n1, n2, n3 and n4 independently are 0-10.

In a further embodiment D1 and D2 are independently selected from —O— or —N(R⁶)— or a valence bond.

In a further embodiment E1 and E2 are independently selected from —O— or —N(R⁶)— or a valence bond.

In a further embodiment $W_1$ through $W_8$ independently are selected from the group consisting of —C(O)NH—, —NHC(O)—, —CH₂NHC(O)—, —C(O)NHS(O)₂—, —S(O)₂NHC(O)—, —NHC(O)C₁₋₆-alkyl, —C(O)NHC₁₋₆-alkyl or a valence bond; wherein the alkyl group is optionally substituted with oxo, pyrrolidine-2,5-dione, —NHC(O)CH*CH₂COOH or —NHC(O)CH₂CH*COOH; wherein (*) indicates the attachment point from the carbon atom of CH to $X_4$.

In a further embodiment R¹, R², R³, R⁴ and R⁵ independently are selected from hydrogen, —C(O)OH, —C(O)NH₂, —S(O)₂OH or C₁₋₆-alkyl; wherein the C₁₋₆-alkyl group optionally is substituted with —C(O)OH, —C(O)NH₂ or —S(O)₂OH.

In a further embodiment —{[(CH₂)ₙ₁E1]ₘ₂—[(CHR²)ₗ₂—W₃]ₘ₃}ₙ₂— and —{[(CH₂)ₙ₃E2]ₘ₅—[(CHR⁴)ₗ₄—W₅]ₘ₆}ₙ₄—, wherein E1 and E2 are —O—, are selected from

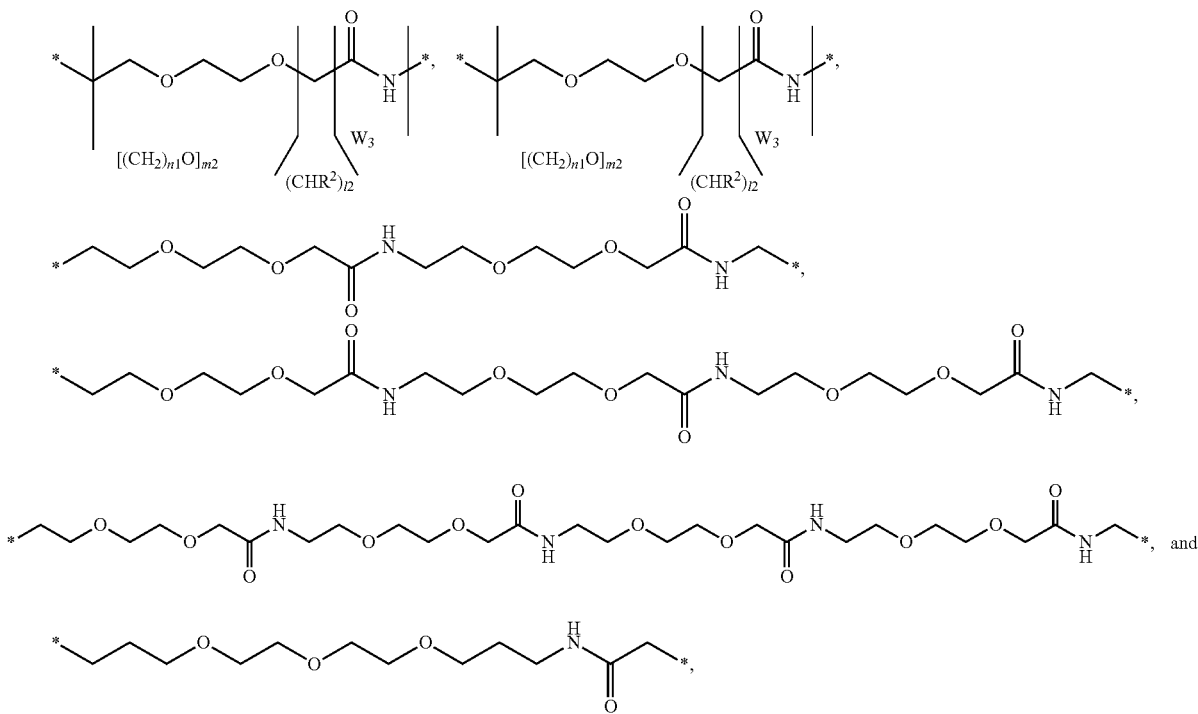

wherein * is intended to denote a point of attachment, ie, an open bond.

In a further embodiment $X_4$ is a valence bond and $W_6$ is selected from either pyrrolidine-2,5-dione, —NHC(O)CH*CH₂COOH or —NHC(O)CH₂CH*COOH wherein (*) indicates the attachment point from the carbon atom of CH to GH.

In a further embodiment B is selected from

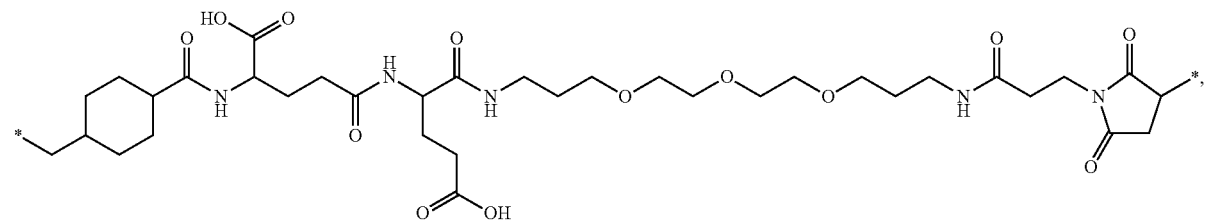

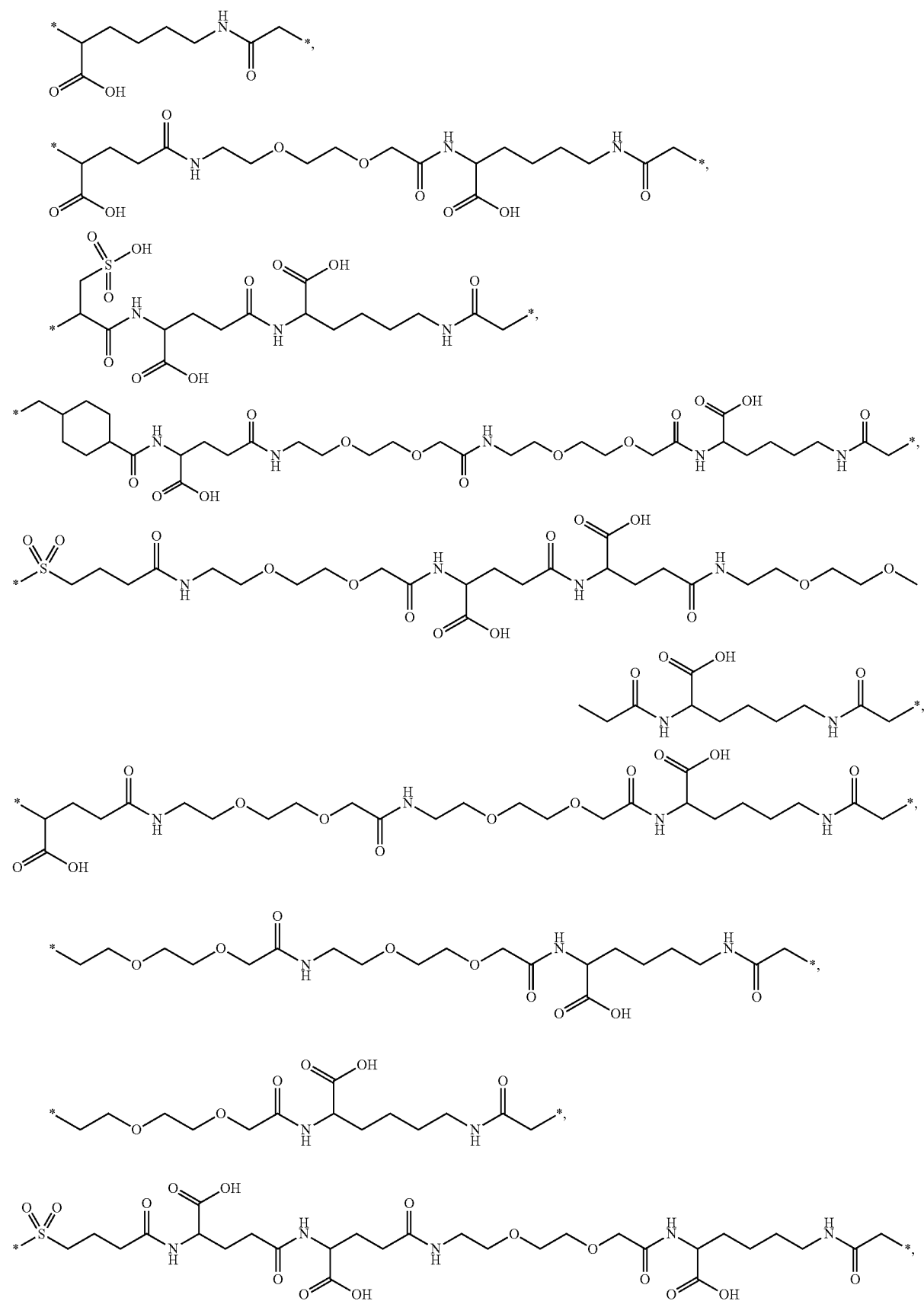

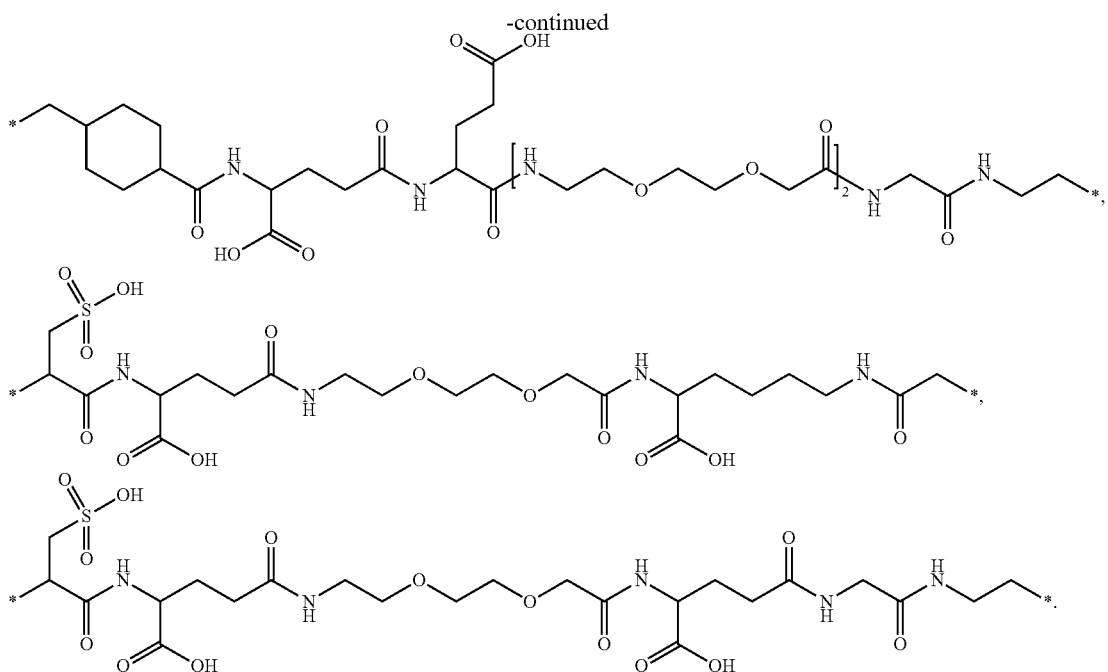
In a further embodiment the GH conjugate is selected from
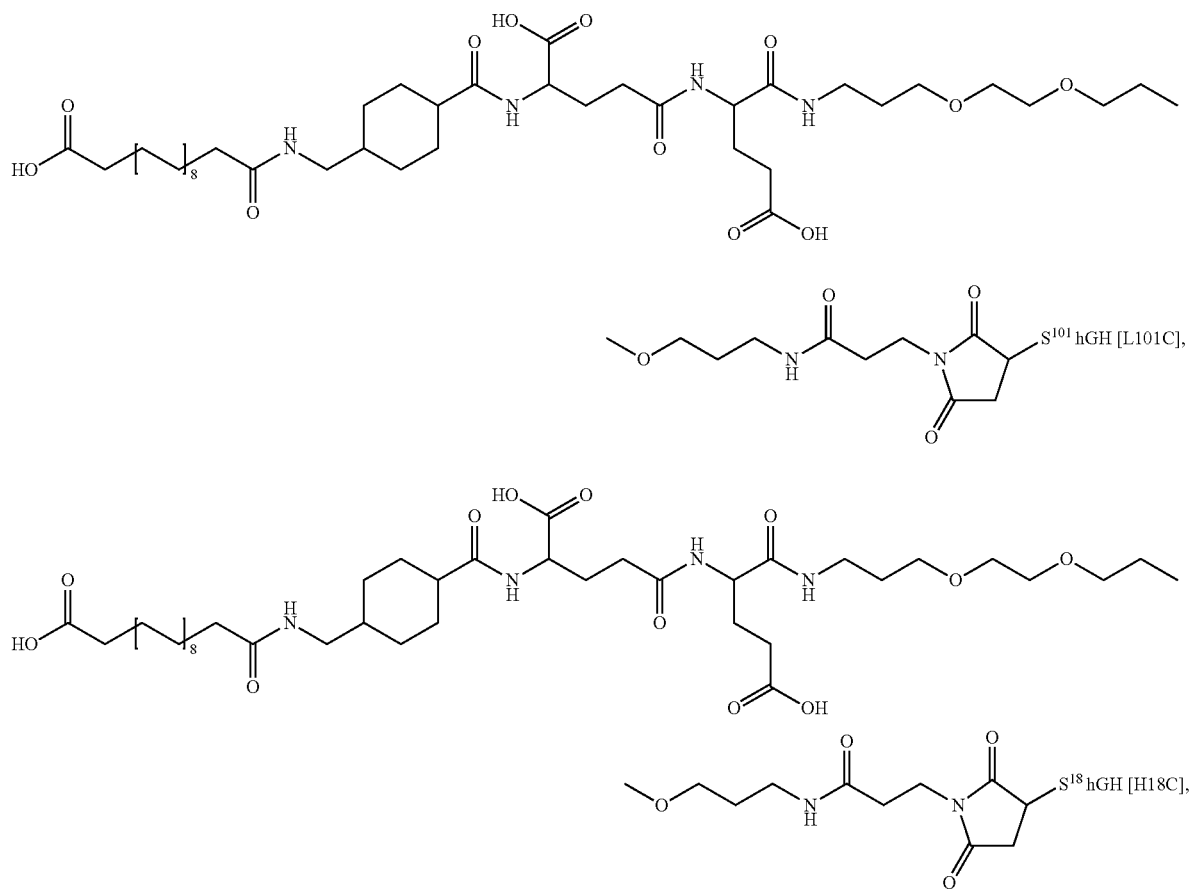

-continued
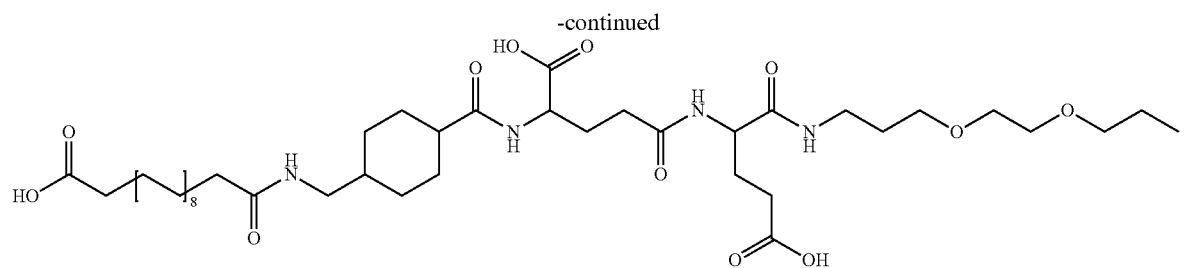

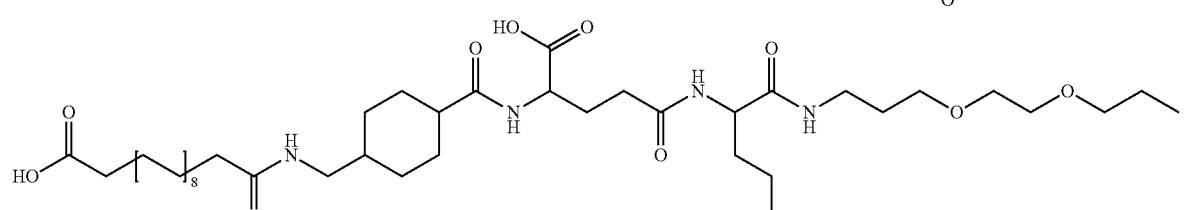
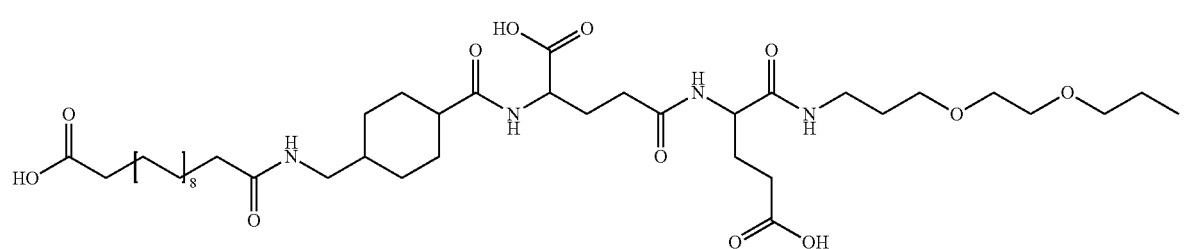

-continued
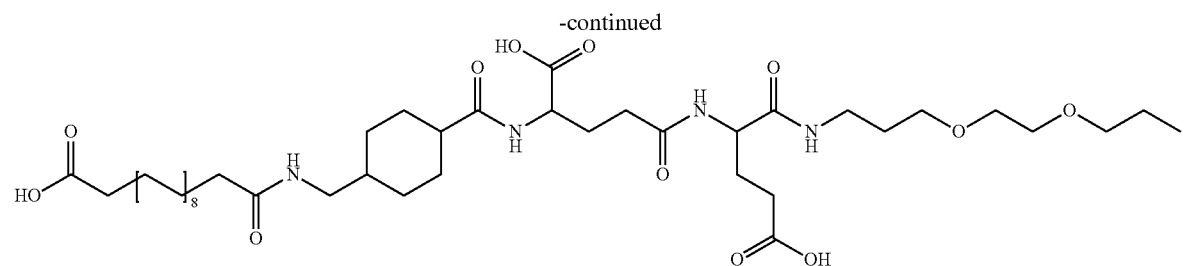
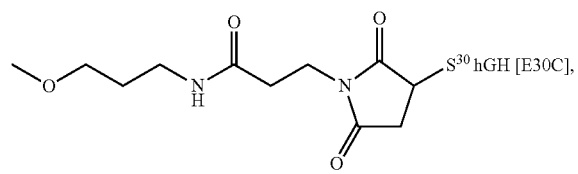
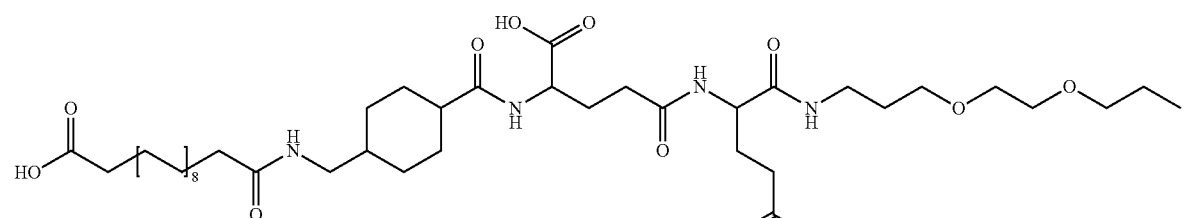
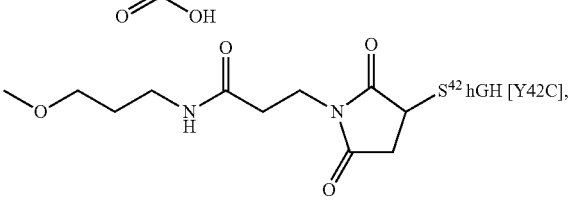
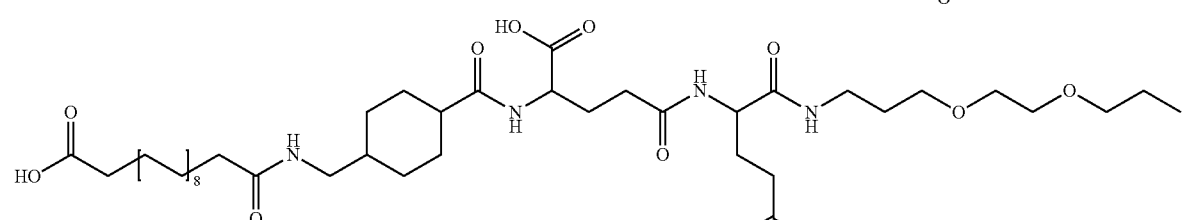
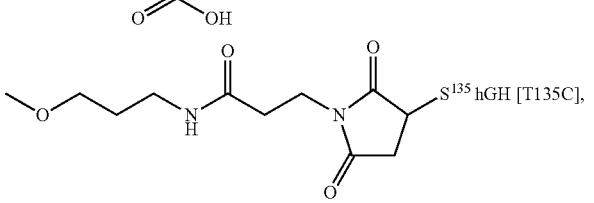
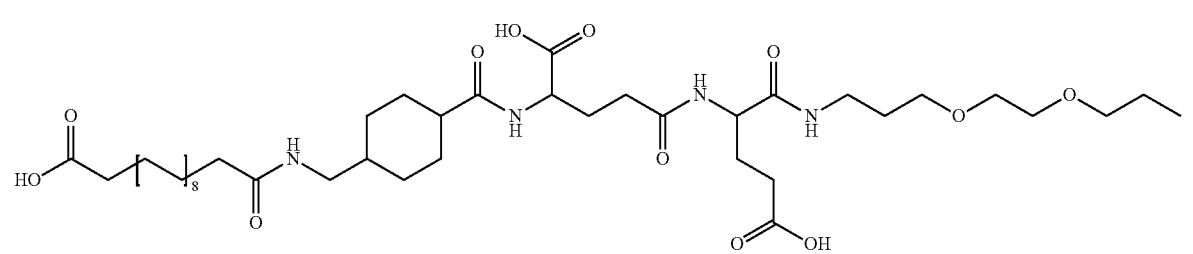
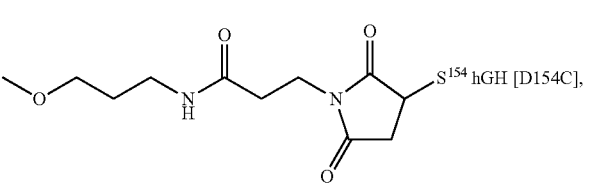

-continued
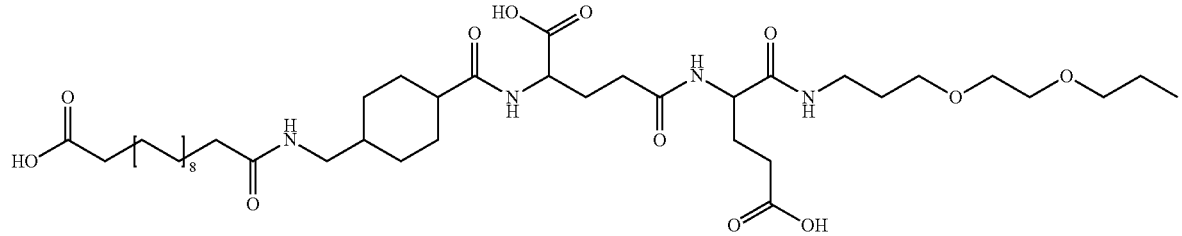
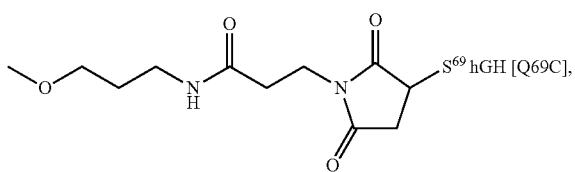
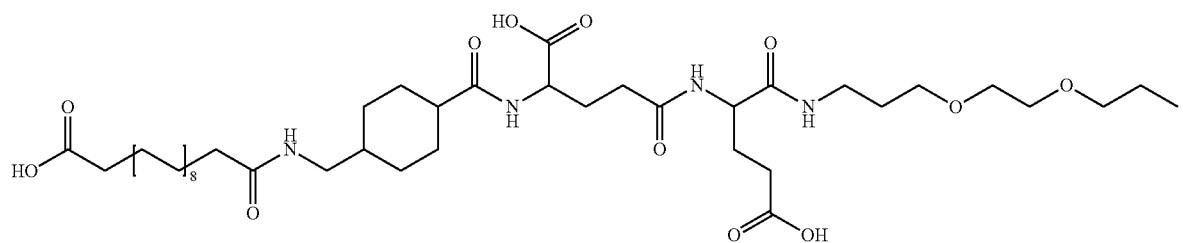
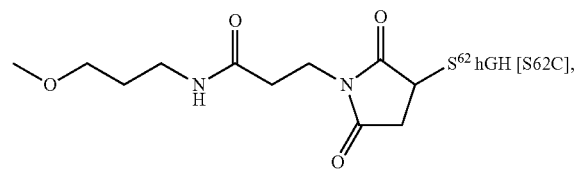
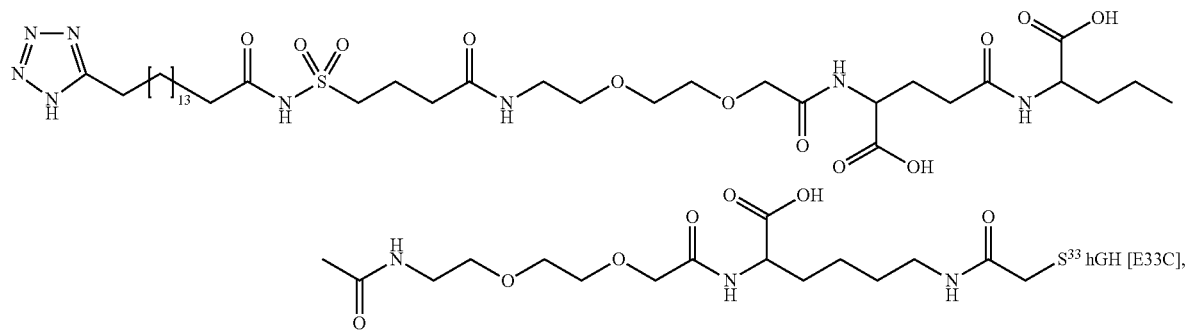
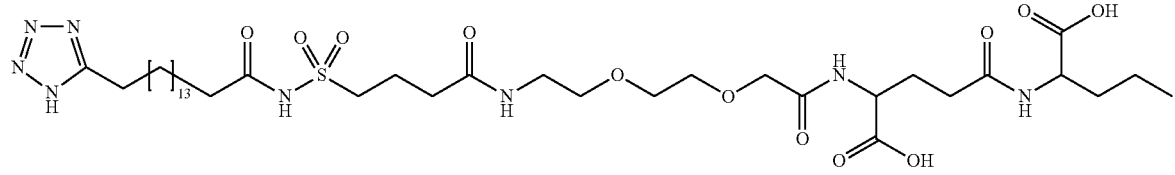
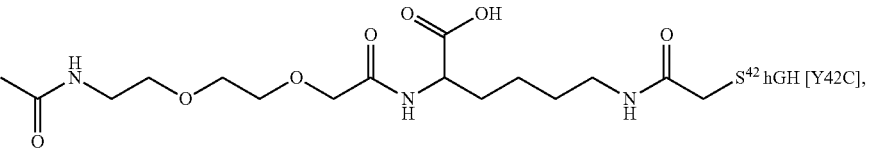
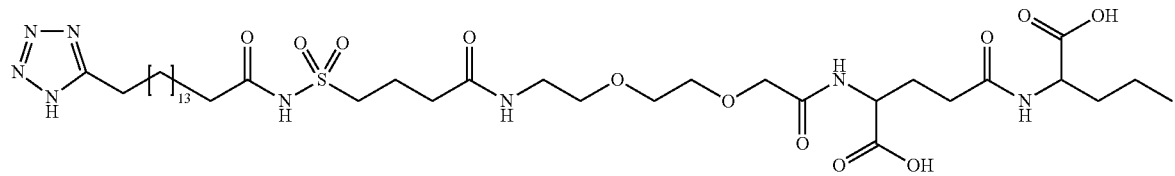

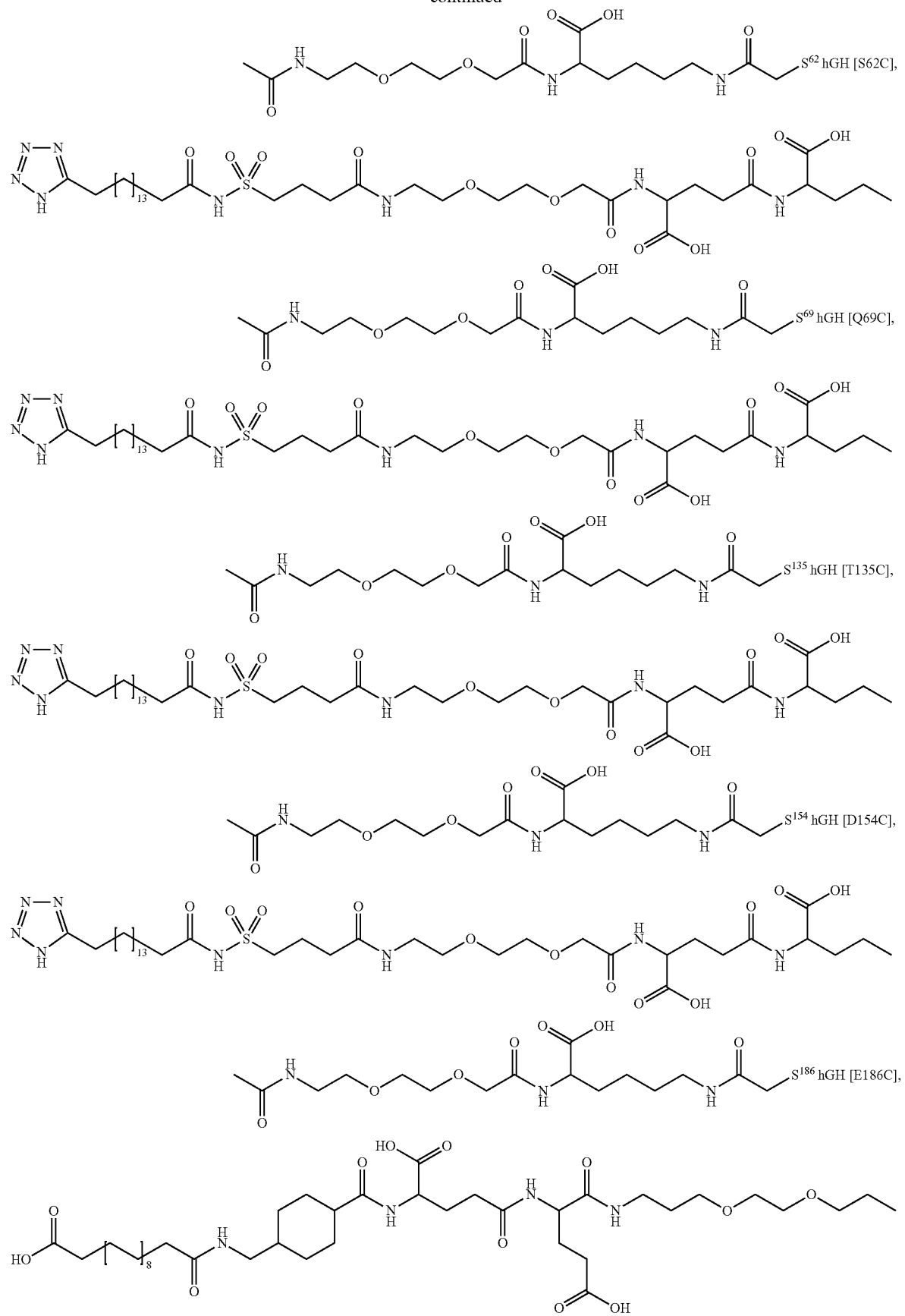

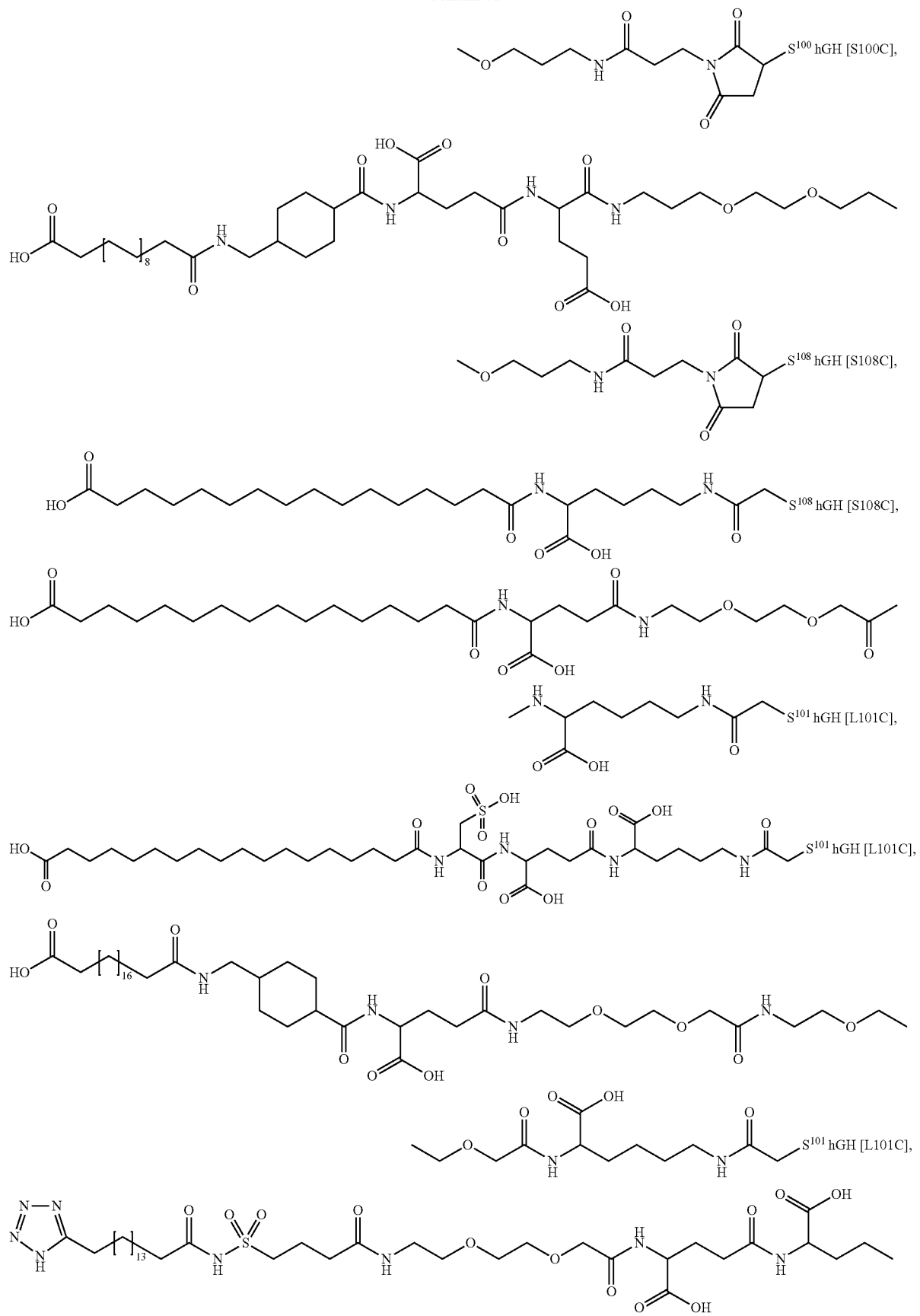

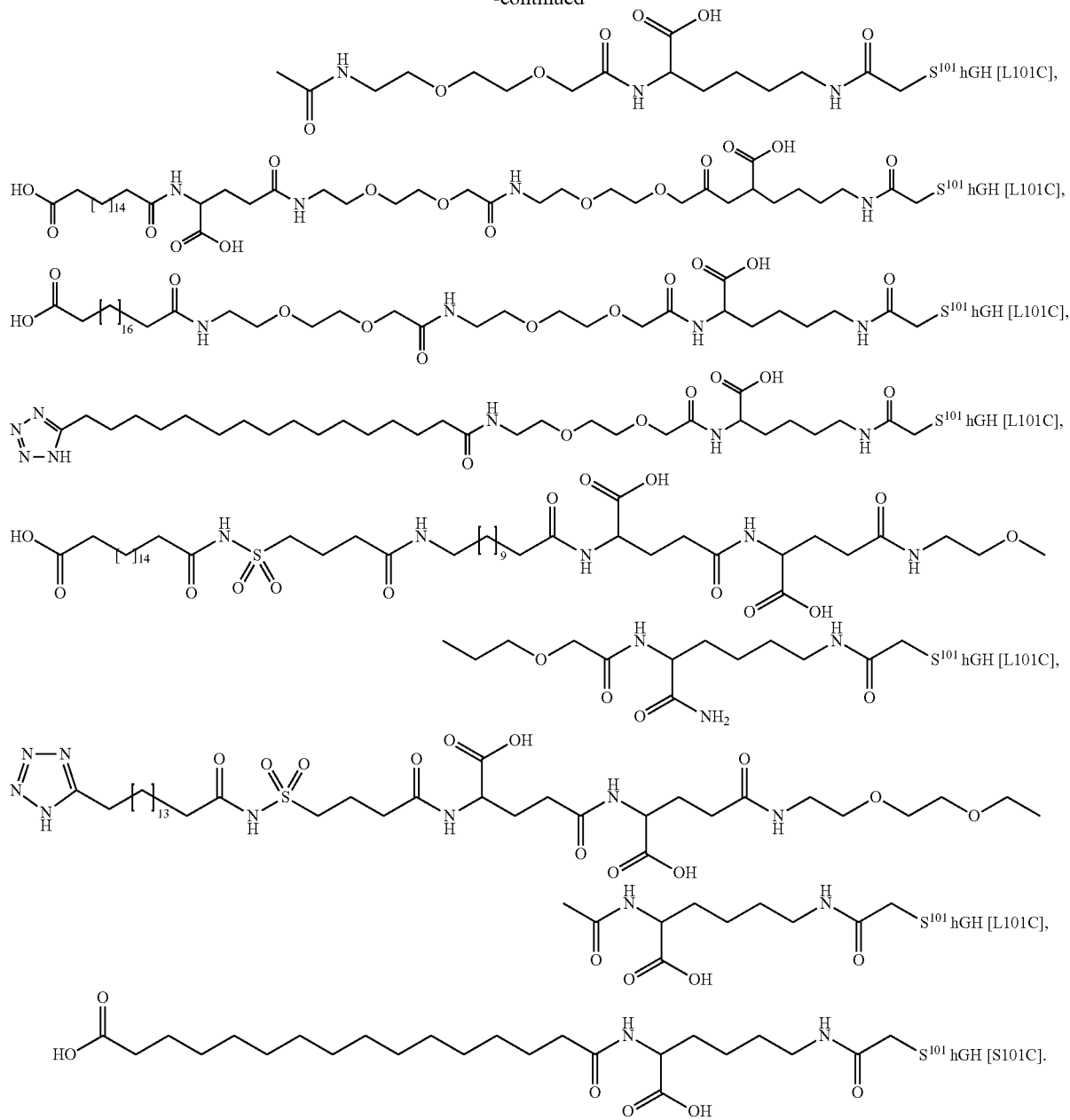

In a further aspect the present invention relates to a growth hormone conjugate having the formula (I):

A-W—B-GH (I)

Wherein
GH represents a growth hormone compound having an additional disulfide bridge,
B represents a hydrophilic spacer,
W is a chemical group linking A and B, and
A represent an albumin binding residue; and
pharmaceutically acceptable salts thereof.

In a further embodiment GH represents a growth hormone compound comprising an amino acid sequence having at least 90% identity to the amino acid sequence of human growth hormone (hGH) (SEQ ID NO: 1). In further embodiments, GH has at least 80%, such as at least 85%, such as at least 95%, such as at least 96%, such as at least 97%, such as at least 98% or such as at least 99% identity with hGH (SEQ ID NO: 1). In further embodiments, said identities to hGH are coupled to at least 10%, such as at least 20%, such as at least 40%, such as at least 60%, such as at least 80% of the growth hormone activity of hGH as determined in assay I herein. Any one of the sequence identity embodiments may be combined with any one of the activity embodiments, such as a GH having at least 80% identity with hGH and coupled to at least 60% of the growth hormone activity of hGH; a GH having at least 90% identity with hGH and coupled to at least 40% of the growth hormone activity of hGH; a GH having at least 95% identity with hGH and coupled to at least 80% of the growth hormone activity of hGH, and so forth.

In a further embodiment the GH of the conjugate comprises additional disulfide bonds between a loop segment and a helical segment or within loop segment or between loop segments or between helical segments.

In a further embodiment the GH of the conjugate comprises an additional disulfide bond wherein at least one of the cysteines is present in a loop segment, such from amino acid residues 128-154.

In a further embodiment the GH of the conjugate comprises an additional disulfide bond wherein the additional disulfide bond which connects a loop segment, such from amino acid residues 128-154 (H3), with a helical segment, such as helix B or helix 2 (corresponding to AA 72-98).

In a further embodiment the GH of the conjugate comprises and additional disulfide bond linking helix 2 (corresponding to AA 72-98) with loop 3 (corresponding to AA 128-154).

In a further embodiment the GH of the conjugate comprise an addition disulfide bond between one of the amino acid pairs in positions corresponding to R16C/L117C, A17C/E174C, H21C/M170C, D26C/V102C, D26C/Y103C, N47C/T50C, Q49C/G161C, F54C/Y143C, F54C/S144C, F54C/F146C, S55C/Y143C, S57C/Y143C, I58C/Q141C, I58C/Y143C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, S85C/Y143C, S85C/S144C, P89C/F146C, F92C/F146C, F92C/T148C, R94C/D107C, V102C/A105C, L156C/F146C, L156C/T148C and/or V185C/S188C in SEQ ID NO: 1.

In a further embodiment the additional disulfide bridge is between at least one of the amino acid pairs in the positions corresponding to R16C/L117C, A17C/E174C, H18C/Y143C, H21C/M170C, N47C/T50C, Q49C/G161C, F54C/S144C, F54C/F146C, I58C/Q141C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, S85C/Y143C, P89C/F146C, F92C/F146C, F92C/T148C, R94C/D107C, V102C/A105C, L156C/F146C, L156C/T148C and/or V185C/S188C in hGH (SEQ ID NO: 1).

In a further embodiment the GH of the conjugate comprises an additional disulfide bond between one of the amino acid pairs in positions corresponding to A17C/E174C, H21C/M170C, D26C/V102C, D26C/Y103C, F54C/Y143C, F54C/S144C, F54C/F146C, S55C/Y143C, S57C/Y143C, I58C/Q141C, I58C/Y143C, I58C/S144C, P59C/Q137C, S71C/S132C, L81C/Y143C, Q84C/Y143C, S85C/Y143C, S85C/S144C, F92C/T148C and/or R94C/D107C in SEQ ID NO: 1.

In a further embodiment the additional disulfide bond is between one of the amino acid pairs in positions corresponding to D26C/V102C, D26C/Y103C, S57C/Y143C, I58C/S144C, P59C/Q137C, S71C/S132C, Q84C/Y143C, S85C/Y143C, S85C/S144C, F92C/T148C and/or R94C/D107C in SEQ ID NO: 1.

In a further embodiment the GH of the conjugate comprise an additional disulfide bond between one of the amino acid pairs in positions corresponding to H21C/M170C, D26C/V102C, D26C/Y103C, F54C/Y143C, F54C/S144C, S55C/Y143C, S57C/Y143C, I58C/Q141C, I58C/Y143C, I58C/S144C, P59C/Q137C, S71C/S132C, L81C/Y143C, Q84C/Y143C, S85C/Y143C and/or S85C/S144C in SEQ ID NO: 1.

In a further embodiment the GH of the conjugate comprises an additional disulfide bond between one of the amino acid pairs in positions corresponding to S57C/Y143C, Q84C/Y143C, S85C/Y143C and/or S85C/S144C in SEQ ID NO: 1.

In a further embodiment A is selected from

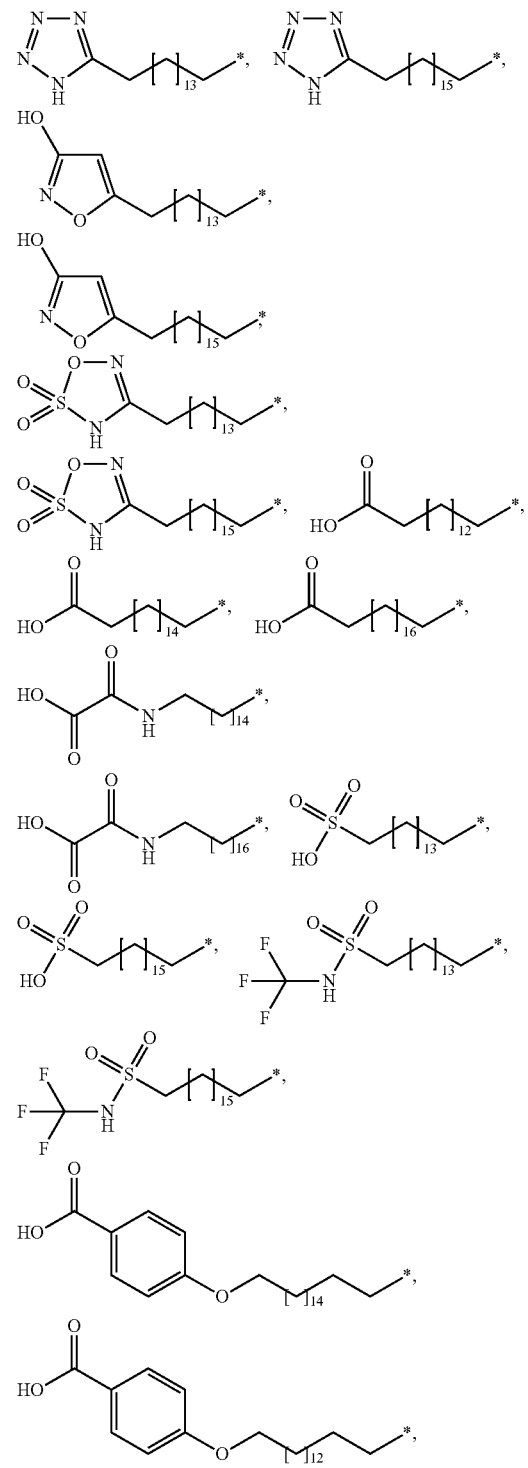

wherein * denotes the attachment to B through W.

In a further embodiment W has the formula wherein

Y is —$(CH_2)_{l7}$—$C_{3-10}$-cycloalkyl-$W_8$— or a valence bond, l7 is 0-6, $W_7$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s3}$—, —C(O)—, —C(O)O—, —OC(O)—, or a valence bond; wherein s3 is 0 or 1, $W_8$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s4}$—, —C(O)—, —C(O)O—, —OC(O)—, or a valence bond; wherein s4 is 0 or 1.

In further embodiments B comprise or consist of one or more OEG, and/or gamma-Glu motiv(s) as described above.

In a further embodiment B has the formula

—X$_1$—X$_2$—X$_3$—X$_4$— wherein $X_1$ is —W$_1$—[(CHR$^1$)$_{l1}$—W$_2$]$_{m1}$—{[(CH$_2$)$_{n1}$E1]$_{m2}$—[(CHR$^2$)$_{l2}$—W$_3$]$_{m3}$}$_{n2}$—, $X_2$ is —[(CHR$^3$)$_{l3}$—W$_4$]$_{m4}$—{[(CH$_2$)$_{n3}$E2]$_{m5}$—[(CHR$^4$)$_{l4}$—W$_5$]$_{m6}$}$_{n4}$—, $X_3$ is —[(CHR$^5$)$_{l5}$—W$_6$]$_{m7}$—, $X_4$ is F-D1-(CH$_2$)$_{l6}$-D2-, l1, l2, l3, l4, l5 and l6 independently are selected from 0-16, m1, m3, m4, m6 and m7 independently are selected from 0-10, m2 and m5 independently are selected from 0-25, n1, n2, n3 and n4 independently are selected from 0-16, F is aryl, hetaryl, pyrrolidine-2,5-dione or a valence bond, wherein the aryl and hetaryl groups are optionally substituted with halogen, —CN, —OH, —C(O)OH, —C(O)NH$_2$, —S(O)$_2$OH or C$_{1-6}$-alkyl, R$^1$, R$^2$, R$^3$, R$^4$ and R$^5$ independently are selected from hydrogen, —C(O)OH, —C(O)NH$_2$, —S(O)OH, —S(O)$_2$OH, —NH—C(=NH)—NH$_2$, C$_{1-6}$-alkyl, aryl or hetaryl; wherein the alkyl, aryl and hetaryl groups optionally are substituted with halogen, —C(O)OH, —C(O)NH$_2$, —S(O)OH, —S(O)$_2$OH, —CN or —OH, D1, D2, E1 and E2 independently are selected from —O—, —N(R$^6$)—, —N(C(O)R$^7$)— or a valence bond; wherein R$^6$ and R$^7$ independently represent hydrogen or C$_{1-6}$-alkyl, W$_1$ to W$_5$ independently are selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s2}$—, —C(O)—, —C(O)O—, —OC(O)—, or a valence bond; wherein s2 is 0 or 1, $W_6$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s1}$—, —C(O)—, —C(O)O—, —OC(O)—, —NHC(O)C$_{1-6}$-alkyl, —C(O)NHC$_{1-6}$-alkyl or a valence bond; wherein s1 is 0 or 1 and the C$_{1-6}$-alkyl group is optionally substituted with oxo, pyrrolidine-2,5-dione, —NHC(O)CH*CH$_2$COOH or —NHC(O)CH$_2$CH*COOH; wherein (*) indicates the attachment point from the carbon atom of CH to X$_4$.

In a further embodiment l1, l2, l3, l4, l5 and l6 independently are 0-6.

In a further embodiment m1, m3, m4, m6 and m7 independently are 0-6.

In a further embodiment m2 and m5 independently are 0-10.

In a further embodiment n1, n2, n3 and n4 independently are 0-10.

In a further embodiment D1 and D2 are independently selected from —O— or —N(R$^6$)— or a valence bond.

In a further embodiment E1 and E2 are independently selected from —O— or —N(R$^6$)— or a valence bond.

In a further embodiment W$_1$ through W$_8$ independently are selected from the group consisting of —C(O)NH—, —NHC(O)—, —CH$_2$NHC(O)—, —C(O)NHS(O)$_2$—, —S(O)$_2$NHC(O)—, —NHC(O)C$_{1-6}$-alkyl, —C(O)NHC$_{1-6}$-alkyl or a valence bond; wherein the alkyl group is optionally substituted with oxo, pyrrolidine-2,5-dione, —NHC(O)CH*CH$_2$COOH or —NHC(O)CH$_2$CH*COOH; wherein (*) indicates the attachment point from the carbon atom of CH to X$_4$.

In a further embodiment R$^1$, R$^2$, R$^3$, R$^4$ and R$^5$ independently are selected from hydrogen, —C(O)OH, —C(O)NH$_2$, —S(O)$_2$OH or C$_{1-6}$-alkyl; wherein the C$_{1-6}$-alkyl group optionally is substituted with —C(O)OH, —C(O)NH$_2$ or —S(O)$_2$OH.

In a further embodiment —{[(CH$_2$)$_{n1}$E1]$_{m2}$—[(CHR$^2$)$_{l2}$—W$_3$]$_{m3}$}$_{n2}$— and —{[(CH$_2$)$_{n3}$E2]$_{m5}$—[(CHR$^4$)$_{l4}$—W$_5$]$_{m6}$}$_{n4}$—, wherein E1 and E2 are —O—, are selected from

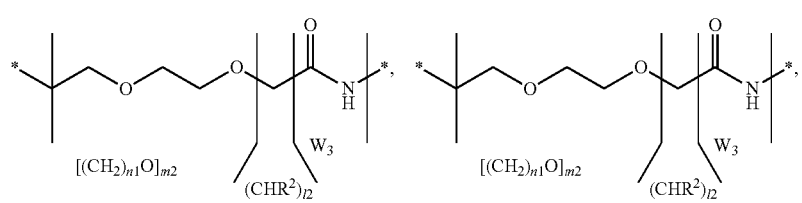

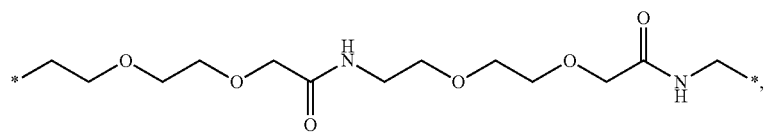

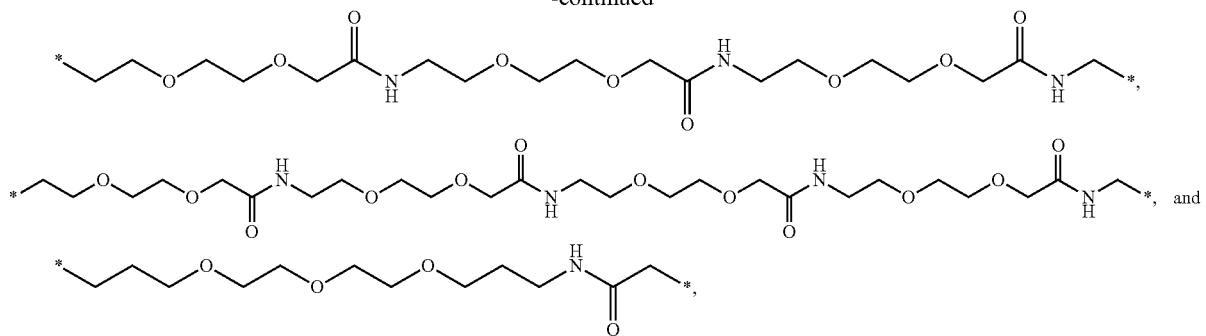
wherein * is intended to denote a point of attachment, ie, an open bond.
In a further embodiment B is selected from
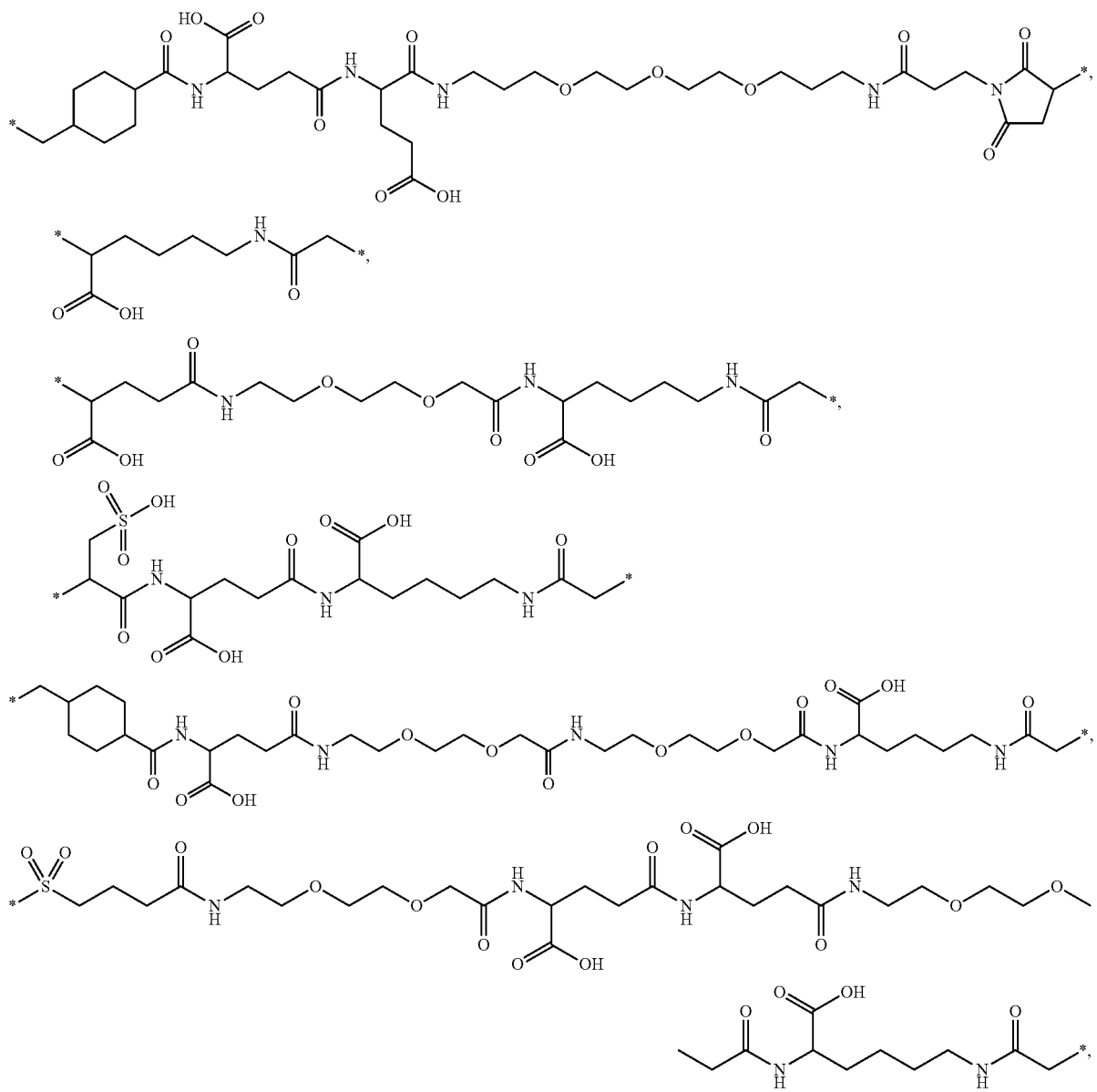

-continued
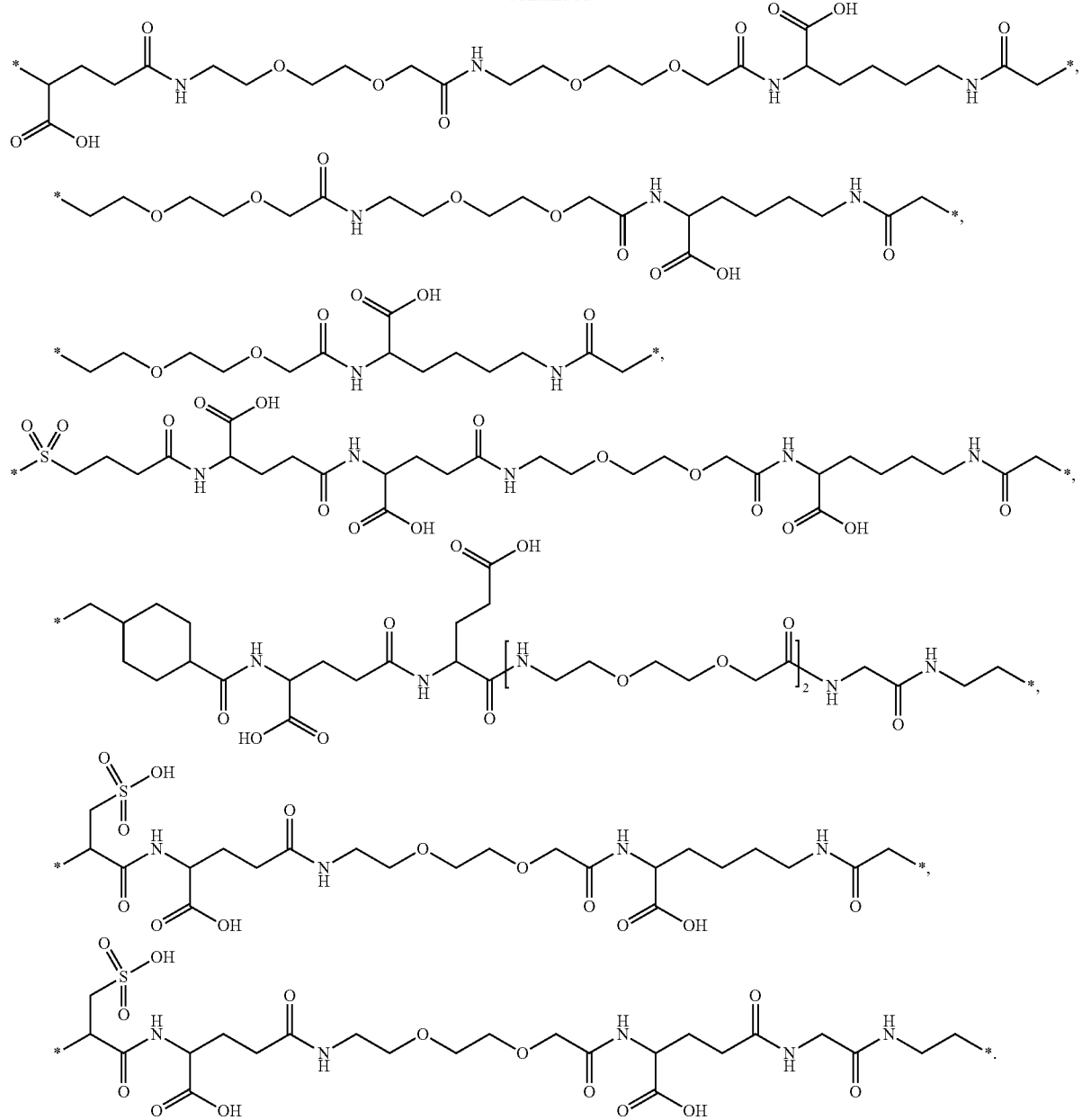
In a further embodiment A via B is attached to the glutamine residue in the position corresponding to position 40, position 141 in SEQ ID NO: 1, or the N-terminal residue of the growth hormone compound.
In a further embodiment the GH conjugate is selected from
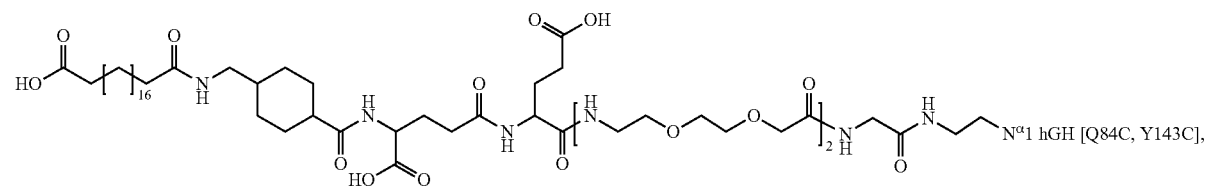

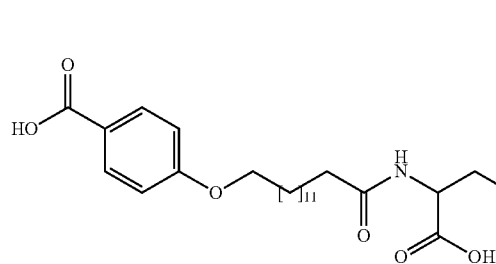

-continued

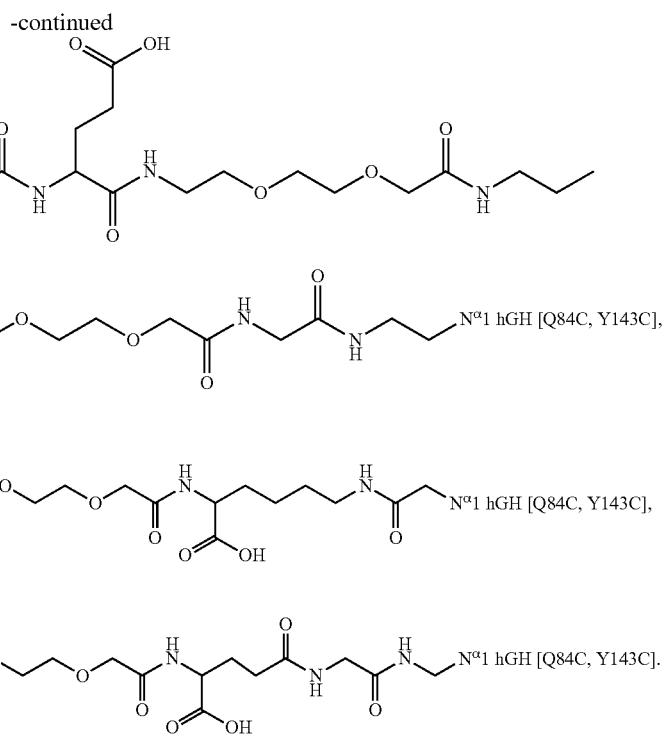

In a further aspect the present invention relates to a growth hormone conjugate wherein the growth hormone conjugate has the formula (I):

A-W—B-GH    (I)

wherein

GH represents a growth hormone compound having a single Cys mutation and an additional disulfide bridge, B represents a hydrophilic spacer linked to the sulphur residue of the Cys mutation, W is a chemical group linking A and B, and A represent an albumin binding residue; and pharmaceutically acceptable salts thereof.

In a further embodiment GH represents a growth hormone compound comprising an amino acid sequence having at least 90% identity to the amino acid sequence of human growth hormone (hGH) (SEQ ID NO: 1). In further embodiments, GH has at least 80%, such as at least 85%, such as at least 95%, such as at least 96%, such as at least 97%, such as at least 98% or such as at least 99% identity with hGH (SEQ ID NO: 1). In further embodiments, said identities to hGH are coupled to at least 10%, such as at least 20%, such as at least 40%, such as at least 60%, such as at least 80% of the growth hormone activity of hGH as determined in assay I herein. Any one of the sequence identity embodiments may be combined with any one of the activity embodiments, such as a GH having at least 80% identity with hGH and coupled to at least 60% of the growth hormone activity of hGH; a GH haying at least 90% identity with hGH and coupled to at least 40% of the growth hormone activity of hGH; a GH having at least 95% identity with hGH and coupled to at least 80% of the growth hormone activity of hGH, and so forth.

In further embodiments the GH of the conjugate has an additional disulfide bond an a single Cys mutation selected from any one of a single Cys mutation in the N-terminal, H1, H2, L2 or H3 regions of GH. In further such embodiments, the single Cys mutation is positioned in the N-terminal, the mutation being such as any one of T3C, P5C, S7C, or in H1 (corresponding to AA 9-35), the mutation being such as any one of D11C, H$_{18}$C, Q29C, E30C, E33C, A34C, Y35C, or in L1 (corresponding to AA36-71), the mutation being such as any one of K38C, E39C, Y42C, S43C, D47C, P48C, S55, S57C, P59C, S62C, E65C, Q69C or preferably any one of Y42C, S55C, S57C, S62C, Q69C or in H2, L2 or H3 (corresponding to AA 72-98, AA 99-106 and AA 107-127), the mutation being such as any one of E88C, Q91C, S95C, A98C, N99C, S100C, L101C, V102C, Y103C, D107C, S108C, D112C, Q122C and G126C of hGH (SEQ ID NO: 1), or in L3 or H4 (corresponding to AA128-154 and AA155-184) In L3 and H4 (128-154 and AA155-184) the mutation being such as any one of E129C, D130C, G131C, P133C, T135C, G136C, T142C, D147C, N149C, D154C, A155C, L156C, R178C, V180C or in the C-terminal the mutation being such as any one of E186C G187C G190C.

If the single Cys mutation is present in a hGH variant the mutation is located in corresponding amino acid residues.

Further embodiments includes GH conjugates having an additional disulfide bond and a single cys mutation in GH is selected from any one of: T3C, P5C, S7C, D11C, H18C, Q29C, E30C, E33C, A34C, Y35C, K38C, E39C, Y42C, S43C, D47C, P48C, S55C, S57C, P59C, S62, E65C, Q69C, E88C, Q91C, S95C, A98C, N99C, S100C, L101C, V102C, Y103C, D107C, S108C, D112C, Q122C, G126C, E129C, D130C, G131C, P133C, T135C, G136C, T142C, D147C, N149C, D154C, A155C, L156C, R178C, E186C, G187C and G190C, such as any one of; T3C, P5C, S7C, D11C, H18C, Q29C, E30C, E33C, A34C, Y35C, E88C, Q91C, S95C, A98C, N99C, S100C, L101C, V102C, Y103C, D107C, S108C, D112C, Q122C and G126C of hGH (SEQ ID NO: 1).

In even further embodiments the single Cys mutation is located within AA 93-106 in hGH or corresponding residues in hGH variants. In further specified embodiments the single Cys mutation is located within L2, such as within AA 99-106 or AA 99-103 or corresponding residues.

In further embodiment the additional disulfide bond may be an additional disulfide bonds between a loop segment and a helical segment or within loop segment or between loop segments or between helical segments.

In a further embodiment the GH comprises a single cys mutant and an additional disulfide bond wherein at least one of the cysteines is present in a loop segment, such from amino acid residues 128-154 (L3).

In a further embodiment the GH comprises a single cys mutant and an additional disulfide bond wherein the additional disulfide bond which connects a loop segment, such from amino acid residues 128-154, with a helical segment, such as helix B or helix 2 (corresponding to AA 72-98).

In a further embodiment the GH of the conjugate comprises a single cys mutant and an additional disulfide bond linking helix 2 (corresponding to AA 72-98) with loop 3 (corresponding to AA 128-154).

In a further embodiment the GH of the conjugate comprise a single cys mutant and an addition disulfide bond between one of the amino acid pairs in positions corresponding to R16C/L117C, A17C/E174C, H21C/M170C, D26C/V102C, D26C/Y103C, N47C/T50C, Q49C/G161C, F54C/Y143C, F54C/S144C, F54C/F146C, S55C/Y143C, S57C/Y143C, I58C/Q141C, I58C/Y143C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C, F92C/T148C, R94C/D107C, V102C/A105C, L156C/F146C, L156C/T148C and/or V185C/S188C in SEQ ID NO: 1.

In a further embodiment the additional disulfide bridge is between at least one of the amino acid pairs in the positions corresponding to R16C/L117C, A17C/E174C, H18C/Y143C, H21C/M170C, N47C/T50C, Q49C/G161C, F54C/S144C, F54C/F146C, I58C/Q141C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, S85C/Y143C, P89C/F146C, F92C/F146C, F92C/T148C, R94C/D107C, V102C/A105C, L156C/F146C, L156C/T148C and/or V185C/S188C in hGH (SEQ ID NO: 1).

In a further embodiment the GH of the conjugate comprises a singly cys mutant and an additional disulfide bond between one of the amino acid pairs in positions corresponding to A17C/E174C, H21C/M170C, D26C/V102C, D26C/Y103C, F54C/Y143C, F54C/S144C, F54C/F146C, S55C/Y143C, S57C/Y143C, I58C/Q141C, I58C/Y143C, I58C/S144C, P59C/Q137C, S71C/S132C, L81C/Y143C, Q84C/Y143C, S85C/Y143C, S85C/S144C, F92C/T148C and/or R94C/D107C in SEQ ID NO: 1.

In a further embodiment the additional disulfide bond is between one of the amino acid pairs in positions corresponding to D26C/V102C, D26C/Y103C, S57C/Y143C, I58C/S144C, P59C/Q137C, S71C/S132C, Q84C/Y143C, S85C/Y143C, S85C/S144C, F92C/T148C and/or R94C/D107C in SEQ ID NO: 1.

In a further embodiment the additional disulfide bond between one of the amino acid pairs in positions corresponding to H21C/M170C, D26C/V102C, D26C/Y103C, F54C/Y143C, F54C/S144C, S55C/Y143C, S57C/Y143C, I58C/Q141C, I58C/Y143C, I58C/S144C, P59C/Q137C, S71C/S132C, L81C/Y143C, Q84C/Y143C, S85C/Y143C and/or S85C/S144C in SEQ ID NO: 1.

In a further embodiment the additional disulfide bond between one of the amino acid pairs in positions corresponding to S57C/Y143C, Q84C/Y143C, S85C/Y143C and/or S85C/S144C in SEQ ID NO: 1.

In a further embodiment the GH comprise a single cysteine mutation in L2 and an additional disulfide bond which connects a loop segment, such as from amino acid residues 128-154 (H3), with a helical segment, such as helix B or helix 2 (corresponding to AA 72-98).

In an embodiment the GH comprise a combination of mutations selected from the following group: A98C/Q84C/Y143C, A98C/S85C/Y143C, A98C/S85C/S144C, N99C/Q84C/Y143C, N99C/S85C/Y143C, N99C/S85C/S144C, S101C/Q84C/Y143C, S101C/S85C/Y143C, S101C/S85C/S144C, L101C/Q84C/Y143C, L101C/S85C/Y143C, L101C/S85C/S144C, C102C/Q84C/Y143C, C102C/S85C/Y143C and C102C/S85C/S144C.

In a further embodiment A is selected from

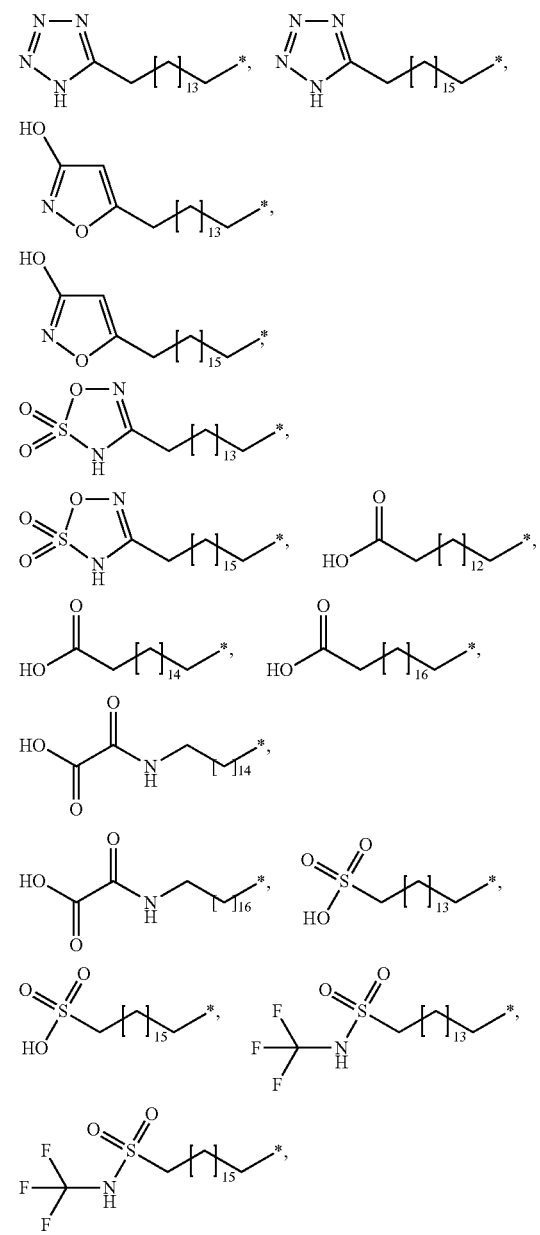

[Structure: HOOC-C6H4-O-(CH2)l4-*]

[Structure: HOOC-C6H4-O-(CH2)l2-*]

wherein * denotes the attachment to B through W.
In a further embodiment W has the formula

—W$_7$—Y—, wherein
Y is —(CH$_2$)$_{l7}$—C$_{3\text{-}10}$-cycloalkyl-W$_8$— or a valence bond,
l7 is 0-6,
W$_7$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s3}$—, —C(O)—, —C(O)O—, —OC(O)—, or a valence bond; wherein s3 is 0 or 1,
W$_8$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s4}$—, —C(O)—, —C(O)O—, —OC(O)—, or a valence bond; wherein s4 is 0 or 1.

In further embodiments B comprise or consist of one or more OEG, and/or gamma-Glu motiv(s) as described above.
In a further embodiment B has the formula

—X$_1$—X$_2$—X$_3$—X$_4$— wherein
X$_1$ is —W$_1$—[(CHR$^1$)$_{l1}$—W$_2$]$_{m1}$—{[(CH$_2$)$_{n1}$E1]$_{m2}$—[(CHR$^2$)$_{l2}$—W$_3$]$_{m3}$}$_{n2}$—,
X$_2$ is —[(CHR$^3$)$_{l3}$—W$_4$]$_{m4}$—{[(CH$_2$)$_{n3}$E2]$_{m5}$—[(CHR$^4$)$_{l4}$—W$_5$]$_{m6}$}$_{n4}$—,
X$_3$ is —[(CHR$^5$)$_{l5}$—W$_6$]$_{m7}$—,
X$_4$ is F-D1-(CH$_2$)$_{l6}$-D2-,
l1, l2, l3, l4, l5 and l6 independently are selected from 0-16,
m1, m3, m4, m6 and m7 independently are selected from 0-10,
m2 and m5 independently are selected from 0-25,
n1, n2, n3 and n4 independently are selected from 0-16,
F is aryl, hetaryl, pyrrolidine-2,5-dione or a valence bond, wherein the aryl and hetaryl groups are optionally substituted with halogen, —CN, —OH, —C(O)OH, —C(O)NH$_2$, —S(O)$_2$OH or C$_{1\text{-}6}$-alkyl,
R$^1$, R$^2$, R$^3$, R$^4$ and R$^5$ independently are selected from hydrogen, —C(O)OH, —C(O)NH$_2$, —S(O)OH, —S(O)$_2$OH, —NH—C(=NH)—NH$_2$, C$_{1\text{-}6}$-alkyl, aryl or hetaryl; wherein the alkyl, aryl and hetaryl groups optionally are substituted with halogen, —C(O)OH, —C(O)NH$_2$, —S(O)OH, —S(O)$_2$OH, —CN or —OH,
D1, D2, E1 and E2 independently are selected from —O—, —N(R$^6$)—, —N(C(O)R$^7$)— or a valence bond; wherein R$^6$ and R$^7$ independently represent hydrogen or C$_{1\text{-}6}$-alkyl,
W$_1$ to W$_5$ independently are selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s2}$—, —C(O)—, —C(O)O—, —OC(O)—, or a valence bond; wherein s2 is 0 or 1,
W$_6$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s1}$—, —C(O)—, —C(O)O—, —OC(O)—, —NHC(O)C$_{1\text{-}6}$-alkyl, —C(O)NHC$_{1\text{-}6}$-alkyl or a valence bond; wherein s1 is 0 or 1 and the C$_{1\text{-}6}$-alkyl group is optionally substituted with oxo, pyrrolidine-2,5-dione, —NHC(O)CH*CH$_2$COOH or —NHC(O)CH$_2$CH*COOH; wherein (*) indicates the attachment point from the carbon atom of CH to X$_4$.

In a further embodiment l1, l2, l3, l4, l5 and l6 independently are 0-6.

In a further embodiment m1, m3, m4, m6 and m7 independently are 0-6.

In a further embodiment m2 and m5 independently are 0-10.

In a further embodiment n1, n2, n3 and n4 independently are 0-10.

In a further embodiment D1 and D2 are independently selected from —O— or —N(R$^6$)— or a valence bond.

In a further embodiment E1 and E2 are independently selected from —O— or —N(R$^6$)— or a valence bond.

In a further embodiment W$_1$ through W$_8$ independently are selected from the group consisting of —C(O)NH—, —NHC(O)—, —CH$_2$NHC(O)—, —C(O)NHS(O)$_2$—, —S(O)$_2$NHC(O)—, —NHC(O)C$_{1\text{-}6}$-alkyl, —C(O)NHC$_{1\text{-}6}$-alkyl or a valence bond; wherein the alkyl group is optionally substituted with oxo, pyrrolidine-2,5-dione, —NHC(O)CH*CH$_2$COOH or —NHC(O)CH$_2$CH*COOH; wherein (*) indicates the attachment point from the carbon atom of CH to X$_4$.

In a further embodiment R$^1$, R$^2$, R$^3$, R$^4$ and R$^5$ independently are selected from hydrogen, —C(O)OH, —C(O)NH$_2$, —S(O)$_2$OH or C$_{1\text{-}6}$-alkyl; wherein the C$_{1\text{-}6}$-alkyl group optionally is substituted with —C(O)OH, —C(O)NH$_2$ or —S(O)$_2$OH.

In a further embodiment —{[(CH$_2$)$_{n1}$E1]$_{m2}$—[(CHR$_2$)$_{l2}$—W$_3$]$_{m3}$}$_{n2}$— and —{[(CH$_2$)$_{n3}$E2]$_{m5}$—[(CHR$^4$)$_{l4}$—W$_5$]$_{m6}$}$_{n4}$—, wherein E1 and E2 are —O—, are selected from

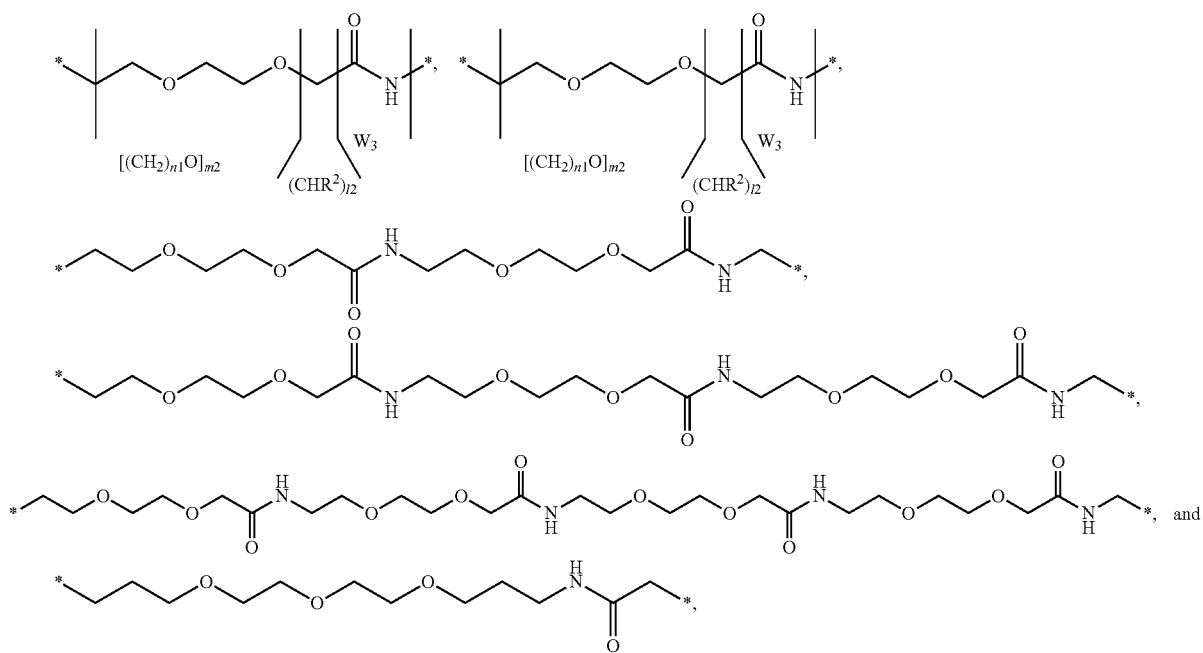
wherein * is intended to denote a point of attachment, ie, an open bond.
In a further embodiment $X_4$ is a valence bond and $W_6$ is selected from either pyrrolidine-2,5-dione, —NHC(O)CH*CH$_2$COOH or —NHC(O)CH$_2$CH*COOH wherein (*) indicates the attachment point from the carbon atom of CH to GH.
In a further embodiment B is selected from
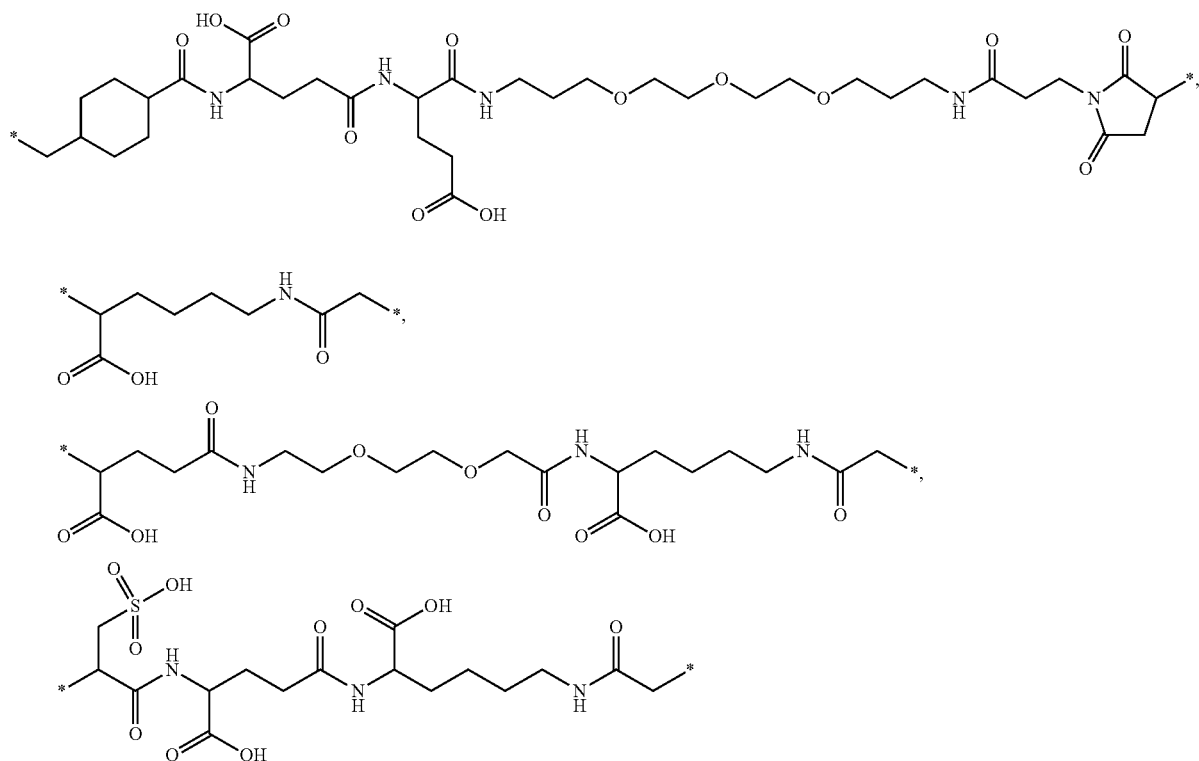

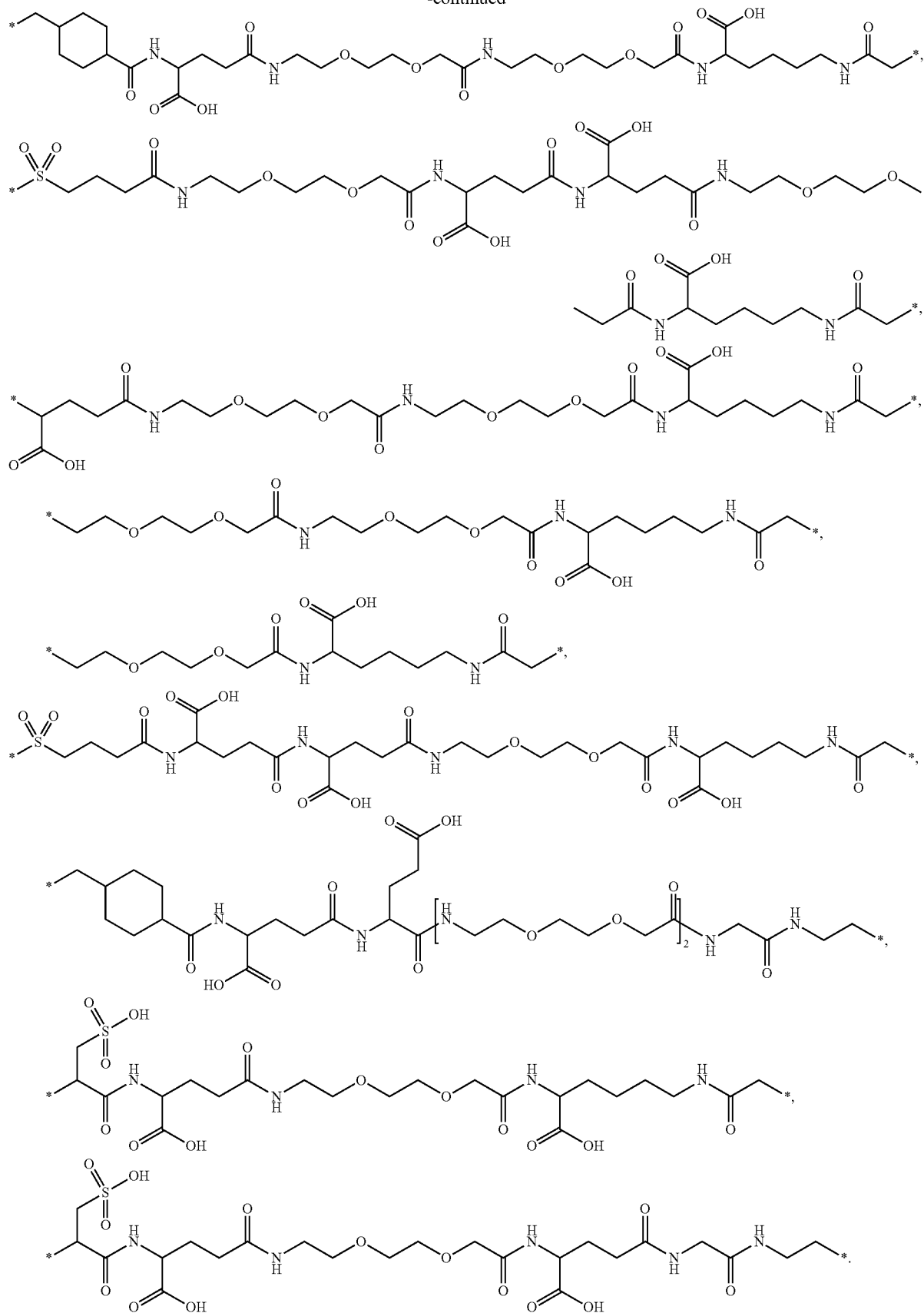

In a further embodiment the GH conjugate is selected from
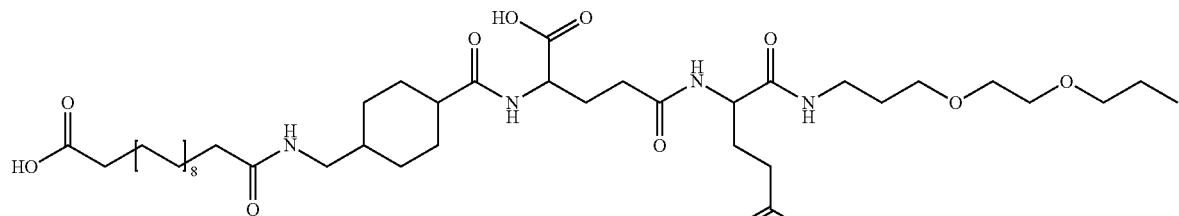
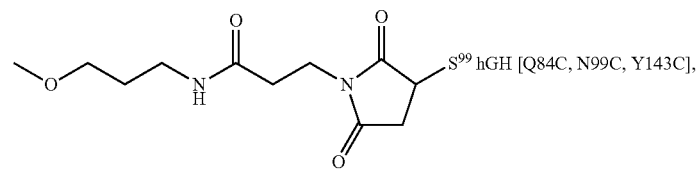
$S^{99}$ hGH [Q84C, N99C, Y143C],
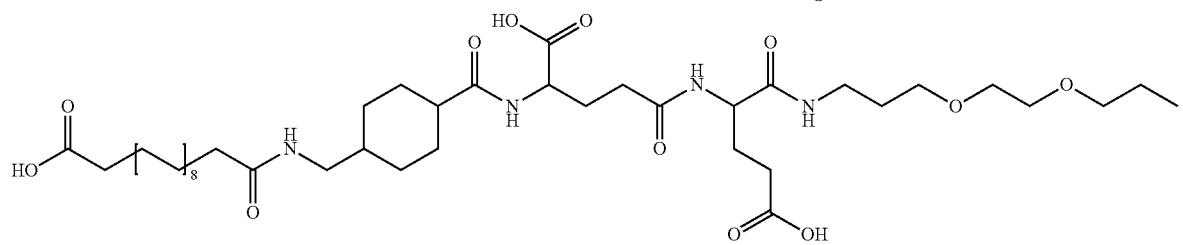
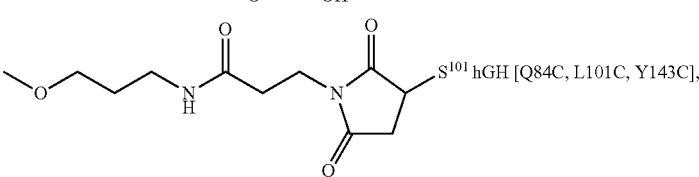
$S^{101}$ hGH [Q84C, L101C, Y143C],
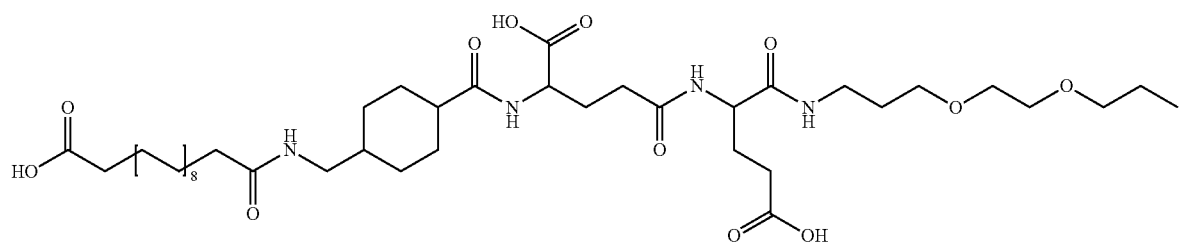
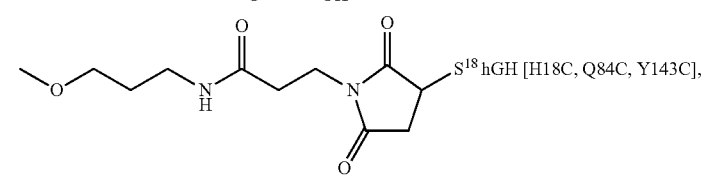
$S^{18}$ hGH [H18C, Q84C, Y143C],
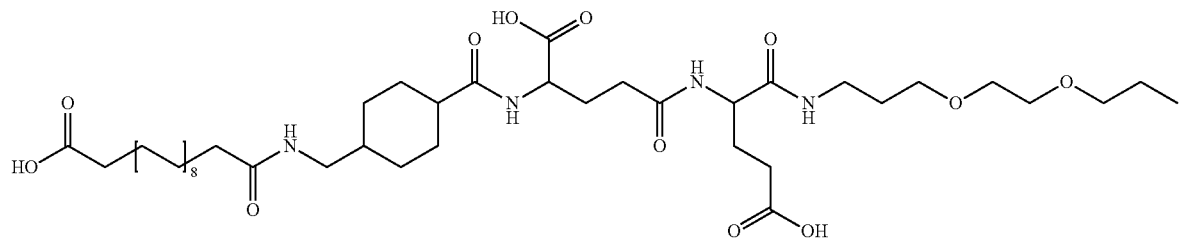
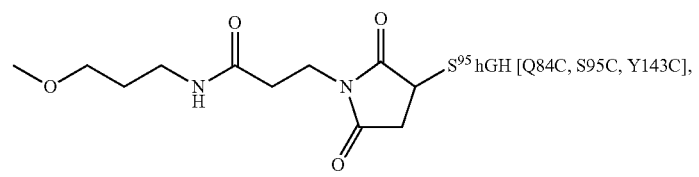
$S^{95}$ hGH [Q84C, S95C, Y143C],

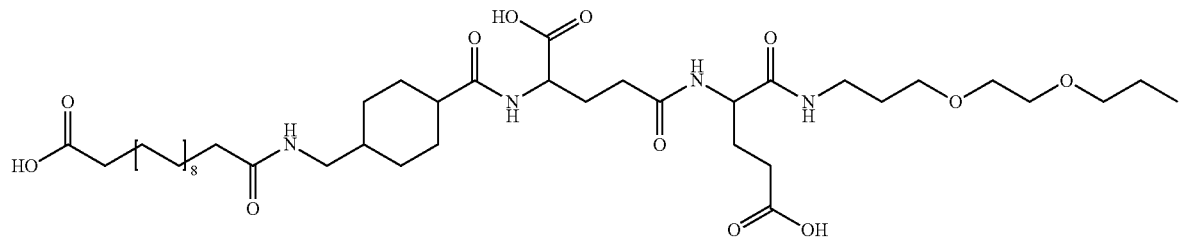
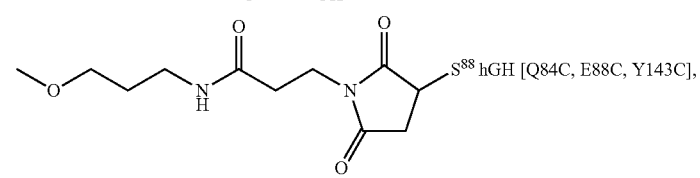
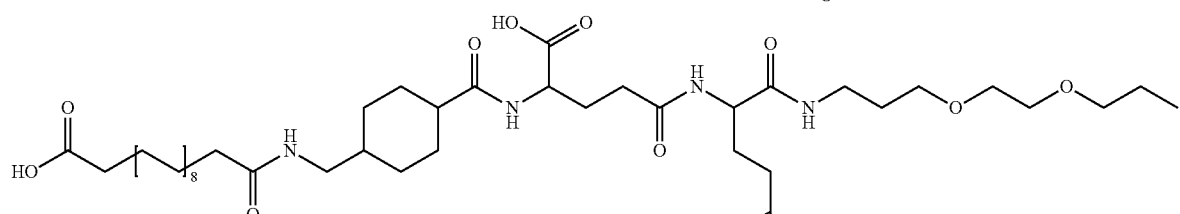
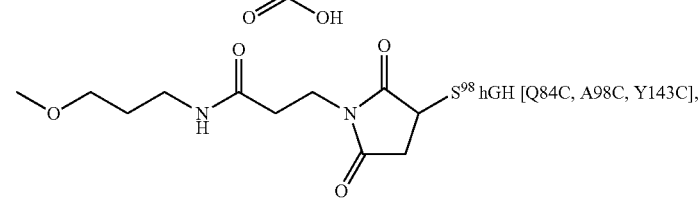
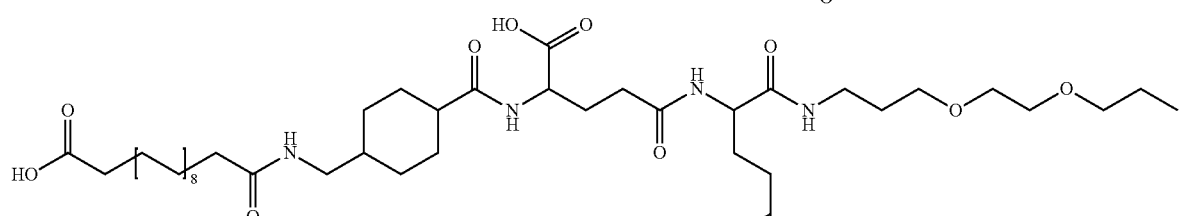
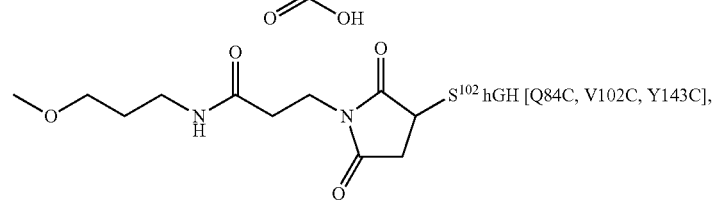
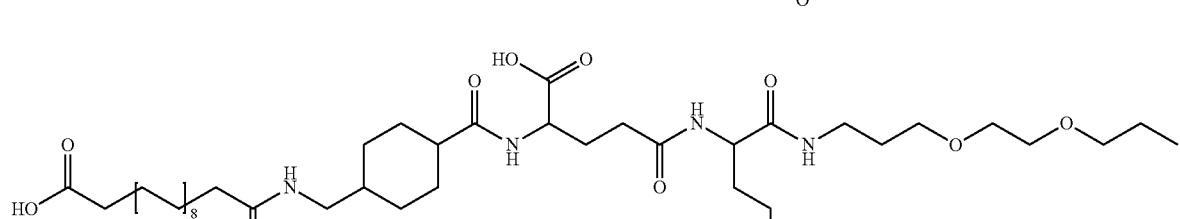
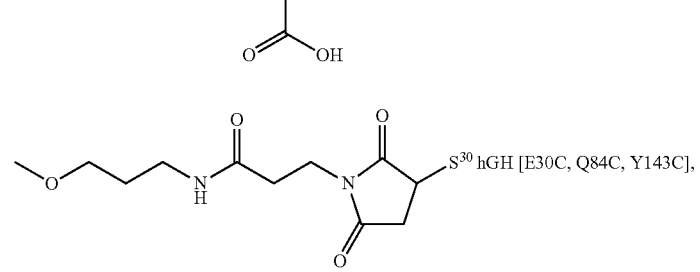

-continued
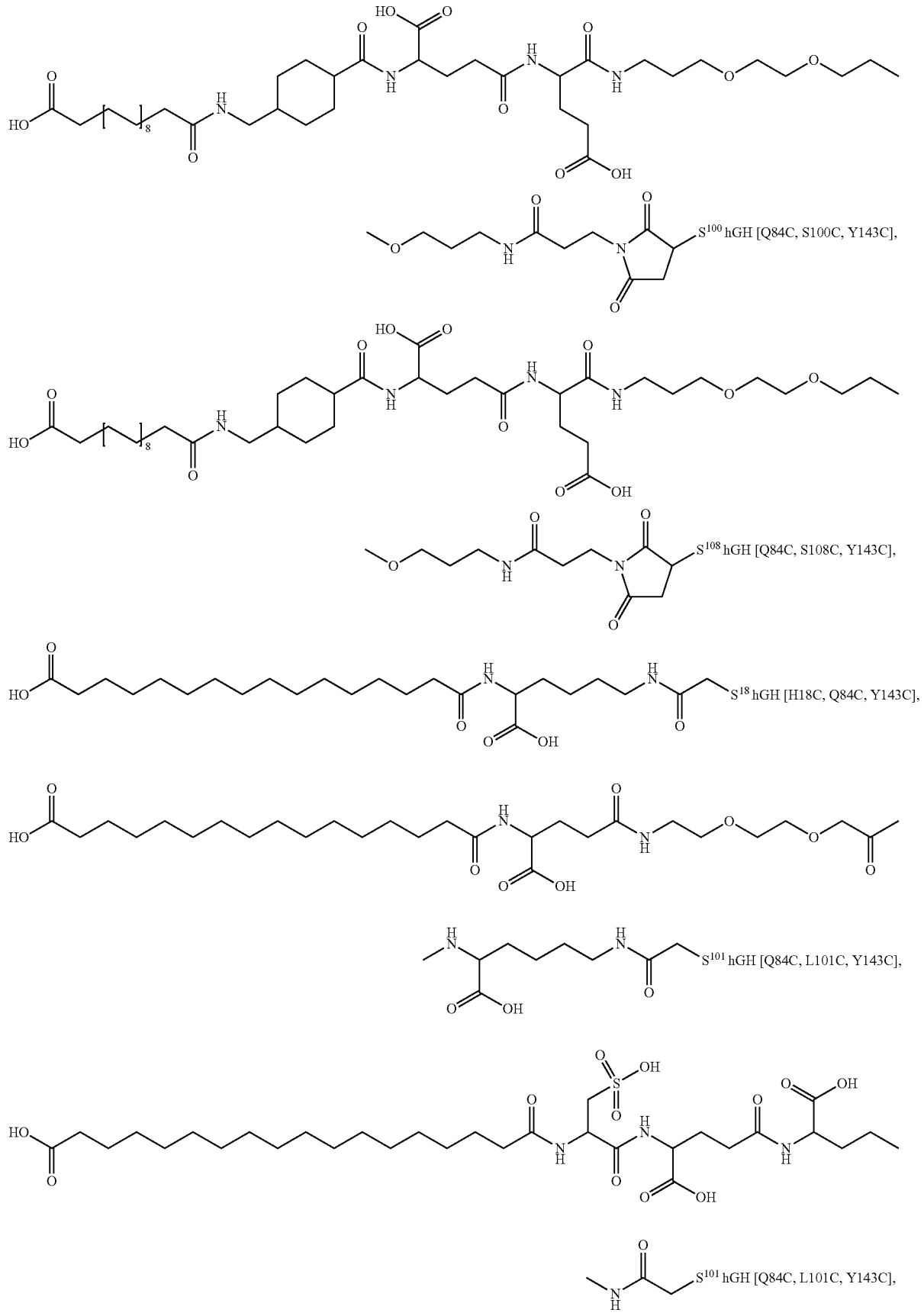

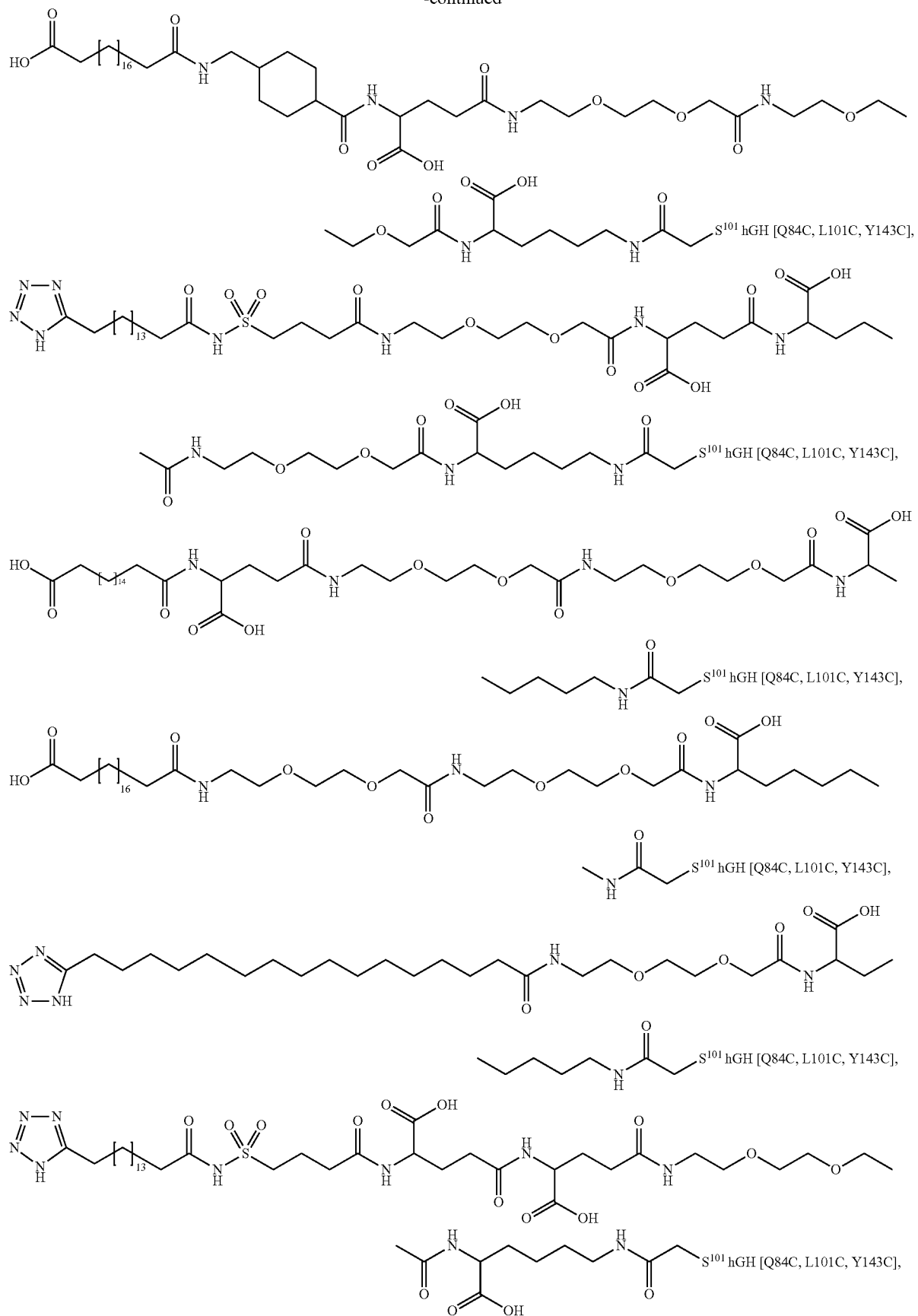

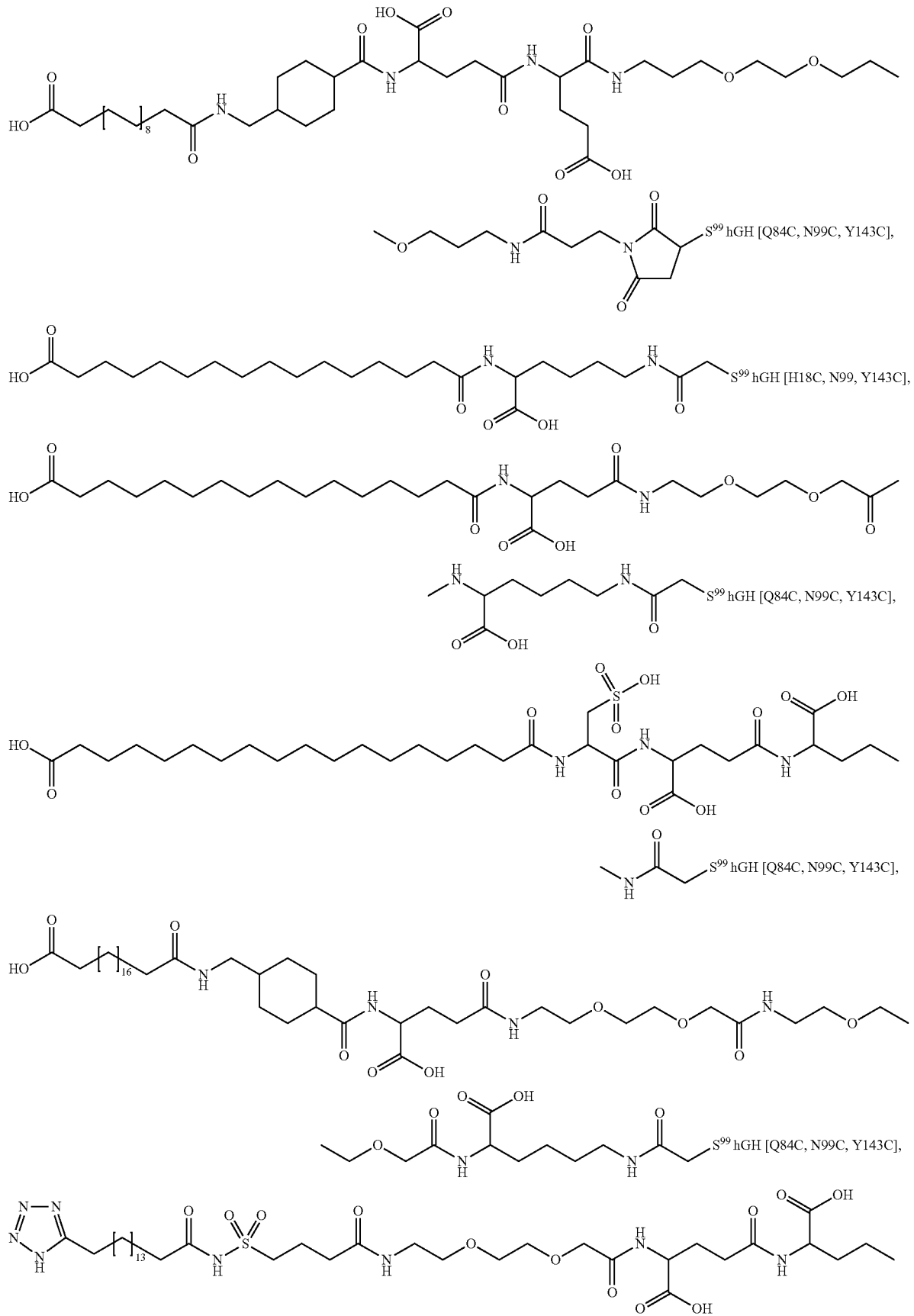

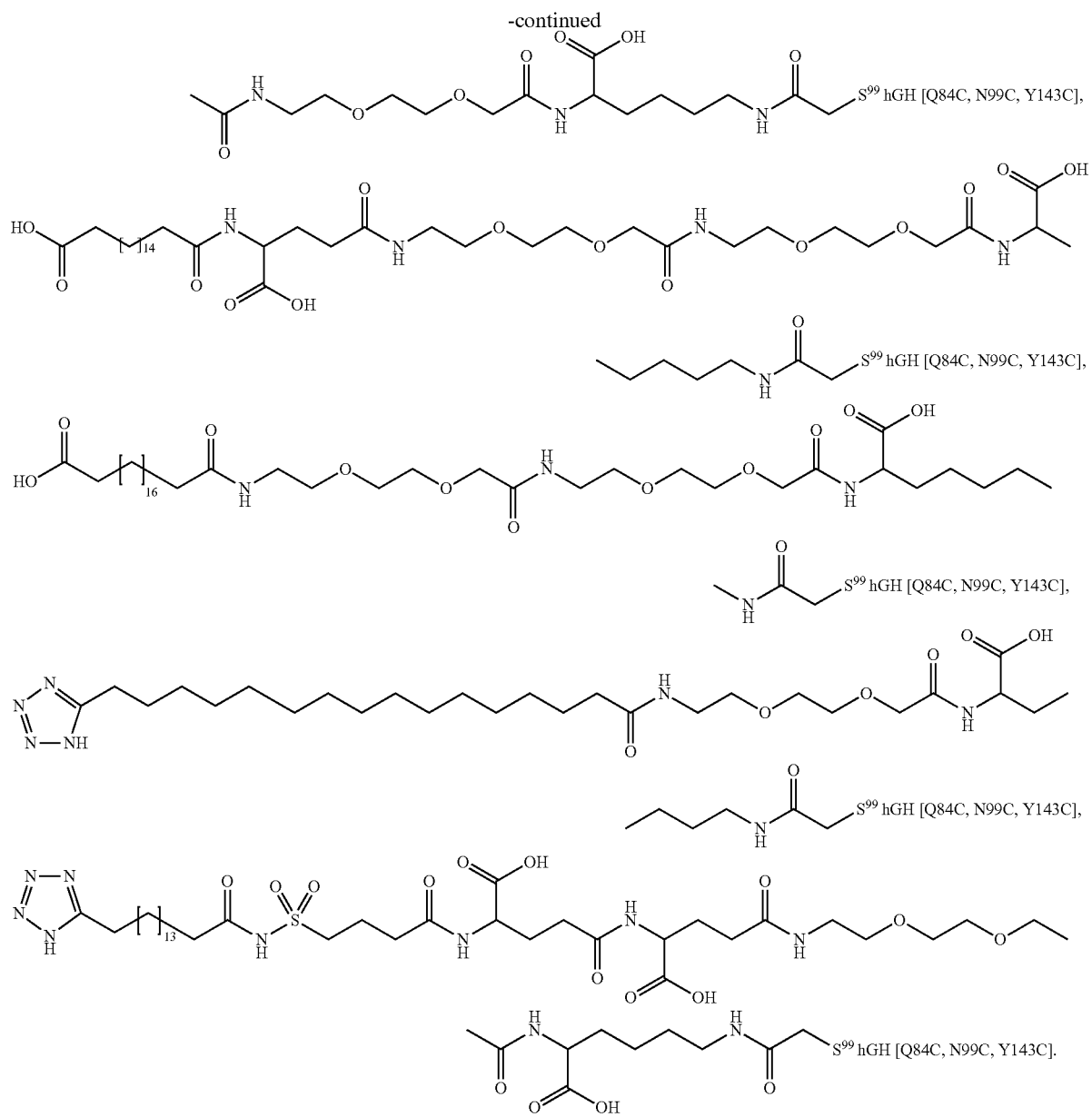

Typically, the conjugate of the present invention has one albumin binding residue (A) linked via a hydrophilic spacer (B), such as one hydrophilic spacer (B), to the growth hormone compound (GH).

However, the growth hormone compound (GH) may be linked to two albumin binding residues via a hydrophilic spacer.

Thus, in a still further aspect the present invention relates to a growth hormone conjugate of the formula (II):

A-W—B-GH—B'—W'-A'  (II)

wherein

GH represents a growth hormone compound having a single Cys mutation,

B and B' independently are hydrophilic spacers linked to the sulphur residue of the Cys mutation, W is a chemical group linking A and B, W' is a chemical group linking A' and B', A and A' independently represents an albumin binding residue, and pharmaceutically acceptable salts thereof.

Further, another aspect the present invention relates to a growth hormone conjugate of the formula (II):

A-W—B-GH—B'—W'-A'  (II)

wherein

GH represents a growth hormone compound having an additional disulfide bridge,

B and B' independently are hydrophilic spacers,

W is a chemical group linking A and B,

W' is a chemical group linking A' and B',

A and A' independently represents an albumin binding residue, and pharmaceutically acceptable salts thereof.

A still further aspect the present invention relates to a growth hormone conjugate of the formula (II):

A-W—B-GH—B'—W'-A'    (II)

wherein

GH represents a growth hormone compound having a single Cys mutation and an additional disulfide bridge, B and B' independently are hydrophilic spacers linked to the sulphur residue of the Cys mutation, W is a chemical group linking A and B, W' is a chemical group linking A' and B', A and A' independently represents an albumin binding residue, and pharmaceutically acceptable salts thereof.

In the conjugate of formula (II) as described above W' is selected from the same groups as W, A' is selected from the same groups as A and B' is selected from the same groups as B, and it should be understood that W and W', A and A', and B and B' are independently selected from any one of the respective groups as defined herein. Thus, any embodiments of W, A, and B herein are also embodiments of W', A', and B'. Furthermore, any one of the embodiments described herein refers independently to both of the conjugates of formula (I) and (II), as well as the broad aspect and embodiments thereof when suitable.

The above embodiments as well as the embodiments to be described hereunder should be seen as referring to any one of the aspects described herein as well as any one of the embodiments described herein unless it is specified that an embodiment relates to a certain aspect or aspects of the present invention.

In one embodiment GH is a variant of hGH, wherein a variant is understood to be the compound obtained by substituting one or more amino acid residues in the hGH sequence with another natural or unnatural amino acid; and/or by adding one or more natural or unnatural amino acids to the hGH sequence; and/or by deleting one or more amino acid residue from the hGH sequence, wherein any of these steps may optionally be followed by further derivatization of one or more amino acid residues.

In a further embodiment GH represents a growth hormone compound comprising an amino acid sequence having at least 90% identity to the amino acid sequence of human growth hormone (hGH) (SEQ ID NO: 1). In further embodiments, GH has at least 80%, such as at least 85%, such as at least 95%, such as at least 96%, such as at least 97%, such as at least 98% or such as at least 99% identity with hGH (SEQ ID NO: 1). In further embodiments, said identities to hGH are coupled to at least 10%, such as at least 20%, such as at least 40%, such as at least 60%, such as at least 80% of the growth hormone activity of hGH as determined in assay I herein. Any one of the sequence identity embodiments may be combined with any one of the activity embodiments, such as a GH having at least 80% identity with hGH and coupled to at least 60% of the growth hormone activity of hGH; a GH having at least 90% identity with hGH and coupled to at least 40% of the growth hormone activity of hGH; a GH having at least 95% identity with hGH and coupled to at least 80% of the growth hormone activity of hGH, and so forth.

In a still further embodiment GH is hGH (SEQ ID NO: 1).

In further embodiments B comprise or or consist of one or more OEG, and/or gamma-Glu motiv(s) as described above.

In a further embodiment of the conjugate of formula (I) or (II), the hydrophilic spacer B has the formula

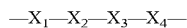

—$X_1$—$X_2$—$X_3$—$X_4$— wherein $X_1$ is —$W_1$—[(CHR$^1$)$_{l1}$—$W_2$]$_{m1}$—{[(CH$_2$)$_{n1}$E1]$_{m2}$—[(CHR$^2$)$_{l2}$—$W_3$]$_{m3}$}$_{n2}$—, $X_2$ is —[(CHR$^3$)$_{l3}$—$W_4$]$_{m4}$—{[(CH$_2$)$_{n3}$E2]$_{m5}$—[(CHR$^4$)$_{l4}$—$W_5$]$_{m6}$}$_{n4}$—, $X_3$ is —[(CHR$^5$)$_{l5}$—$W_6$]$_{m7}$—, $X_4$ is F-D1-(CH$_2$)$_{l6}$-D2-, l1, l2, l3, l4, l5 and l6 independently are selected from 0-16, m1, m3, m4, m6 and m7 independently are selected from 0-10, m2 and m5 independently are selected from 0-25, n1, n2, n3 and n4 independently are selected from 0-16, F is aryl, hetaryl, pyrrolidine-2,5-dione or a valence bond, wherein the aryl and hetaryl groups are optionally substituted with halogen, —CN, —OH, —C(O)OH, —C(O)NH$_2$, —S(O)$_2$OH or C$_{1-6}$-alkyl, R$^1$, R$^2$, R$^3$, R$^4$ and R$^5$ independently are selected from hydrogen, —C(O)OH, —C(O)NH$_2$, —S(O)OH, —S(O)$_2$OH, —NH—C(=NH)—NH$_2$, C$_{1-6}$-alkyl, aryl or hetaryl; wherein the alkyl, aryl and hetaryl groups optionally are substituted with halogen, —C(O)OH, —C(O)NH$_2$, —S(O)OH, —S(O)$_2$OH, —CN or —OH, D1, D2, E1 and E2 independently are selected from —O—, —N(R$^6$)—, —N(C(O)R$^7$)— or a valence bond; wherein R$^6$ and R$^7$ independently represent hydrogen or C$_{1-6}$-alkyl, $W_1$ to $W_5$ independently are selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s2}$—, —C(O)—, —C(O)O—, —OC(O)—, or a valence bond; wherein s2 is 0 or 1, $W_6$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s1}$—, —C(O)—, —C(O)O—, —OC(O)—, —NHC(O)C$_{1-6}$-alkyl, —C(O)NHC$_{1-6}$-alkyl or a valence bond; wherein s1 is 0 or 1 and the alkyl group is optionally substituted with oxo, pyrrolidine-2,5-dione, —NHC(O)CH*CH$_2$COOH or —NHC(O)CH$_2$CH*COOH; wherein (*) indicates the attachment point from the carbon atom of CH to $X_4$.

In a further embodiment $W_1$ is selected from —C(O)NH—, —NHC(O)—, —C(O)NHCH$_2$—, —CH$_2$NHC(O)—, —C(O)NHS(O)$_2$—, —S(O)$_2$NHC(O)— or a valence bond. Typically, $W_1$ is selected from —C(O)NH—, —NHC(O)— or —C(O)NHS(O)$_2$—.

In a further embodiment $W_2$ is selected from —C(O)NH—, —NHC(O)—, —C(O)NHCH$_2$—, —CH$_2$NHC(O)—, —C(O)NHS(O)$_2$—, —S(O)$_2$NHC(O)— or a valence bond. Typically, $W_2$ is selected from —C(O)NH—, —NHC(O)— or —C(O)NHS(O)$_2$—.

In a further embodiment $W_3$ is selected from —C(O)NH—, —NHC(O)—, —C(O)NHCH$_2$—, —CH$_2$NHC(O)—, —C(O)NHS(O)$_2$—, —S(O)$_2$NHC(O)— or a valence bond. Typically, $W_3$ is selected from —C(O)NH—, —NHC(O)— or —C(O)NHS(O)$_2$—.

In a further embodiment $W_4$ is selected from —C(O)NH—, —NHC(O)—, —C(O)NHCH$_2$—, —CH$_2$NHC(O)—, —C(O)NHS(O)$_2$—, —S(O)$_2$NHC(O)— or a valence bond. Typically, $W_4$ is selected from —C(O)NH—, —NHC(O)— or —C(O)NHS(O)$_2$—.

In a further embodiment $W_5$ is selected from —C(O)NH—, —NHC(O)—, —C(O)NHCH$_2$—, —CH$_2$NHC(O)—

(O)—, —C(O)NHS(O)$_2$—, —S(O)$_2$NHC(O)— or a valence bond. Typically, W$_5$ is selected from —C(O)NH—, —NHC(O)— or —C(O)NHS(O)$_2$—.

In a further embodiment W$_6$ is selected from —C(O)NH—, —NHC(O)—, —CH$_2$NHC(O)—, —C(O)NHS(O)$_2$—, —S(O)$_2$NHC(O)—, —NHC(O)C$_{1-6}$-alkyl, —C(O)NHC$_{1-6}$-alkyl or a valence bond; wherein the alkyl group is optionally substituted with pyrrolidine-2,5-dione, —NHC(O)CH*CH$_2$COOH or —NHC(O)CH$_2$CH*COOH; wherein (*) indicates the attachment point from the carbon atom of CH to X$_4$. Typically, W$_6$ is selected from —C(O)NH—, —NHC(O)—, —C(O)NHS(O)$_2$— or —NHC(O)C$_{1-6}$-alkyl.

In a further embodiment, D1, D2, F are all valence bonds, l6 is 0, and W6 is selected from either pyrrolidine-2,5-dione, —NHC(O)CH*CH$_2$COOH or —NHC(O)CH$_2$CH*COOH wherein (*) indicates the attachment point from the carbon atom of CH to GH.

In a further embodiment R$^1$ selected from hydrogen, —C(O)OH, —C(O)NH$_2$, —S(O)$_2$OH or C$_{1-6}$-alkyl; wherein the alkyl group optionally is substituted with —C(O)OH, —C(O)NH$_2$, —S(O)$_2$OH. Typically, R$^1$ is selected from —C(O)OH, —C(O)NH$_2$, or C$_{1-6}$-alkyl; wherein the alkyl group optionally is substituted with —C(O)OH, —C(O)NH$_2$, or —S(O)$_2$OH.

In a further embodiment R$^2$ is selected from hydrogen, —C(O)OH, —C(O)NH$_2$, —S(O)$_2$OH or C$_{1-6}$-alkyl; wherein the alkyl group optionally is substituted with —C(O)OH, —C(O)NH$_2$, —S(O)$_2$OH. Typically, R$^2$ is selected from —C(O)OH, —C(O)NH$_2$, or C$_{1-6}$-alkyl; wherein the alkyl group optionally is substituted with —C(O)OH, —C(O)NH$_2$, or —S(O)$_2$OH.

In a further embodiment R$^3$ is selected from hydrogen, —C(O)OH, —C(O)NH$_2$, —S(O)$_2$OH or C$_{1-6}$-alkyl; wherein the alkyl group optionally is substituted with —C(O)OH, —C(O)NH$_2$, —S(O)$_2$OH. Typically, R$^3$ is selected from —C(O)OH, —C(O)NH$_2$, or C$_{1-6}$-alkyl; wherein the alkyl group optionally is substituted with —C(O)OH, —C(O)NH$_2$, or —S(O)$_2$OH.

In a further embodiment R$^4$ is selected from hydrogen, —C(O)OH, —C(O)NH$_2$, —S(O)$_2$OH or C$_{1-6}$-alkyl; wherein the alkyl group optionally is substituted with —C(O)OH, —C(O)NH$_2$, —S(O)$_2$OH. Typically, R$^4$ is selected from —C(O)OH, —C(O)NH$_2$, or C$_{1-6}$-alkyl; wherein the alkyl group optionally is substituted with —C(O)OH, —C(O)NH$_2$, or —S(O)$_2$OH.

In a further embodiment R$^5$ is selected from hydrogen, —C(O)OH, —C(O)NH$_2$, —S(O)$_2$OH or C$_{1-6}$-alkyl; wherein the alkyl group optionally is substituted with —C(O)OH, —C(O)NH$_2$, —S(O)$_2$OH. Typically, R$^5$ is selected from —C(O)OH, —C(O)NH$_2$, or C$_{1-6}$-alkyl; wherein the alkyl group optionally is substituted with —C(O)OH, —C(O)NH$_2$, or —S(O)$_2$OH.

In a further embodiment E1 is selected from —O— or —N(R$^6$)—, or a valence bond. Typically, E1 is selected from —O—.

In a further embodiment E2 is selected from —O— or —N(R$^6$)—, or a valence bond. Typically, E2 is selected from —O—.

In a further embodiment E1 and E2 are both —O—.

In a further embodiment E1 and E2 are both —N(R$^6$)—.

In a further embodiment F is phenyl, pyrrolidine-2,5-dione or a valence bond.

In a further embodiment D1 is selected from —O— or —N(R$^6$)—, or a valence bond. Typically, D1 is selected from —N(R$^6$)—.

In a further embodiment D2 is selected from —O— or —N(R$^6$)—, or a valence bond. Typically, D1 is selected from —N(R$^6$)—.

In a further embodiment l1 is 0-6, such as 0, 1, 2, 3, 4, 5 or 6.

In a further embodiment l2 is 0-6, such as 0, 1, 2, 3, 4, 5 or 6.

In a further embodiment l3 is 0-6, such as 0, 1, 2, 3, 4, 5 or 6.

In a further embodiment l4 is 0-6, such as 0, 1, 2, 3, 4, 5 or 6. In a further embodiment l5 is 0-6, such as 0, 1, 2, 3, 4, 5 or 6.

In a further embodiment l6 is 0-6, such as 0, 1, 2, 3, 4, 5 or 6.

In a further embodiment m1 is 0-6, such as 0, 2, 3, 4, 5 or 6.

In a further embodiment m2 is 0-10, such as 0, 1, 2, 3, 4, 5, 6, 7, 8, 9, or 10.

In a further embodiment m3 is 0-5, such as 0, 1, 2, 3, 4, 5 or 6.

In a further embodiment m4 is 0-5, such as 0, 1, 2, 3, 4, 5 or 6.

In a further embodiment m5 is 0-10, such as 0, 2, 3, 4, 5, 6, 7, 8, 9, or 10.

In a further embodiment m6 is 0-5, such as 0, 1, 2, 3, 4, 5 or 6.

In a further embodiment m7 is 0-5, such as 0, 1, 2, 3, 4, 5 or 6.

In a further embodiment n1 is 0-10, such as 0, 1, 2, 3, 4, 5 or 6.

In a further embodiment n2 is 0-10, such as 0, 1, 2, 3, 4, 5 or 6.

In a further embodiment n3 is 0-10, such as 0, 1, 2, 3, 4, 5 or 6.

In a further embodiment n4 is 0-10, such as 0, 1, 2, 3, 4, 5 or 6.

In a further embodiment X$_1$ is —W$_1$—[(CHR$^1$)$_{l1}$—W$_2$]$_{m1}$—{[(CH$_2$)$_{n1}$O]$_{m2}$—[(CHR$^2$)$_{l2}$—W$_3$]$_{m3}$}$_{n2}$— and X$_2$ is —[(CHR$^3$)$_{l3}$—W$_4$]$_{m4}$—{[(CH$_2$)$_{n3}$O]$_{m5}$—[(CHR$^4$)$_{l4}$—W$_5$]$_{m6}$}$_{n4}$—, wherein —{[(CH$_2$)$_{n1}$O]$_{m2}$—[(CHR$^2$)$_{l2}$—W$_3$]$_{m3}$}$_{n2}$— and —{[(CH$_2$)$_{n3}$O]$_{m5}$—[(CHR$^4$)$_{l4}$—W$_5$]$_{m6}$}$_{n4}$— are selected from,

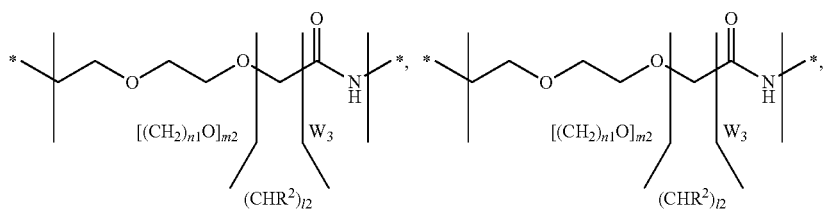

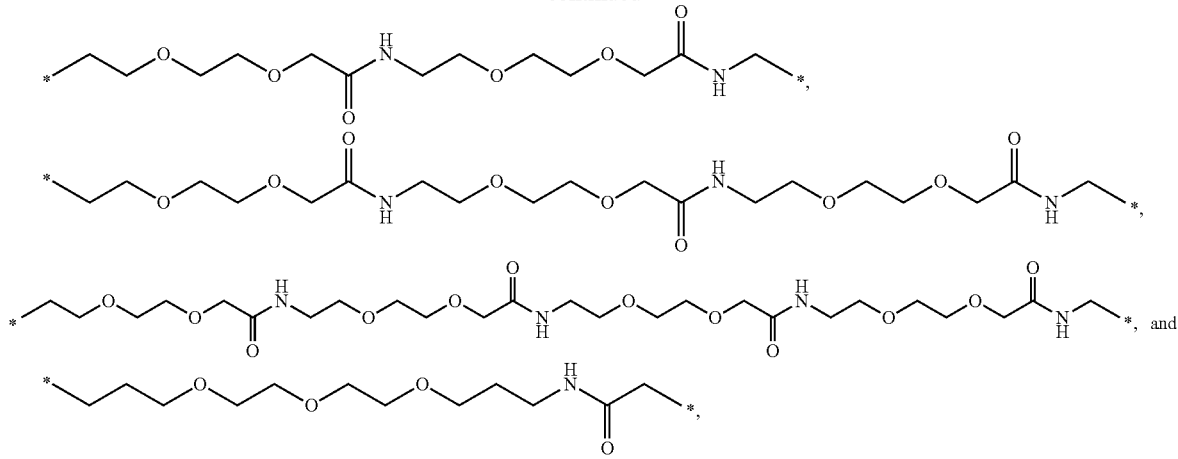

wherein * is intended to denote a point of attachment, ie, an open bond.

In a further embodiment the molar weight of said hydrophilic spacer is in the range from 80 Daltons (D) to 1500 D or in the range from 300 D to 1100 D.

In a still further embodiment W has the formula

—W$_7$—Y—, wherein

Y is —(CH$_2$)$_{l7}$—C$_{3-10}$-Cycloalkyl-W$_8$— or a valence bond, l7 is 0-6, W$_7$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s3}$—, —C(O)—, —C(O)O—, —OC(O)—, or a valence bond; wherein s3 is 0 or 1, W$_8$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s4}$—, —C(O)—, —C(O)O—, —OC(O)—, or a valence bond; wherein s4 is 0 or 1.

In an embodiment of W Y is —(CH$_2$)$_7$-cyclohexyl-W$_8$—.

In a further embodiment Y is a valence bond.

In an embodiment W$_7$ is selected from —C(O)NH—, —NHC(O)—, —C(O)NHCH$_2$—, —CH$_2$NHC(O)—, —C(O)NHS(O)$_2$—, —S(O)$_2$NHC(O)— or a valence bond. Typically, W$_7$ is selected from —C(O)NH—, —NHC(O)—, or —C(O)NHS(O)$_2$.

In a further embodiment W$_8$ is selected from —C(O)NH—, —NHC(O)—, —C(O)NHCH$_2$—, —CH$_2$NHC(O)—, —C(O)NHS(O)$_2$—, —S(O)$_2$NHC(O)— or a valence bond. Typically, W$_8$ is selected from —C(O)NH—, —NHC(O)—, or —C(O)NHS(O)$_2$.

In a further embodiment l7 is 0 or 1.

In a further embodiment the hydrophilic spacer B of the present invention is selected from

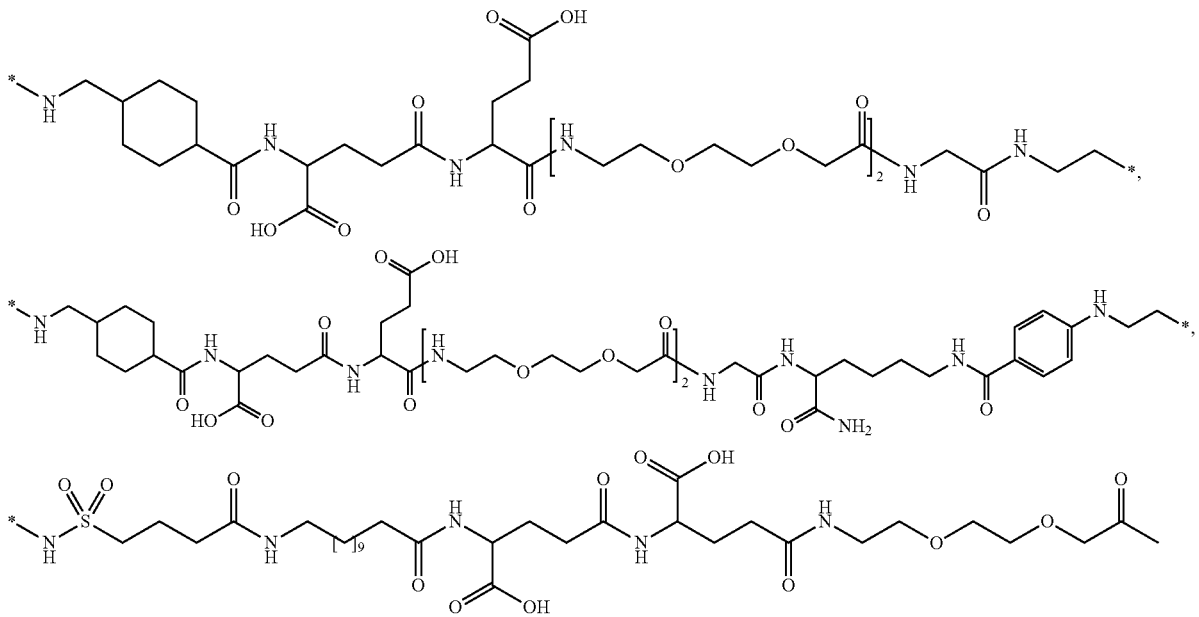

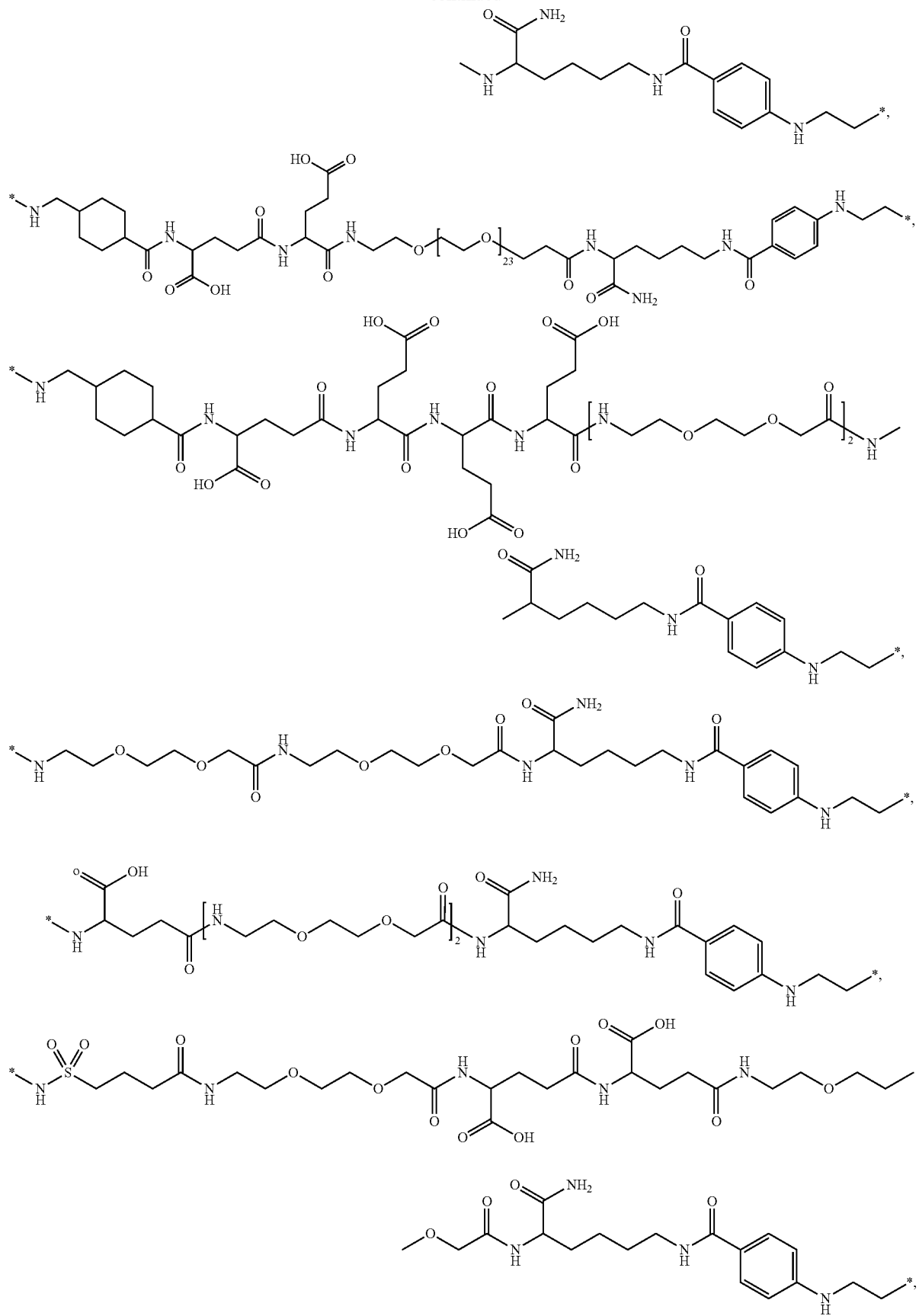

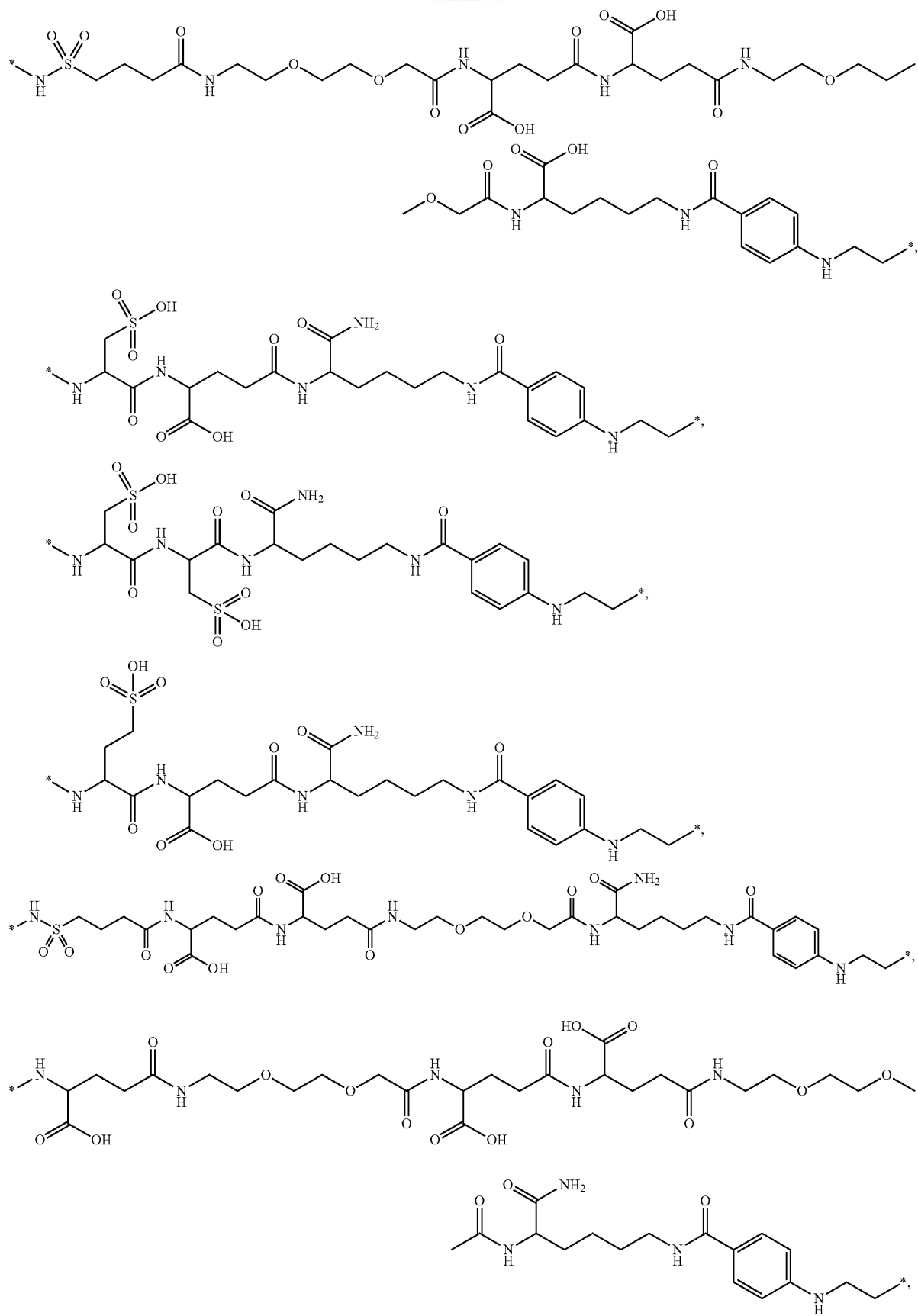

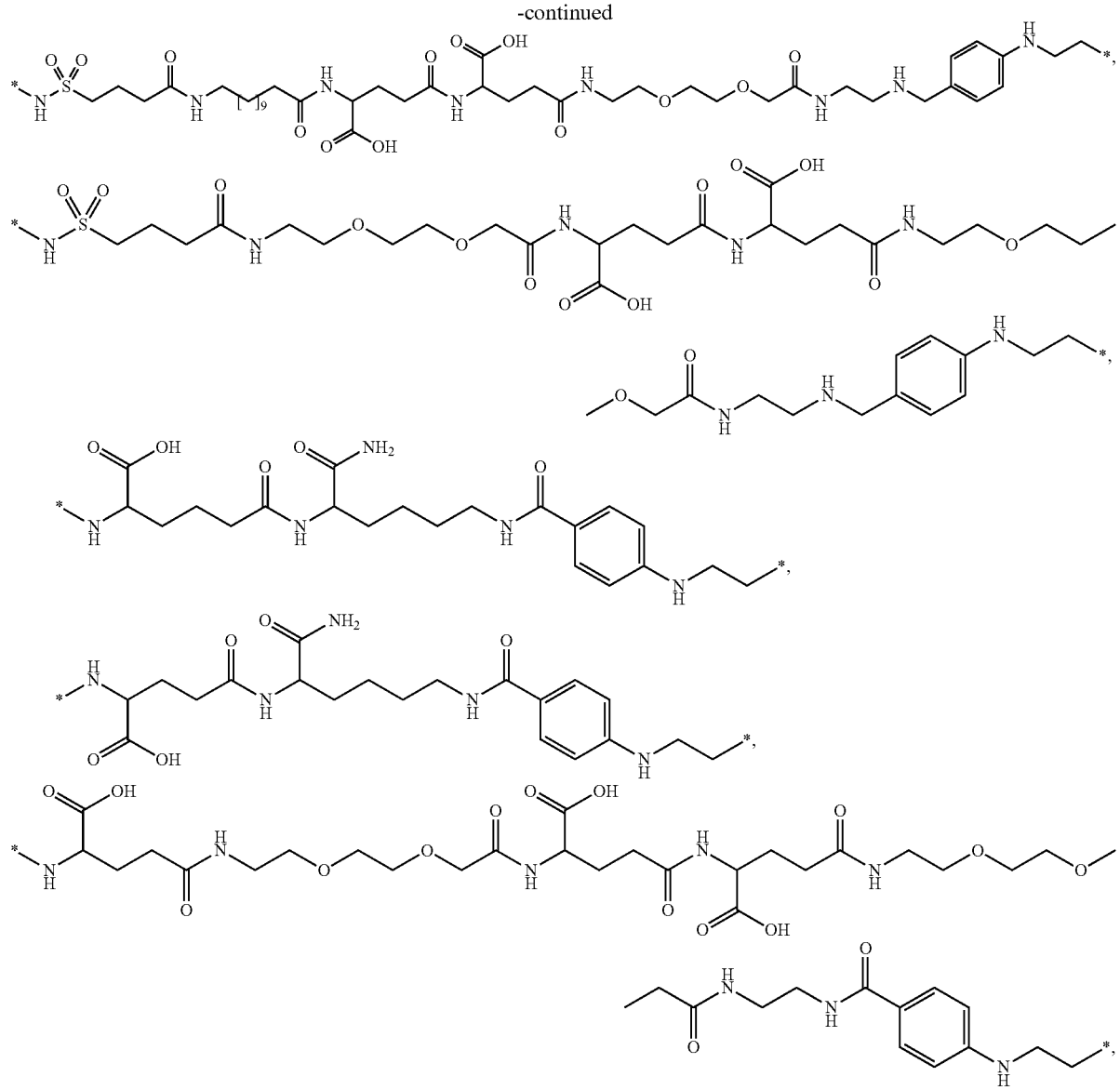

wherein * is intended to denote a point of attachment, ie, an open bond.

The albumin binding residue (substituent A in formula (I) or (II) above) attached to the growth hormone compound of the present invention is a lipophilic residue, which binds non-covalently to albumin. Typically, albumin binding residue is negatively charged at physiological pH, and has a binding affinity towards human serum albumin that is below about 10 μM or even below about 1 μM.

In a further embodiment of the growth hormone compound of the present invention the albumin binding residue is selected from a straight chain alkyl group, a branched alkyl group, a group which has a ω-carboxylic acid group or a ω-carboxylic acid isoster. Typically, the albumin binding residue has from 6 to 40 carbon atoms. In a further embodiment the albumin binding residue has from 8 to 26 carbon atoms. In a further embodiment the albumin binding residue has from 8 to 20 carbon atoms.

In a further embodiment A has 14 to 26 carbon atoms and comprises an ω-carboxylic acid group. In a further embodiment A has 14 to 26 carbon atoms and comprises an ω-carboxylic acid isoster, such as a tetrazol.

In a further embodiment A is selected from

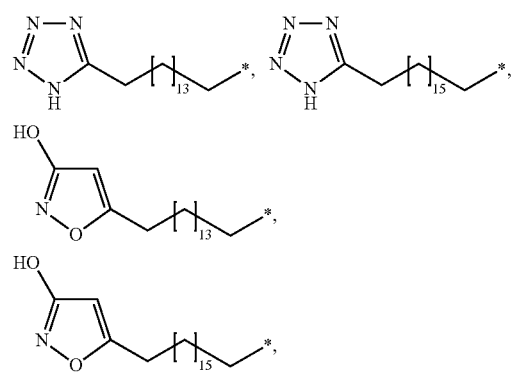

81
-continued

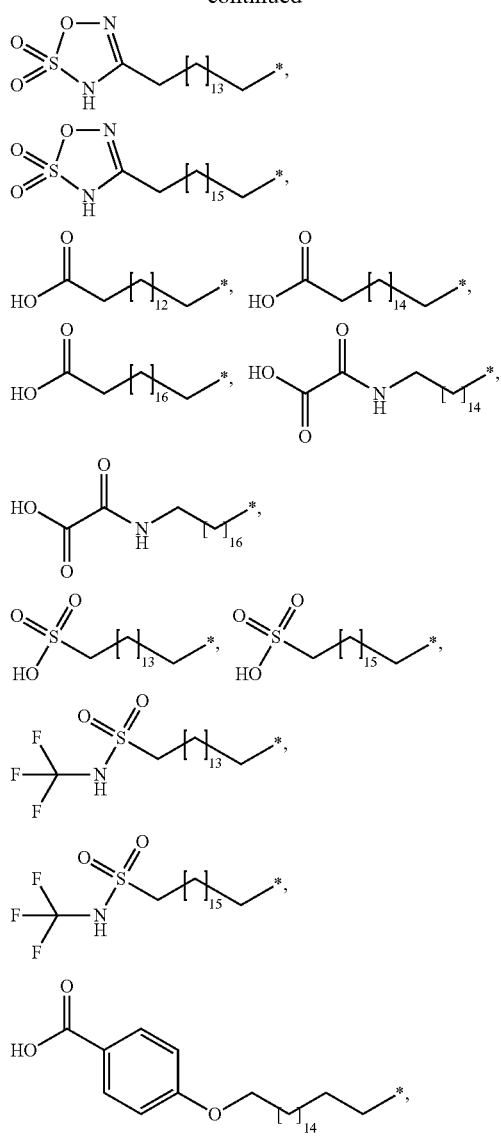

82
-continued

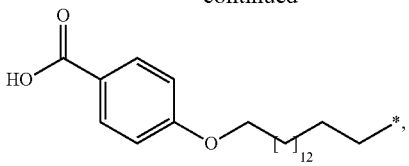

wherein * denotes the attachment to B through W.

The hydrophilic spacer (B) is preferably introduced in a position of the growth hormone compound (GH) in a selective manner in order to be able to control whether one or two albumin binding residues (A) should be incorporated in the growth hormone compound. The hydrophilic spacer (B) may be attached to an amino acid side-chain of the GH compound. Such amino acid side-chain may be a chemically modified amino acid side-chain of the GH compound. Another, such amino acid side-chain may be an enzymatically modified amino acid side-chain of the GH compound. Preferably, a transglutaminase is used to introduce a hydrophilic spacer in the glutamine residue in the position corresponding to position 40 or position 141 in SEQ ID NO: 1. Another way of selectively introducing a hydrophilic spacer is in the N-terminal residue of the growth hormone compound, such as hGH (SEQ ID NO: 1).

In the growth hormone conjugate of the formula (I) the fragment A-W—B may be linear or branched. In one embodiment, A-W—B is not a linear peptide.

In a further embodiment the albumin binding residue via a hydrophilic spacer is attached to the glutamine residue in the position corresponding to position 40 in SEQ ID NO: 1.

In a further embodiment the albumin binding residue via a hydrophilic spacer is attached to the glutamine residue in the position corresponding to position 141 in SEQ ID NO: 1.

In a further embodiment the albumin binding residue via a hydrophilic spacer is attached to the N-terminal residue of the growth hormone compound, such as hGH (SEQ ID NO: 1).

In a further embodiment the albumin binding residue via a hydrophilic spacer is attached to the glutamine residue in the position corresponding to position 40, position 141 and to the N-terminal residue of the growth hormone compound, such as hGH (SEQ ID NO: 1).

The growth hormone conjugates of the present invention are selected from,

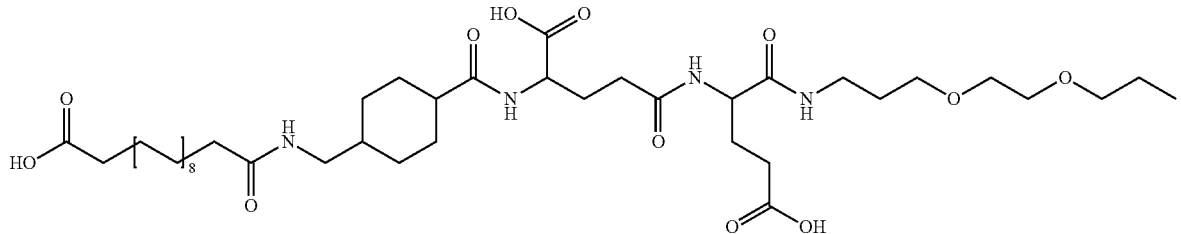

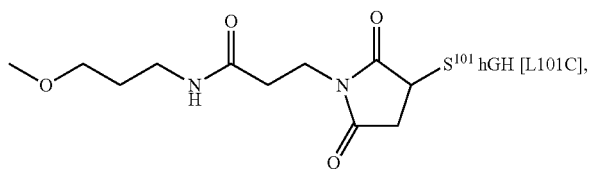

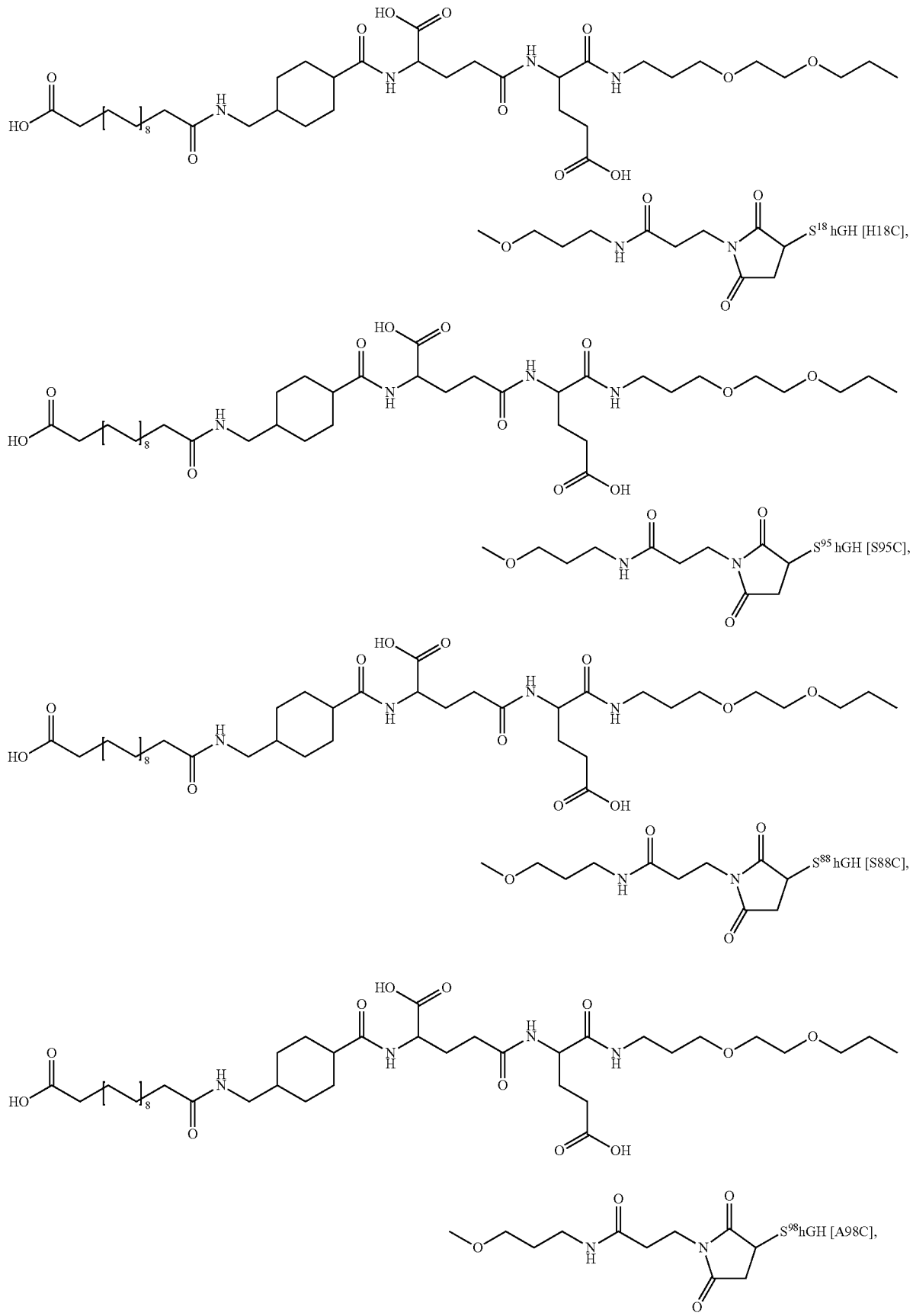

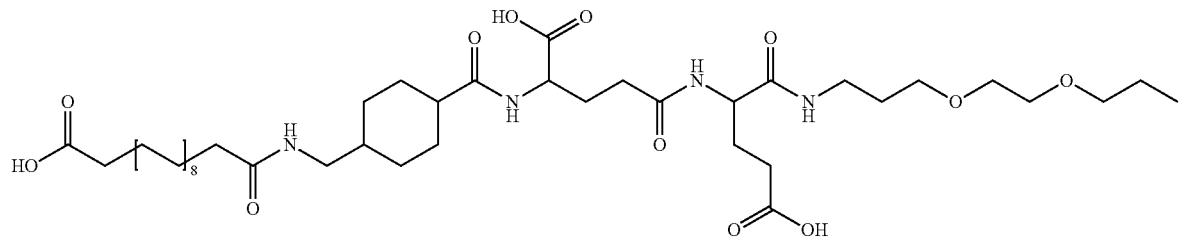
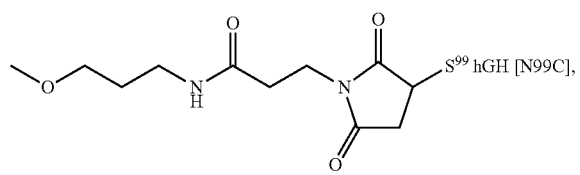
S⁹⁹ hGH [N99C],
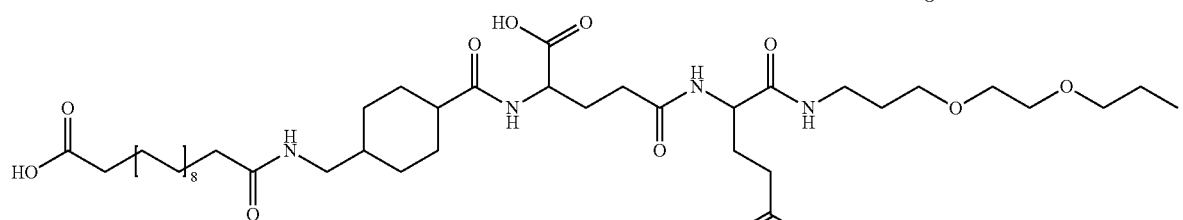
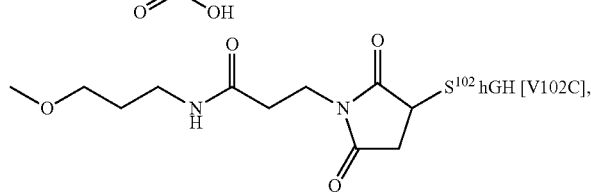
S¹⁰² hGH [V102C],
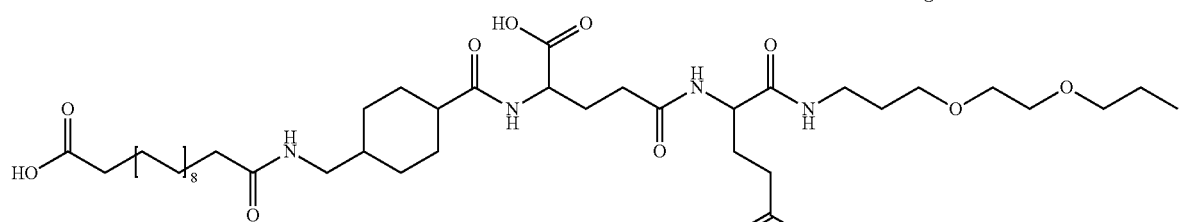
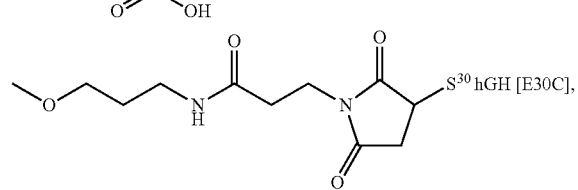
S³⁰ hGH [E30C],
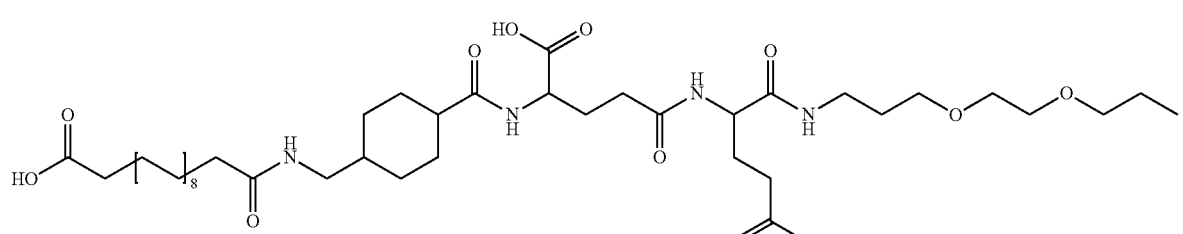
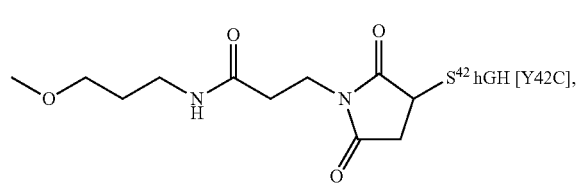
S⁴² hGH [Y42C], -continued
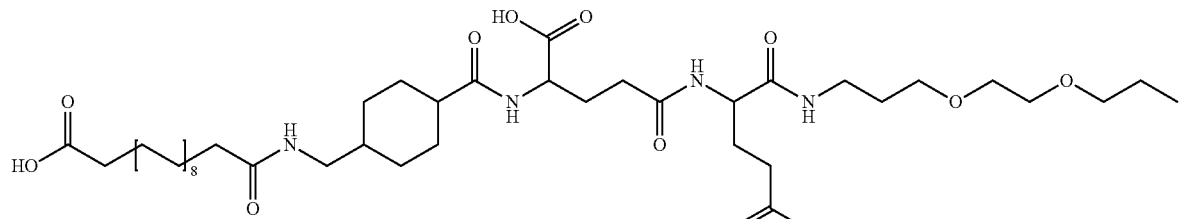
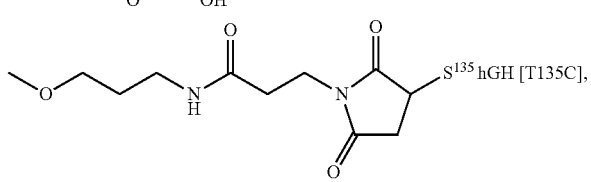
$S^{135}$ hGH [T135C],
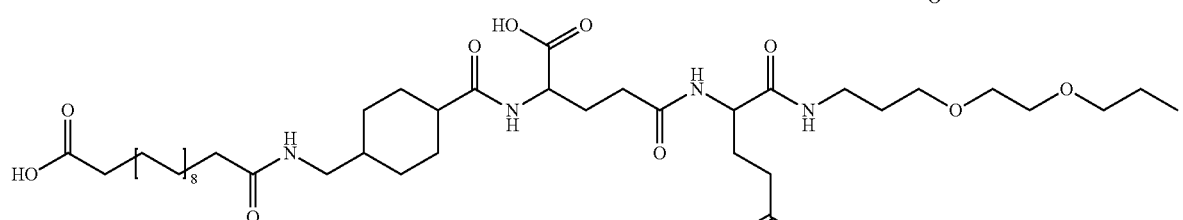
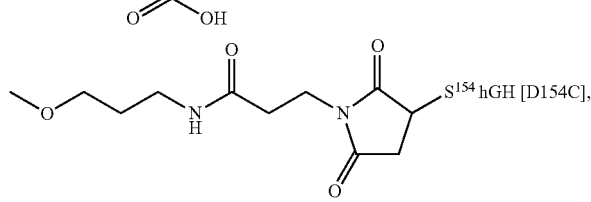
$S^{154}$ hGH [D154C],
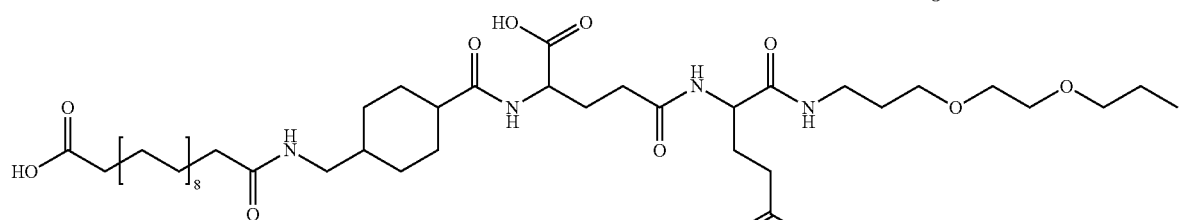
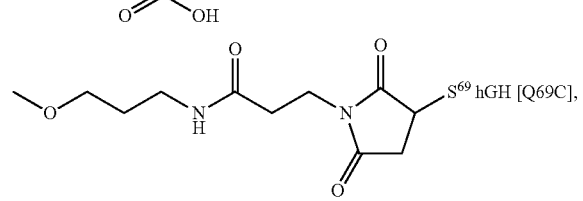
$S^{69}$ hGH [Q69C],
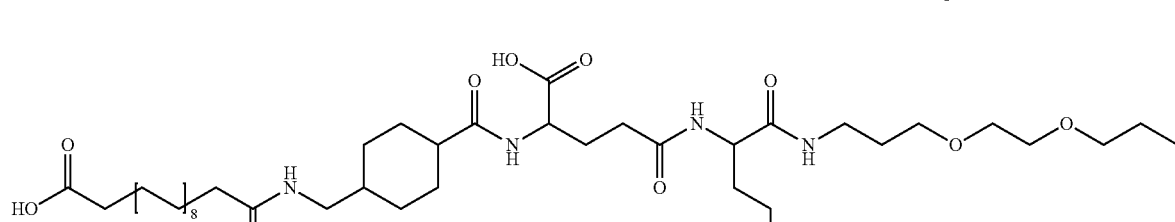
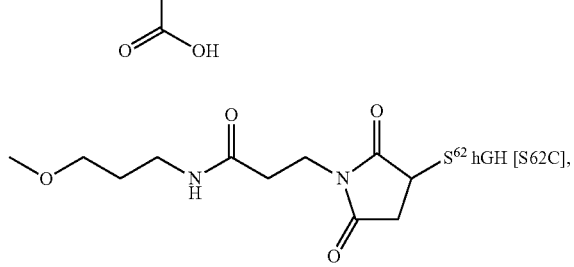
$S^{62}$ hGH [S62C],

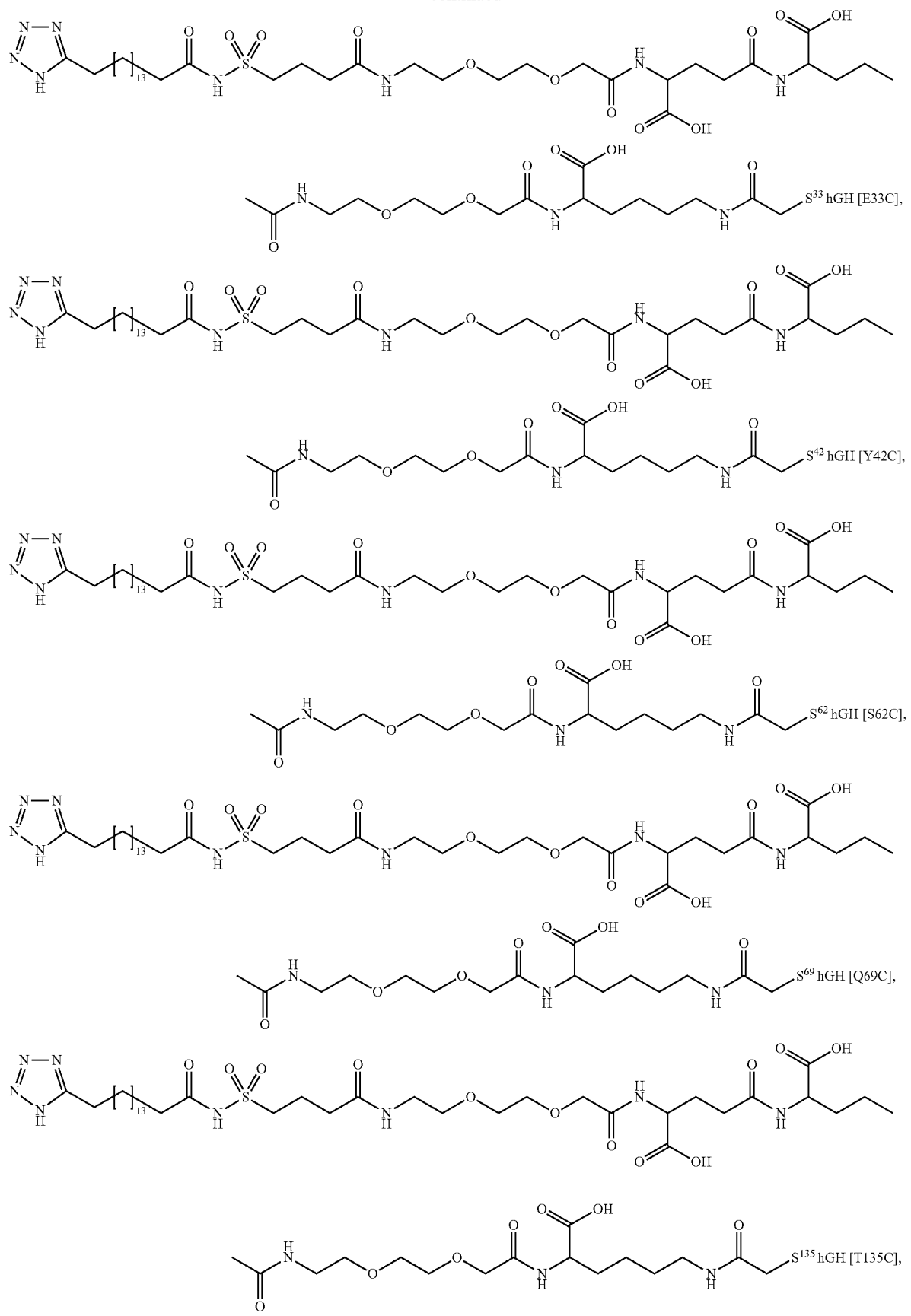

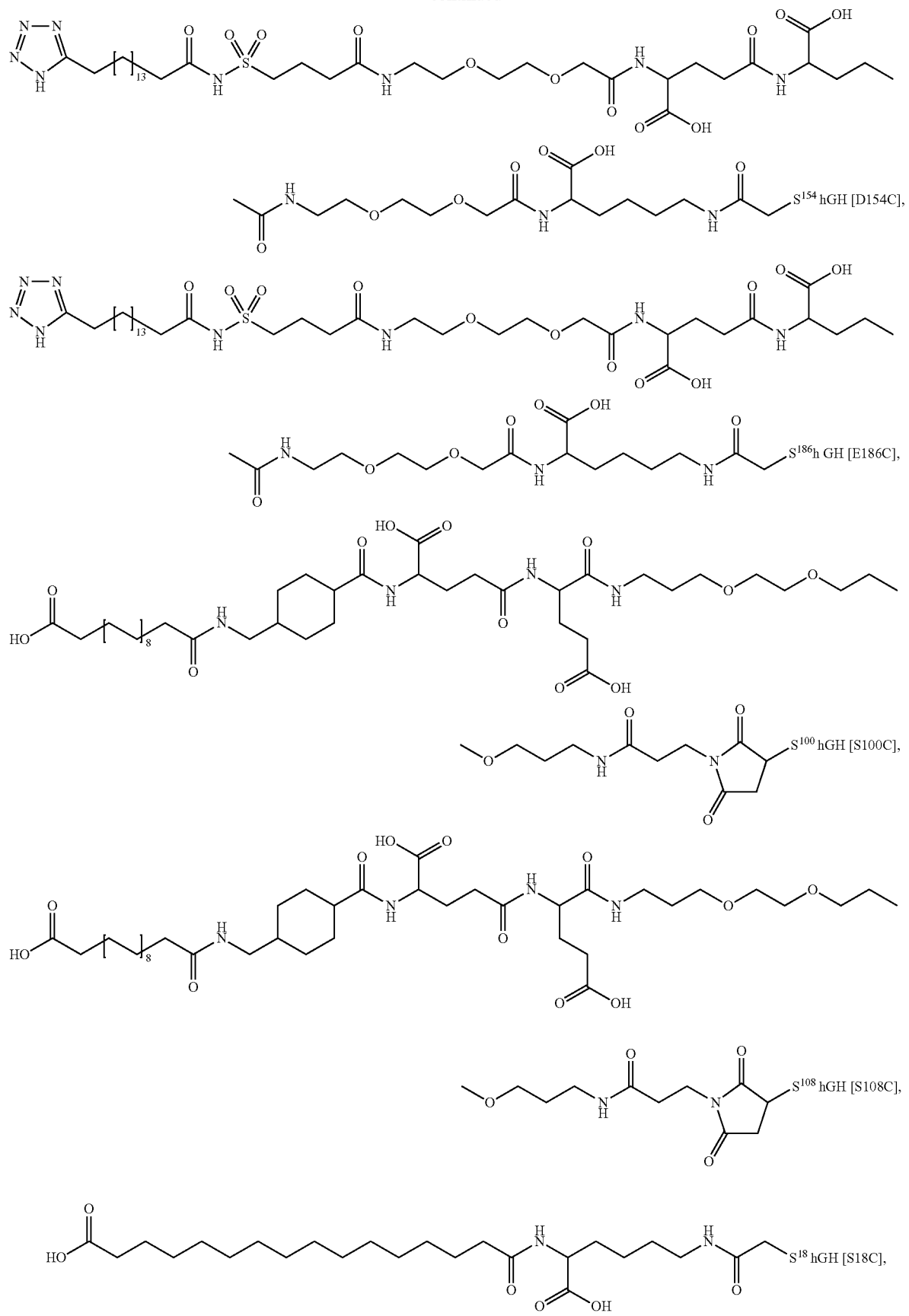

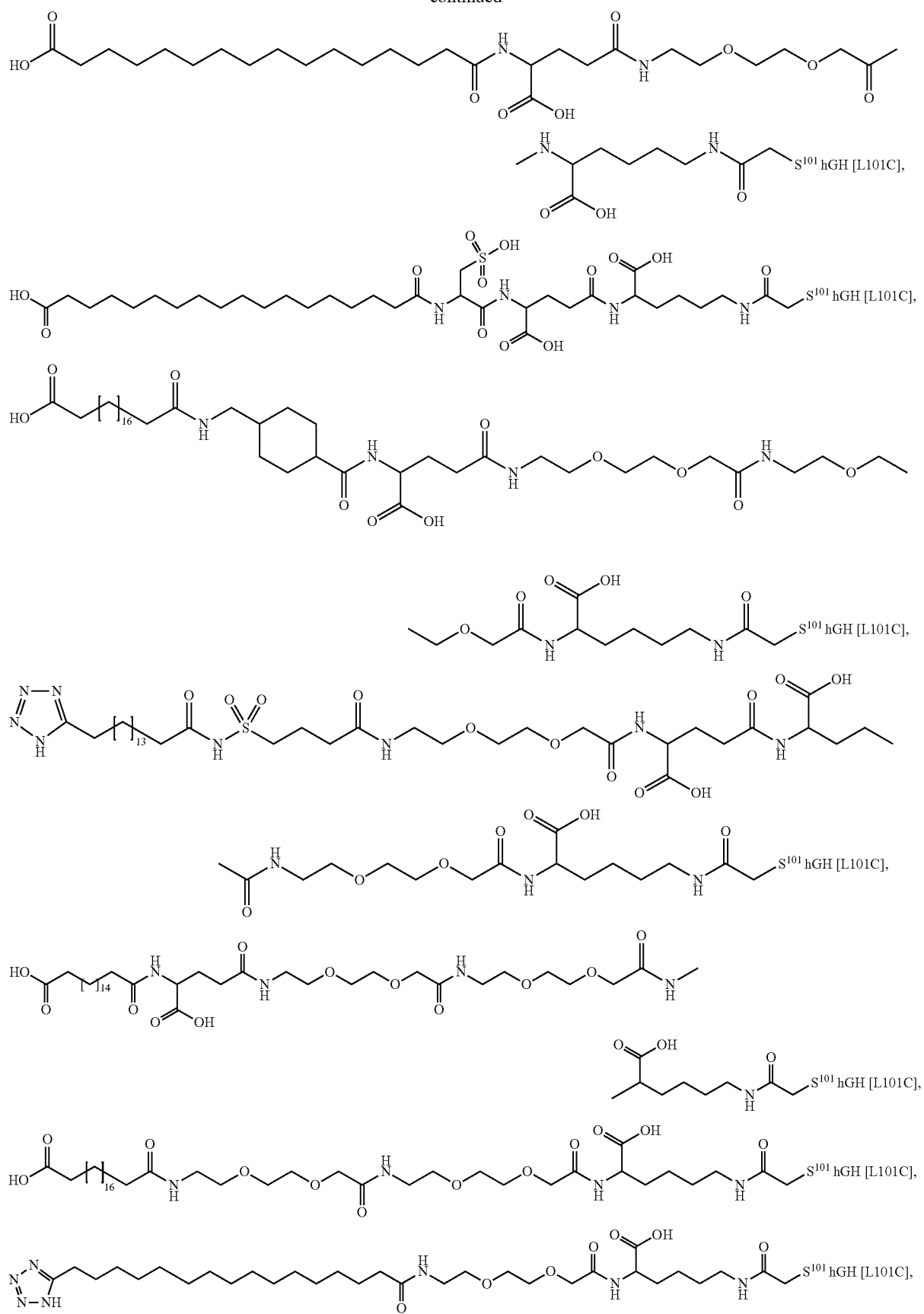

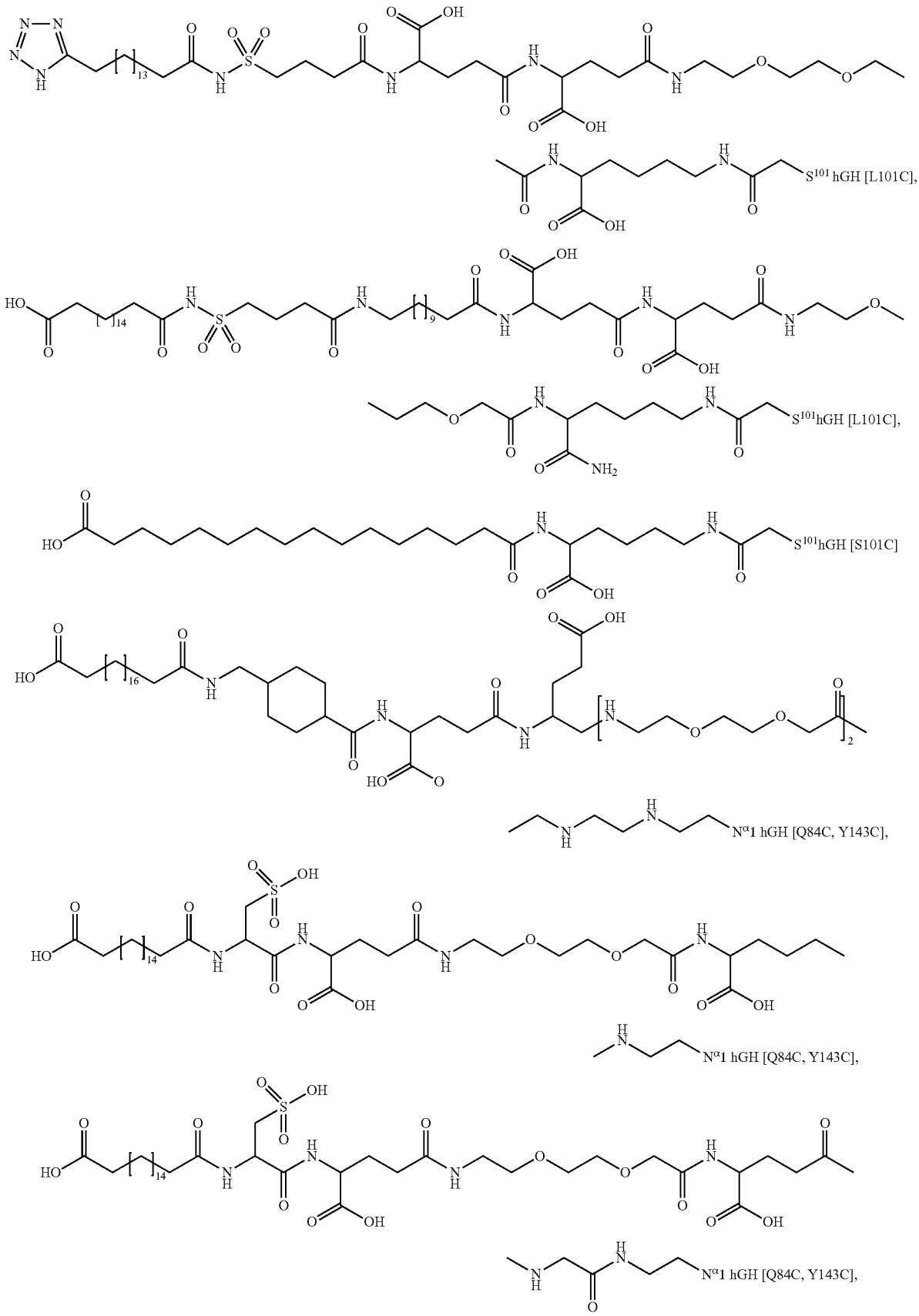

-continued
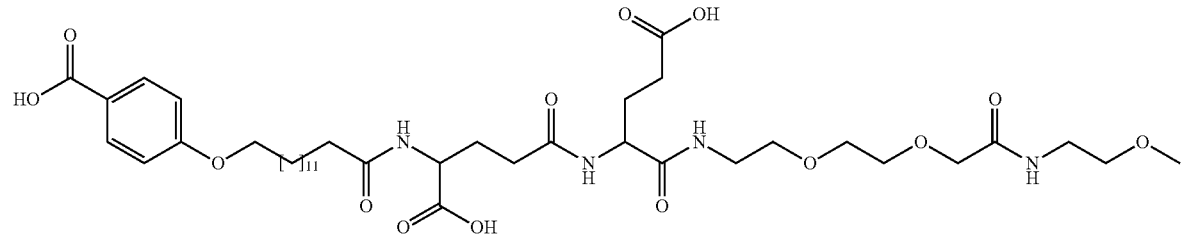
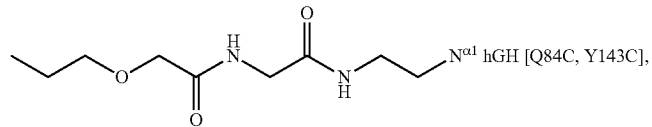
Nα1 hGH [Q84C, Y143C],
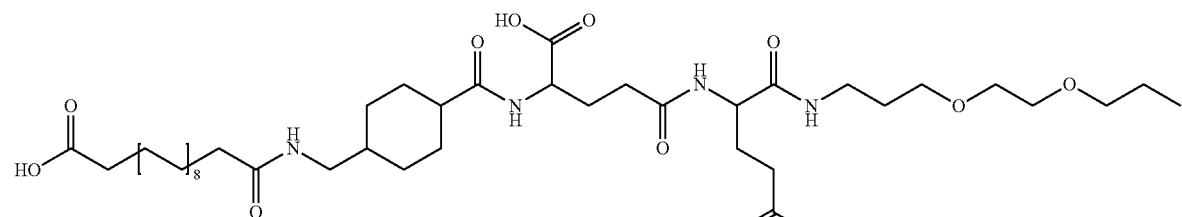
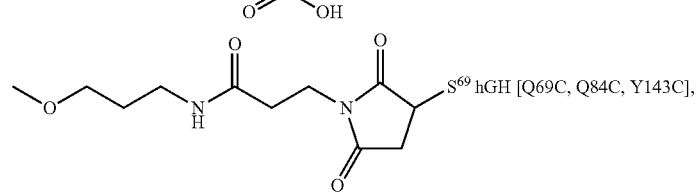
S69 hGH [Q69C, Q84C, Y143C],
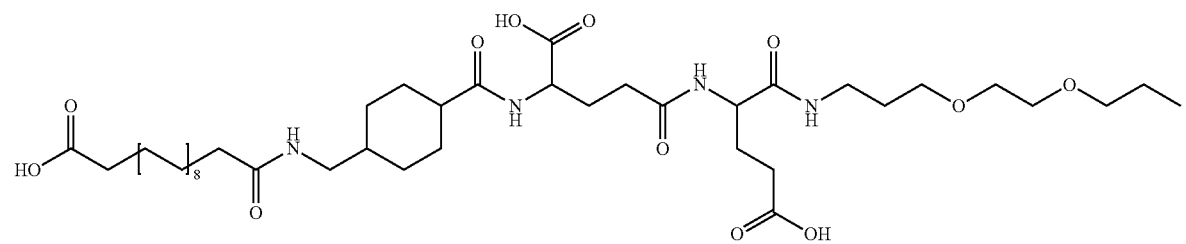
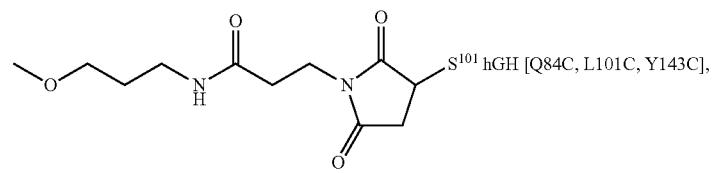
S101 hGH [Q84C, L101C, Y143C],
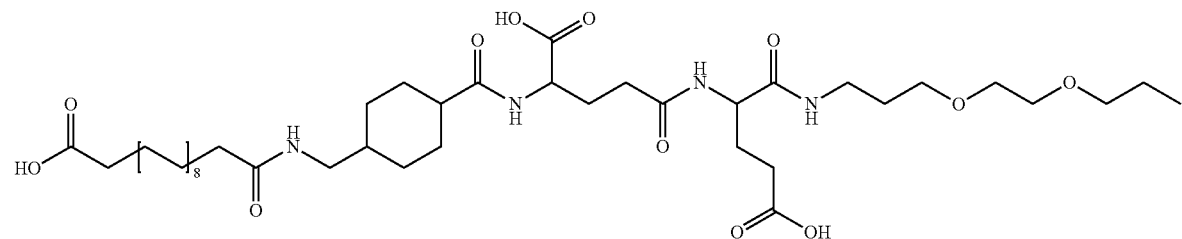
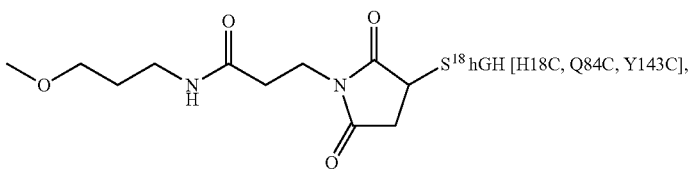
S18 hGH [H18C, Q84C, Y143C], -continued
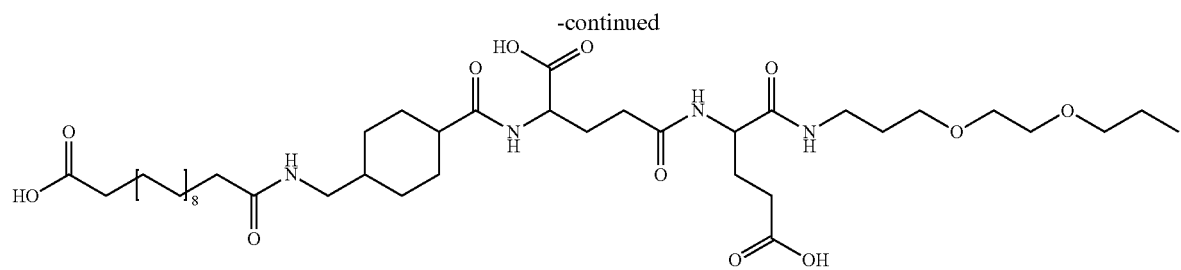
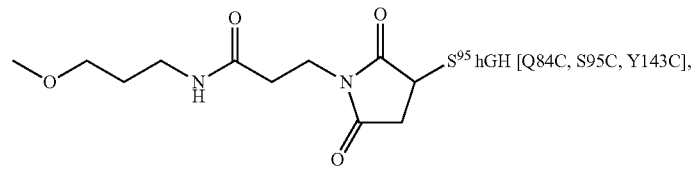 S⁹⁵ hGH [Q84C, S95C, Y143C],
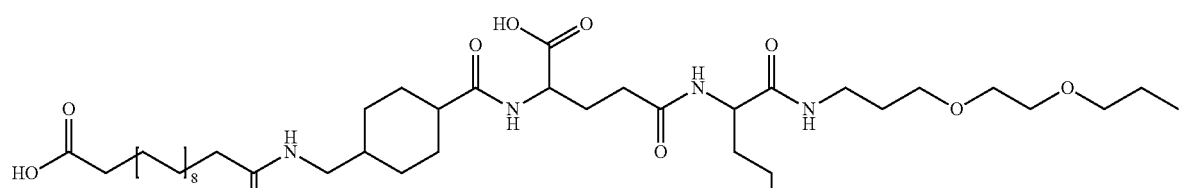
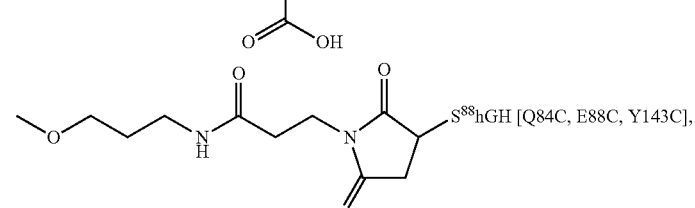 S⁸⁸ hGH [Q84C, E88C, Y143C],
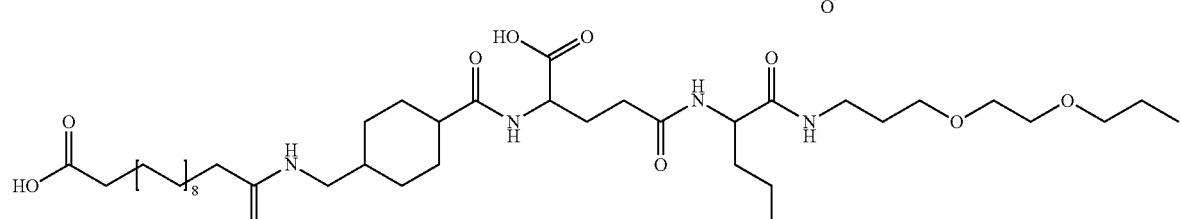
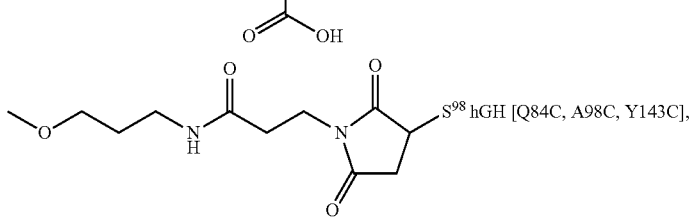 S⁹⁸ hGH [Q84C, A98C, Y143C],
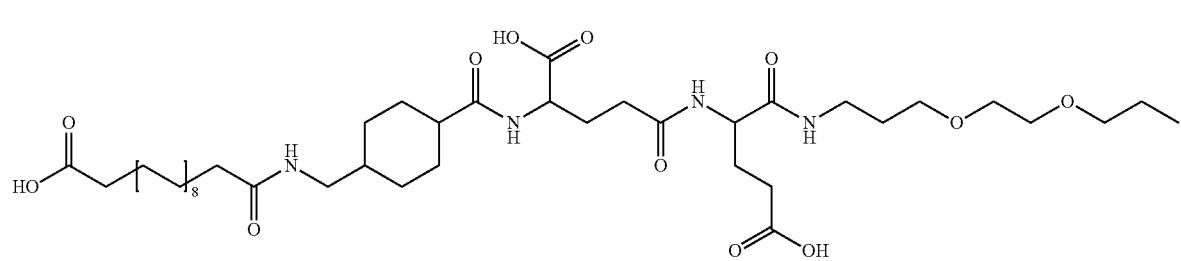
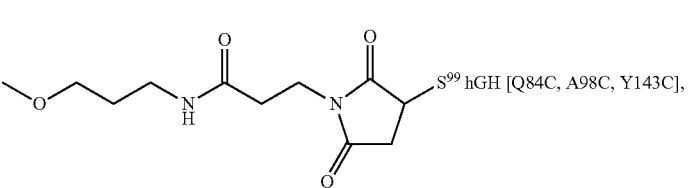 S⁹⁹ hGH [Q84C, A98C, Y143C], -continued
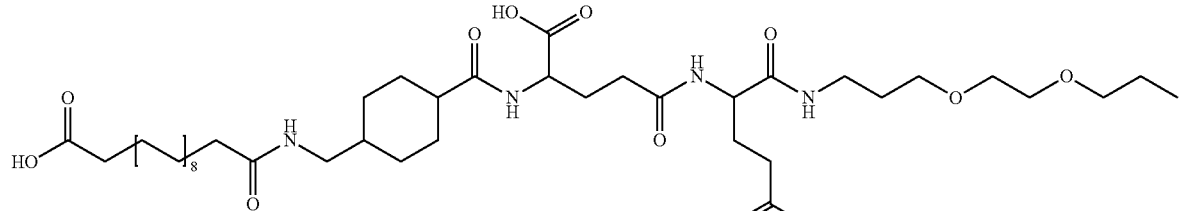
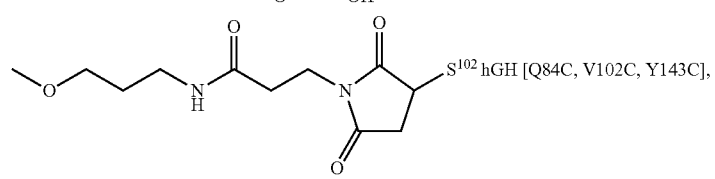 S¹⁰² hGH [Q84C, V102C, Y143C],
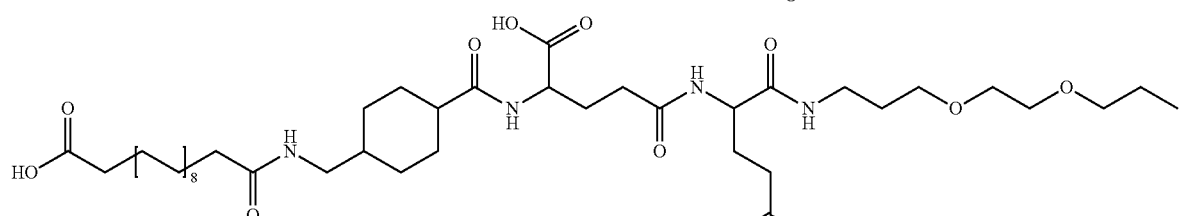
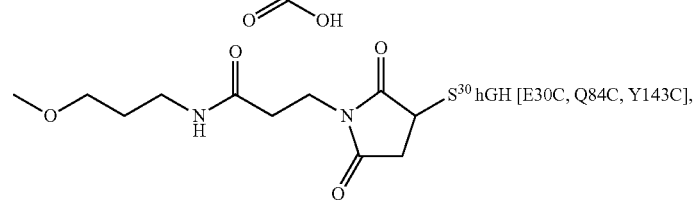 S³⁰ hGH [E30C, Q84C, Y143C],
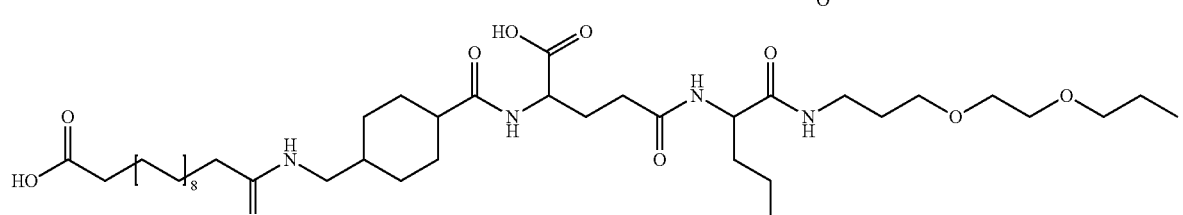
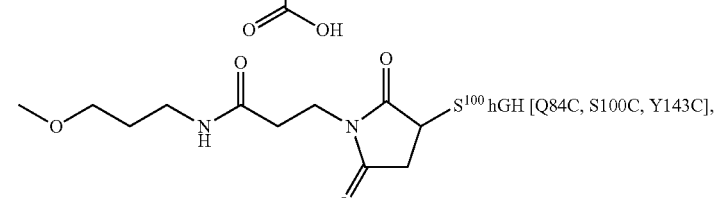 S¹⁰⁰ hGH [Q84C, S100C, Y143C],
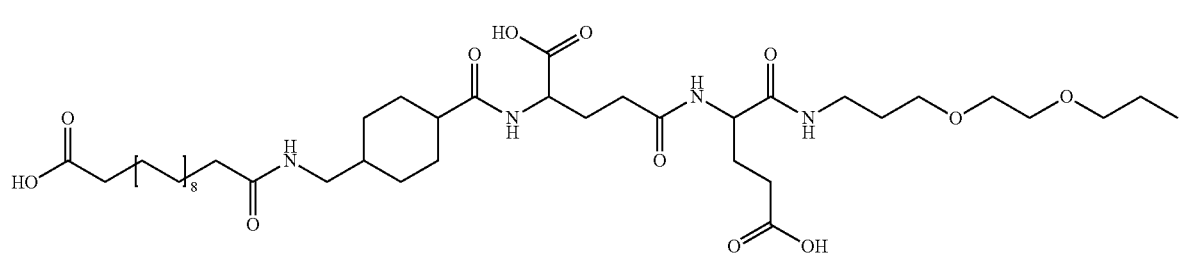
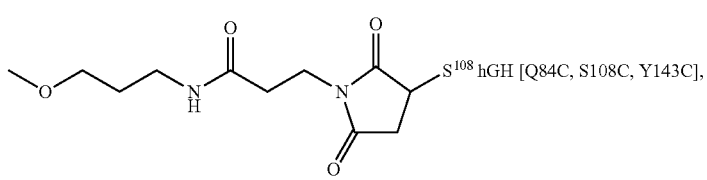 S¹⁰⁸ hGH [Q84C, S108C, Y143C],

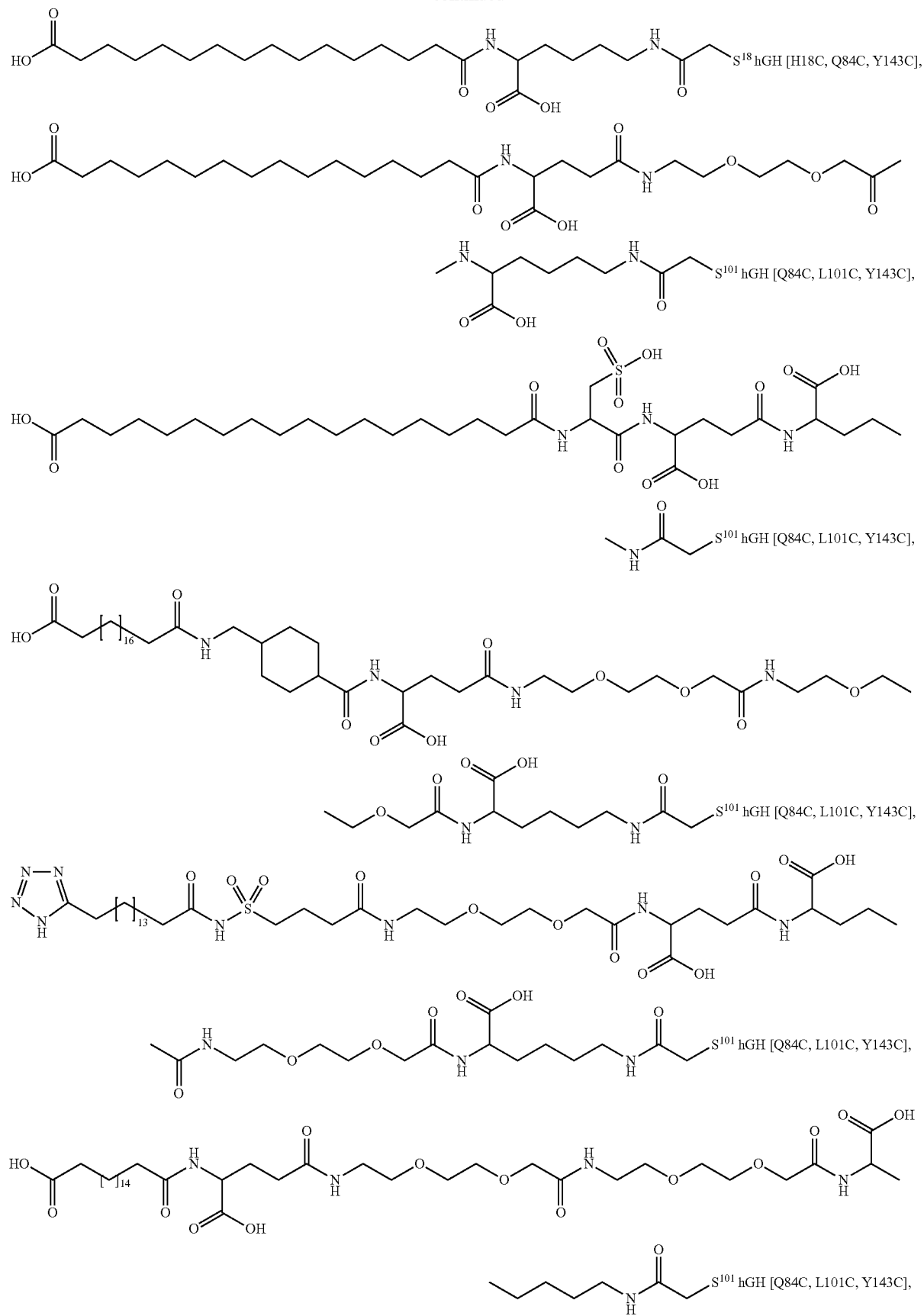

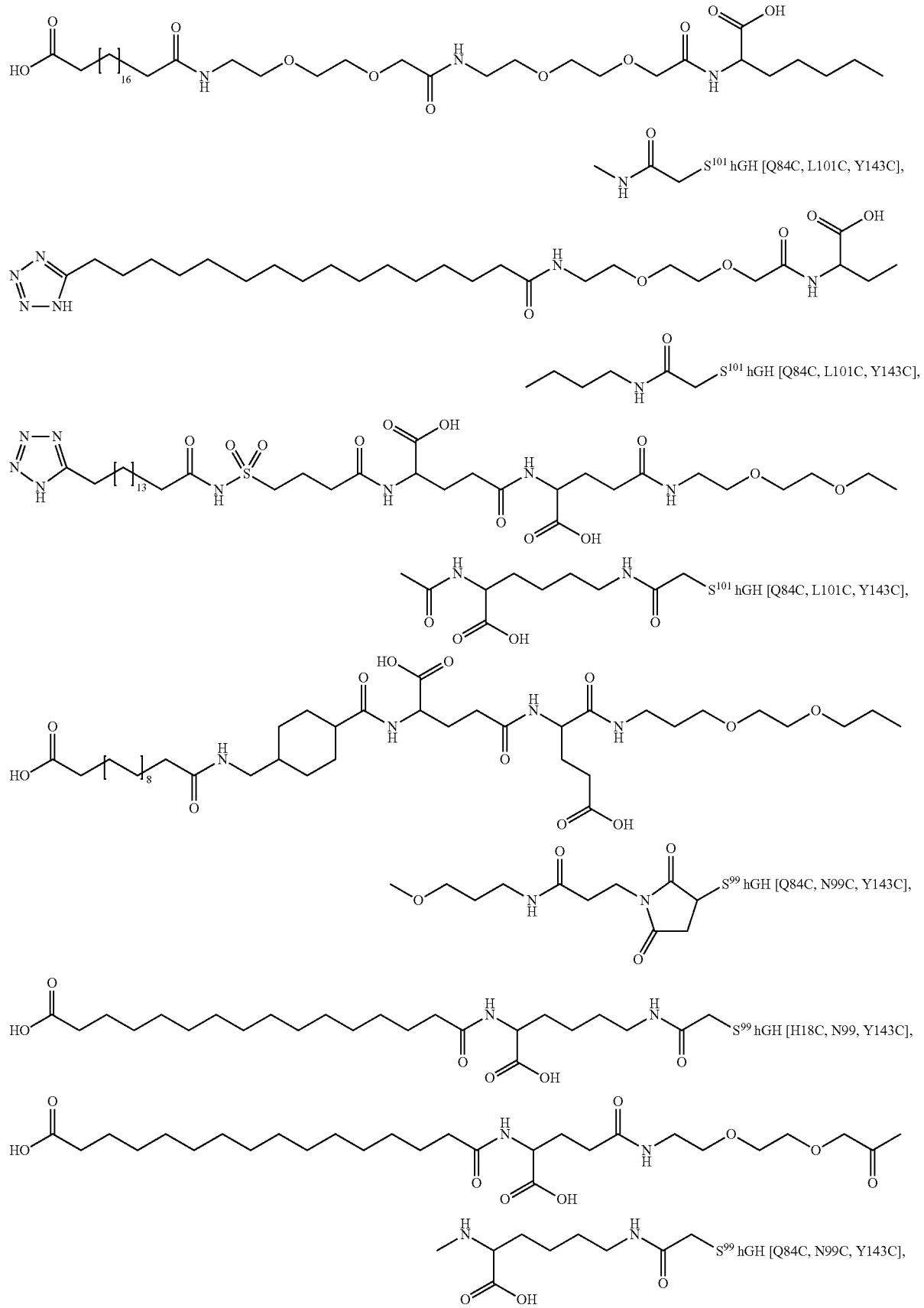

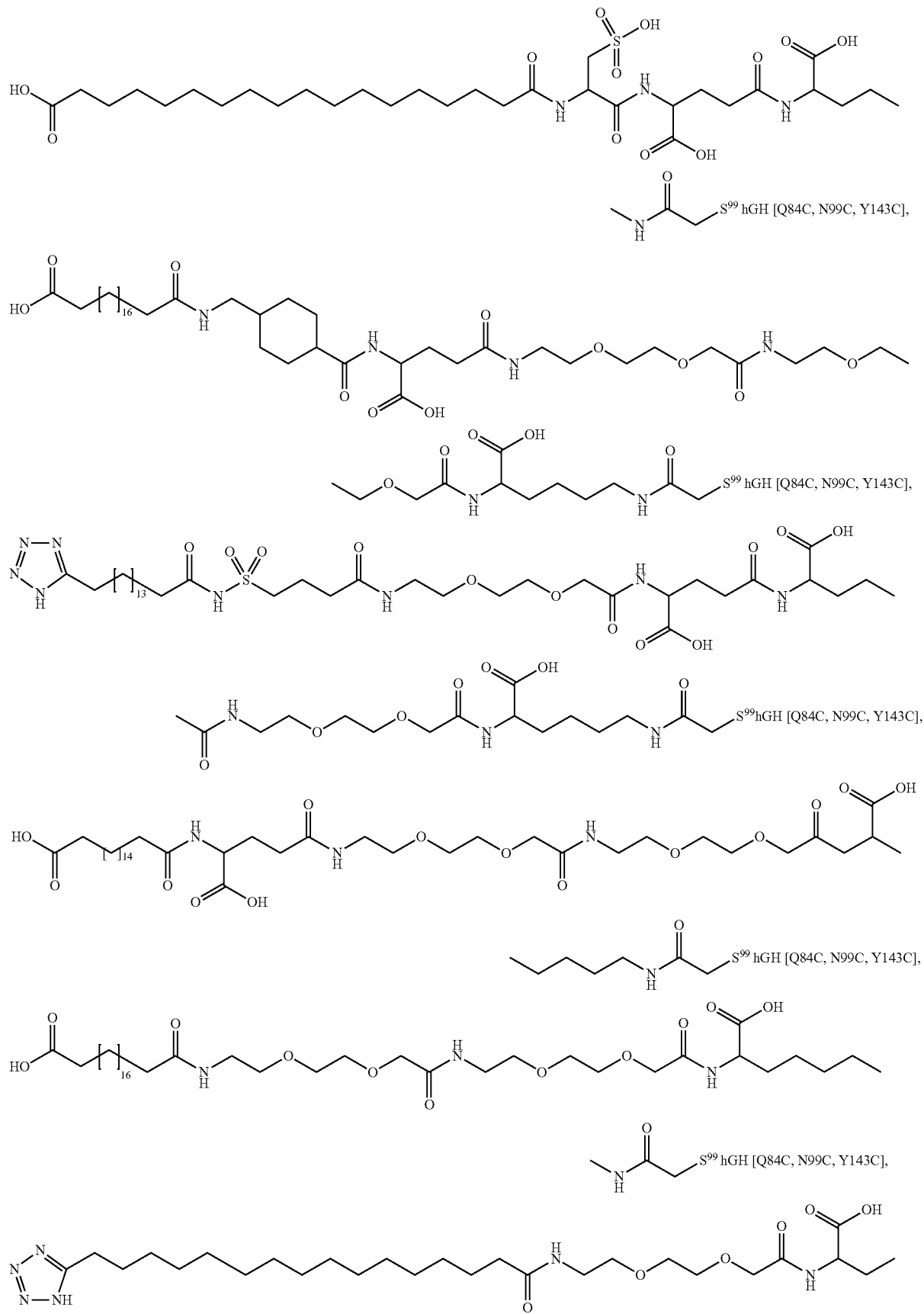

-continued

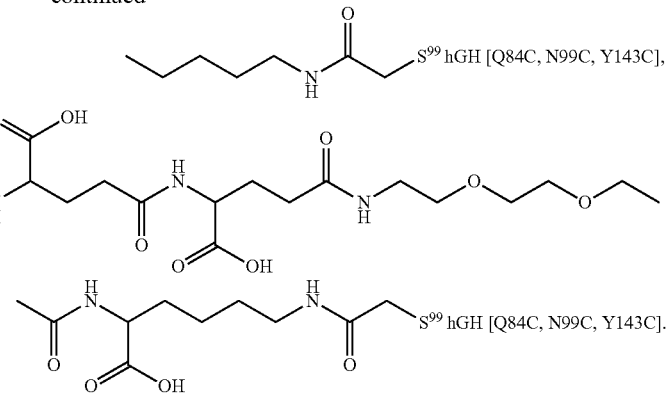

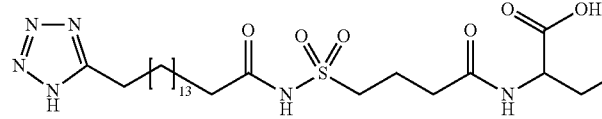

In a further aspect the present invention relates to a growth hormone variants such as the growth hormone compounds (GH) described herein. The growth hormone variants may be useful as therapeutic agents or as intermediates in the preparation of growth hormone conjugates. The growth hormone compounds may be produces by recombinant methods known in the art or as described herein. In an embodiment the growth hormone variant is soluble.

In a further aspect the invention relates to a composition comprising a growth hormone variant as described herein.

In an embodiment the composition comprises a growth hormone variant comprising a single cys mutation selected from the group of: P5C, S7C, D11C, H18C, Q29C, E30C, E33C, A34C, Y35C, E88C, Q91C, S95C, A98C, N99C, S100C, L101C, V102C, Y103C, D107C, S108C, D112C, Q122C and G126C.

In an embodiment of the invention the growth hormone variant of the composition has a single Cys mutation in the N-terminal (AA 1-8), in Helix 1, in Loop 1, in Helix 2, in Loop 2 or in Helix 3 of the growth hormone compound.

In an embodiment the single Cys mutation is positioned in the N-terminal, the mutation being such as any one of P5C, S7C. In an embodiment the single Cys mutation is positioned in H1 (corresponding to AA 9-35), such as any one of D11C, H18C, Q29C, E30C, E33C, A34C, Y35C. In an embodiment the single Cys mutation is positioned in L1 (corresponding to AA36-71), the mutation being such as any one of K38C, E39C, Y42C, S43C, D47C, P48C, S55, S57C, P59C, S62C, E65C, Q69C or preferably any one of Y42C, S55C, S57C, S62C, Q69C. In an embodiment the single Cys mutation is positioned in H2 (AA 72-98), such as any one of E88C, Q91C, S95C and A98C. In an embodiment the single Cys mutation is positioned within AA 99-127. In an embodiment the single Cys mutation is positioned in L2 (AA 99-106), such as any one of N99C, S100C, L101C, V102C and Y103C. In an embodiment the single Cys mutation is positioned in H3 (AA 107-127), the mutation being such as any one of D107C, S108C, D112C, Q122C and G126C of hGH (SEQ ID NO: 1) or in L3 or H4 (corresponding to AA128-154 and AA155-184) the mutation being such as any one of E129C, D130C, G131C, P133C, T135C, G136C, T142C, D147C, N149C, D154C, A155C, L156C, R178C, V180C or in the C-terminal the mutation being such as any one of E186C G187C and G190C. If the single Cys mutation is present in a hGH variant the mutation is located in corresponding amino acid residues. In even further embodiments the single Cys mutation is located within AA 93-106 in hGH or corresponding residues in hGH variants. In further specified embodiments the single Cys mutation is located within L2, such as within AA 99-106 or AA 99-104 or corresponding residues.

In an embodiment the composition according to the invention comprises a growth hormone variant comprising a single cys mutation and an additional disulfide bond. In an embodiment the single cys mutation is any one of the above described single cys mutations. In an embodiment the single cys mutation in GH is selected from any one of: T3C, P5C, S7C, D11C, H18C, Q29C, E30C, E33C, A34C, Y35C, K38C, E39C, Y42C, S43C, D47C, P48C, S55C, S57C, P59C, S62, E65C, Q69C, E88C, Q91C, S95C, A98C, N99C, S100C, L101C, V102C, Y103C, D107C, S108C, D112C, Q122C, G126C, E129C, D130C, G131C, P133C, T135C, G136C, T142C, D147C, N149C, D154C, A155C, L156C, R178C, E186C, G187C and G190C, such as any one of; P5C, S7C, D11C, H18C, Q29C, E30C, E33C, A34C, Y35C, E88C, Q91C, S95C, A98C, N99C, S100C, L101C, V102C, Y103C, D107C, S108C, D112C, Q122C and G126C of hGH (SEQ ID NO: 1) or corresponding residues. In an embodiment the additional disulfide bond is selected from the following group of pairs of cystein mutations: R16C/L117C, A17C/E174C, H21C/M170C, D26C/V102C, D26C/Y103C, N47C/T50C, Q49C/G161C, F54C/Y143C, F54C/S144C, F54C/F146C, S55C/Y143C, S57C/Y143C, I58C/Q141C, I58C/Y143C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, S85C/Y143C, S85C/S144C, P89C/F146C, F92C/F146C, F92C/T148C, R94C/D107C, V102C/A105C, L156C/F146C, L156C/T148C and/or V185C/S188C. In an embodiment the growth hormone variant comprise a single cystein and an additional disulfide bond selected from the following pairs of cystein mutations: S57C/Y143C, Q84C/Y143C, S85C/Y143C and/or S85C/S144C.

In an embodiment the growth hormone variant comprise a single cysteine mutation in L2 and an additional disulfide bond which connects a loop segment, such as from amino acid residues 128-154 (H3), with a helical segment, such as helix B or helix 2 (corresponding to AA 72-98). In an embodiment the growth hormone variant comprise a combination of mutations selected from the following group: A98C/Q84C/Y143C, A98C/S85C/Y143C, A98C/S85C/S144C, N99C/Q84C/Y143C, N99C/S85C/Y143C, N99C/S85C/S144C, S101C/Q84C/Y143C, S101C/S85C/Y143C, S101C/S85C/S144C, L101C/Q84C/Y143C, L101C/S85C/Y143C, L101C/S85C/S144C, C102C/Q84C/Y143C, C102C/S85C/Y143C and C102C/S85C/S144C. In an embodiment the growth hormone variant comprise a combination of mutations selected from the following group: A98C/Q84C/Y143C, N99C/Q84C/Y143C, S101C/Q84C/Y143C, L101C/Q84C/Y143C and C102C/Q84C/Y143C. In an embodiment the growth hormone variant comprise the mutations L101C, Q84C and Y143C.

In a further aspect the present invention relates to a growth hormone conjugate which comprises a growth hormone compound (GH) linked to an albumin binding residue via a hydrophilic spacer, or a pharmaceutically acceptable salt thereof for use in therapy. Furthermore, in the growth hormone conjugate of the present invention GH, the albumin binding residue, and the hydrophilic spacer are selected from any one of the above embodiments, in particular the growth hormone conjugate has the formula (I) or (II).

In a further aspect the present invention relates to a pharmaceutical composition comprising a growth hormone conjugate which comprises a growth hormone compound (GH) linked to an albumin binding residue via a hydrophilic spacer, or a pharmaceutically acceptable salt optionally in combination with a pharmaceutical acceptable excipient.

The term "identity" as known in the art, refers to a relationship between the sequences of two or more proteins, as determined by comparing the sequences. In the art, "identity" also means the degree of sequence relatedness between proteins, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related proteins can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM *J. Applied Math.*, 48, 1073, (1988).

Preferred methods to determine identity are designed to give the largest match between the sequences tested. Methods to determine identity are described in publicly available computer programs. Preferred computer program methods to determine identity between two sequences include the GCG program package, including GAP (Devereux et al., *Nucl. Acid. Res.*, 12, 387, (1984)); Genetics Computer Group, University of Wisconsin, Madison, Wis.), BLASTP, BLASTN, and FASTA (Altschul et al., *J. Mol. Biol.*, 215, 403-410, (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

For example, using the computer algorithm GAP (Genetics Computer Group, University of Wisconsin, Madison, Wis.), two proteins for which the percent sequence identity is to be determined are aligned for optimal matching of their respective amino acids (the "matched span", as determined by the algorithm). A gap opening penalty (which is calculated as 3.times. the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, suppl. 3, (1978) for the PAM 250 comparison matrix; Henikoff et al., *Proc. Natl. Acad. Sci USA*, 89, 10915-10919, (1992) for the BLOSUM 62 comparison matrix) is also used by the algorithm.

Preferred parameters for a protein sequence comparison include the following:

Algorithm: Needleman et al., *J. Mol. Biol*, 48, 443-453, (1970); Comparison matrix: BLOSUM 62 from Henikoff et al., *Proc. Natl. Acad. Sci. USA*, 89, 10915-10919, (1992); Gap Penalty: 12, Gap Length Penalty: 4, Threshold of Similarity: 0.

The GAP program is useful with the above parameters. The aforementioned parameters are the default parameters for protein comparisons (along with no penalty for end gaps) using the GAP algorithm.

The compounds of the present invention have improved pharmacological properties compared to the corresponding un-conjugated growth hormone, which is also referred to as the parent compound. Examples of such pharmacological properties include functional in vivo half-life, immunogenicity, renal filtration, protease protection and albumin binding.

The term "functional in vivo half-life" is used in its normal meaning, i.e., the time at which 50% of the biological activity of the GH or GH conjugate is still present in the body/target organ, or the time at which the activity of the GH or GH conjugate is 50% of its initial value. As an alternative to determining functional in vivo half-life, "in vivo plasma half-life" may be determined, i.e., the time at which 50% of the GH or GH conjugate circulate in the plasma or bloodstream prior to being cleared. Determination of plasma half-life is often more simple than determining functional half-life and the magnitude of plasma half-life is usually a good indication of the magnitude of functional in vivo half-life. Alternative terms to plasma half-life include serum half-life, circulating half-life, circulatory half-life, serum clearance, plasma clearance, and clearance half-life.

The term "increased" as used in connection with the functional in vivo half-life or plasma half-life is used to indicate that the relevant half-life of the GH conjugate is statistically significantly increased relative to that of the parent GH, as determined under comparable conditions. For instance the relevant half-life may be increased by at least about 25%, such as by at lest about 50%, e.g., by at least about 100%, 150%, 200%, 250%, or 500%. In one embodiment, the compounds of the present invention exhibit an increase in half-life of at least about 5 h, preferably at least about 24 h, more preferably at least about 72 h, and most preferably at least about 7 days, relative to the half-life of the parent GH.

Measurement of in vivo plasma half-life can be carried out in a number of ways as described in the literature. An increase in in vivo plasma half-life may be quantified as a decrease in clearance (CL) or as an increase in mean residence time (MRT). Conjugated GH of the present invention for which the CL is decreased to less than 70%, such as less than 50%, such than less than 20%, such than less than 10% of the CL of the parent GH as determined in a suitable assay is said to have an increased in vivo plasma half-life. Conjugated GH of the present invention for which MRT is increased to more than 130%, such as more than 150%, such as more than 200%, such as more than 500% of the MRT of the parent GH in a suitable assay is said to have an increased in vivo plasma half-life. Clearance and mean residence time can be assessed in standard pharmacokinetic studies using suitable test animals. It is within the capabilities of a person skilled in the art to choose a suitable test animal for a given protein. Tests in human, of course, represent the ultimate test. Suitable test animals include normal, Sprague-Dawley male rats, mice and cynomolgus monkeys. Typically the mice and rats are in injected in a single subcutaneous bolus, while monkeys may be injected in a single subcutaneous bolus or in a single iv dose. The amount injected depends on the test animal. Subsequently, blood samples are taken over a period of one to five days as appropriate for the assessment of CL and MRT. The blood samples are conveniently analysed by ELISA techniques.

The term "Immunogenicity" of a compound refers to the ability of the compound, when administered to a human, to elicit a deleterious immune response, whether humoral, cellular, or both. In any human sub-population, there may be individuals who exhibit sensitivity to particular administered proteins. Immunogenicity may be measured by quantifying the presence of growth hormone antibodies and/or growth hormone responsive T-cells in a sensitive individual, using conventional methods known in the art. In one embodiment, the conjugated GH of the present invention exhibit a decrease in immunogenicity in a sensitive individual of at least about 10%, preferably at least about 25%, more preferably at least about 40% and most preferably at least about 50%, relative to the immunogenicity for that individual of the parent GH. The term "protease protection" or "protease protected" as used herein is intended to indicate that the conjugated GH of the present invention is more resistant to the plasma peptidase or proteases than is the parent GH. Protease and peptidase enzymes present in plasma are known to be involved in the degradation of circulating proteins, such as e.g. circulating peptide hormones, such as growth hormone. Such protease protection may be measured by the method of Example A described herein.

Growth hormone may be susceptible to degradation by for instance thrombin, plasmin, subtilisin, and chymotrypsin-like serine proteinase. Assays for determination of degradation of these proteases are described in *J. Biotech.*, 65, 183, (1998). In one embodiment, the rate of hydrolysis of the GH conjugate is less than 70%, such as less than 40%, such as less than 10% of that of the parent GH.

The most abundant protein component in circulating blood of mammalian species is serum albumin, which is normally present at a concentration of approximately 3 to 4.5 grams per 100 milliters of whole blood. Serum albumin is a blood protein of approximately 65,000 daltons which has several important functions in the circulatory system. It functions as a transporter of a variety of organic molecules found in the blood, as the main transporter of various metabolites such as fatty acids and bilirubin through the blood, and, owing to its abundance, as an osmotic regulator of the circulating blood. Serum albumin has a half-life of more than one week, and one approach to increasing the plasma half-life of proteins has been to conjugate to the protein a group that binds to serum albumin. Albumin binding property may be determined as described in *J. Med. Chem.*, 43, 1986, (2000) which is incorporated herein by reference.

The growth hormone conjugates of formula (I) or (II) exert growth hormone activity and may as such be used in the treatment of diseases or states which will benefit from an increase in the amount of circulating growth hormone. In particular, the invention provides a method for the treatment of growth hormone deficiency (GHD); Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short children born short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in e.g. hand, knee, or shoulder; patients having or going through distraction oteogenesis; patients after hip or discus replacement, meniscus repair, spinal fusions or prosthesis fixation, such as in the knee, hip, shoulder, elbow, wrist or jaw; patients into which osteosynthesis material, such as nails, screws and plates, have been fixed; patients with non-union or mal-union of fractures; patients after osteatomia, e.g. from tibia or $1^{st}$ toe; patients after graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Crohn's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; or short stature due to glucucorticoid treatment inchildren, the method comprising administering to a patient in need thereof a therapeutically effective amount of a growth hormone conjugate according to formula (I) or (II).

In a further aspect, the invention provides a method for the acceleration of the healing of muscle tissue, nervous tissue or wounds; the acceleration or improvement of blood flow to damaged tissue; or the decrease of infection rate in damaged tissue, the method comprising administration to a patient in need thereof an effective amount of a therapeutically effective amount of a growth hormone conjugate of formula (I) or (II).

In a further embodiment, the invention relates to the use of a growth hormone conjugate of formula (I) or (II) in the manufacture of diseases benefiting from an increase in the growth hormone plasma level, such as the disease mentioned above.

A typical parenteral dose is in the range of $10^{-9}$ mg/kg to about 100 mg/kg body weight per administration. Typical administration doses are from about 0.0000001 to about 10 mg/kg body weight per administration. The exact dose will depend on e.g. indication, medicament, frequency and mode of administration, the sex, age and general condition of the subject to be treated, the nature and the severity of the disease or condition to be treated, the desired effect of the treatment and other factors evident to the person skilled in the art.

Typical dosing frequencies are twice daily, once daily, bi-daily, twice weekly, once weekly or with even longer dosing intervals. Due to the prolonged half-lifes of the fusion proteins of the present invention, a dosing regime with long dosing intervals, such as twice weekly, once weekly or with even longer dosing intervals is a particular embodiment of the invention.

Many diseases are treated using more than one medicament in the treatment, either concomitantly administered or sequentially administered. It is therefore within the scope of the present invention to use a growth hormone conjugate of formula (I) or (II) in therapeutic methods for the treatment of one of the above mentioned diseases in combination with one or more other therapeutically active compound(s) normally used in the treatment said diseases. By analogy, it is also within the scope of the present invention to use a growth hormone conjugate of formula (I) or (II) in combination with other therapeutically active compounds normally used in the treatment of one of the above mentioned diseases in the manufacture of a medicament for said disease.

General Methods

Enzyme Conjugation:

In the preparation of a growth hormone conjugate of the present invention, typically at least one of the covalent bonds established in the preparation of a A-W—B-GH conjugate of formula (I) is prepared by use of an enzyme as illustrated in the examples below. Such an enzyme may for instance be selected from the group consisting of transglutaminases, serine proteases and cysteine proteases. Typically, said enzyme is a transglutaminase. Such transglutaminase may for instance be selected from the group consisting of microbial transglutaminases, tissue transglutaminases and factor XIII and variants thereof. In another embodiment, said enzyme is a cysteine protease. The growth hormone conjugate of the present invention may be prepared by many different methods, non-limiting examples are shown below.

The present invention also provides methods for preparing A-W—B-GH conjugates of formula (I).

Transglutaminase

As stated above, at least one of the covalent bonds established in the preparation of a A-W—B-GH conjugate of the present invention may be prepared by use of a transglutaminase. Transglutaminases may include microbial transglutaminases such as that isolated from the *Streptomyces* species; *S. mobaraense*, *S. cinnamoneum*, *S. griseocarneum* (U.S. Pat. No. 5,156,956 incorporated herein by reference), *S. lavendulae* (U.S. Pat. No. 5,252,469 incorporated herein by reference) and *S. ladakanum* (JP2003/199569 incorporated herein by reference). Other useful microbial transglutaminases have been isolated from *Bacillus subtilis* (disclosed in U.S. Pat. No. 5,731,183, which is incorporated herein by reference) and from various Myxomycetes.

Other examples of useful microbial transglutaminases are those disclosed in WO1996/06931 (e.g. transglutaminase from *Bacilus lydicus*) and WO1996/22366, both of which are incorporated herein by reference. Useful non-microbial transglutaminases include guinea-pig liver transglutaminase, and transglutaminases from various marine sources like the flat fish Pagrus major (disclosed in EP0555649, which is incorporated herein by reference), and the Japanese oyster *Crassostrea gigas* (disclosed in U.S. Pat. No. 5,736,356, which is incorporated herein by reference). Functional analogues and derivatives thereof may also be useful.

Typically, the TGase used in the methods of the invention is a microbial transglutaminase. In one embodiment, the TGase is from *S. mobaraense* or a variant thereof, for instance as described in WO2007/020290 and WO2008/020075. In another embodiment, the TGase is from *S. ladakanum* or a variant thereof, for instance as described in WO2008/020075.

The conjugation of GH to A-W—B according to the present invention may be achieved by TGase-mediated modification leading to selective alteration at specific lysine (Lys) or glutamine (Gln) positions in the sequence of the GH compound depending on the substrate used. Use of amines as substrates will leade to modification of Glutamines whereas the use of primary amides will lead to modification of Lysines. hGH (SEQ ID NO: 1) has 9 lysine residues at positions 38, 41, 70, 115, 140, 145, 158, 168 and 172 and 13 glutamine residues at positions 22, 29, 40, 46, 49, 68, 69, 84, 91, 122, 137, 141 and 181, although not all of these are readily available for modification nor suitably for modifications as this will lead to diminished binding potency to the growth hormone binding protein hence leading to reduced biological activity. The x-ray protein crystal structure between hGH and its binding protein (pdb: 3HHR) reveals that at least 4 lysines (38, 41, 168 and 172) takes part in binding to the binding protein and potentially only one of the glutamines (Gln 46). This renders the glutamines more attractive as target for selective introduction of an albumin binder linker. These structural considerations are further supported by findings summarised by N. Cheme et al in *Reprod. Nutr. Develop.* 29, 1-25 (1989) where it's concluded that chemical modifications affecting lysines have been found to have a negative effect on the in vivo biological activity and on the binding capacity to the liver receptors of GH.

Chemistry I

In an aspect the present invention relates to preparation of a growth hormone conjugate of formula (I) wherein a GH compound is treated with a property-modifying group using TGase catalyzed chemistry. Initially, an aldehyde or a ketone functionality is installed by a two step reaction using amino alcohols that subsequently are treated with periodate to generate an aldehyde or keto functionality by oxidative cleavage. Non limited examples of amino alcohols for illustration only includes 1,3-diamino-2-propanol and 1-amino-2,3-dihydroxypropane.

In a further aspect the present invention relates to preparation of a growth hormone conjugate of formula (I) comprising treatment of an aldehyde or ketone derived from the GH compound with a property-modifying group-derived aniline or heteroaryl amine to yield an amine (III→IV).

In an embodiment, aldehyde derived from the GH compound is treated with property-modifying group-derived aniline or heteroarylamine.

The term "GH compound derived aldehyde (or ketone)" or "an aldehyde or ketone derived from the GH compound" is intented to indicate a GH compound to which an aldehyde or ketone functional group has been covalently attached, or a GH compound on which an aldehyde or ketone functional group has been generated. The preparation of GH compound-derived aldehydes, such as compound (III) illustrated below is well known to those skilled in the art, and any of these known procedures may be used to prepare the GH compound-derived aldehyde (III) required for the realization of the invention disclosed herein.

In one embodiment, the conjugate A-W—B-GH (IV) is prepared as illustrated below:

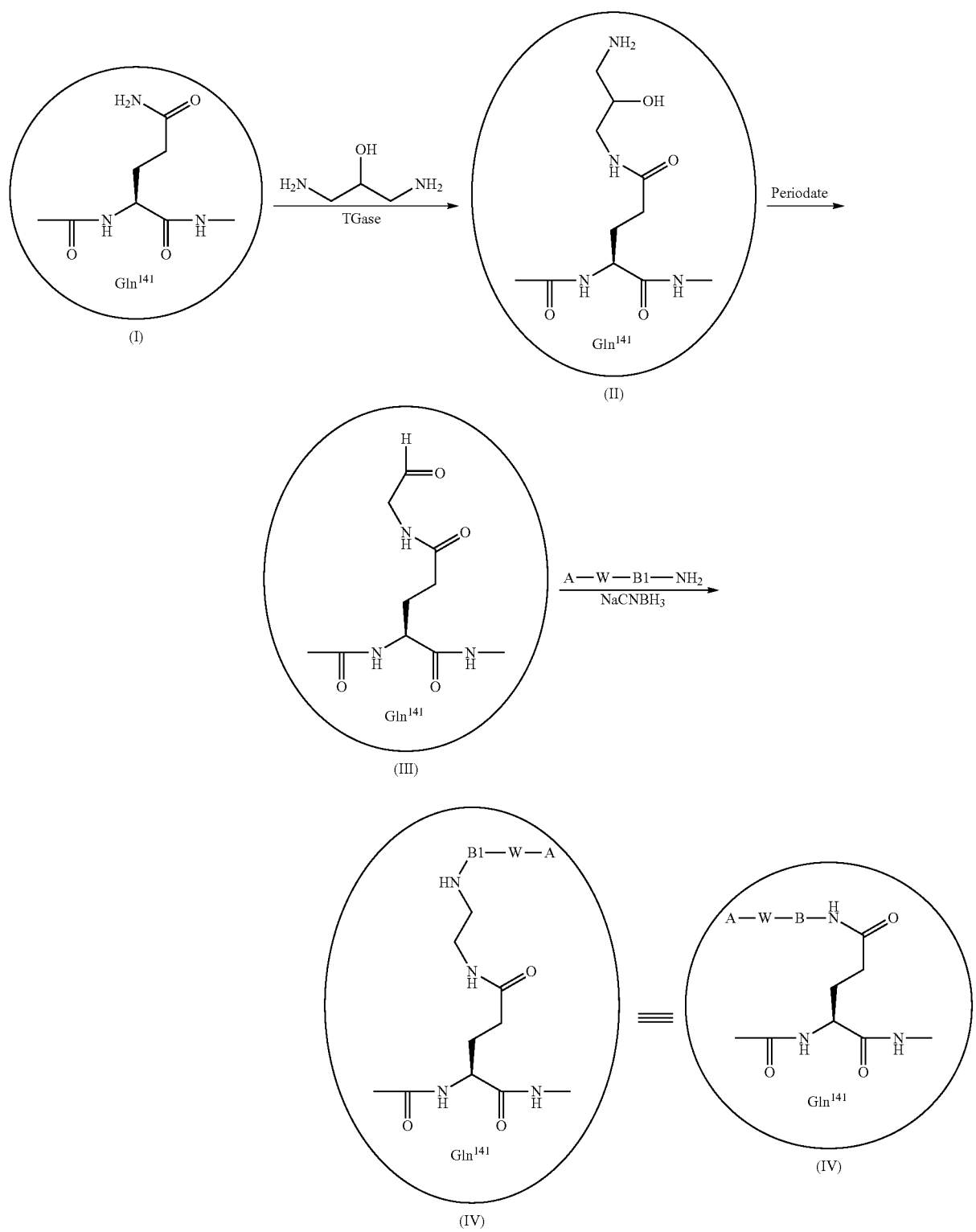

The TGase-mediated enzymatic reaction with GH (I) results in the modification of Gln at position 141 and/or 40 affording (II). The modified GH (II) is treated with periodate to cleave the aminoalcohol to provide a GH derived aldehyde (III). Conjugation of GH aldehyde (III) with A-W—B1-NH$_2$ occurs via reductive alkylation (III→IV). Reductive alkylation as exemplified herein is well-recognized in the art and results in GH compounds (IV) modified in position Gln(141) and/or 40.

Chemistry II

In one embodiment, the conjugate A-W—B-GH is prepared using reductive amination in GH's N-terminal as illustrated below:

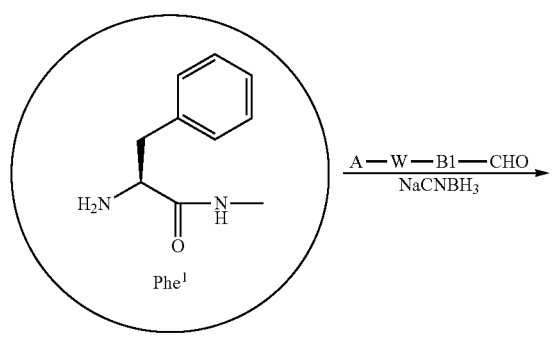
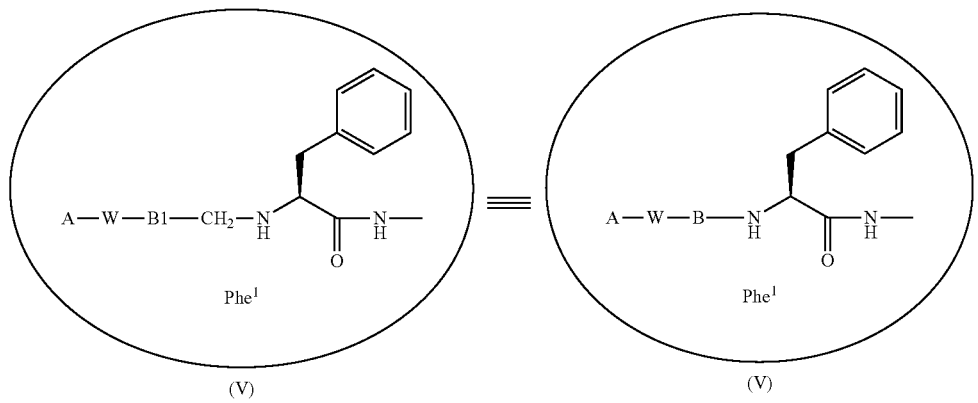
Conjugation of GH to A-W—B1-CHO occurs via reductive alkylation (GH→V). Reductive alkylation as exemplified above is well-recognized in the art for modifying the N-terminal of GH.
Chemistry III
In one embodiment, the conjugate A-W—B-GH is prepared as illustrated below:
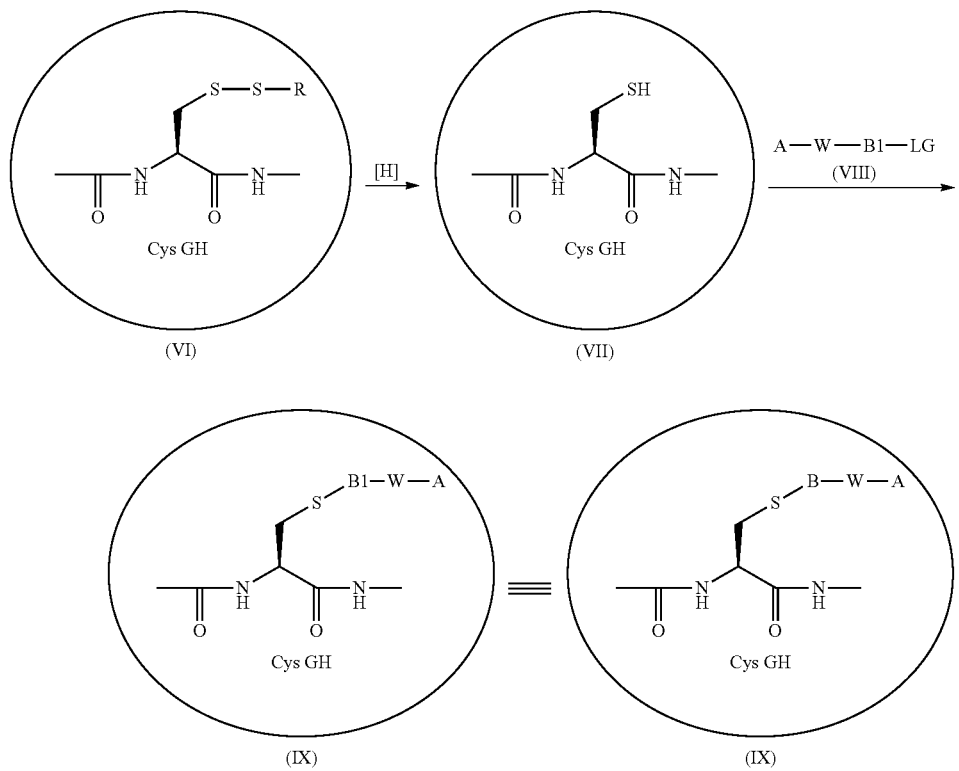

Wherein the cysteine residue optionally is protected as a mixed disulfide (VI) (GH-S—S—R) with R being a small organic moiety. Non limited examples of mixed disulfides may include disulfides between cystamine (R=—CH$_2$CH$_2$NH$_2$); cysteine (R=—CH$_2$CH(C(O)OH)NH$_2$); homocysteine (R=—CH$_2$CH$_2$CH(C(O)OH)NH$_2$); and glutathione (R=—CH$_2$CH(C(O)NH—CH$_2$C(O)OH)NH—C(O)CH$_2$CH$_2$CH(C(O)OH)NH$_2$).

The derivatization process utilise an albumin binding linker A-W—B1-LG wherein LG represent an inorganic leaving group such as —Cl, —Br, —I or an organic leaving group such as mesylate or tosylate. Conjugation of GH with A-W—B1-LG occurs via nucleophilic substitution (VII→IX).

Chemistry IV

In one embodiment, the conjugate A-W—B-GH is prepared as illustrated below:

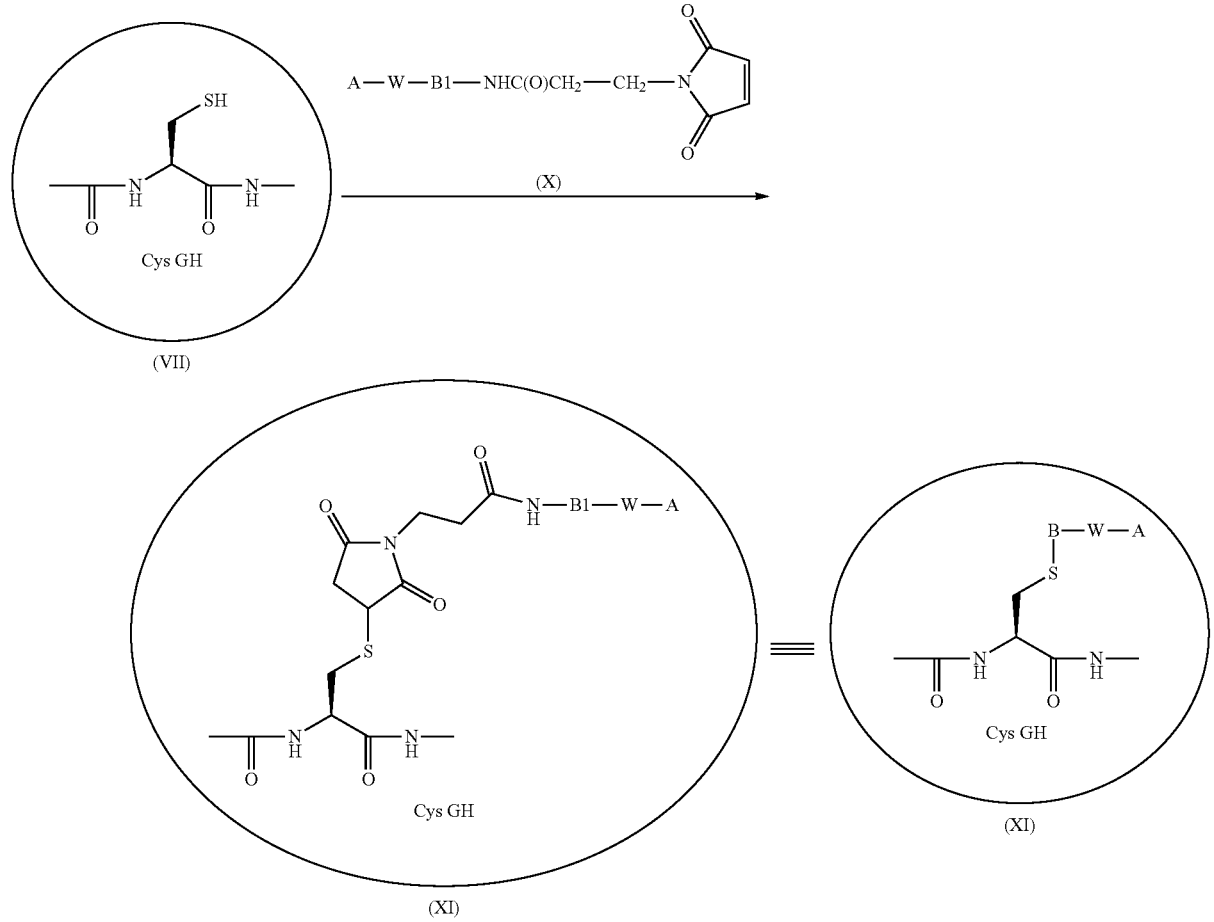

Deprotected Cys GH compound (VII) as obtained from (VI) above can be reacted with a malimide substituted albumin binder linker (X) affording GH conjugate A-W—B1-NHC(O)CH$_2$CH$_2$-pyrrolidin-2,5-dione-3-GH (XI).

wherein the hydrophilic spacer B1 has the formula

—X$_1$—X$_2$—X$_3$—X$_4$— wherein

X$_1$ is —W$_1$—[(CHR$^1$)$_{l1}$—W$_2$]$_{m1}$—{[(CH$_2$)$_{n1}$E1]$_{m2}$—[(CHR$^2$)$_{l2}$—W$_3$]$_{m3}$}$_{n2}$—,

X$_2$ is —[(CHR$^3$)$_{l3}$—W$_4$]$_{m4}$—{[(CH$_2$)$_{n3}$E2]$_{m5}$—[(CHR$^4$)$_{l4}$—W$_5$]$_{m6}$}$_{n4}$—,

X$_3$ is —[(CHR$^5$)$_{l5}$]$_{m7}$—,

X$_4$ is a valence bond, l1, l2, l3, l4, and l5 independently are selected from 0-16, m1, m3, m4, m6 and m7 independently are selected from 0-10, m2 and m5 independently are selected from 0-25, n1, n2, n3 and n4 independently are selected from 0-16, R$^1$, R$^2$, R$^3$, R$^4$ and R$^5$ independently are selected from hydrogen, —C(O)OH, —C(O)NH$_2$, —S(O)OH, —S(O)$_2$OH, —NH—C(=NH)—NH$_2$, C$_{1-6}$-alkyl, aryl or hetaryl; wherein the alkyl, aryl and hetaryl groups optionally are substituted with halogen, —C(O)OH, —C(O)NH$_2$, —S(O)OH, —S(O)$_2$OH, —CN or —OH, E1 and E2 independently are selected from —O—, —NR$^6$—, —N(COR$^7$)— or a valence bond; wherein R$^6$ and R$^7$ independently represent hydrogen or C$_{1-6}$-alkyl, W$_1$ to W$_5$ independently are selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s2}$—, —C(O)—, —C(O)O—, —OC(O)—, or a valence bond; wherein s2 is 0 or 1.

Chemistry V

In one embodiment, the conjugate A-W—B-GH is prepared as illustrated below:

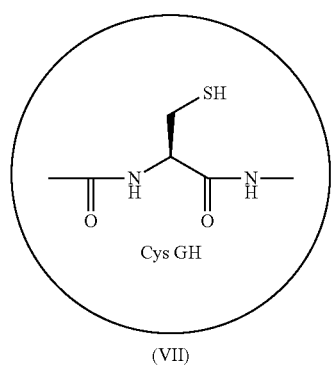
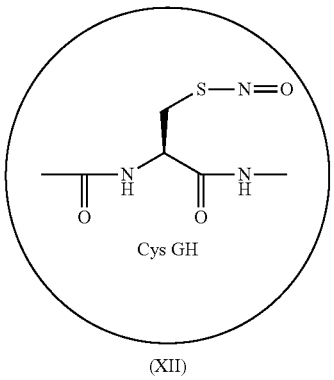
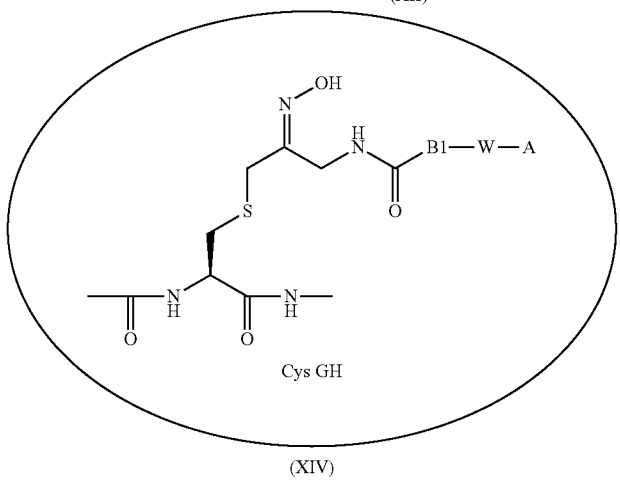
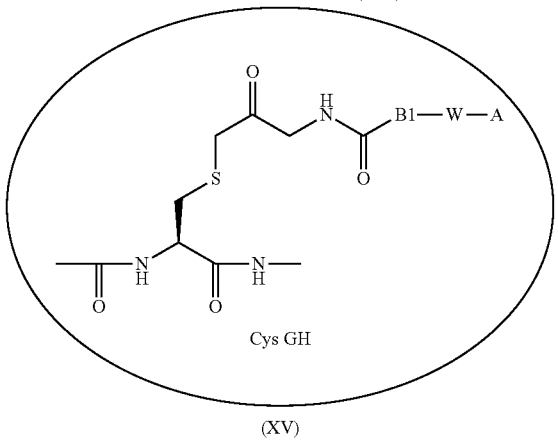
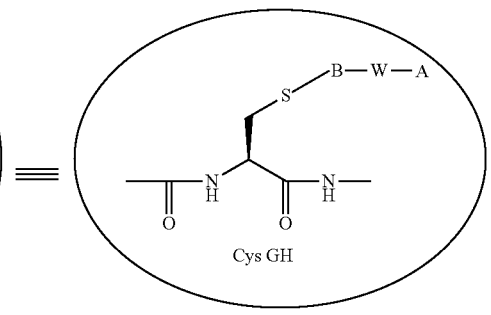

Albumine binders may be attached to single cys GH derivatives using S-nitrosyl chemistry as described in WO2009/024791.

Deprotected Cys GH compound (VII) is subjected to S-nitrosylation by addition of a NO donor such as DEA NOnate (Sigma Aldrich). Nitrosylated single cys GH (XII) is then reacted with an allyl amine substituted albumine binder (XIII) affording oxime (XIV) which after hydrolysis affords GH conjugate A-W—B1-C(O)NHCH$_2$C(O)CH$_2$-Cys GH (XV)

wherein the hydrophilic spacer B1 has the formula

—X$_1$—X$_2$—X$_3$—X$_4$— wherein

X$_1$ is —W$_1$—[(CHR$^1$)$_{l1}$—W$_2$]$_{m1}$—{[(CH$_2$)$_{n1}$E1]$_{m2}$—[(CHR$^2$)$_{l2}$—W$_3$]$_{m3}$}$_{n2}$—,

X$_2$ is —[(CHR$^3$)$_{l3}$—W$_4$]$_{m4}$—{[(CH$_2$)$_{n3}$E2]$_{m5}$—[(CHR$^4$)$_{l4}$—W$_5$]$_{m6}$}$_{n4}$—,

X$_3$ is —[(CHR$^5$)$_{l5}$]$_{m7}$—,

X$_4$ is a valence bond, l1, l2, l3, l4, and l5 independently are selected from 0-16, m1, m3, m4, m6 and m7 independently are selected from 0-10, m2 and m5 independently are selected from 0-25, n1, n2, n3 and n4 independently are selected from 0-16, R$^1$, R$^2$, R$^3$, R$^4$ and R$^5$ independently are selected from hydrogen, —C(O)OH, —C(O)NH$_2$, —S(O)OH, —S(O)$_2$OH, —NH—C(=NH)—NH$_2$, C$_{1-6}$-alkyl, aryl or hetaryl; wherein the alkyl, aryl and hetaryl groups optionally are substituted with halogen, —C(O)OH, —C(O)NH$_2$, —S(O)OH, —S(O)$_2$OH, —CN or —OH, E1 and E2 independently are selected from —O—, —N(R⁶)—, —N(C(O)R⁷)— or a valence bond; wherein R⁶ and R⁷ independently represent hydrogen or $C_{1-6}$-alkyl, $W_1$ to $W_5$ independently are selected from —C(O)NH—, —NHC(O)—, —C(O)NHCH₂—, —CH₂NHC(O)—, —C(O)NHS(O)₂—, —S(O)₂NHC(O)—, —OC(O)NH—, —NHC(O)O—, —C(O)CH₂—, —CH₂C(O)—, —C(O)CH═CH—, —CH═CHC(O)—, —(CH₂)$_{s2}$—, —C(O)—, —C(O)O—, —OC(O)—, or a valence bond; wherein s2 is 0 or 1.

A close relationship to the natural peptide is generally regarded as an advantage with therapeutic interventions comprising administration of variants or analogues of this natural peptide as it minimizes the risk of e.g. any unwanted antibody generation.

GH may be modified in their C-terminal by use of carboxypeptidase Y (EC. 3.4.16.5), and suitable modified substrates as described in WO2007/093594. A two step procedure as described by B. Peschke et al. "C-Terminally PEGylated GH derivatives" *Bioorg. Med. Chem.* 15, 4382-4395, (2007), where C terminal alanine is enzymatically exchanged with N$^∈$-(4-acetylbenzoyl)lysine, followed by reaction with albumin binder derivatives according to the invention.

As apparent from the above the invention further relates to the intermediate linker applied in preparation of the conjugate A-W—B-GH. Said linker compound may be described by us of formula (III)

wherein A represent an albumin binding residue,

B1 represents a hydrophilic spacer,

W is a chemical group linking A and B1, and U represent a conjugating moiety.

Based on the above the conjugating moiety will vary depending on the method of conjugation applied which may in the end also be visible in the final hGH compound (A-W—B-GH).

In further embodiments of the compound, A-W—B1-U, A and W are as defined in any of the above embodiments.

When the method described herein above as Chemistry IV, is applied the compound A-W—B1-U, may further be defined, as an embodiment, wherein U comprises or consists of an aryl, an heteraryl, a substituted malimide or a pyrrolidine-2,5-dione such as —NHC(O)CH₂CH₂-pyrrolidin-2,5-dione.

In alternative embodiments of compound A-W—B1-U, U comprises D1-(CH₂)$_{l6}$-D2, wherein D1 and D2 are independently selected from —O—, —N(R⁶)—, —NC(O)R⁷— or a valence bond; wherein R6 and R7 independently represent hydrogen or $C_{1-6}$-alkyl.

Likewise application of Chemistry III as described herein above will apply linker compounds wherein U comprises or consists of a leaving group, such as Cl, Br, I, —OH, —OS(O)₂Me, —OS(O)₂CF₃ or —OTs, or preferably compounds according to formula (III), wherein the leaving group is a halogen compound selected from Cl, Br and I, preferably Br.

Further embodiments of the linker compounds (which are applied in Chemistry V) are according to the invention defined by formula (III), wherein U comprises or consists of an allyl amine (H₂C═CH—CH2-NH₂), such as —C(O)NHCH₂—CH═CH₂.

When the method described herein above as Chemistry I, is applied the compound A-W—B1-U, may further be defined, as an embodiment, wherein U comprises or consists of an amine (—NH₂).

In alternative embodiments, U may comprises or consists of an aldehyde, such as —CHO.

The compounds may following be conjugated to any sort of therapeutic compound which include an acceptor group to which "U" may enable conjugation. In a preferred embodiment the therapeutic compound is a polypeptide. Peptides may naturally include AA residues which may function as an acceptor group, such as Gln residues, Phe residues and Cys residues. Alternatively such amino acid residues may be introduced in an appropriate position in the polypeptide.

Pharmaceutical Compositions

Another purpose is to provide a pharmaceutical composition comprising a growth hormone conjugate of the present invention, such as a growth hormone conjugate of formula (I) or (II), which is present in a concentration from $10^{-15}$ mg/mL to 200 mg/mL, such as e.g. $10^{-10}$ mg/mL to 5 mg/mL and wherein said composition has a pH from 2.0 to 10.0. The composition may further comprise pharmaceutical exhibits, such as a buffer system, preservative(s), tonicity agent(s), chelating agent(s), stabilizers and surfactants. In one embodiment of the invention the pharmaceutical composition is an aqueous composition, i.e. composition comprising water. Such composition is typically a solution or a suspension. In a further embodiment of the invention the pharmaceutical composition is an aqueous solution. The term "aqueous composition" is defined as a composition comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical composition is a freeze-dried composition, whereto the physician or the patient adds solvents and/or diluents prior to use.

In another embodiment the pharmaceutical composition is a dried composition (e.g. freeze-dried or spray-dried) ready for use without any prior dissolution.

In a further aspect the invention relates to a pharmaceutical composition comprising an aqueous solution of a growth hormone conjugate, such as a growth hormone conjugate of formula (I) or (II), and a buffer, wherein said GH conjugate is present in a concentration from 0.1-100 mg/mL or above, and wherein said composition has a pH from about 2.0 to about 10.0.

In a another embodiment of the invention the pH of the composition is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the composition further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3-(p-chlorphenoxy)propane-1,2-diol) or mixtures thereof. In a further embodiment of the invention the preservative is present in a concentration from 0.1 mg/mL to 20 mg/mL. In a further embodiment of the invention the preservative is present in a concentration from 0.1 mg/mL to 5 mg/mL. In a further embodiment of the invention the preservative is present in a concentration from 5 mg/mL to 10 mg/mL. In a further embodiment of the invention the preservative is present in a concentration from 10 mg/mL to 20 mg/mL. Each one of these specific preservatives constitutes an alternative embodiment of the invention. The use of a preservative in pharmaceutical compositions is well-known to the skilled person. For convenience reference is made to Remington: *The Science and Practice of Pharmacy*, 20$^{th}$ edition, 2000.

In a further embodiment of the invention the composition further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG 400), or mixtures thereof. Any sugar such as mono, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects obtained using the methods of the invention. In one embodiment, the sugar or sugar alcohol concentration is between about 1 mg/mL and about 150 mg/mL. In a further embodiment of the invention the isotonic agent is present in a concentration from 1 mg/mL to 50 mg/mL. In a further embodiment of the invention the isotonic agent is present in a concentration from 1 mg/mL to 7 mg/mL. In a further embodiment of the invention the isotonic agent is present in a concentration from 8 mg/mL to 24 mg/mL. In a further embodiment of the invention the isotonic agent is present in a concentration from 25 mg/mL to 50 mg/mL. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 20$^{th}$ edition, 2000.

In a further embodiment of the invention the composition further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/mL to 5 mg/mL. In a further embodiment of the invention the chelating agent is present in a concentration from 0.1 mg/mL to 2 mg/mL. In a further embodiment of the invention the chelating agent is present in a concentration from 2 mg/mL to 5 mg/mL. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 20$^{th}$ edition, 2000.

In a further embodiment of the invention the composition further comprises a stabilizer. The use of a stabilizer in pharmaceutical compositions is well-known to the skilled person. For convenience reference is made to Remington: *The Science and Practice of Pharmacy*, 20$^{th}$ edition, 2000.

More particularly, compositions of the invention are stabilized liquid pharmaceutical compositions whose therapeutically active components include a protein that possibly exhibits aggregate formation during storage in liquid pharmaceutical compositions. By "aggregate formation" is intended a physical interaction between the protein molecules that results in formation of oligomers, which may remain soluble, or large visible aggregates that precipitate from the solution. By "during storage" is intended a liquid pharmaceutical composition or composition once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or composition is dried either by freeze drying (i.e., lyophilization; see, for example, Williams and Polli, *J. Parenteral Sci. Technol.*, 38, 48-59, (1984)), spray drying (see Masters (1991) in Spray-Drying Handbook (5$^{th}$ ed; Longman Scientific and Technical, Essez, U.K.), pp. 491-676; Broadhead et al. *Drug Devel. Ind. Pharm.* 18, 1169-1206, (1992); and Mumenthaler et al., *Pharm. Res.*, 11, 12-20, (1994)), or air drying (Carpenter and Crowe, *Cryobiology* 25, 459-470, (1988); and Roser, *Biopharm.* 4, 47-53, (1991)). Aggregate formation by a protein during storage of a liquid pharmaceutical composition can adversely affect biological activity of that protein, resulting in loss of therapeutic efficacy of the pharmaceutical composition. Furthermore, aggregate formation may cause other problems such as blockage of tubing, membranes, or pumps when the protein-containing pharmaceutical composition is administered using an infusion system.

The pharmaceutical compositions of the invention may further comprise an amount of an amino acid base sufficient to decrease aggregate formation by the protein during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L or D isomer, or mixtures thereof) of a particular amino acid (methionine, histidine, arginine, lysine, isoleucine, aspartic acid, tryptophan, threonine and mixtures thereof) or combinations of these stereoisomers or glycine or an organic base such as but not limited to imidazole, may be present in the pharmaceutical compositions of the invention so long as the particular amino acid or organic base is present either in its free base form or its salt form. In one embodiment the L-stereoisomer of an amino acid is used. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the protein during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the protein acting as the therapeutic agent is a protein comprising at least one methionine residue susceptible to such oxidation. By "inhibit" is intended minimal accumulation of methionine oxidized species over time. Inhibiting methionine oxidation results in greater retention of the protein in its proper molecular form. Any stereoisomer of methionine (L or D isomer) or any combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be obtained by adding methionine such that the ratio of methionine added to methionine residues ranges from about 1:1 to about 1000:1, such as 10:1 to about 100:1.

In a further embodiment of the invention the composition further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active protein therein. Stabilizing agents of particular interest to the present invention include, but are not limited to, methionine and EDTA, which protect the protein against methionine oxidation, and a nonionic surfactant, which protects the protein against aggregation associated with freeze-thawing or mechanical shearing.

In a further embodiment of the invention the composition further comprises a surfactant. In a further embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof. $C_6$-$C_{12}$ (eg. oleic acid and caprylic acid), acylcarnitines and derivatives, Na-acylated derivatives of lysine, arginine or histidine, or side-chain acylated derivatives of lysine or arginine, Na-acylated derivatives of dipeptides comprising any combination of lysine, arginine or histidine and a neutral or acidic amino acid, Na-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethyl-ammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), non-ionic surfactants (eg. dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 20th edition, 2000.

It is possible that other ingredients may be present in the pharmaceutical composition of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical composition of the present invention.

Pharmaceutical compositions containing a growth hormone conjugate according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the growth hormone conjugate, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the composition of solids, semisolids, powder and solutions for pulmonary administration of growth hormone conjugate, using, for example a metered dose inhaler, dry powder inhaler and a nebulizer, all being devices well known to those skilled in the art.

Compositions of the current invention are specifically useful in the composition of controlled, sustained, protracting, retarded, and slow release drug delivery systems. More specifically, but not limited to, compositions are useful in composition of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of *Pharmaceutical Controlled Release* (Wise, D. L., ed. Marcel Dekker, New York, 2000) and Drug and the Pharmaceutical Sciences vol. 99: *Protein Composition and Delivery* (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the growth hormone conjugate in the form of a nasal or pulmonal spray. As a still further option, the pharmaceutical compositions containing the growth hormone conjugate of the invention can also be adapted to transdermal administration, e.g. by needle-free injection or from a patch, optionally an iontophoretic patch, or transmucosal, e.g. buccal, administration.

The term "stabilized composition" refers to a composition with increased physical stability, increased chemical stability or increased physical and chemical stability.

The term "physical stability" of the protein composition as used herein refers to the tendency of the protein to form biologically inactive and/or insoluble aggregates of the protein as a result of exposure of the protein to thermomechanical stresses and/or interaction with interfaces and surfaces that are destabilizing, such as hydrophobic surfaces and interfaces. Physical stability of the aqueous protein compositions is evaluated by means of visual inspection and/or turbidity measurements after exposing the composition filled in suitable containers (e.g. cartridges or vials) to mechanical/physical stress (e.g. agitation) at different temperatures for various time periods. Visual inspection of the compositions is performed in a sharp focused light with a dark background. The turbidity of the composition is characterized by a visual score ranking the degree of turbidity for instance on a scale from 0 to 3 (a composition showing no turbidity corresponds to a visual score 0, and a composition showing visual turbidity in daylight corresponds to visual score 3). A composition is classified physical unstable with respect to protein aggregation, when it shows visual turbidity in daylight. Alternatively, the turbidity of the composition can be evaluated by simple turbidity measurements well-known to the skilled person. Physical stability of the aqueous protein compositions can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein composition as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein composition as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein composition can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized composition" refers to a composition with increased physical stability, increased chemical stability or increased physical and chemical stability. In general, a composition must be stable during use and storage (in compliance with recommended use and storage conditions) until the expiration date is reached.

In one embodiment of the invention the pharmaceutical composition comprising the growth hormone conjugate of formula (I) or (II) is stable for more than 6 weeks of usage and for more than 3 years of storage.

In another embodiment of the invention the pharmaceutical composition comprising the growth hormone conjugate of formula (I) or (II) is stable for more than 4 weeks of usage and for more than 3 years of storage.

In a further embodiment of the invention the pharmaceutical composition comprising the growth hormone conjugate of formula (I) or (II) is stable for more than 4 weeks of usage and for more than two years of storage.

In an even further embodiment of the invention the pharmaceutical composition comprising the growth hormone conjugate of formula (I) or (II) is stable for more than 2 weeks of usage and for more than two years of storage.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural (i.e. one or more), unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

A non-exhaustive list of embodiment describing the invention is provided here below.

LIST OF EMBODIMENTS

Embodiment 1

A growth hormone conjugate which comprises a growth hormone compound (GH) having
a) a single Cys mutation,
b) an additional disulfide bridge, or
c) a single Cys mutation and an additional disulfide bridge,
wherein an albumin binding residue via a hydrophilic spacer is linked to said GH, or a pharmaceutically acceptable salt thereof.

2. The conjugate of embodiment 1, wherein GH represents a growth hormone compound comprising an amino acid sequence having at least 80% identity to the amino acid sequence of human growth hormone (hGH) (SEQ ID NO: 1), such as at least 80%, at least 85%, at least 90%, or at least 95% identity with hGH, or GH is hGH (SEQ ID NO: 1).

3. The conjugate of embodiment 1, wherein GH or the GH conjugate has at least 80% of the growth hormone activity of hGH.

4. The conjugate of any one of embodiments 1-3 wherein the albumin binding residue via a hydrophilic spacer is linked to a GH having a single Cys mutation.

5. The conjugate of embodiment 4, wherein the single Cys mutation is positioned in any one of the regions selected from the N-terminal, H1, H2, L2 or H3 of GH.

6. The conjugate of embodiment 5, wherein the GH has a single Cys mutation selected from any one of T3C, P5C, S7C, D11C, H18C, Q29C, E30C, E33C, A34C, Y35C, E88C, Q91C, S95C, A98C, N99C, S100C, L101C, V102C, Y103C, D107C, S108C, D112C, Q122C and G126C.

7. The conjugate of any one of embodiments 1-3 wherein the albumin binding residue via a hydrophilic spacer is linked to a GH having an additional disulfide bridge.

8. The conjugate of embodiment 7, wherein the additional disulfide bond is between a loop segment and a helical segment or within loop segment or between loop segments or between helical segments.

9. The conjugate of any one of embodiments 7-8, wherein the GH comprises an additional disulfide bond wherein at least one of the cysteines is present in a loop segment, such from amino acid residues 128-154 (L3).

10. The conjugate of any one of embodiments 7-9, wherein the GH comprises an additional disulfide bond wherein the additional disulfide bond which connects a loop segment with a helical segment, such as helix B or H2.

11. The conjugate of any one of embodiments 7-10, wherein the additional disulfide bond connects L3 with H2.

12. The conjugate of any one of embodiments 7-11, wherein the additional disulfide bridge is between at least one of the amino acid pairs in the positions corresponding to R16C/L117C, A17C/E174C, H21C/M170C, D26C/V102C, D26C/Y103C, N47C/T50C, Q49C/G161C, F54C/Y143C, F54C/S144C, F54C/F146C, S55C/Y143C, S57C/Y143C, I58C/Q141C, I58C/Y143C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C, F92C/T148C, R94C/D107C, V102C/A105C, L156C/F146C, L156C/T148C and/or V185C/S188C in hGH (SEQ ID NO: 1), such as Q84C/Y143C.

13. The conjugate of any one of embodiments 1-3 wherein the albumin binding residue via a hydrophilic spacer is linked to a GH having a single Cys mutation and an additional disulfide bridge.

14. The conjugate of embodiment 13 wherein the GH has a single Cys mutation selected from any one of T3C, P5C, S7C, D11C, H18C, Q29C, E30C, E33C, A34C, Y35C, Y42C, S55C, S57C, S62C, Q69C, E88C, Q91C, S95C, A98C, N99C, S100C, L101C, V102C, Y103C, D107C, S108C, D112C, Q122C and G126C.

15. The conjugate of any one of embodiments 13-14, wherein the additional disulfide bond is between a loop segment and a helical segment or within loop segment or between loop segments or between helical segments.

16. The conjugate of any one of embodiments 13-15, wherein the GH comprises an additional disulfide bond wherein at least one of the cysteines is present in a loop segment, such from amino acid residues 128-154 (L3).

17. The conjugate of any one of embodiments 13-16, wherein the GH comprises an additional disulfide bond wherein the additional disulfide bond which connects a loop segment, with a helical segment, such as helix B or H2.

18. The conjugate of any one of embodiments 13-17, wherein the additional disulfide bond connects a loop segment, such from amino acid residues 128-154 (L3), with helix B or H2.

19. The conjugate of any one of embodiments 13-18, wherein the additional disulfide bridge is between at least one of the amino acid pairs in the positions corresponding to R16C/L117C, A17C/E174C, H21C/M170C, D26C/V102C, D26C/Y103C, N47C/T50C, Q49C/G161C, F54C/Y143C, F54C/S144C, F54C/F146C, S55C/Y143C, S57C/Y143C, I58C/Q141C, I58C/Y143C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C, F92C/T148C, R94C/D107C, V102C/A105C, L156C/F146C, L156C/T148C and/or V185C/S188C in hGH (SEQ ID NO: 1), such as Q84C/Y143C.

20. The conjugate of any one of embodiments 1-19, wherein the albumin binding residue is selected from

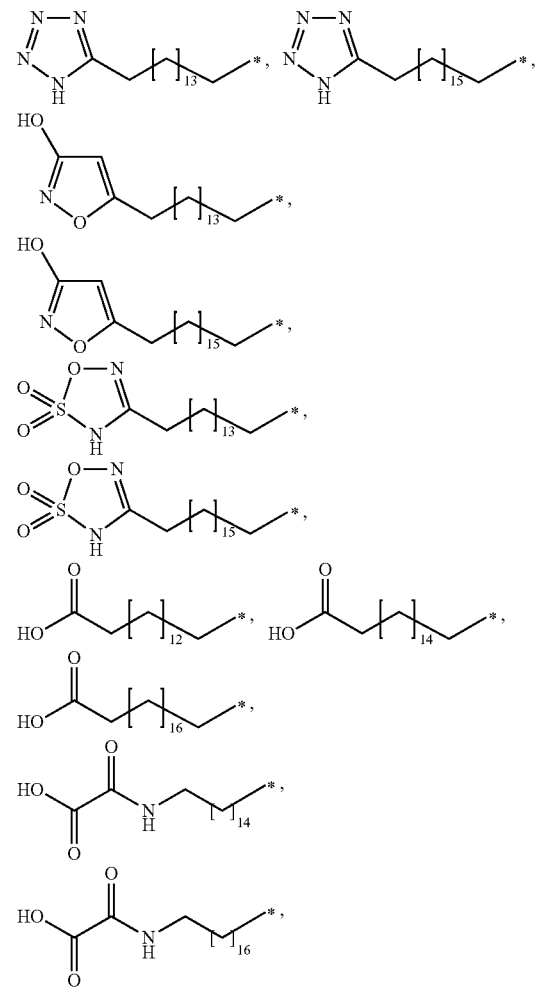

-continued

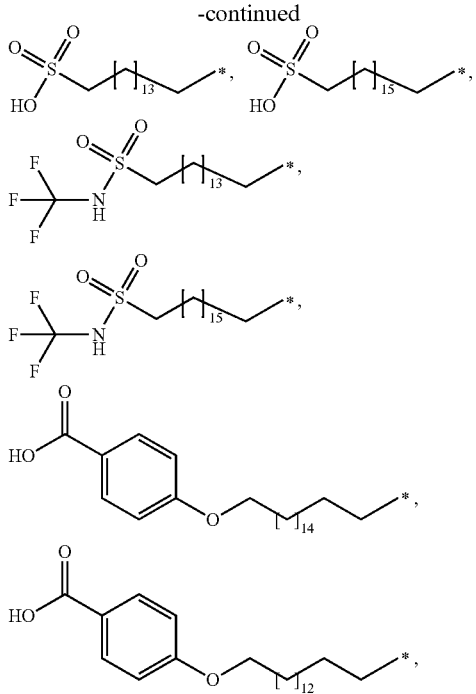

wherein * denotes the attachment to the hydrophilic spacer through a chemical group linking the albumin binding residue and the hydrophilic spacer.

21. The conjugate of any one of embodiments 1-20, wherein the chemical group linking the albumin binding residue and the hydrophilic spacer has the formula $$—W_7—Y—,$$

wherein
Y is $—(CH_2)_{l7}—C_{3-10}$-cycloalkyl-$W_8$— or a valence bond,
l7 is 0-6,
$W_7$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s3}$—, —C(O)—, —C(O)O—, —OC(O)—, or a valence bond; wherein s3 is 0 or 1,
$W_8$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s4}$—, —C(O)—, —C(O)O—, —OC(O)—, or a valence bond; wherein s4 is 0 or 1.

22. The conjugate of any one of embodiments 1-21 wherein the hydrophilic spacer has the formula $$—X_1—X_2—X_3—X_4—$$

wherein
$X_1$ is $—W_1—[(CHR^1)_{l1}—W_2]_{m1}—\{[(CH_2)_{n1}E1]_{m2}—[(CHR^2)_{l2}—W_3]_{m3}\}_{n2}—$,
$X_2$ is $—[(CHR^3)_{l3}—W_4]_{m4}—\{[(CH_2)_{n3}E2]_{m5}—[(CHR^4)_{l4}—W_5]_{m6}\}_{n4}—$,
$X_3$ is $—[(CHR^5)_{l5}—W_6]_{m7}—$,
$X_4$ is F-D1-(CH$_2$)$_{l6}$-D2-,
l1, l2, l3, l4, l5 and l6 independently are selected from 0-16,
m1, m3, m4, m6 and m7 independently are selected from 0-10,
m2 and m5 independently are selected from 0-25,
n1, n2, n3 and n4 independently are selected from 0-16,
F is aryl, hetaryl, pyrrolidine-2,5-dione or a valence bond, wherein the aryl and hetaryl groups are optionally substituted with halogen, —CN, —OH, —C(O)OH, —C(O)NH$_2$, —S(O)$_2$OH or C$_{1-6}$-alkyl,
$R^1$, $R^2$, $R^3$, $R^4$ and $R^5$ independently are selected from hydrogen, —C(O)OH, —C(O)NH$_2$, —S(O)OH, —S(O)$_2$OH, —NH—C(=NH)—NH$_2$, C$_{1-6}$-alkyl, aryl or hetaryl; wherein the alkyl, aryl and hetaryl groups optionally are substituted with halogen, —C(O)OH, —C(O)NH$_2$, —S(O)OH, —S(O)$_2$OH, —CN or —OH,
D1, D2, E1 and E2 independently are selected from —O—, —N(R$^6$)—, —N(C(O)R$^7$)— or a valence bond; wherein R$^6$ and R$^7$ independently represent hydrogen or C$_{1-6}$-alkyl,
$W_1$ to $W_5$ independently are selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s2}$—, —C(O)—, —C(O)O—, —OC(O)—, or a valence bond; wherein s2 is 0 or 1,
$W_6$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s1}$—, —C(O)—, —C(O)O—, —OC(O)—, —NHC(O)C$_{1-6}$-alkyl, —C(O)NHC$_{1-6}$-alkyl or a valence bond; wherein s1 is 0 or 1 and the C$_{1-6}$-alkyl group is optionally substituted with oxo, pyrrolidine-2,5-dione, —NHC(O)CH*CH$_2$COOH or —NHC(O)CH$_2$CH*COOH; wherein (*) indicates the attachment point from the carbon atom of CH to $X_4$.

23. The conjugate of any one of embodiments 1-22, wherein $X_4$ is a valence bond and $W_6$ is selected from either pyrrolidine-2,5-dione, —NHC(O)CH*CH$_2$COOH or —NHC(O)CH$_2$CH*COOH wherein (*) indicates the attachment point from the carbon atom of CH to GH.

24. The conjugate of embodiment 22 wherein the hydrophilic spacer is selected from

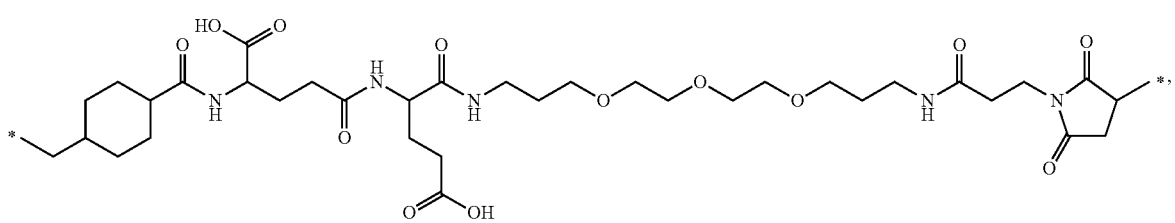

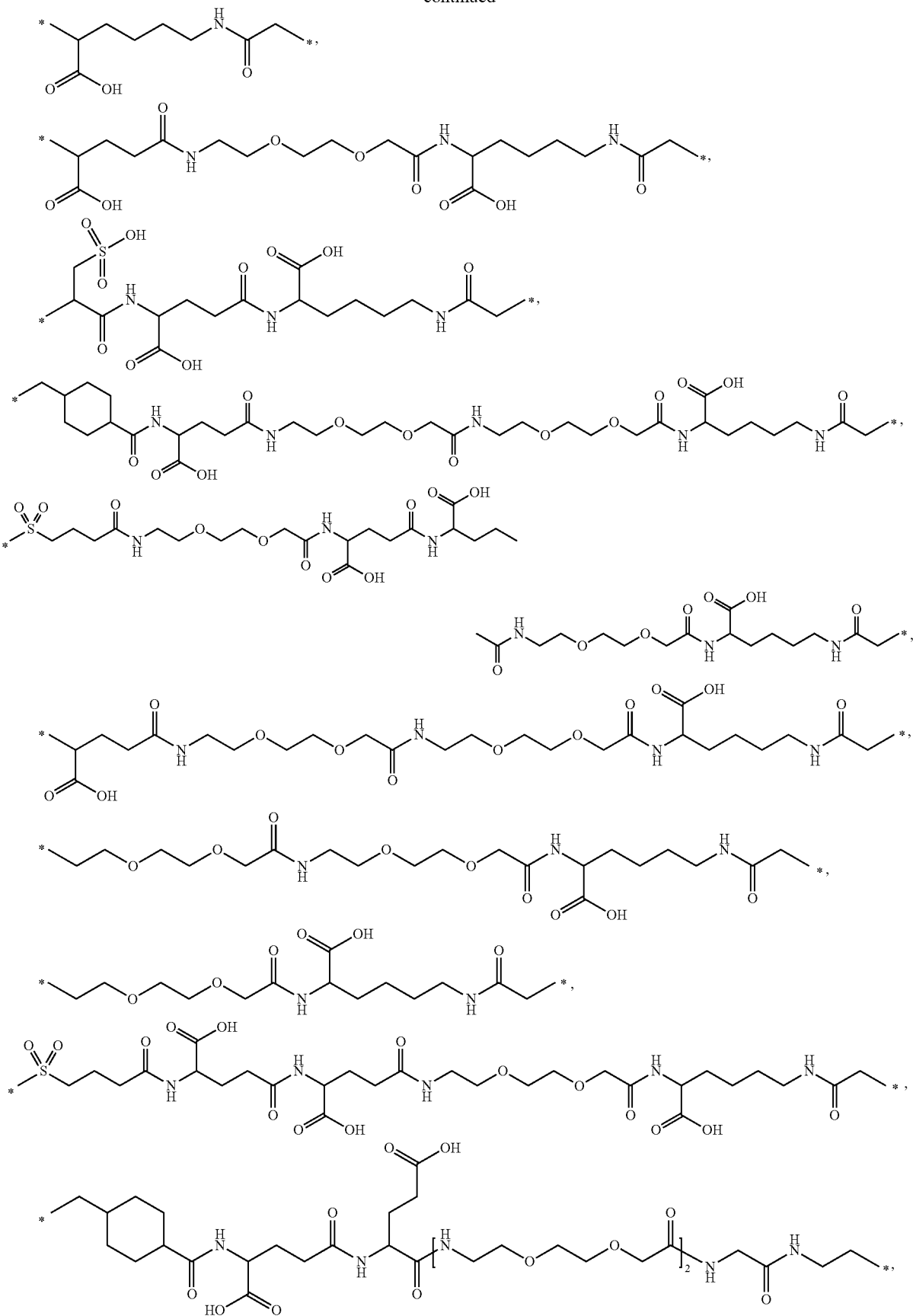

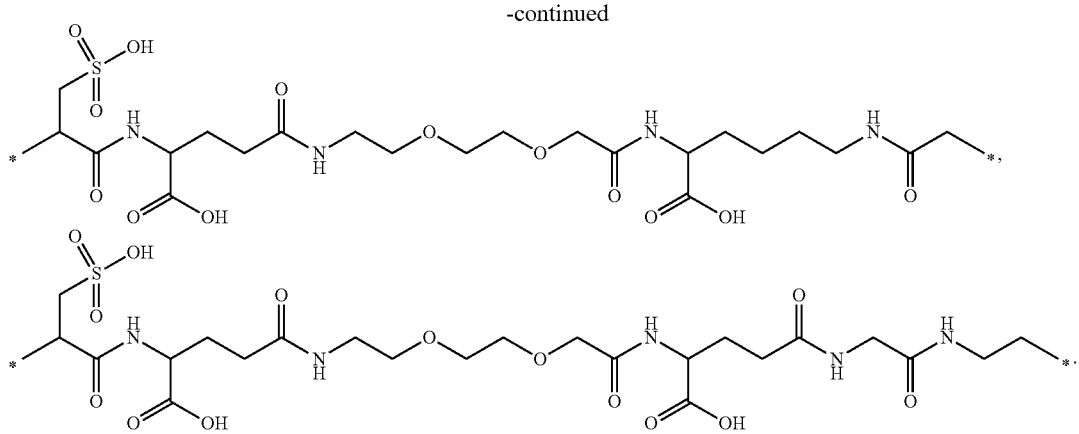

25. A growth hormone conjugate wherein the growth hormone conjugate has the formula (I):

A-W—B-GH  (I)

Wherein
GH represents a growth hormone compound having a single Cys mutation,
B represents a hydrophilic spacer linked to the sulphur residue of the Cys mutation,
W is a chemical group linking A and B, and
A represent an albumin binding residue; and
pharmaceutically acceptable salts thereof.

26. The conjugate of embodiment 25, wherein GH represents a growth hormone compound comprising an amino acid sequence having at least 80% identity to the amino acid sequence of human growth hormone (hGH) (SEQ ID NO: 1), such as at least 80%, at least 85%, at least 90%, or at least 95% identity with hGH, or GH is hGH (SEQ ID NO: 1).

27. The conjugate of embodiment 25, wherein GH or the GH conjugate has at least 80% of the growth hormone activity of hGH.

28. The conjugate of any one of embodiments 25-27, wherein the single Cys mutation is positioned in any one of the regions selected from the N-terminal, H1, H2, L2 or H3 of GH.

29. The conjugate of any one of embodiments 25-28 wherein the GH has a single Cys mutation selected from any one of: T3C, PSC, S7C, D11C, H18C, Q29C, E30C, E33C, A34C, Y35C, E88C, Q91C, S95C, A98C, N99C, S100C, L101C, V102C, Y103C, D107C, S108C, D112C, Q122C and G126C.

30. The conjugate of any one of embodiments 25-29, wherein A is selected from

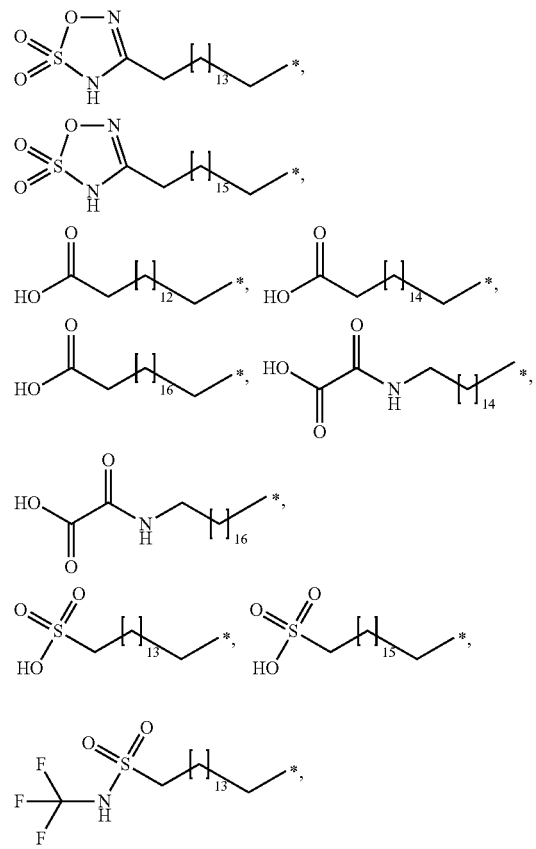

-continued

[Structure: 4-hydroxycarbonyl-phenyl-O-(CH2)12-*]

wherein * denotes the attachment to B through W.

31. The conjugate of any one of embodiments 25-30, wherein W has the formula

—W$_7$—Y—, wherein
Y is —(CH$_2$)$_{l7}$—C$_{3-10}$-cycloalkyl-W$_8$— or a valence bond,
l7 is 0-6,
W$_7$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s3}$—, —C(O)—, —C(O)O—, —OC(O)—, or a valence bond; wherein s3 is 0 or 1,
W$_8$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s4}$—, —C(O)—, —C(O)O—, —OC(O)—, or a valence bond; wherein s4 is 0 or 1.

32. The conjugate of any one of embodiments 25-31 wherein B has the formula

—X$_1$—X$_2$—X$_3$—X$_4$— wherein
X$_1$ is —W$_1$—[(CHR$^1$)$_{l1}$—W$_2$]$_{m1}$—{[(CH$_2$)$_{n1}$E1]$_{m2}$—[(CHR$^2$)$_{l2}$—W$_3$]$_{m3}$}$_{n2}$—,
X$_2$ is —[(CHR$^3$)$_{l3}$—W$_4$]$_{m4}$—{[(CH$_2$)$_{n3}$E2]$_{m5}$—[(CHR$^4$)$_{l4}$—W$_5$]$_{m6}$}$_{n4}$—,
X$_3$ is —[(CHR$^5$)$_{l5}$—W$_6$]$_{m7}$—,
X$_4$ is F-D1-(CH$_2$)$_{l6}$-D2-,
l1, l2, l3, l4, l5 and l6 independently are selected from 0-16,
m1, m3, m4, m6 and m7 independently are selected from 0-10,
m2 and m5 independently are selected from 0-25,
n1, n2, n3 and n4 independently are selected from 0-16,
F is aryl, hetaryl, pyrrolidine-2,5-dione or a valence bond, wherein the aryl and hetaryl groups are optionally substituted with halogen, —CN, —OH, —C(O)OH, —C(O)NH$_2$, —S(O)$_2$OH or C$_{1-6}$-alkyl,
R$^1$, R$^2$, R$^3$, R$^4$ and R$^5$ independently are selected from hydrogen, —C(O)OH, —C(O)NH$_2$, —S(O)OH, —S(O)$_2$OH, —NH—C(=NH)—NH$_2$, C$_{1-6}$-alkyl, aryl or hetaryl; wherein the alkyl, aryl and hetaryl groups optionally are substituted with halogen, —C(O)OH, —C(O)NH$_2$, —S(O)OH, —S(O)$_2$OH, —CN or —OH,
D1, D2, E1 and E2 independently are selected from —O—, —N(R$^6$)—, —N(C(O)R$^7$)— or a valence bond; wherein R$^6$ and R$^7$ independently represent hydrogen or C$_{1-6}$-alkyl,
W$_1$ to W$_5$ independently are selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s2}$—, —C(O)—, —C(O)O—, —OC(O)—, or a valence bond; wherein s2 is 0 or 1,
W$_6$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s1}$—, —C(O)—, —C(O)O—, —OC(O)—, —NHC(O)C$_{1-6}$-alkyl, —C(O)NHC$_{1-6}$-alkyl or a valence bond; wherein s1 is 0 or 1 and the C$_{1-6}$-alkyl group is optionally substituted with oxo, pyrrolidine-2,5-dione, —NHC(O)CH*CH$_2$COOH or —NHC(O)CH$_2$CH*COOH; wherein (*) indicates the attachment point from the carbon atom of CH to X$_4$.

33. The conjugate of any one of embodiments 25-32, wherein
l1, l2, l3, l4, l5 and l6 independently are 0-6,
m1, m3, m4, m6 and m7 independently are 0-6,
m2 and m5 independently are 0-10, and
n1, n2, n3 and n4 independently are 0-10.

34. The conjugate of any one of embodiments 25-33, wherein D1 and D2 are independently selected from —O— or —N(R$^6$)— or a valence bond.

35. The conjugate of any one of embodiments 25-34, wherein E1 and E2 are independently selected from —O— or —N(R$^6$)— or a valence bond.

36. The conjugate of any one of embodiments 25-35, wherein W$_1$ through W$_8$ independently are selected from the group consisting of —C(O)NH—, —NHC(O)—, —CH$_2$NHC(O)—, —C(O)NHS(O)$_2$—, —S(O)$_2$NHC(O)—, —NHC(O)C$_{1-6}$-alkyl, —C(O)NHC$_{1-6}$-alkyl or a valence bond; wherein the alkyl group is optionally substituted with oxo, pyrrolidine-2,5-dione, —NHC(O)CH*CH$_2$COOH or —NHC(O)CH$_2$CH*COOH; wherein (*) indicates the attachment point from the carbon atom of CH to X$_4$.

37. The conjugate of any one of embodiments 25-36, wherein R$^1$, R$^2$, R$^3$, R$^4$ and R$^5$ independently are selected from hydrogen, —C(O)OH, —C(O)NH$_2$, —S(O)$_2$OH or C$_{1-6}$-alkyl; wherein the alkyl group optionally is substituted with —C(O)OH, —C(O)NH$_2$ or —S(O)$_2$OH.

38. The conjugate of any one of embodiments 25-37, wherein —{[(CH$_2$)$_{n1}$E1]$_{m2}$-[(CHR$^2$)$_{l2}$—W$_3$]$_{m3}$}$_{n2}$— and —{[(CH$_2$)$_{n3}$E2]$_{m5}$—[(CHR$^4$)$_{l4}$—W$_5$]$_{m6}$}$_{n4}$—, wherein E1 and E2 are —O—, are selected from

[Two chemical structures showing PEG-like repeating units with [(CH$_2$)$_{n1}$O]$_{m2}$, (CHR$^2$)$_{l2}$, and W$_3$ groups]

-continued

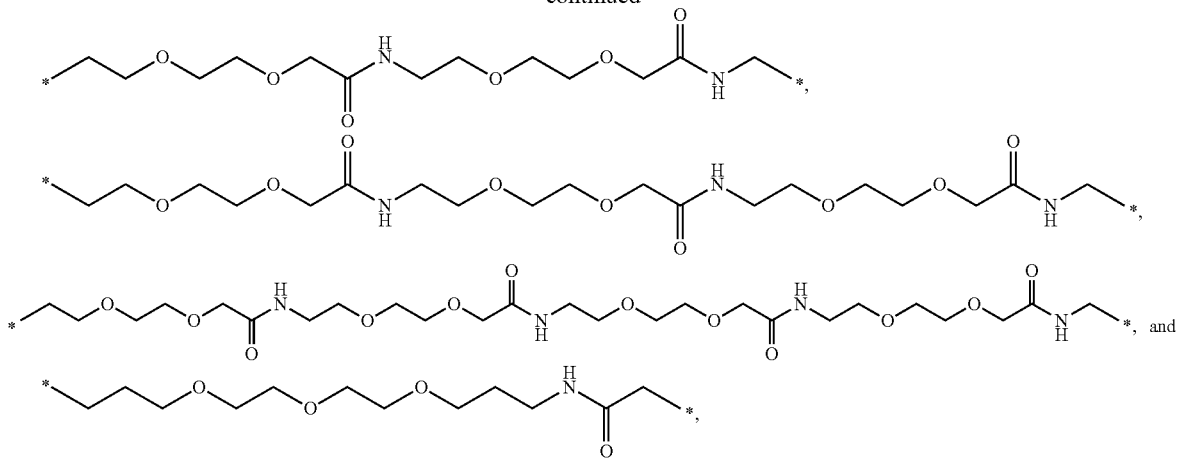

wherein * is intended to denote a point of attachment, ie, an open bond.

39. The conjugate of any one of embodiments 25-38, wherein $X_4$ is a valence bond and $W_6$ is selected from either pyrrolidine-2,5-dione, —NHC(O)CH*CH$_2$COOH or —NHC(O)CH$_2$CH*COOH wherein (*) indicates the attachment point from the carbon atom of CH to GH.

40. The conjugate of any one of embodiments 25-39 wherein B is selected from

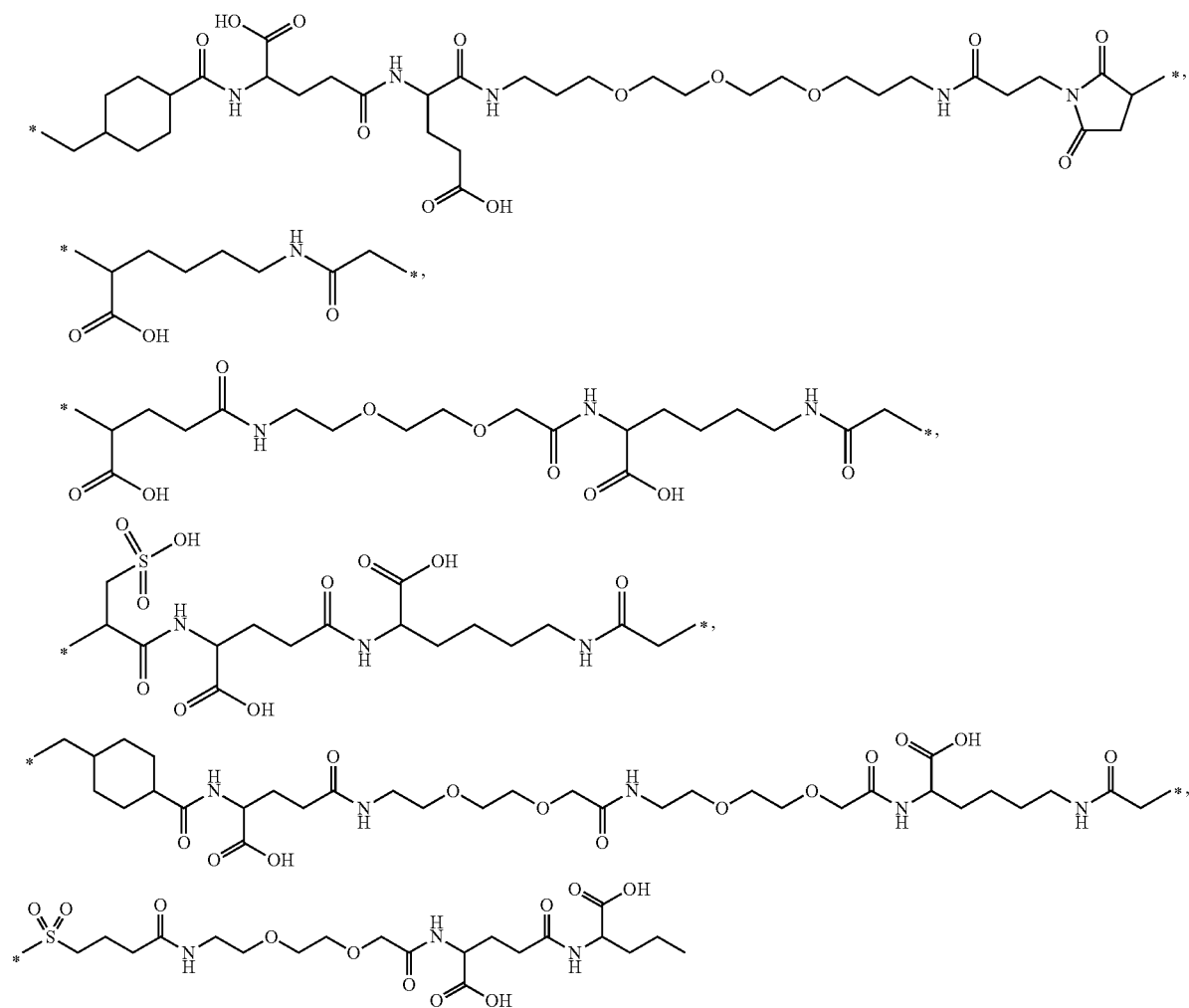

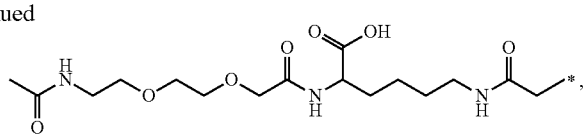
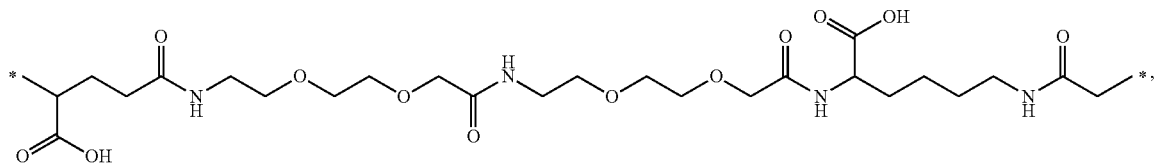
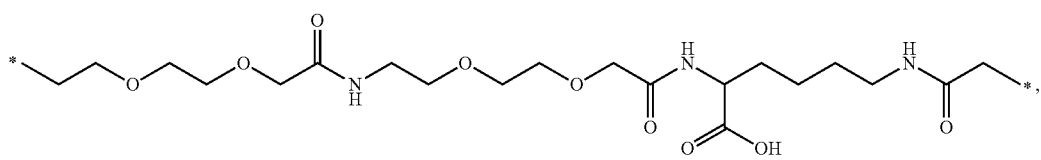
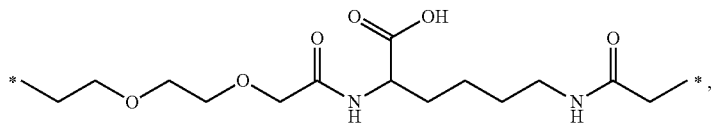
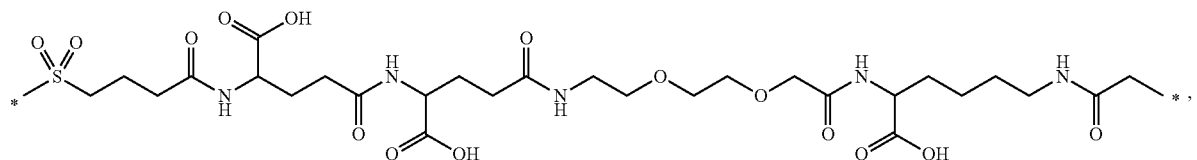
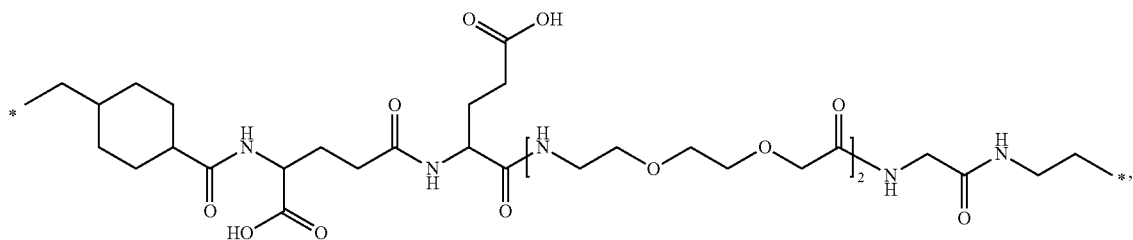
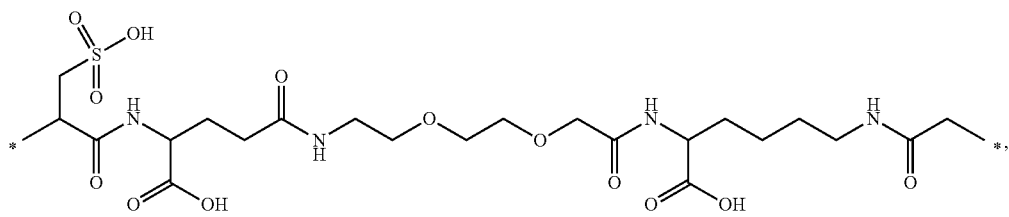
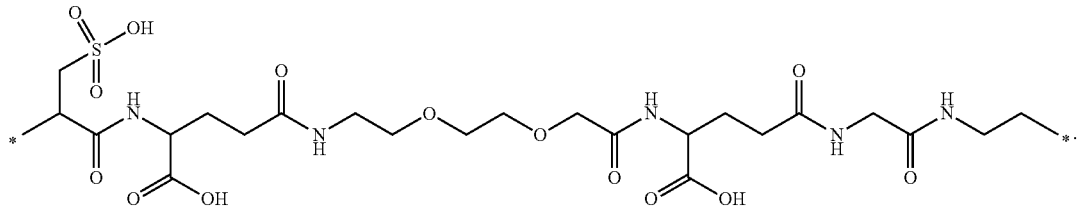

41. The conjugate of any one of embodiments 25-40, wherein said compound is selected from
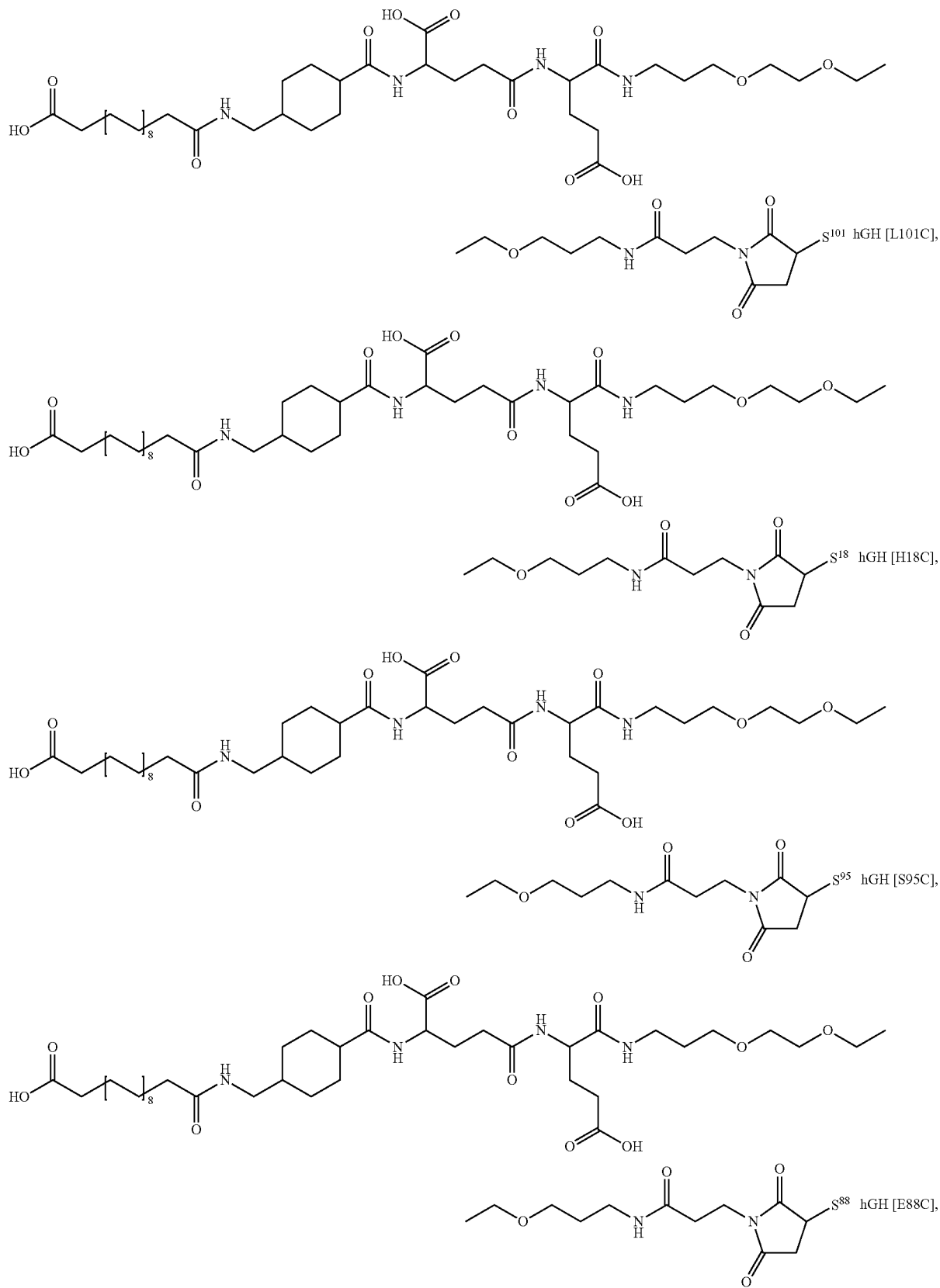

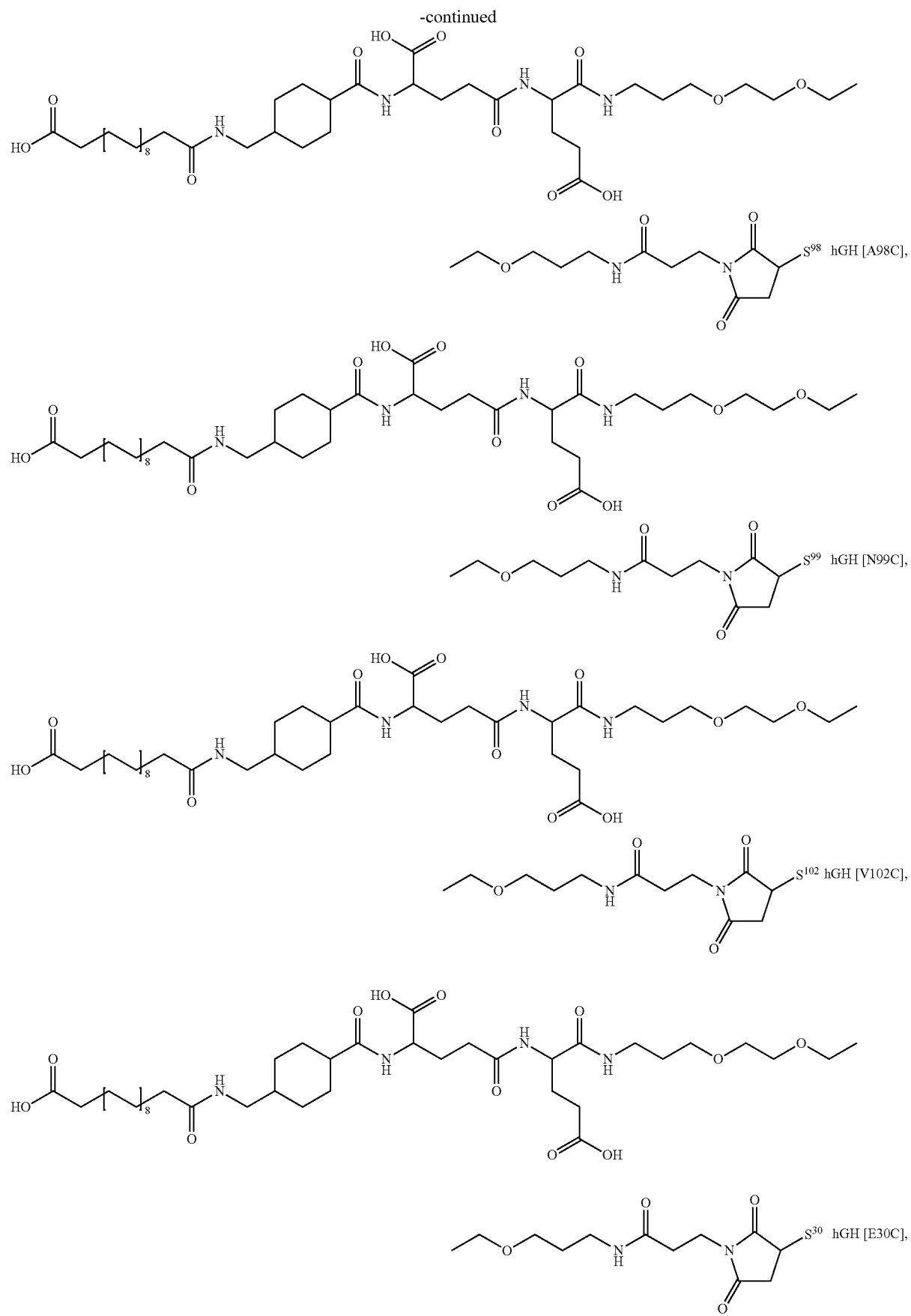

-continued
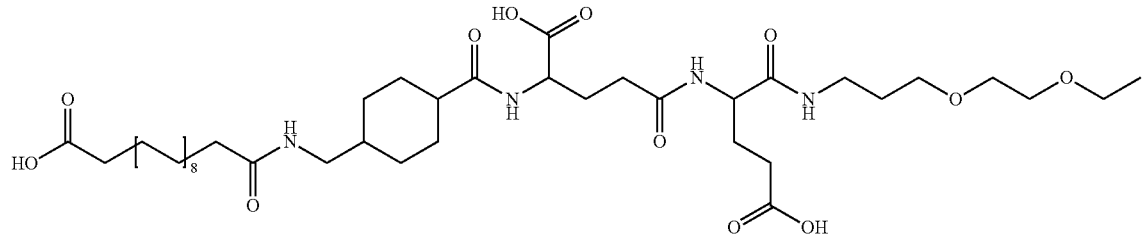
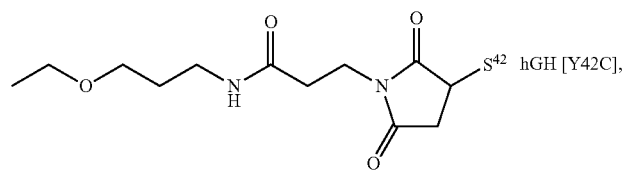 hGH [Y42C],
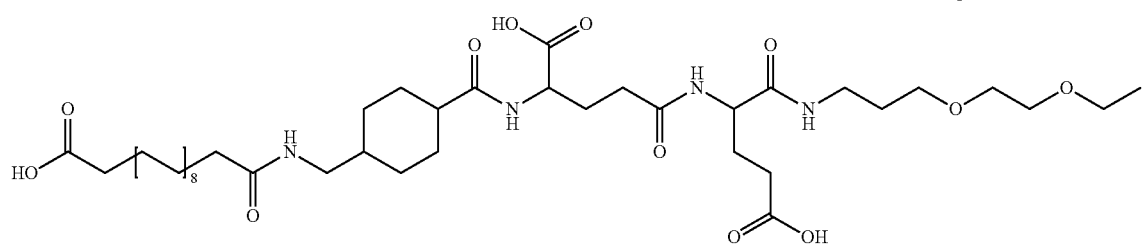
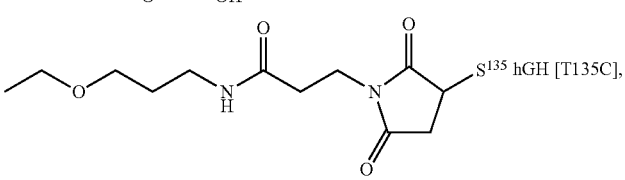 hGH [T135C],
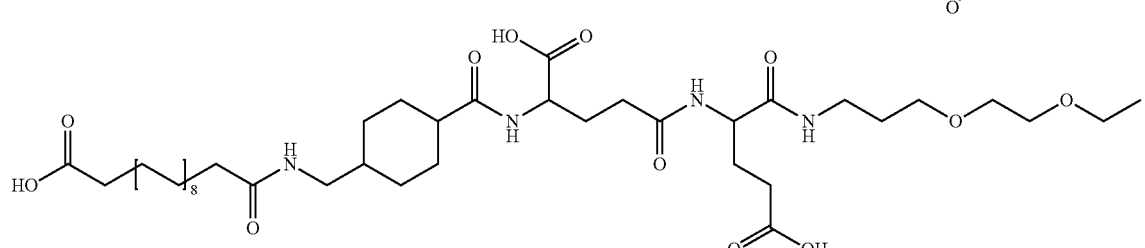
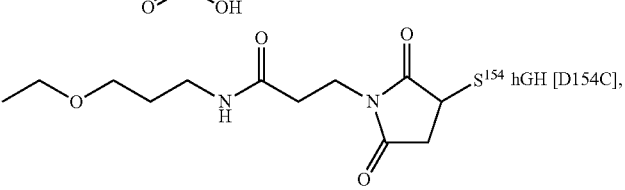 hGH [D154C],
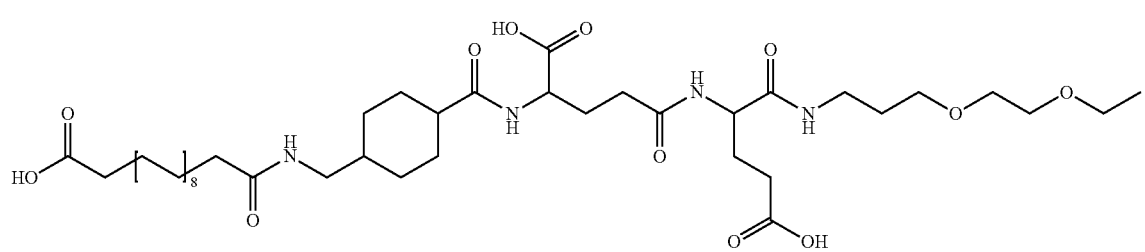
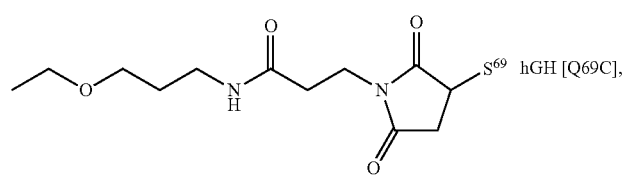 hGH [Q69C], -continued
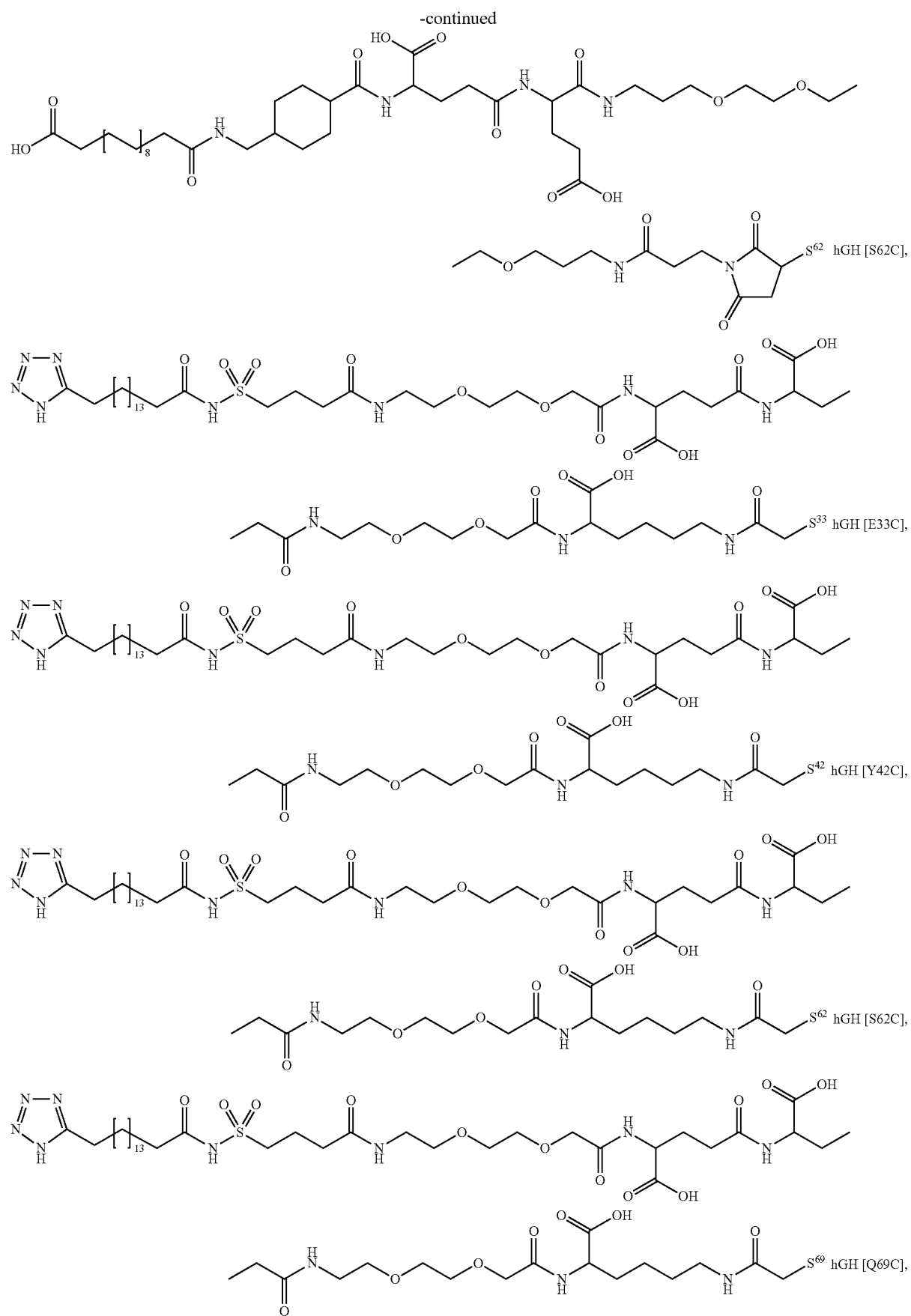

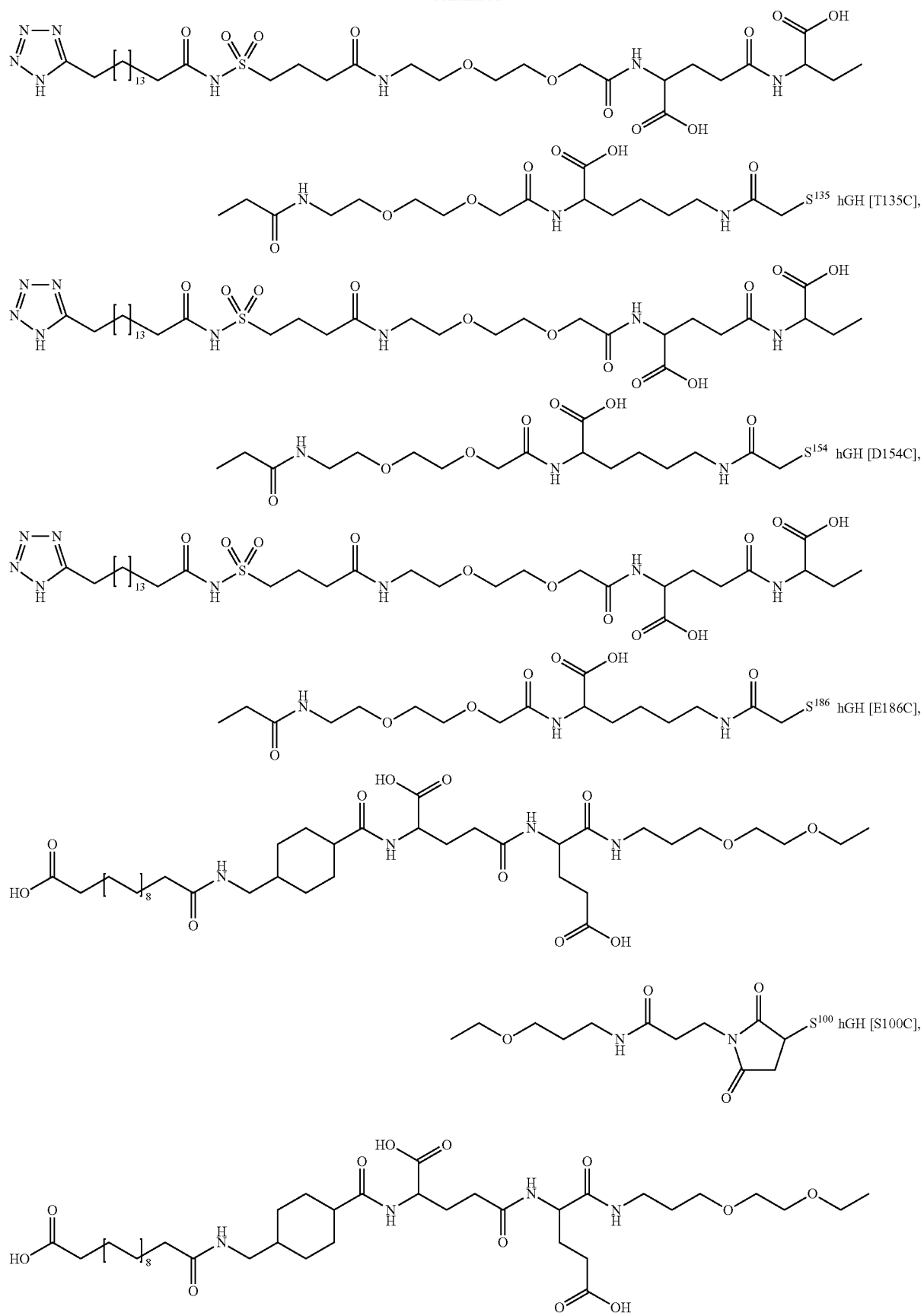

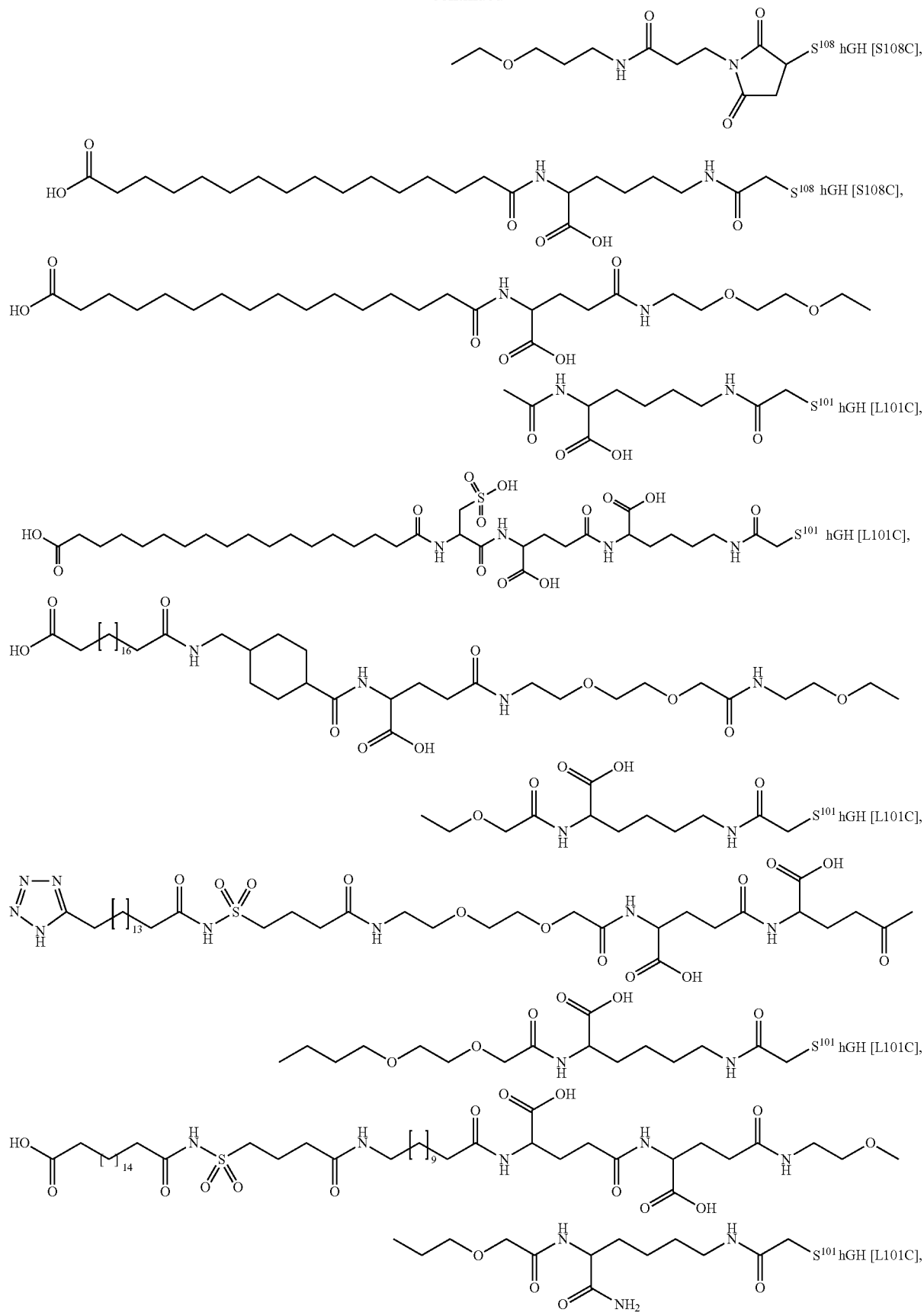

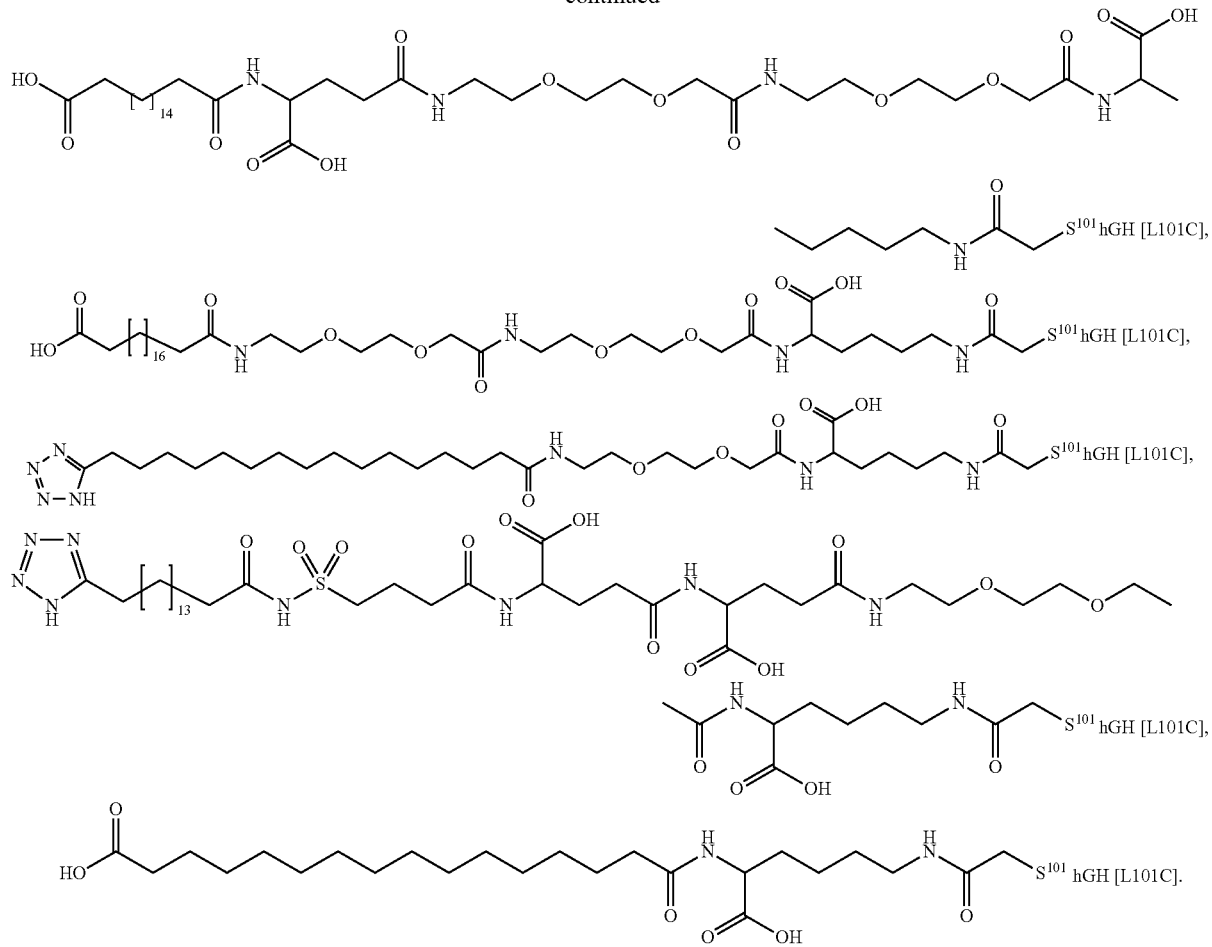

42. A growth hormone conjugate wherein the growth hormone conjugate has the formula (I):

A-W—B-GH  (I)

Wherein
GH represents a growth hormone compound having an additional disulfide bridge,
B represents a hydrophilic spacer,
W is a chemical group linking A and B, and
A represent an albumin binding residue; and
pharmaceutically acceptable salts thereof.

43. The conjugate of embodiment 42, wherein GH represents a growth hormone compound comprising an amino acid sequence having at least 80% identity to the amino acid sequence of human growth hormone (hGH) (SEQ ID NO: 1), such as at least 80%, at least 85%, at least 90%, or at least 95% identity with hGH, or GH is hGH (SEQ ID NO: 1).

44. The conjugate of embodiment 42, wherein GH or the GH conjugates has at least 80% of the growth hormone activity of hGH.

45. The conjugate of embodiment 44, wherein the activity is measured in an in vitro BAF assay (assay I)

46. The conjugate of any one of embodiments 42-45, wherein the GH comprises additional disulfide bonds between a loop segment and a helical segment or within loop segment or between loop segments or between helical segments.

47. The conjugate of any one of embodiments 42-46, wherein the GH comprises an additional disulfide bond wherein at least one of the cysteines is present in a loop segment, such from amino acid residues 128-154 (L3).

48. The conjugate of any one of embodiments 42-47, wherein the GH comprises an additional disulfide bond wherein the additional disulfide bond which connects a loop segment, with a helical segment, such as helix B or helix 2.

49. The conjugate of any one of embodiments 42-48, wherein the GH comprises an additional disulfide bond wherein the additional disulfide bond connects L3 (128-154), with helix B or helix 2.

50. The conjugate of any one of embodiments 42-49, wherein the additional disulfide bridge is between at least one of the amino acid pairs in the positions corresponding to R16C/L117C, A17C/E174C, H21C/M170C, D26C/V102C, D26C/Y103C, N47C/T50C, Q49C/G161C, F54C/Y143C, F54C/S144C, F54C/F146C, S55C/Y143C, S57C/Y143C, I58C/Q141C, I58C/Y143C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C, F92C/T148C, R94C/D107C, V102C/A105C, L156C/F146C, L156C/T148C and/or V185C/S188C in hGH (SEQ ID NO: 1), such as Q84C/Y143C.

51. The conjugate of any one of embodiments 42-50, wherein A is selected from

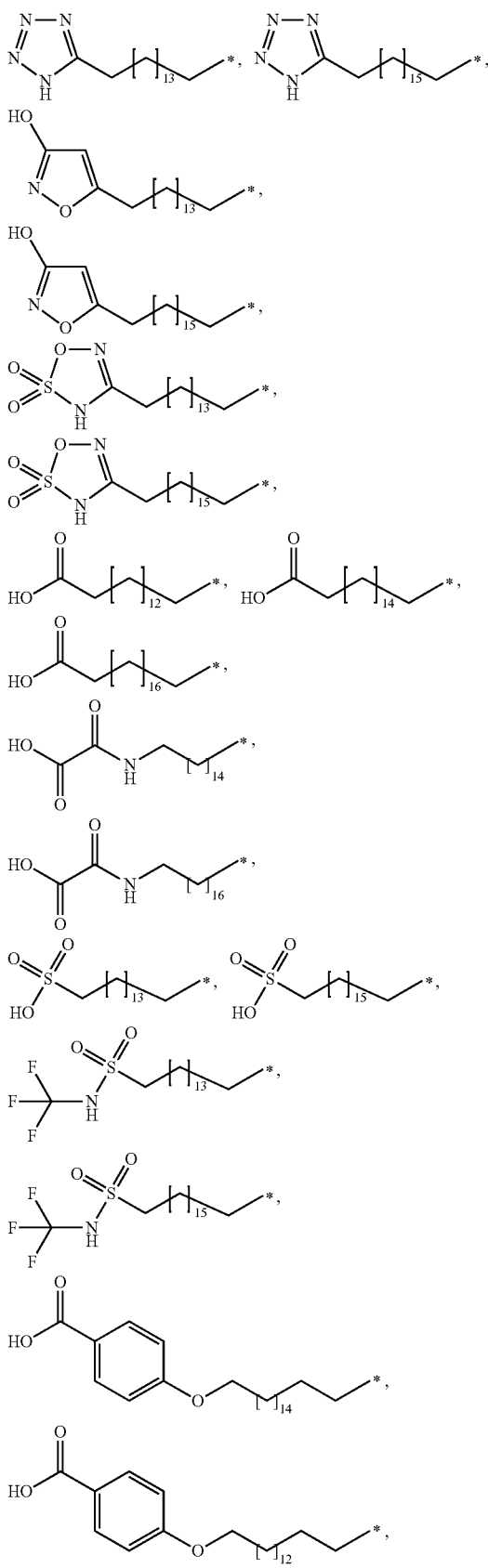

wherein * denotes the attachment to B through W.

52. The conjugate of any one of embodiments 42-51, wherein W has the formula

—W$_7$—Y—, wherein

Y is —(CH$_2$)$_{l7}$—C$_{3-10}$-cycloalkyl-W$_8$— or a valence bond, l7 is 0-6, W$_7$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s3}$—, —C(O)—, —C(O)O—, —OC(O)—, or a valence bond; wherein s3 is 0 or 1, W$_8$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s4}$—, —C(O)—, —C(O)O—, —OC(O)—, or a valence bond; wherein s4 is 0 or 1.

53. The conjugate of any one of embodiments 42-52 wherein B has the formula

—X$_1$—X$_2$—X$_3$—X$_4$— wherein

X$_1$ is —W$_1$—[(CHR$^1$)$_{l1}$—W$_2$]$_{m1}$—{[(CH$_2$)$_{n1}$E1]$_{m2}$—[(CHR$^2$)$_{l2}$—W$_3$]$_{m3}$}$_{n2}$—,

X$_2$ is —[(CHR$^3$)$_{l3}$—W$_4$]$_{m4}$—{[(CH$_2$)$_{n3}$E2]$_{m5}$—[(CHR$^4$)$_{l4}$—W$_5$]$_{m6}$}$_{n4}$—,

X$_3$ is —[(CHR$^5$)$_{l5}$—W$_6$]$_{m7}$—,

X$_4$ is F-D1-(CH$_2$)$_{l6}$-D2-, l1, l2, l3, l4, l5 and l6 independently are selected from 0-16, m1, m3, m4, m6 and m7 independently are selected from 0-10, m2 and m5 independently are selected from 0-25, n1, n2, n3 and n4 independently are selected from 0-16, F is aryl, hetaryl, pyrrolidine-2,5-dione or a valence bond, wherein the aryl and hetaryl groups are optionally substituted with halogen, —CN, —OH, —C(O)OH, —C(O)NH$_2$, —S(O)$_2$OH or C$_{1-6}$-alkyl, R$^1$, R$^2$, R$^3$, R$^4$ and R$^5$ independently are selected from hydrogen, —C(O)OH, —C(O)NH$_2$, —S(O)OH, —S(O)$_2$OH, —NH—C(=NH)—NH$_2$, C$_{1-6}$-alkyl, aryl or hetaryl; wherein the alkyl, aryl and hetaryl groups optionally are substituted with halogen, —C(O)OH, —C(O)NH$_2$, —S(O)OH, —S(O)$_2$OH, —CN or —OH, D1, D2, E1 and E2 independently are selected from —O—, —N(R$^6$)—, —N(C(O)R$^7$)— or a valence bond; wherein R$^6$ and R$^7$ independently represent hydrogen or C$_{1-6}$-alkyl, W$_1$ to W$_5$ independently are selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s2}$—, —C(O)—, —C(O)O—, —OC(O)—, or a valence bond; wherein s2 is 0 or 1, W$_6$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s1}$—, —C(O)—, —C(O)O—, —OC(O)—, —NHC(O)C$_{1-6}$-alkyl, —C(O)NHC$_{1-6}$-alkyl or a valence bond; wherein s1 is 0 or 1 and the $C_{1-6}$-alkyl group is optionally substituted with oxo, pyrrolidine-2,5-dione, —NHC(O)CH*CH$_2$COOH or —NHC(O)CH$_2$CH*COOH; wherein (*) indicates the attachment point from the carbon atom of CH to $X_4$.

54. The conjugate of any one of embodiments 42-53, wherein
l1, l2, l3, l4, l5 and l6 independently are 0-6,
m1, m3, m4, m6 and m7 independently are 0-6,
m2 and m5 independently are 0-10, and
n1, n2, n3 and n4 independently are 0-10.

55. The conjugate of any one of embodiments 42-54, wherein D1 and D2 are independently selected from —O— or —N($R^6$)— or a valence bond.

56. The conjugate of any one of embodiments 42-55, wherein E1 and E2 are independently selected from —O— or —N($R^6$)— or a valence bond.

57. The conjugate of any one of embodiments 42-56, wherein $W_1$ through $W_8$ independently are selected from the group consisting of —C(O)NH—, —NHC(O)—, —CH$_2$NHC(O)—, —C(O)NHS(O)$_2$—, —S(O)$_2$NHC (O)—, —NHC(O)C$_{1-6}$-alkyl or —C(O)NHC$_{1-6}$-alkyl or a valence bond; wherein the alkyl group is optionally substituted with oxo, pyrrolidine-2,5-dione, —NHC(O) CH*CH$_2$COOH or —NHC(O)CH$_2$CH*COOH; wherein (*) indicates the attachment point from the carbon atom of CH to $X_4$.

58. The conjugate of any one of embodiments 42-57, wherein $R^1$, $R^2$, $R^3$, $R^4$ and $R^5$ independently are selected from hydrogen, —C(O)OH, —C(O)NH$_2$, —S(O)$_2$OH or $C_{1-6}$-alkyl; wherein the alkyl group optionally is substituted with —C(O)OH, —C(O)NH$_2$ or —S(O)$_2$OH.

59. The conjugate of any one of embodiments 42-58, wherein —{[(CH$_2$)$_{n1}$E1]$_{m2}$-[(CHR$^2$)$_{l2}$—W$_3$]$_{m3}$}$_{n2}$— and —{[(CH$_2$)$_{n3}$E2]$_{m5}$—[(CHR$^4$)$_{l4}$—W$_5$]$_{m6}$}$_{n4}$—, wherein E1 and E2 are —O—, are selected from

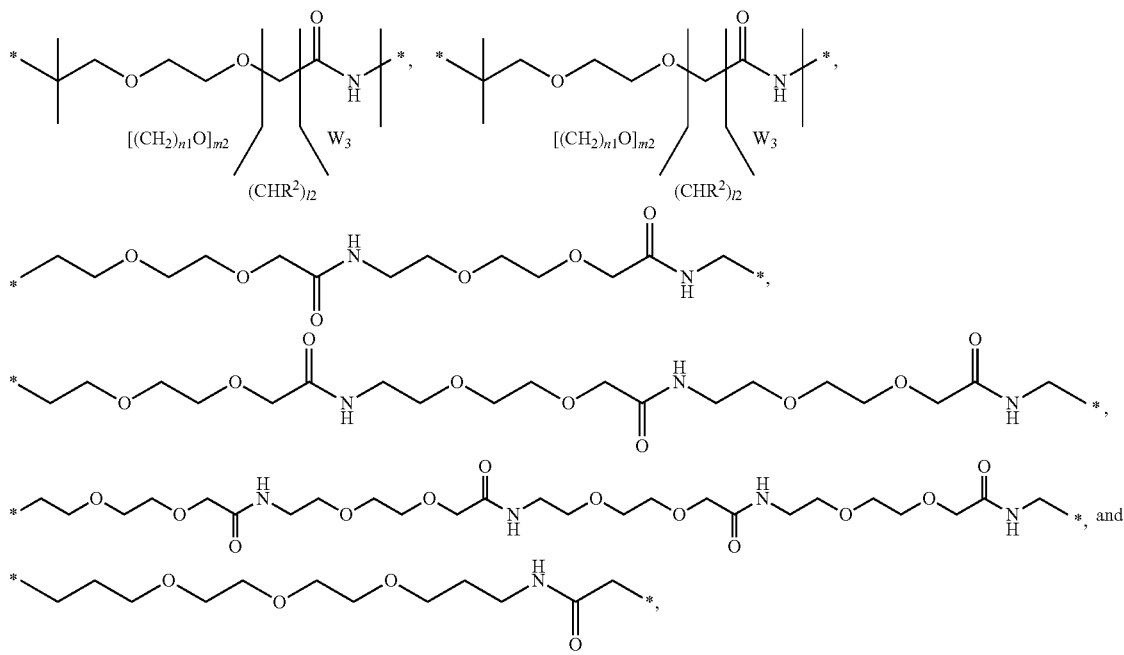

wherein * is intended to denote a point of attachment, ie, an open bond.

60. The conjugate of any one of embodiments 42-59 wherein B is selected from

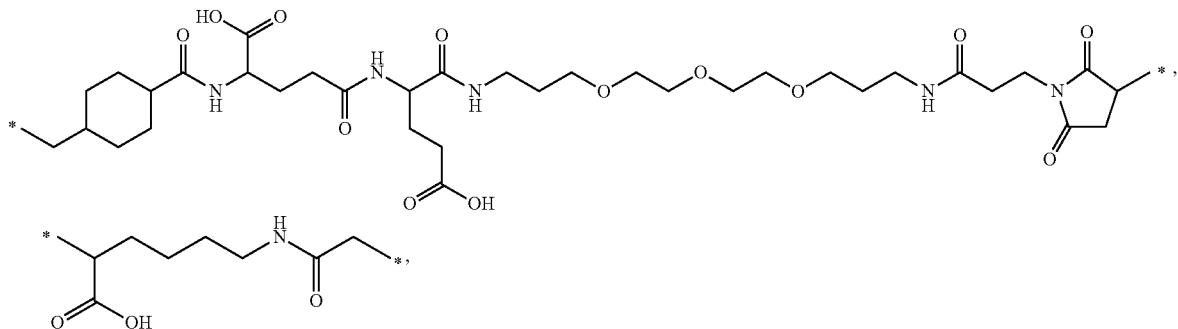

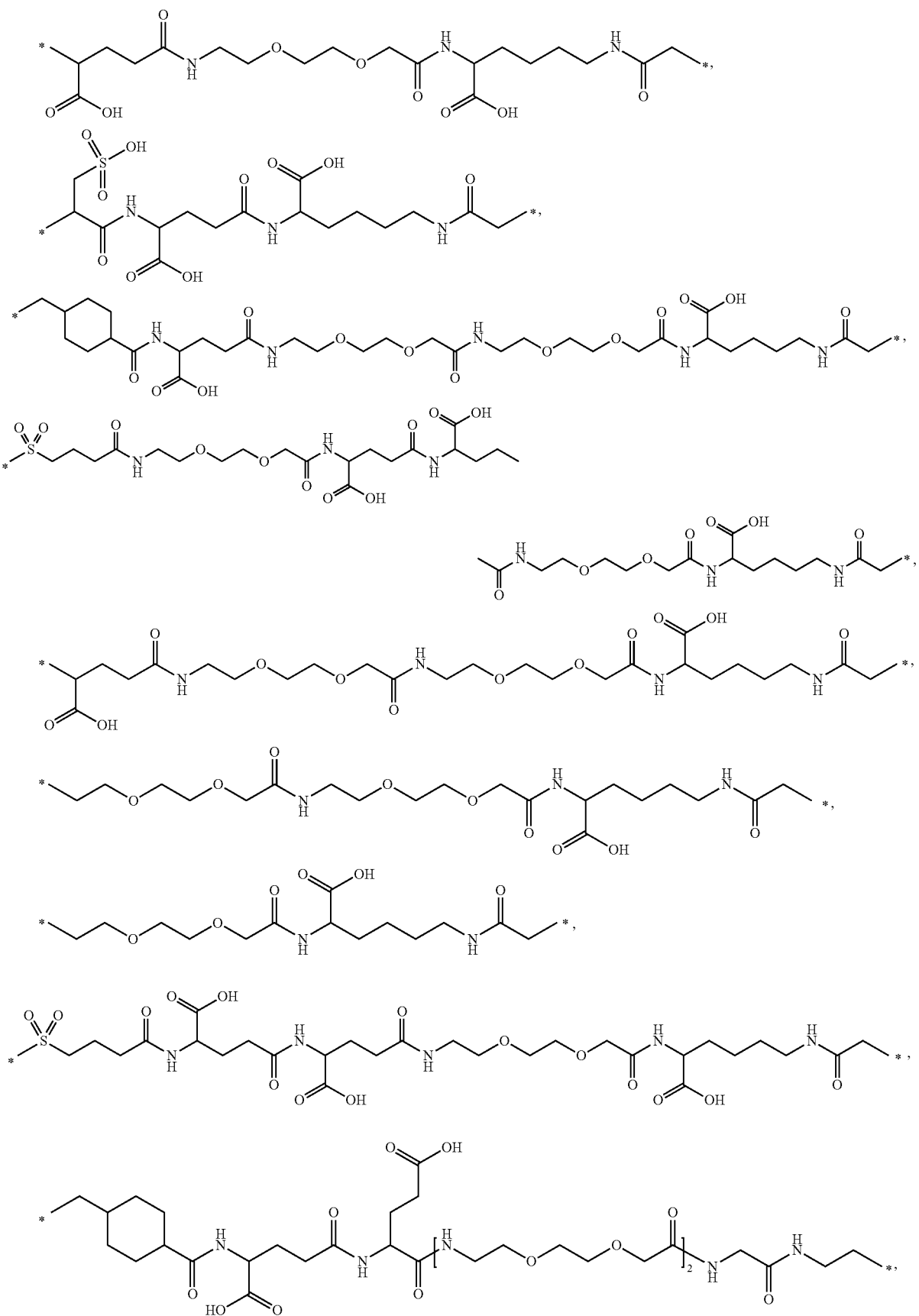

-continued
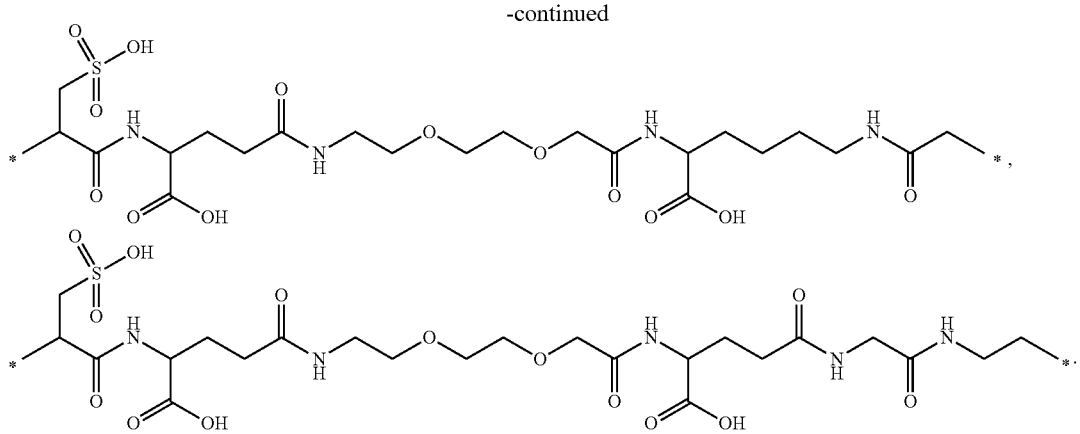
61. The conjugate of any one of embodiments 42-60, wherein A via B is attached to the glutamine residue in the position corresponding to position 40, position 141 in hGH SEQ ID NO: 1, or the N-terminal residue of the growth hormone compound.
62. The conjugate of any one of embodiments 42-61, wherein said compound is selected from
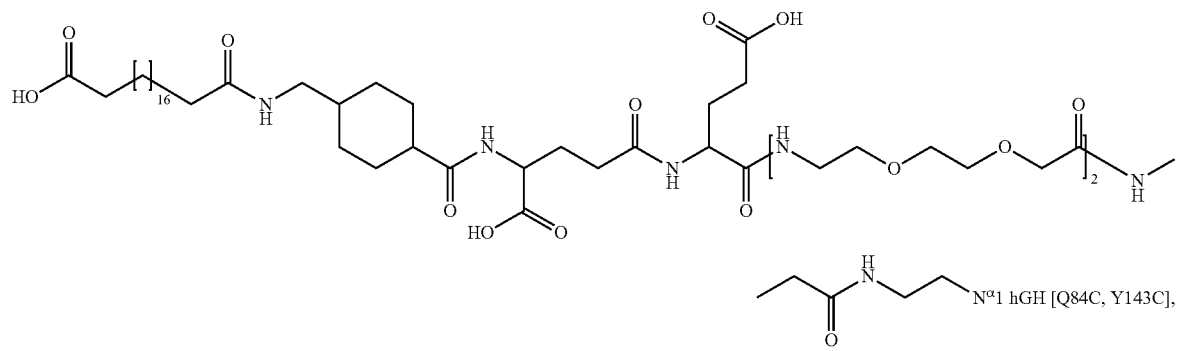
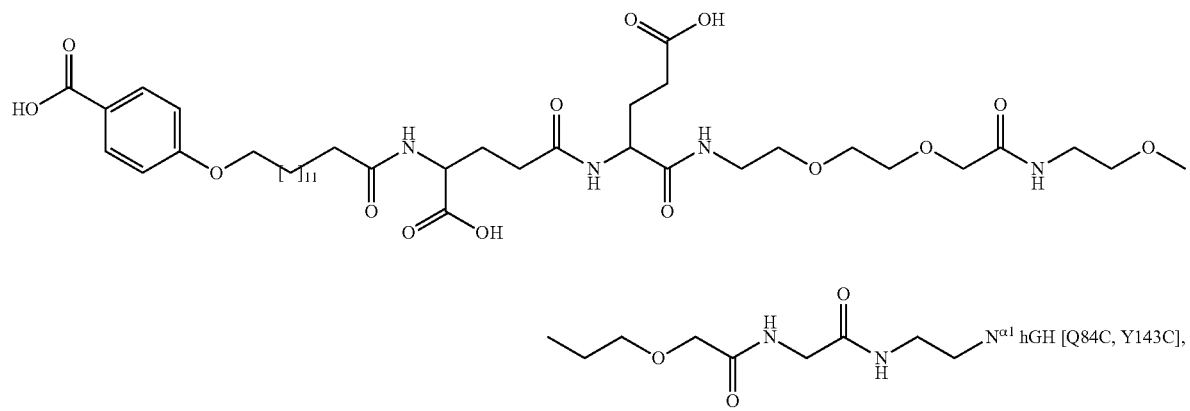
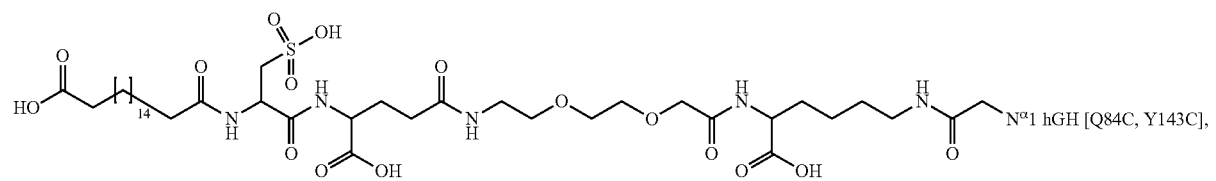

-continued

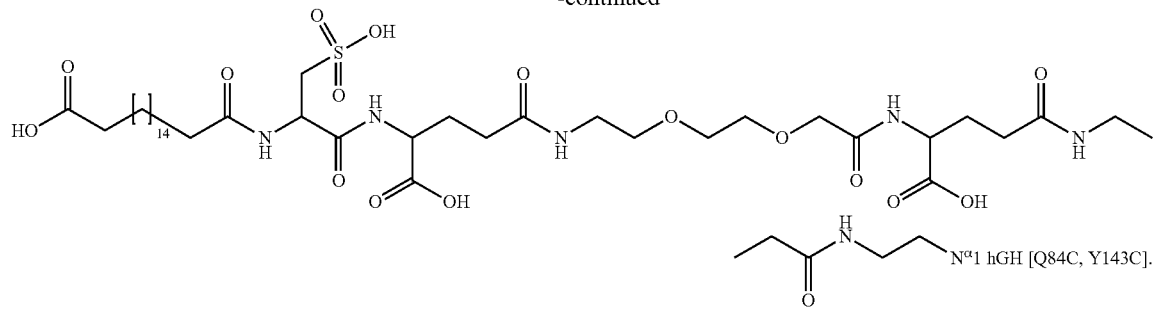

63. A growth hormone conjugate wherein the growth hormone conjugate has the formula (I):

A-W—B-GH    (I)

wherein

GH represents a growth hormone compound having a single Cys mutation and an additional disulfide bridge, B represents a hydrophilic spacer linked to the sulphur residue of the Cys mutation, W is a chemical group linking A and B, and A represent an albumin binding residue; and pharmaceutically acceptable salts thereof.

64. The conjugate of embodiment 63, wherein GH represents a growth hormone compound comprising an amino acid sequence having at least 80% identity to the amino acid sequence of human growth hormone (hGH) (SEQ ID NO: 1), such as at least 80%, at least 85%, at least 90%, or at least 95% identity with hGH, or GH is hGH (SEQ ID NO: 1).

65. The conjugate of embodiment 64, wherein GH or the GH conjugate has at least 80% of the growth hormone activity of hGH.

66. The conjugate of any of the embodiments 63-65, wherein the single Cys mutation is positioned in any one of the regions selected from the N-terminal, H1, H2, L2 or H3 of GH.

67. The conjugate of any one of embodiments 63-66 wherein the GH has a single Cys mutation selected from any one of: T3C, P5C, S7C, D11C, H$_{18}$C, Q29C, E30C, E33C, A34C, Y35C, K38C, E39C, Y42C, S43C, D47C, P48C, S55C, S57C, P59C, S62, E65C, Q69C, E88C, Q91C, S95C, A98C, N99C, S100C, L101C, V102C, Y103C, D107C, S108C, D112C, Q122C, G126C, E129C, D130C, G131C, P133C, T135C, G136C, T142C, D147C, N149C, D154C, A155C, L156C, R178C, E186C, G187C and G190C, such as any one of: T3C, P5C, S7C, D11C, H$_{18}$C, Q29C, E30C, E33C, A34C, Y35C, E88C, Q91C, S95C, A98C, N99C, S100C, L101C, V102C, Y103C, D107C, S108C, D112C, Q122C and G126C.

68. The conjugate of any one of embodiments 63-67, wherein the additional disulfide bond is between a loop segment and a helical segment or within loop segment or between loop segments or between helical segments.

69. The conjugate of any one of embodiments 63-68, wherein the GH comprises an additional disulfide bond wherein at least one of the cysteines is present in a loop segment, such from amino acid residues 128-154 (L3).

70. The conjugate of any one of embodiments 63-69, wherein the additional disulfide bond connects a loop segment, with a helical segment, such as H2.

71. The conjugate of any one of embodiments 63-70, wherein the additional disulfide bond connects L3, with helix H2.

72. The conjugate of any one of embodiments 63-71, wherein the additional disulfide bridge is between at least one of the amino acid pairs in the positions corresponding to R16C/L117C, A17C/E174C, H21C/M170C, D26C/V102C, D26C/Y103C, N47C/T50C, Q49C/G161C, F54C/Y143C, F54C/S144C, F54C/F146C, S55C/Y143C, S57C/Y143C, I58C/Q141C, I58C/Y143C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C, F92C/T148C, R94C/D107C, V102C/A105C, L156C/F146C, L156C/T148C and/or V185C/S188C in hGH (SEQ ID NO: 1), such as Q84C/Y143C.

73. The conjugate of any one of embodiments 63-72, wherein A is selected from

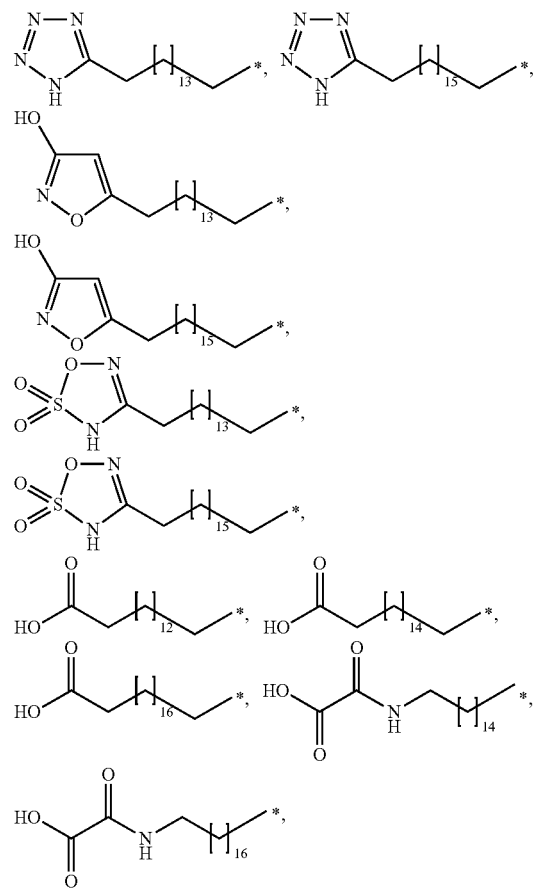

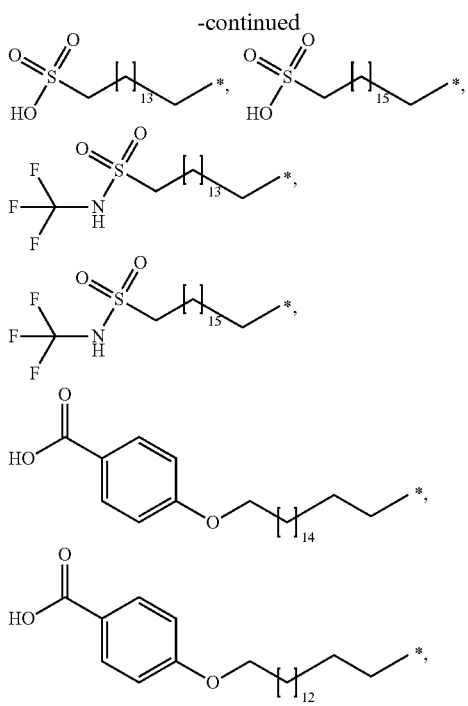

wherein * denotes the attachment to B through W.

74. The conjugate of any one of embodiments 63-73, wherein W has the formula

—W₇—Y—, wherein
Y is —(CH₂)$_{l7}$—C$_{3-10}$-cycloalkyl-W₈— or a valence bond,
l7 is 0-6,
W₇ is selected from —C(O)NH—, —NHC(O)—, —C(O)NHCH₂—, —CH₂NHC(O)—, —C(O)NHS(O)₂—, —S(O)₂NHC(O)—, —OC(O)NH—, —NHC(O)O—, —C(O)CH₂—, —CH₂C(O)—, —C(O)CH=CH—, —CH=CHC(O)—, —(CH₂)$_{s3}$—, —C(O)—, —C(O)O—, —OC(O)—, or a valence bond; wherein s3 is 0 or 1,
W₈ is selected from —C(O)NH—, —NHC(O)—, —C(O)NHCH₂—, —CH₂NHC(O)—, —C(O)NHS(O)₂—, —S(O)₂NHC(O)—, —OC(O)NH—, —NHC(O)O—, —C(O)CH₂—, —CH₂C(O)—, —C(O)CH=CH—, —CH=CHC(O)—, —(CH₂)$_{s4}$—, —C(O)—, —C(O)O—, —OC(O)—, or a valence bond; wherein s4 is 0 or 1.

75. The conjugate of any one of embodiments 63-74 wherein B has the formula

—X₁—X₂—X₃—X₄— wherein
X₁ is —W₁—[(CH)$_{l1}$—W₂]$_{m1}$—{[(CH₂)$_{n1}$E1]$_{m2}$—[(CHR²)$_{l2}$—W₃]$_{m3}$}$_{n2}$—,
X₂ is —[(CHR³)$_{l3}$—W₄]$_{m4}$—{[(CH₂)$_{n3}$E2]$_{m5}$—[(CHR⁴)$_{l4}$—W₅]$_{m6}$}$_{n4}$—,
X₃ is —[(CHR⁵)$_{l5}$—W₆]$_{m7}$—,
X₄ is F-D1-(CH₂)$_{l6}$-D2-,
l1, l2, l3, l4, l5 and l6 independently are selected from 0-16,
m1, m3, m4, m6 and m7 independently are selected from 0-10,
m2 and m5 independently are selected from 0-25,
n1, n2, n3 and n4 independently are selected from 0-16,
F is aryl, hetaryl, pyrrolidine-2,5-dione or a valence bond, wherein the aryl and hetaryl groups are optionally substituted with halogen, —CN, —OH, —C(O)OH, —C(O)NH₂, —S(O)₂OH or C$_{1-6}$-alkyl,
R¹, R², R³, R⁴ and R⁵ independently are selected from hydrogen, —C(O)OH, —C(O)NH₂, —S(O)OH, —S(O)₂OH, —NH—C(=NH)—NH₂, C$_{1-6}$-alkyl, aryl or hetaryl; wherein the alkyl, aryl and hetaryl groups optionally are substituted with halogen, —C(O)OH, —C(O)NH₂, —S(O)OH, —S(O)₂OH, —CN or —OH,
D1, D2, E1 and E2 independently are selected from —O—, —N(R⁶)—, —N(C(O)R⁷)— or a valence bond; wherein R⁶ and R⁷ independently represent hydrogen or C$_{1-6}$-alkyl,
W₁ to W₅ independently are selected from —C(O)NH—, —NHC(O)—, —C(O)NHCH₂—, —CH₂NHC(O)—, —C(O)NHS(O)₂—, —S(O)₂NHC(O)—, —OC(O)NH—, —NHC(O)O—, —C(O)CH₂—, —CH₂C(O)—, —C(O)CH=CH—, —CH=CHC(O)—, —(CH₂)$_{s2}$—, —C(O)—, —C(O)O—, —OC(O)—, or a valence bond; wherein s2 is 0 or 1,
W₆ is selected from —C(O)NH—, —NHC(O)—, —C(O)NHCH₂—, —CH₂NHC(O)—, —C(O)NHS(O)₂—, —S(O)₂NHC(O)—, —OC(O)NH—, —NHC(O)O—, —C(O)CH₂—, —CH₂C(O)—, —C(O)CH=CH—, —CH=CHC(O)—, —(CH₂)$_{s1}$—, —C(O)—, —C(O)O—, —OC(O)—, —NHC(O)C$_{1-6}$-alkyl, —C(O)NHC$_{1-6}$-alkyl or a valence bond; wherein s1 is 0 or 1 and the C$_{1-6}$-alkyl group is optionally substituted with oxo, pyrrolidine-2,5-dione, —NHC(O)CH*CH₂COOH or —NHC(O)CH₂CH*COOH; wherein (*) indicates the attachment point from the carbon atom of CH to X₄.

76. The conjugate of any one of embodiments 63-75, wherein
l1, l2, l3, l4, l5 and l6 independently are 0-6,
m1, m3, m4, m6 and m7 independently are 0-6,
m2 and m5 independently are 0-10, and
n1, n2, n3 and n4 independently are 0-10.

77. The conjugate of any one of embodiments 63-75, wherein D1 and D2 are independently selected from —O— or —N(R⁶)— or a valence bond.

78. The conjugate of any one of embodiments 63-77, wherein E1 and E2 are independently selected from —O— or —N(R⁶)— or a valence bond.

79. The conjugate of any one of embodiments 63-78, wherein W₁ through W₈ independently are selected from the group consisting of —C(O)NH—, —NHC(O)—, —CH₂NHC(O)—, —C(O)NHS(O)₂—, —S(O)₂NHC(O)—, —NHC(O)C$_{1-6}$-alkyl or —C(O)NHC$_{1-6}$-alkyl or a valence bond; wherein the alkyl group is optionally substituted with oxo, pyrrolidine-2,5-dione, —NHC(O)CH*CH₂COOH or —NHC(O)CH₂CH*COOH; wherein (*) indicates the attachment point from the carbon atom of CH to X₄.

80. The conjugate of any one of embodiments 63-79, wherein R¹, R², R³, R⁴ and R⁵ independently are selected from hydrogen, —C(O)OH, —C(O)NH₂, —S(O)₂OH or C$_{1-6}$-alkyl; wherein the alkyl group optionally is substituted with —C(O)OH, —C(O)NH₂ or —S(O)₂OH.

81. The conjugate of any one of embodiments 63-80, wherein —{[(CH₂)$_{n1}$E1]$_{m2}$—[(CHR²)$_{l2}$—W₃]$_{m3}$}$_{n2}$— and —{[(CH₂)$_{n3}$E2]$_{m5}$—[(CHR⁴)$_{l4}$—W₅]$_{m6}$}$_{n4}$—, wherein E1 and E2 are —O—, are selected from

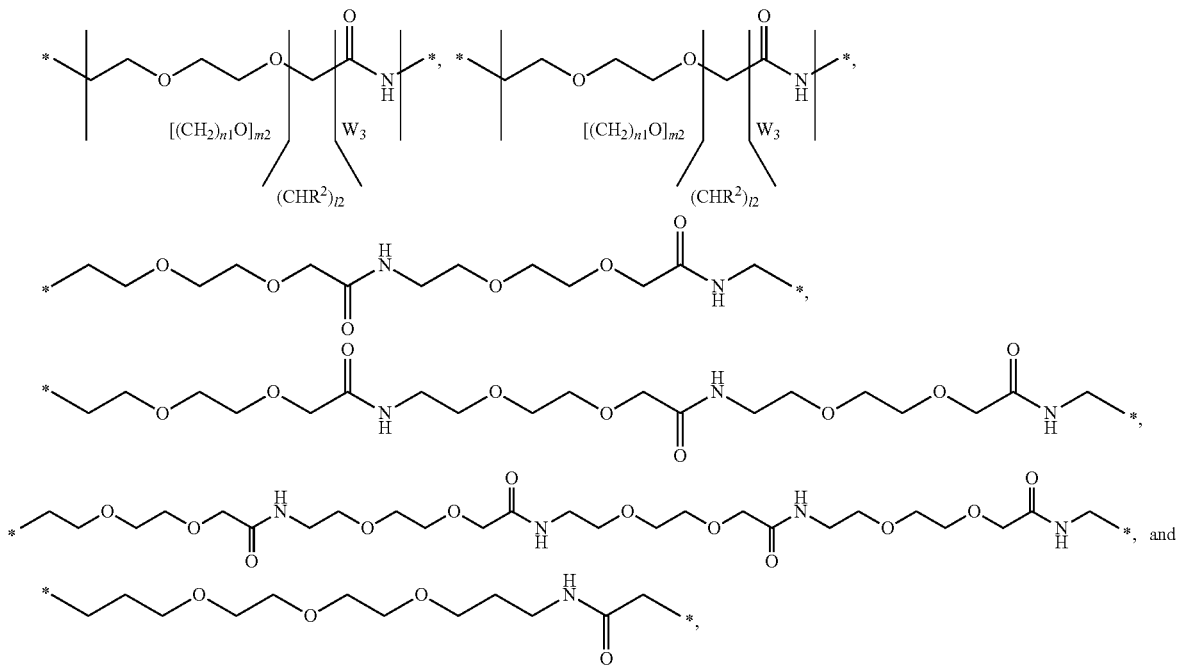
wherein * is intended to denote a point of attachment, ie, an open bond.
82. The conjugate of any one of embodiments 63-81, wherein $X_4$ is a valence bond and $W_6$ is selected from either pyrrolidine-2,5-dione, —NHC(O)CH*CH$_2$COOH or —NHC(O)CH$_2$CH*COOH wherein (*) indicates the attachment point from the carbon atom of CH to GH.
83. The conjugate of any one of embodiments 63-82 wherein B is selected from
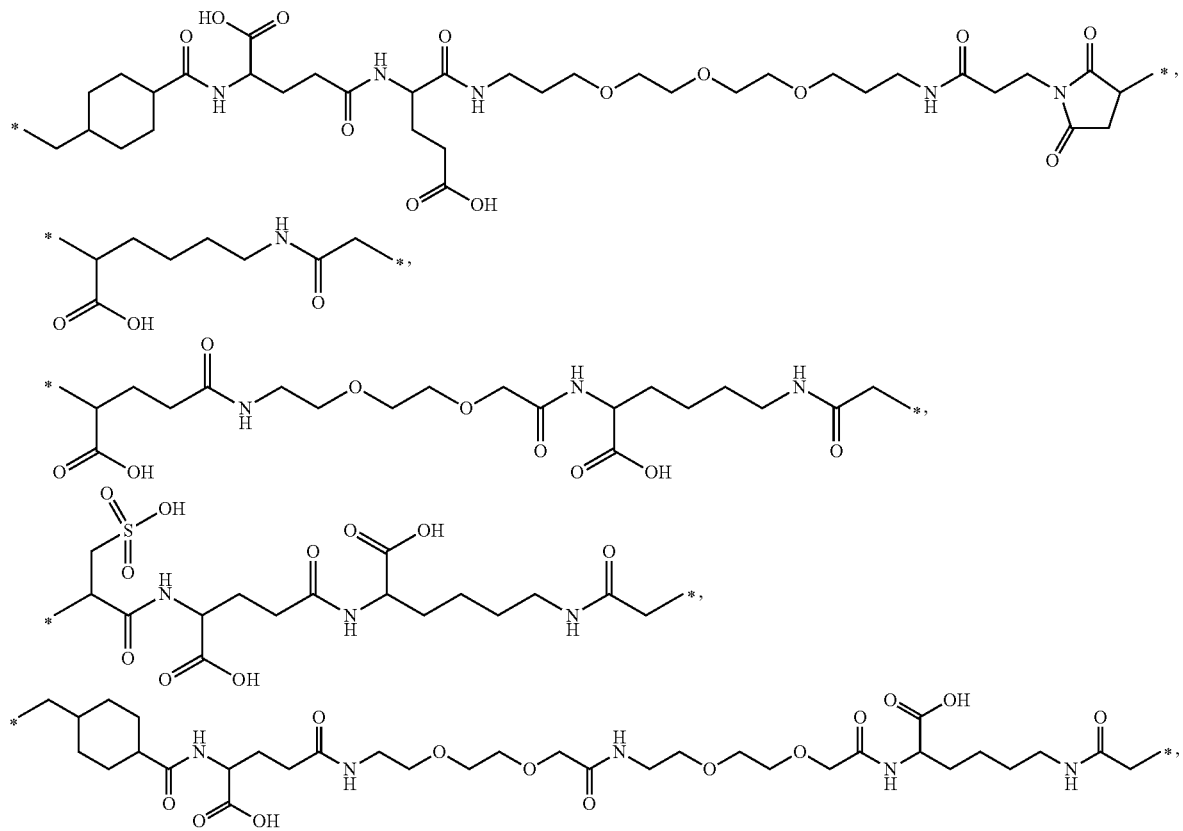

177    178
-continued
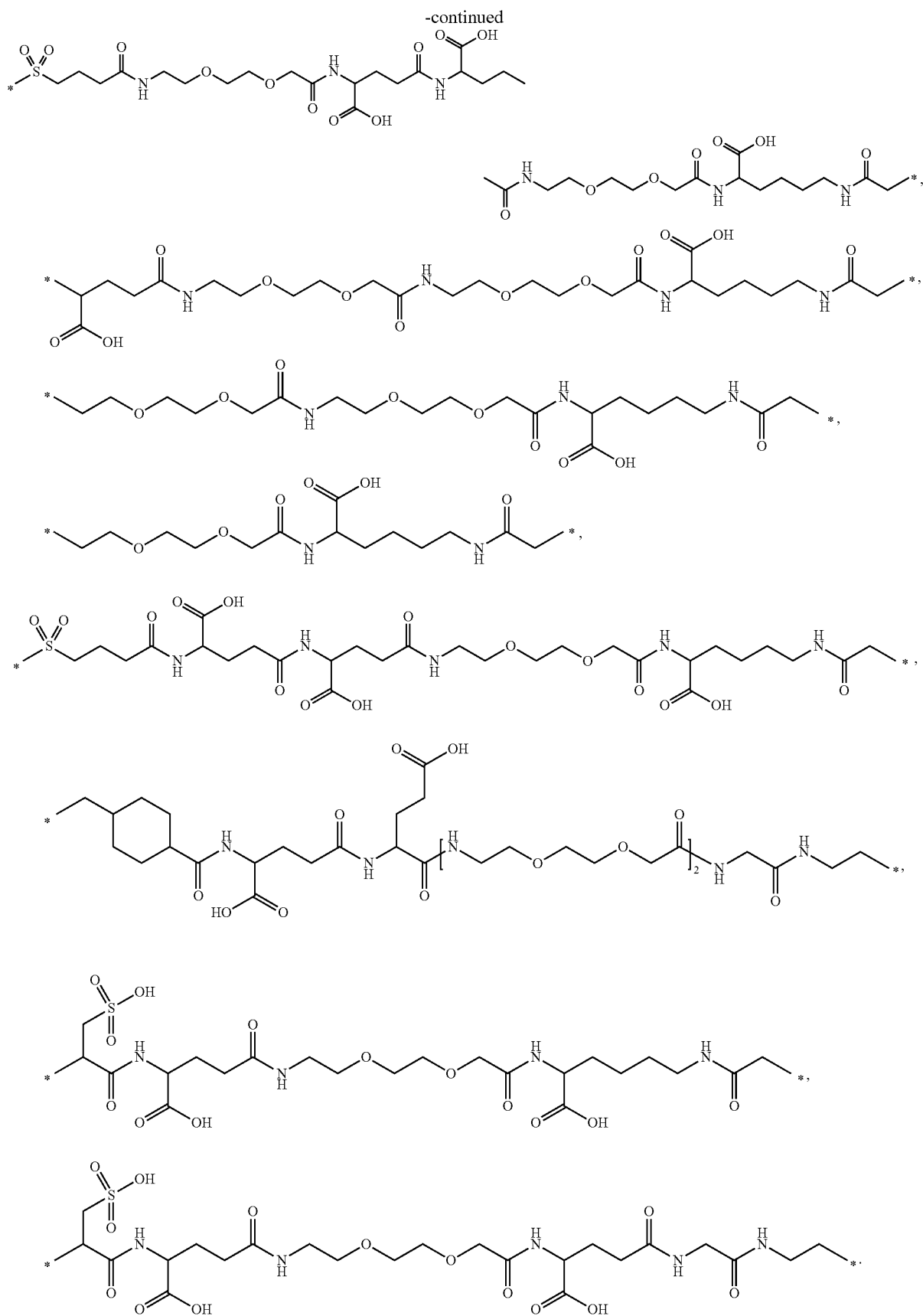

84. The conjugate of any one of embodiments 1-83, wherein one albumin binding residue (A) via a hydrophilic spacer (B) is linked to said GH.
85. The conjugate of any one of embodiments 63-84, wherein said compound is selected from
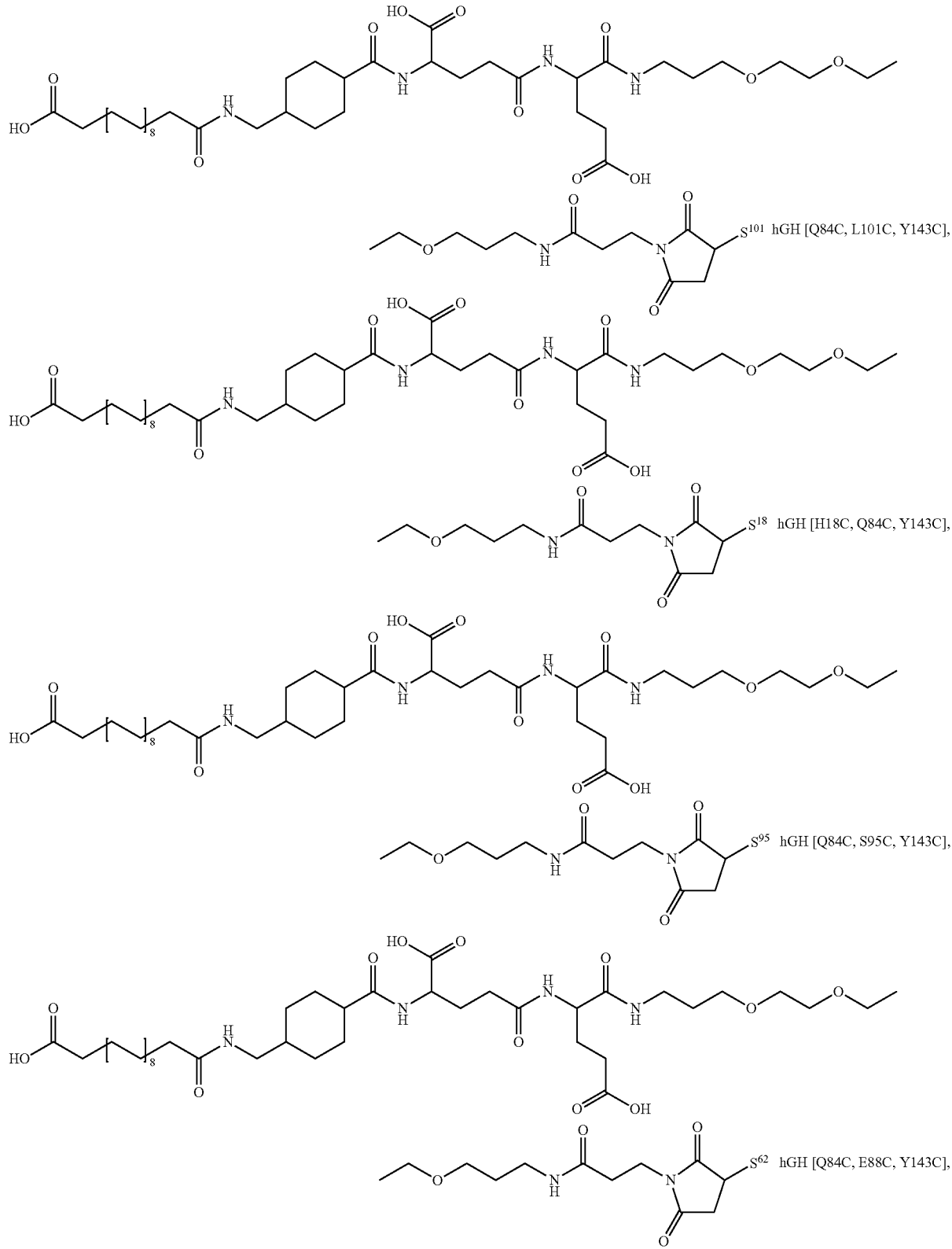

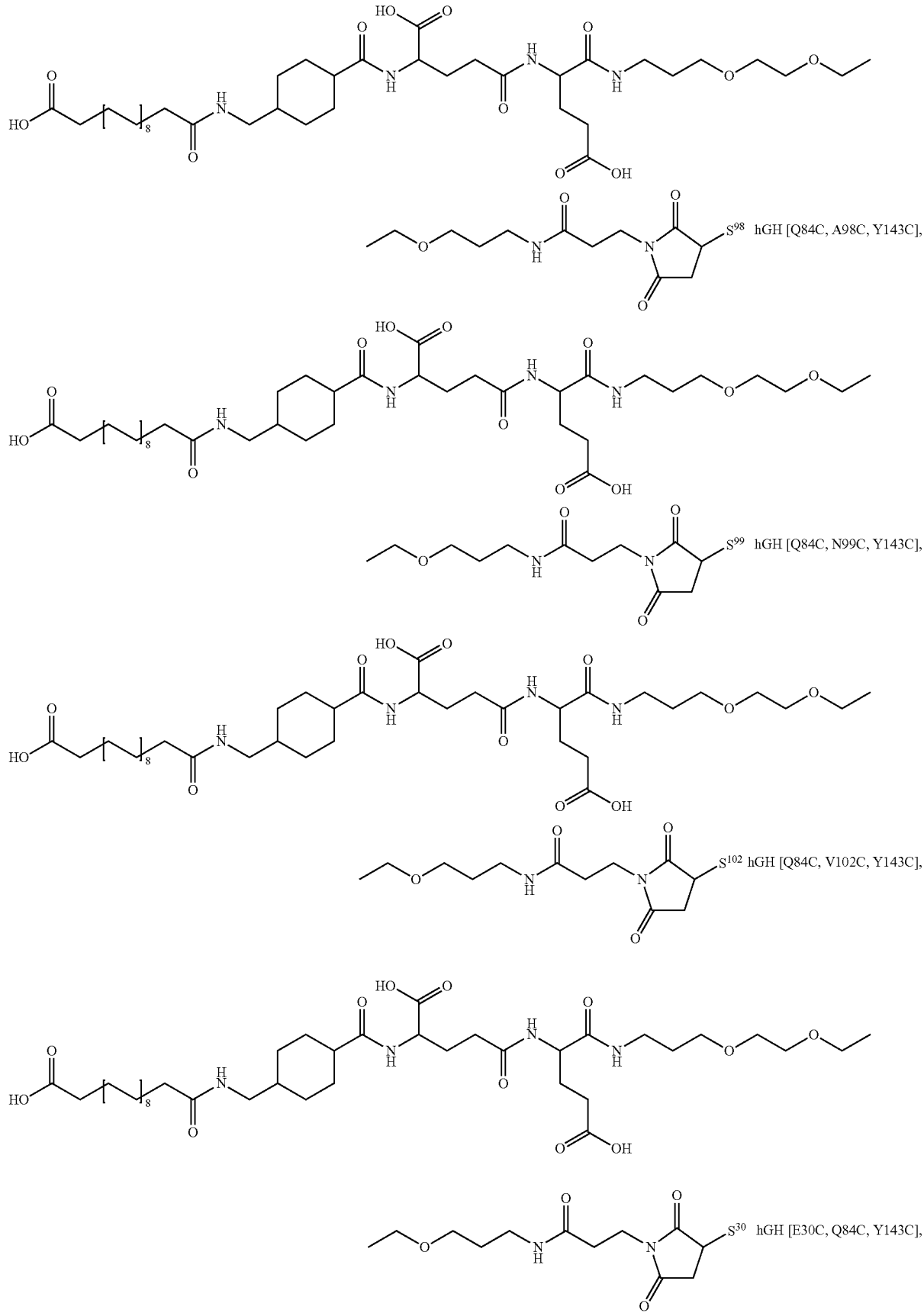

-continued
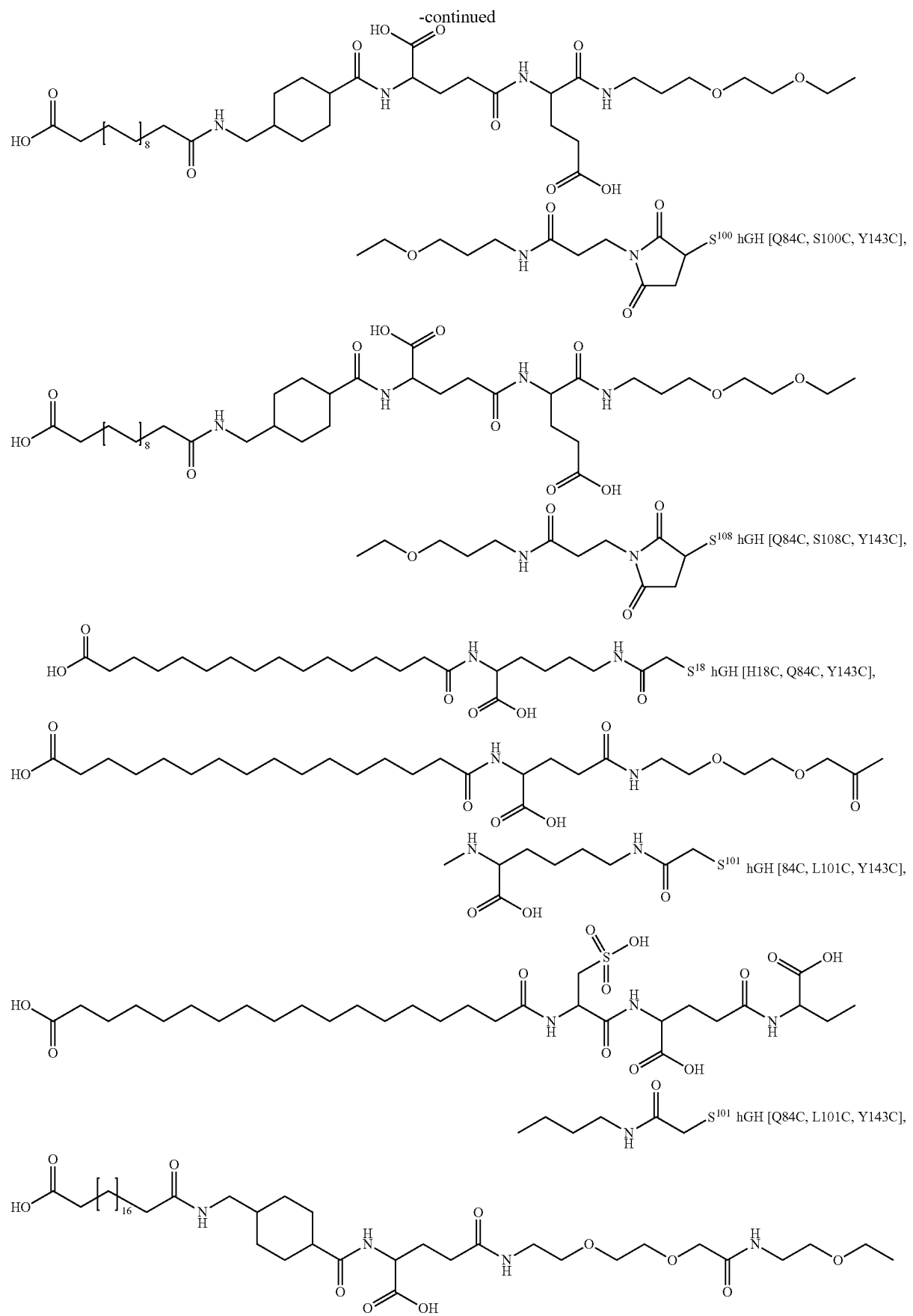

-continued
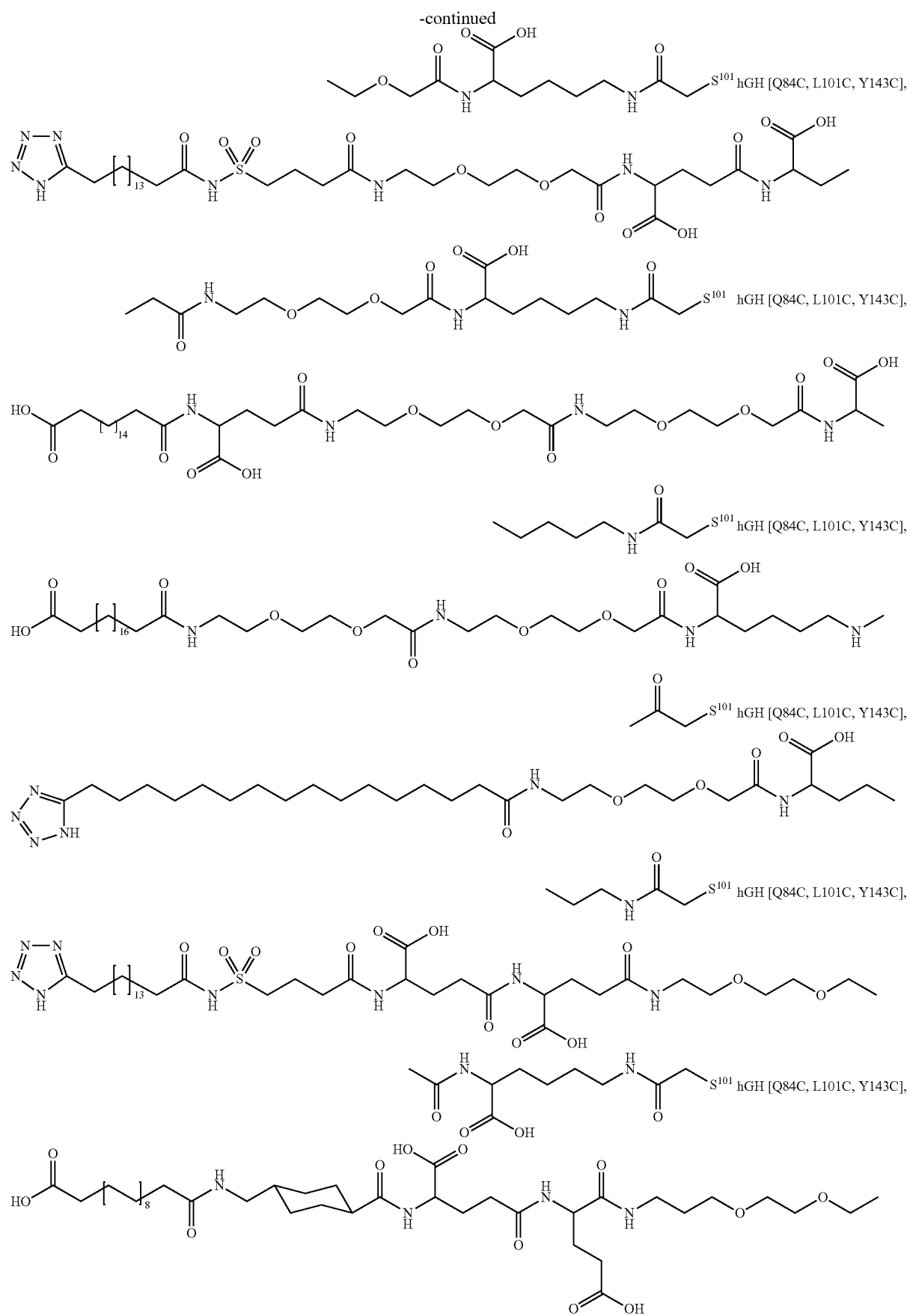

-continued
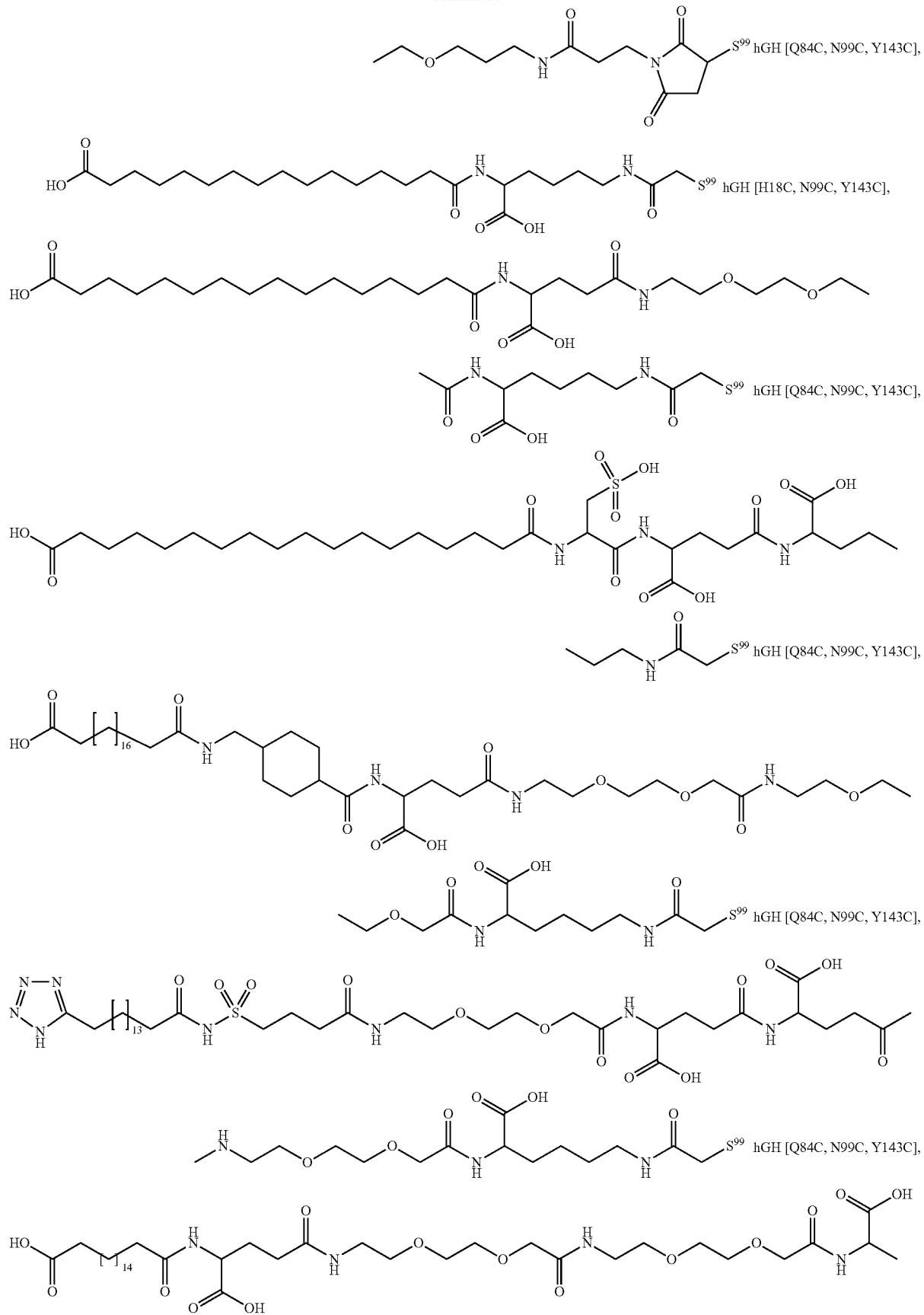

-continued

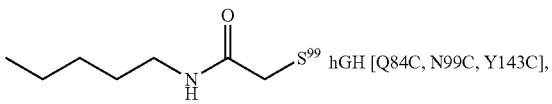
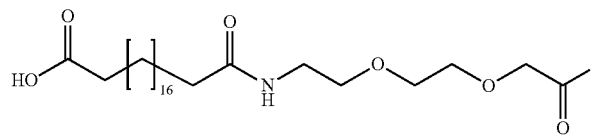
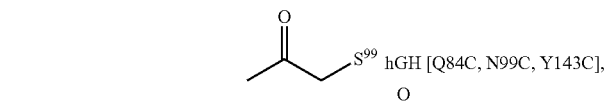
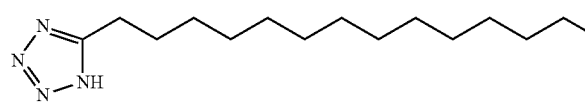
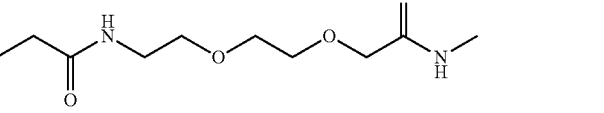
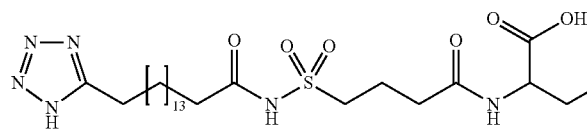
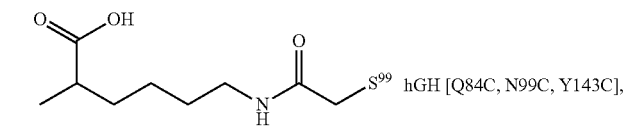
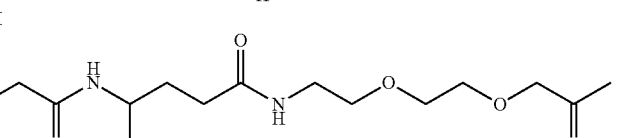
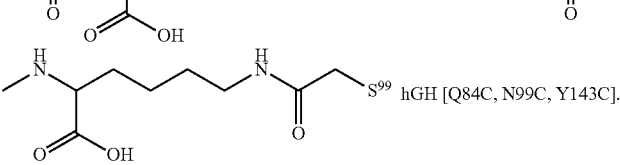

86. The conjugate of any one of embodiments 1-85 wherein the hydrophilic spacer has mLog P<0.

87. The conjugate of any one of embodiments 1-86, wherein the molar weight of said hydrophilic spacer is in the range from 80 D to 1500 D or in the range from 300 D to 1100 D.

88. The conjugate of any one of embodiments 1-87, wherein said albumin binding residue is a lipophilic residue.

89. The conjugate of any one of embodiments 1-88, wherein said albumin binding residue binds non-covalently to albumin.

90. The conjugate of any one of embodiments 1-89, wherein said albumin binding residue is negatively charged at physiological pH.

91. The conjugate of any one of embodiments 1-90, wherein said albumin binding residue has a binding affinity towards human serum albumin that is below about 10 μM or below about 1 μM.

92. The conjugate of any one of embodiments 1-91, wherein said albumin binding residue is selected from a straight chain alkyl group, a branched alkyl group, a group which has an ω-carboxylic acid group or an ω-carboxylic acid isoster.

93. The conjugate of any one of embodiments 1-92, wherein said albumin binding residue has from 6 to 40 carbon atoms, from 8 to 26 carbon atoms or from 8 to 20 carbon atoms.

94. The conjugate of any one of embodiments 1-93, wherein said albumin binding residue is a peptide, such as a peptide comprising less than 40 amino acid residues.

95. The conjugate of any one of embodiments 1-94, wherein two albumin binding residues (A) via a hydrophilic spacer (B) is linked to said GH.

96. The conjugate of any one of embodiments 1-95 for use in therapy.

97. A pharmaceutical composition comprising a conjugate of any one of embodiments 1-95, optionally in combination with a pharmaceutical acceptable excipient.

98. A pharmaceutical composition of embodiment 97, wherein said composition can be administered through lingual, sublingual, buccal, in the mouth, oral, in the stomach and intestine, nasal, pulmonary, epidermal, dermal, transdermal, and parenteral to patients.

99. A method of treating growth hormone deficiency (GHD), the method comprising administrating to a patient in need thereof an effective amount of a therapeutically effective amount of a conjugate of any one of embodiments 1-95.

100. A method of treating Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short children born short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in e.g. hand, knee, or shoulder; patients having or going through distraction oteogenesis; patients after hip or discus replacement, meniscus repair, spinal fusions or prosthesis fixation, such as in the knee, hip, shoulder, elbow, wrist or jaw; patients into which osteosynthesis material, such as nails, screws and plates, have been fixed; patients with non-union or mal-union of fractures; patients after osteatomia, e.g. from tibia or $1^{st}$ toe; patients after graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Crohn's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; short stature due to glucucorticoid treatment inchildren, the acceleration of the healing of muscle tissue, nervous tissue or wounds; the acceleration or improvement of blood flow to damaged tissue; or the decrease of infection rate in damaged tissue, the method comprising administrating to a patient in need thereof an effective amount of a therapeutically effective amount of a conjugate of any one of embodiments 1-95.

101. The use of a conjugate of any one of embodiments 1-95 in the manufacture of a medicament for the treatment of growth hormone deficiency (GHD).

102. The use of a conjugate of any one of embodiments 1-95 in the manufacture of a medicament for the treatment of Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short children born short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in, e.g., hand, knee, or shoulder; patients having or going through distraction oteogenesis; patients after hip or discus replacement, meniscus repair, spinal fusions or prosthesis fixation, such as in the knee, hip, shoulder, elbow, wrist or jaw; patients into which osteosynthesis material, such as nails, screws and plates, have been fixed; patients with non-union or mal-union of fractures; patients after osteatomia, e.g., from tibia or $1^{st}$ toe; patients after graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Crohn's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; short stature due to glucucorticoid treatment inchildren, the acceleration of the healing of muscle tissue, nervous tissue or wounds; the acceleration or improvement of blood flow to damaged tissue; or the decrease of infection rate in damaged tissue.

103. A compound of formula (III)

$$A\text{-}W\text{—}B1\text{-}U \quad (III)$$

wherein A represent an albumin binding residue,

B1 represents a hydrophilic spacer,

W is a chemical group linking A and B1, and U represent a conjugating moiety.

104. The compound according to embodiment 103, wherein A and W are as defined in any of the above embodiments.

105. The compound according to embodiment 103 or embodiment 104, wherein U comprises or consists of an aryl, an heteraryl, a substituted malimide or a pyrrolidine-2,5-dione such as —NHC(O)CH$_2$CH$_2$-pyrrolidin-2,5-dione.

106. The compound according to embodiment 103 or embodiment 104, wherein U comprises D1-(CH$_2$)$_{16}$-D2, wherein D1 and D2 are independently selected from —O—, —N(R6)-, —NC(O)R7- or a valence bond; wherein R6 and R7 independently represent hydrogen or C$_{1-6}$-alkyl.

107. The compound according to embodiment 103 or embodiment 104, wherein U comprises or consists of a leaving group, such as Cl, Br, I, —OH, —OS(O)$_2$Me, —OS(O)$_2$CF$_3$, —Ots.

108. The compound according to embodiments 107, wherein the leaving group is a halogen compound selected from Cl, Br and I, preferably Br.

109. The compound according to embodiment 103 or embodiment 104, wherein U comprises or consists of an allyl amine (H$_2$C=CH—CH$_2$—NH$_2$), such as —C(O)NHCH$_2$—CH=CH$_2$.

110. The compound according to embodiment 103 or embodiment 104, wherein U comprises or consists of an amine, such as —NH$_2$.

111. The compound according to any of the embodiments 103-110, wherein the therapeutic compound is a polypeptide.

112. The compound according to any of the embodiments 103-110, wherein the therapeutic compound is a polypeptide with a single free cystine.

113. The compound according to embodiment 103 or embodiment 104, wherein U comprises or consists of an aldehyde, such as —CHO.

114. The compound according to any of the embodiment 103-113, wherein the hydrophilic spacer B1 has the formula

—X$_1$—X$_2$—X$_3$—X$_4$— wherein

X$_1$ is —W$_1$—[(CHR$^1$)$_{l1}$—W$_2$]$_{m1}$—{[(CH$_2$)$_{n1}$E1]$_{m2}$—[(CHR$^2$)$_{l2}$—W$_3$]$_{m3}$}$_{n2}$—,

X$_2$ is —[(CHR$^3$)$_{l3}$—W$_4$]$_{m4}$—{[(CH$_2$)$_{n3}$E2]$_{m5}$—[(CHR$^4$)$_{l4}$—W$_5$]$_{m6}$}$_{n4}$—,

X$_3$ is —[(CHR$^5$)$_{l5}$]$_{m7}$—,

X$_4$ is a valence bond, l1, l2, l3, l4, and l5 independently are selected from 0-16, m1, m3, m4, m6 and m7 independently are selected from 0-10, m2 and m5 independently are selected from 0-25, n1, n2, n3 and n4 independently are selected from 0-16, $R^1$, $R^2$, $R^3$, $R^4$ and $R^5$ independently are selected from hydrogen, —C(O)OH, —C(O)NH$_2$, —S(O)OH, —S(O)$_2$OH, —NH—C(=NH)—NH$_2$, $C_{1-6}$-alkyl, aryl or hetaryl; wherein the alkyl, aryl and hetaryl groups optionally are substituted with halogen, —C(O)OH, —C(O)NH$_2$, —S(O)OH, —S(O)$_2$OH, —CN or —OH, E1 and E2 independently are selected from —O—, —N($R^6$)—, —N(C(O)$R^7$)— or a valence bond; wherein $R^6$ and $R^7$ independently represent hydrogen or $C_{1-6}$-alkyl, $W_1$ to $W_5$ independently are selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s2}$—, —C(O)—, —C(O)O—, —OC(O)—, or a valence bond; wherein s2 is 0 or 1.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

Abbreviations:
amu=atomic mass units
CV=column volumes
hr(s)=hour(s)
Hz=hertz
L=liter(s)
M=molar
mbar=millibar
mg=milligram(s)
min.=minute(s)
mL=milliliter(s)
mM=millimolar
mm=milimeter(s)
mmol=millimole(s)
nmol=nanomole(s)
mol=mole(s)
μL=microliters
N=normal
nm=nanometer(s)
sec=second(s)
ppm=parts per million
ESI=electrospray ionization
i.v.=intravenous
m/z=mass to charge ratio
MS=mass spectrometry
HPLC=high pressure liquid chromatography
RP=reverse phase
HPLC-MS=high pressure liquid chromatography—mass spectrometry
NMR=nuclear magnetic resonance spectroscopy
p.o.=per oral
rt or RT=room temperature
s.c.=subcutaneous
tr=retention time
Boc=tert butyloxycarbonyl
O-t-Bu=tert butyl ester
t-Bu=tert butyl
Boc-4-ABZ—OH=4-tert-Butoxycarbonylamino-benzoic acid
DCM=dichloromethane, CH$_2$Cl$_2$, methylenechloride
DIC=diisopropylcarbdiimide
DIPEA=N,N-diisopropylethylamine
DMF=N,N-dimethylformamide
DMSO=dimethylsulfoxide
DTT=dithiothreitol
EDAC=1-ethyl-3-(3-dimethylaminopropyl)carbodiimide hydrochloride
Et$_2$O=diethyl ether
EtOAc=ethyl acetate
Fmoc=9H-fluoren-9-ylmethoxycarbonyl
Fmoc-Glu-O-t-Bu=N-Fmoc-glutamic acid-1-t-butyl ester
Fmoc-Lys(Mtt)-OH=(S)-6-[(Diphenyl-p-tolyl-methyl)-amino]-2-(9H-fluoren-9-ylmethoxycarbonylamino)-hexanoic acid
Fmoc-OEG-OH=(2[2-(Fmoc-amino)ethoxy]ethoxy)acetic acid
OEG=(2[2-(amino)ethoxy]ethoxy)acetyl
Fmoc-Thx-OH=N-Fmoc-trans-4-aminomethylcyclohexan-carboxylic acid
H$_2$O=water
HOBt=1-hydroxybenzotriazole
MeCN=acetonitrile
MeOH=methanol
MTP=3-methyl-thio-1-propanol
NaCl=sodium chloride
NaOH=sodium hydroxide
NMP=N-methylpyrrolidin-2-one
OEG=(2[2-(amino)ethoxy]ethoxy)acetic acid
TFA=trifluoroacetic acid
THF=tetrahydrofuran
TIS=triisopropylsilane
CDCl$_3$=deuterio chloroform
CD$_3$OD=tetradeuterio methanol
DMSO-d$_6$=hexadeuterio dimethylsulfoxide
TNBS=trinitrobenzensulfonic acid
TSTU=O—(N-Succinimidyl)-1,1,3,3-tetramethyl uranium tetrafluoroborate The examples also make use of the following general methods:

General Method for Preparing a hGH Compounds.

The gene coding for the growth hormone compound was inserted recombinantly into a plasmid vector. A suitable *E. coli* strain was subsequently transformed using the plasmid vector. hGH or GH variants may be expressed with an N-terminal methionine or as a MEAE fusion from which the MEAE sequence is subsequently cleaved off.

Cell stock was prepared in 25% glycerol and stored at −80° C. Glycerol stock strain was inoculated into LB plates and subsequently incubated at 37° C. overnight. The content of each plate was washed with LB medium and diluted into 500 mL LB medium for expression.

The cultures were incubated at 37° C. with shaking at 220 rpm until $OD_{600}$ 0.6 was reached. Succeeding induction was performed using 0.2 mM IPTG at 25° C. for 6 hours. Cells were finally harvested by centrifugation.

Cells were subsequently suspended in 10 mM Tris-HCl, pH=9.0 containing 0.05% Tween 20, 2.5 mM EDTA, 10 mM cysteamine and 4M urea, and disrupted using a cell disrupter at 30 kPSI. The supernatant was collected by centrifugation and subsequently subjected to chromatographic purification.

The purification was performed using ion-exchange chromatography and hydrophibic interaction, followed by removal of the peptide tag using human dipeptidyl peptidase I (hDPPI) expressed from CHO cell. Final purification was achieved by isoprecipitation and ion-exchange chromatography. The purification could also be achieved by using but not limited to ion-exchange chromatography, hydrophobic interaction chromatography, affinity chromatography, size exclusion chromatography and membrane based separation techniques known to a person skilled in the art.

Protein Chemical Characterization of Purified Growth Hormone Compounds.

The intact purified protein was analysed using MALDI-MS. The observed mass corresponded to the theoretical mass deduced from the amino acid sequence. The expected linkage disulfide bonds may be demonstrated by peptide mapping using trypsin and AspN digestion followed by MALDI-MS analysis of the digest before and after reduction of the disulfide bonds with DTT.

Assay for Measuring Rate of Protease Degradation of GH and hGH Compound Conjugates The compound of interest is digested by a relevant protease (Trypsin, Chymotrypsin, Pepsin, Elastase, Factor VIIa, Factor Xa, Proteinase K, Carboxy peptidase, DPPIV, Neutral Endopeptidase, Granzyme B, Proline-endopeptidase, Staphylococcal peptidase I, Thermolysin, Thrombin, Arg-C proteinase, Asp-N endopeptidase, Caspase 1-10, Clostripain, Enterokinase, Glutamyl endopeptidase, Granzyme B, LysC, LysN, Proline-endopeptidase and Staphylococcal peptidase I or tissue extracts.) in an appropriate buffer (e.g. PBS or ammonium bicarbonate) at 37° C. for up till 24 hrs. Proteolytic degradation is assessed by a HPLC assay.

Proteolytic Digestion:

100 µL of test compound solution at 1 mg/mL in ammonium bicarbonate buffer is degraded by enzyme for up till 24 hrs at 37° C. Sub-samples are taken to various time points and the proteolytic reaction is stopped by acidifying the sample by 10 times dilution into 1% TFA. These diluted samples are analysed by reversed phase HPLC to estimate the degree of proteolytic digestion.

HPLC Method:

10 µL of the above solution is injected on a reversed phase Vydac C4 2×150 mm column eluted with a linear gradient from 0.1% TFA in water to 100% acetonitrile containing 0.1% TFA over a period of 30 min at a flow rate of 0.2 ml/min. Detection of peaks is performed at 214 nm UV absorption. Percentage (%) intact compound at time point t=T is calculated from the peak area at time point t=T ($A_T$) and the peak area at t=0 ($A_0$) as ($A_T/A_0$)×100%. Percentage (%) intact compound is plotted against time using GraphPad Prisms software ver. 5.01. Half life ($T_{1/2}$) is calculated as one phase decay also by GraphPad Prism software. Examples of enzymes that may be used are elastase (Sigma from porcine pancrease) and chymotrypsin (Roche sequencing grade). Example of buffer is 50 mM ammonium bicarbonate, pH=8.5.

Capillary Electrophoresis:

Capillary electrophoresis was carried out using an Agilent Technologies 3DCE system (Agilent Technologies). Data acquisition and signal processing were performed using Agilent Technologies 3DCE ChemStation. The capillary was a 64.5 cm (56.0 cm efficient length) 50 µm i.d. "Extended Light Path Capillary" from Agilent. UV detection was performed at 200 nm (16 nm Bw, Reference 380 nm and 50 nm Bw). The running electrolyte was phosphate buffer 50 mM pH 7 (method A). The capillary was conditioned with 0.1M NaOH for 3 min, then with Milli-Q water for 2 min and with the electrolyte for 3 min. After each run, the capillary was flushed with milli-Q water for 2 min, then with phosphoric acid for 2 min, and with milli-Q water for 2 min. The hydrodynamic injection was done at 50 mbar for 4.0 sec. The voltage was +25 kV. The capillary temperature was 30° C. and the runtime was 10.5 min.

Maldi-T of Mass Spectrometry:

Molecular weights were determined using the Autoflex Maldi-T of instrument (Bruker). Samples were prepared using alfa-cyano-4-hydroxy-cinnamic acid as matrix.

RP-HPLC:

RP-HPLC analysis was performed on a Agilent 1100 system using a Vydac 218TP54 4.6 mm×250 mm 5 µm C-18 silica column (The Separations Group, Hesperia). Detection was by UV at 214 nm, 254 nm, 280 nm and 301 nm. The column was equilibrated with 0.1% trifluoracetic acid/$H_2O$ and the sample was eluted by a suitable gradient of 0 to 90% acetonitrile against 0.1% trifluoracetic acid/$H_2O$.

LC-MS:

LC-MS analysis was performed on a PE-Sciex API 100 or 150 mass spectrometer equipped with two Perkin Elmer Series 200 Micropumps, a Perkin Elmer Series 200 autosampler, an Applied Biosystems 785A UV detector and a Sedex 75 Evaporative Light scattering detector. A Waters Xterra 3.0 mm×50 mm 5µ C-18 silica column was eluted at 1.5 ml/min at room temperature. It was equilibrated with 5% MeCN/0.1% TFA/$H_2O$ and eluted for 1.0 min with 5% MeCN/0.1% TFA/$H_2O$ and then with a linear gradient to 90% MeCN/0.1% TFA/$H_2O$ over 7 min. Detection was by UV detection at 214 nm and Evaporative light Scattering. A fraction of the column eluate was introduced into the ion-spray interface of a PE-Sciex API 100 mass spectrometer. The mass range 300-2000 amu was scanned every 2 seconds during the run.

Quantification of Protein:

Protein concentrations were estimated by measuring absorbance at 280 nm using a NanoDrop ND-1000 UV-spectrofotometer.

Enzymatic Peptide Mapping for Determination of Site(s) of Derivatization:

Peptide mapping was performed using Asp-N digestion of the reduced and alkylated protein. First the protein was treated with DTT and iodoacetamide according to standard procedures. The alkylated product was purified using HPLC. Subsequently the alkylated purified product was digested overnight with endoprotease Asp-N (Boehringer) at an enzyme:substrate ratio of 1:100. The digest was HPLC separated using a C-18 column and standard TFA/MeCN buffer system. The resulting peptide map was compared to that of underivatized hGH and fractions with different retention times were collected and further analyzed using Maldi-tof mass spectrometry.

SDS Page:

SDS poly-acrylamide gel electrophoresis was performed using NuPAGE 4%-12% Bis-Tris gels (Invitrogen NP0321BOX). The gels were silver stained (Invitrogen LC6100) or Coomassie stained (Invitrogen LC6065) and where relevant also stained for PEG with barium iodide as described by M. M. Kurfurst in *Anal. Biochem.* 200(2), 244-248, (1992).

Protein Chromatography:

Protein chromatography was performed on an Äkta Explorer chromatographic system and columns from GE Health Care. Anion exchange was done using a Q-Sepharose HP 26/10 column. Starting buffer was 20 mM triethanolamine buffer pH 8.5 and eluting buffer was starting buffer+0.2 M NaCl. The compounds were typically eluted with a gradient of 0-75% eluting buffer over 15 column volumes. De-salting and buffer exchange was performed using a HiPrep 26/10 column.

TNBS Test

A solution of 10% DIPEA in DMF (solution 1) and a solution of 1 M aqueous TNBS (solution 2) was prepared. A few resin beads were placed in a small test tube and 1-3 drops of each solution (1 and 2) were added. After a short mixing the mixture was left at room temperature for 10 min. and the beads inspected. Intensely orange or red beads indicate positive results (i.e presence of free amines); yellow or slightly orange beads indicate slightly positive and colorless beads are negative.

Log P Calculation

Log P values can be calculated as mLog P and/or cLog P for the albumin binder part and/or the hydrophilic spacer part using published algorithms (*J. Am. Chem. Soc.*, 86, 5175-5180, (1964) "A New Substituent Constant, $\notin$, Derived from Partition Coefficients", C. A. Lipinski et al. *Advanced Drug Delivery Reviews*, 23, 3-25 (1997), "Experimental and Computational Approaches to Estimate Solubility and Permeability in Drug Discovery and Development Settings" and I. Moriguchi, S. Hirono, I. Nakagome, H. Hirano, *Chem. and Pharm.* 42, 976-978, (1994) "Comparison of Reliability of log P Values for Drugs Calculated by Several Methods". Herein clog P—Pomona College log P (octanol/water partition coefficient) is calculated with Sybyl 7.0 from Tripos (http://www.tripos.com) version 4.2 of the clog P algorithm and version 22 of its associated fragment database as provided by BioByte Corp (http://www.biobyte.com/).

Preparation of Albumin Binders

Example 1

4-(1H-Tetrazol-16-yl-hexadecanoylsulfamoyl)butanoyl-OEG-γGlu-γGlu-OEG-N$^\in$(C(O)CH$_2$Br) OLys-OH (I)

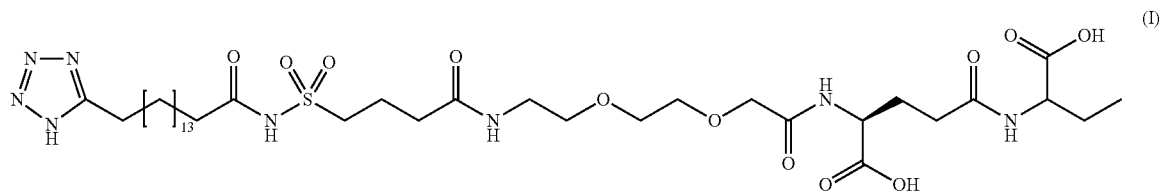

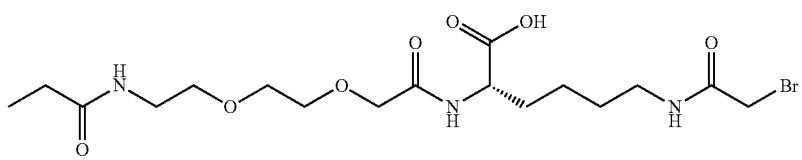

The compound (I) was synthesised on solid support according to scheme 1, in 1 mM scale using standard Fmoc-peptide chemistry on an ABI433 synthetizer. Peptide was assembled on a Fmoc-Lys(MTT)-Wang resin using Fmoc-OEG-OH and Fmoc-Glu-OtBu protected amino acids. 4-(16-1H-Tetrazol-5-yl-hexadecanoylsulfamoyl)butyric acid was manual coupled using DIC/NHS in DCM/NMP, 2 eq. over night, TNBS test showed the reaction to be completed. The resin was then treated with 50 mL DCM/TFA/TIS/water (94:2:2:2) in a flow-through arrangement until the yellow colour disappeared, ~20 min. followed by washing and neutralizing with DIPEA/DMF. Bromo acetic acid (4 mM) in DCM/NMP (1:1) was activated with a 1 mM mixture of NHS and DIC, filtered and added to the resin with addition of further 1 mM of DIPEA. After 1 hr the reaction was completed. The resin was treated with 80 mL TFA/TIS/water (95:2,5:2,5) for 1 hr. Evaporated with a stream of $N_2$, precipitated by addition of $Et_2O$ and washed with $Et_2O$ and dried. Crude product was purified on preparative HPLC (2 runs), with a gradient from 30-80% 0.1 TFA/MeCN against 0.1% TFA in water. Fractions were collected and lyophilized with ~50% MeCN affording compound (I).

TOF-MS: mass 1272.52 (M+1)

Scheme 1

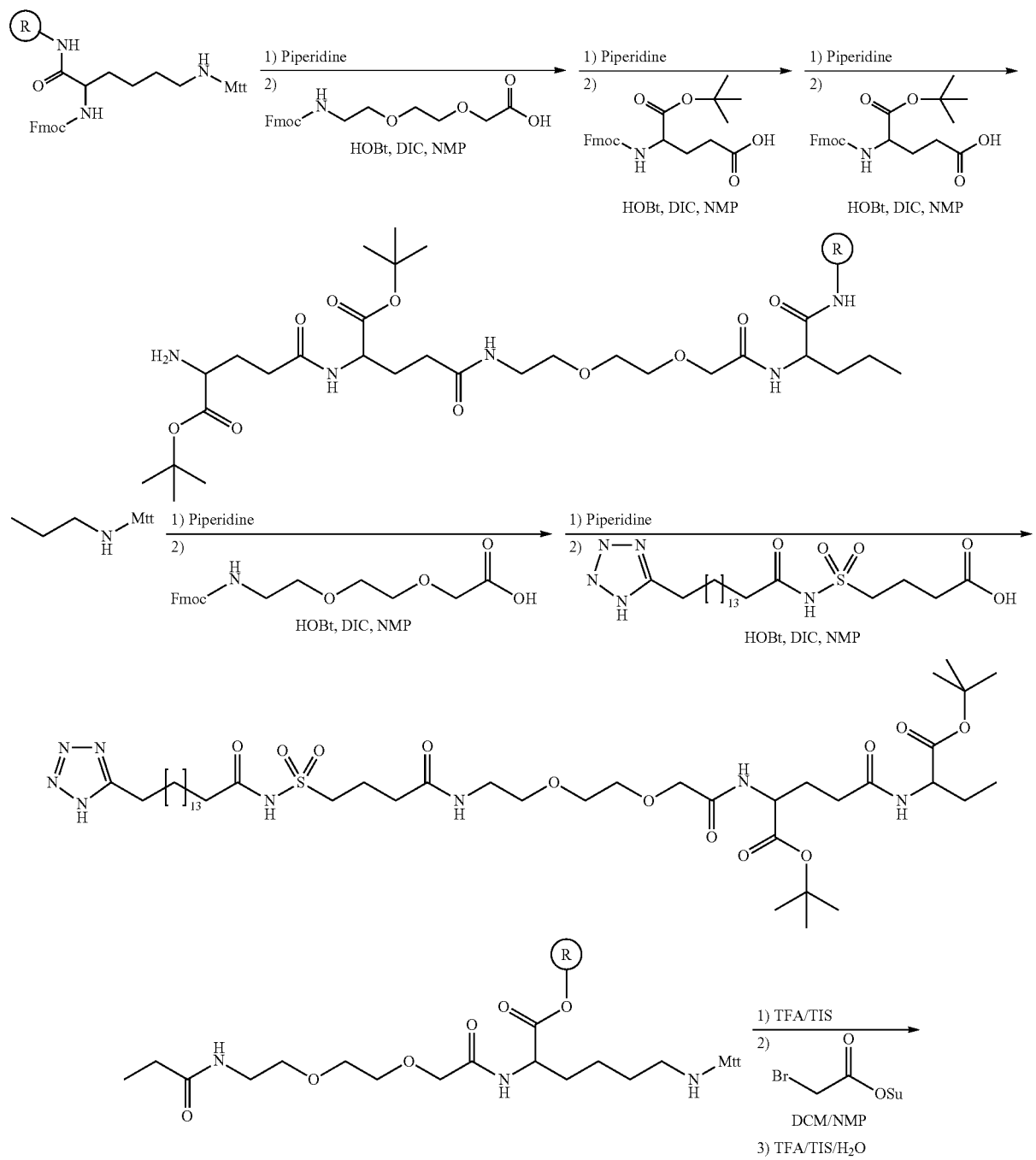

-continued

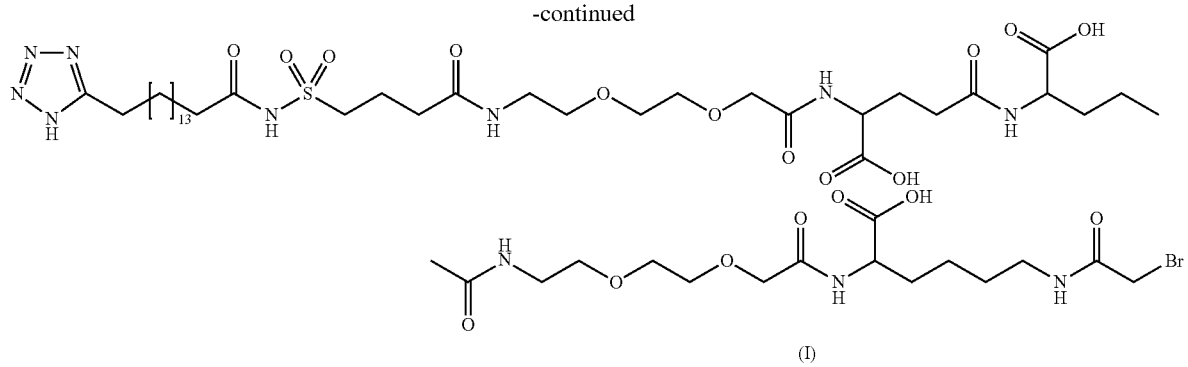

(I)

Example 2

In a similar way as described in Example 1 above the following compound was prepared using Fmoc-Lys(Mtt)-OH and Wang Resin.

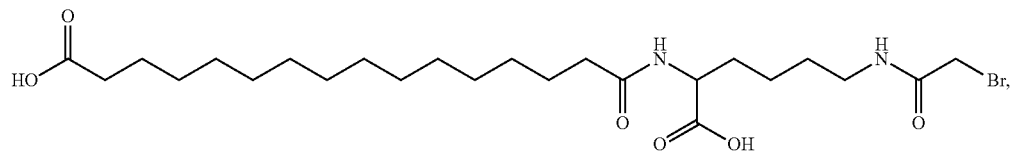 [SMILES: O=C(O)CCCCCCCCCCCCCCC(=O)NC(CCCCNC(=O)CBr)C(=O)O]

TOF-MS: mass 536.52 (M+1)

Example 3

In a similar way as described in Example 1 above the following compound was prepared using Fmoc-Lys(Mtt)-OH and Wang Resin.

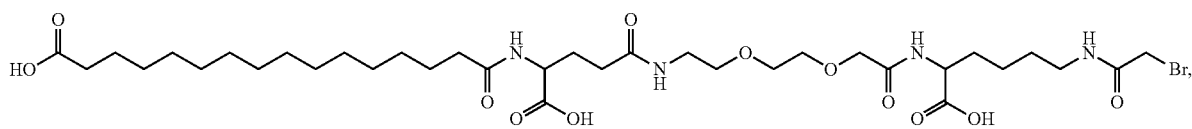 [SMILES: O=C(O)CCCCCCCCCCCCCCC(=O)NC(CCC(=O)NCCOCCOCC(=O)NC(CCCCNC(=O)CBr)C(=O)O)C(=O)O]

TOF-MS: mass 810.80 (M+1)

Example 4

In a similar way as described in Example 1 above the following compound was prepared using Fmoc-Lys(Mtt)-OH and Wang Resin.

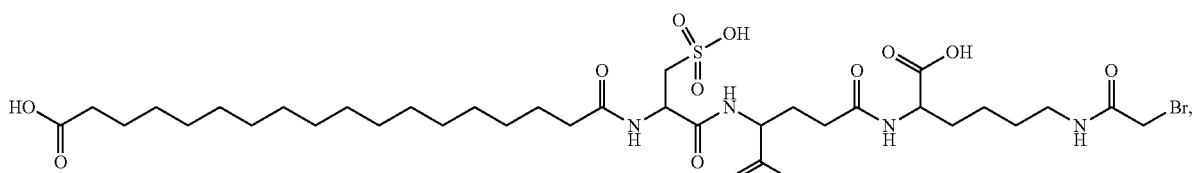

TOF-MS: mass 844.84 (M+1)

Example 5

In a similar way as described in Example 1 above the following compound was prepared using Fmoc-Lys(Mtt)-OH and Wang Resin.

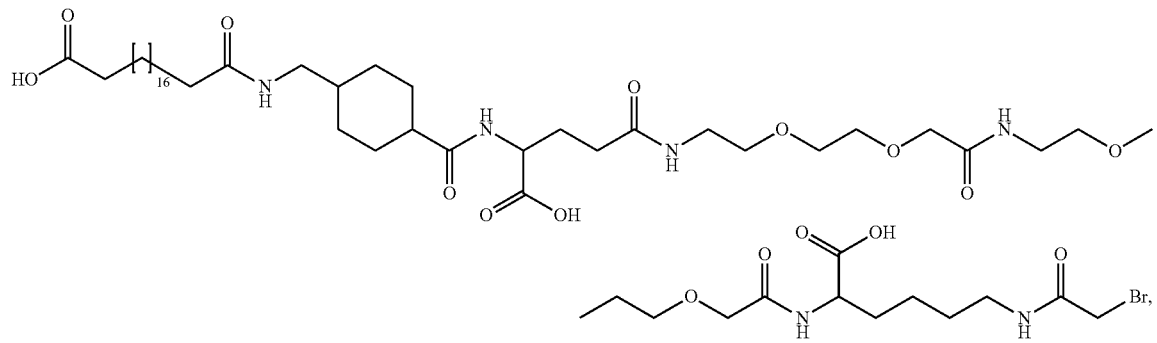

TOF-MS: mass 1151.27 (M+1)

Example 6

In a similar way as described in Example 1 above the following compound was prepared using Fmoc-Lys(Mtt)-OH and Wang Resin.

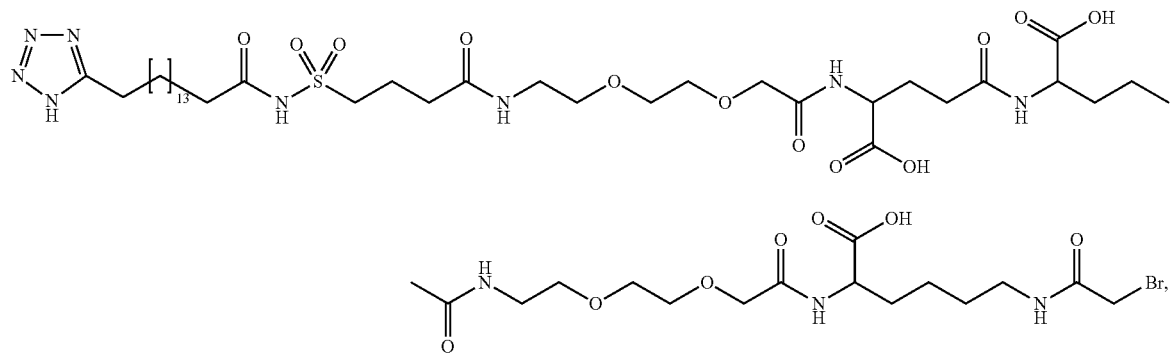

TOF-MS: mass 1272.30 (M+1)

Example 7

In a similar way as described in Example 1 above the following compound was prepared using Fmoc-Lys(Mtt)-OH and Wang Resin.

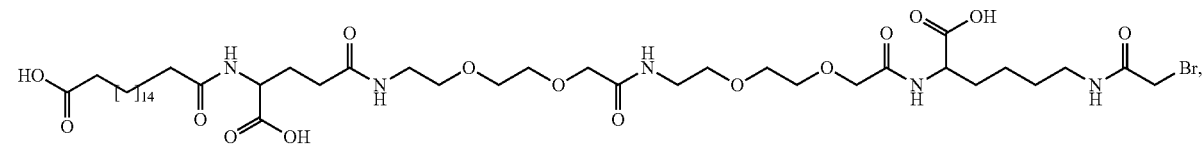

TOF-MS: mass 984.01 (M+1)

Example 8

In a similar way as described in Example 1 above the following compound was prepared using Fmoc-Lys(Mtt)-OH and Wang Resin.

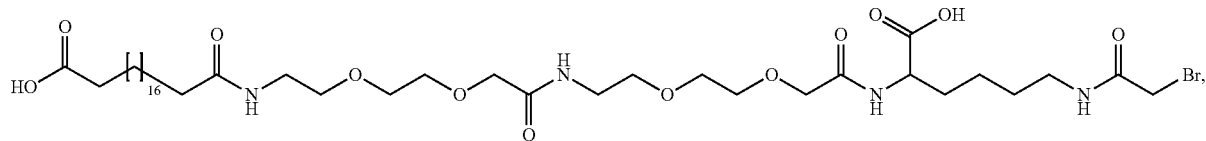

TOF-MS: mass 882.95 (M+1)

Example 9

In a similar way as described in Example 1 above the following compound was prepared using Fmoc-Lys(Mtt)-OH and Wang Resin.

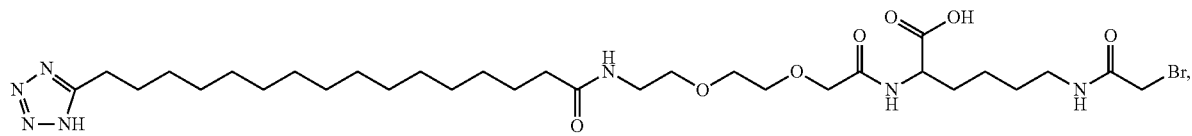 [SMILES: O=C(CBr)NCCCCC(NC(=O)COCCOCCNC(=O)CCCCCCCCCCCCCCCc1nnn[nH]1)C(=O)O]

TOF-MS: mass 782.74 (M+1)

Example 10

In a similar way as described in Example 1 above the following compound was prepared using Fmoc-Lys(Mtt)-OH and Wang Resin.

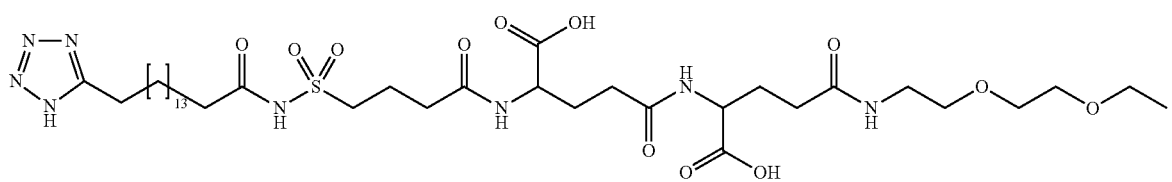

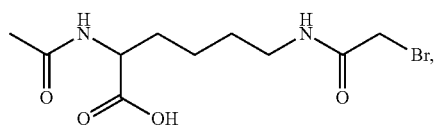

TOF-MS: mass 1127.14 (M+1)

Example 11

In a similar way as described in Example 1 above the following compound was prepared using Fmoc-Lys(Mtt)-OH, iodoacetic acid and Wang Resin.

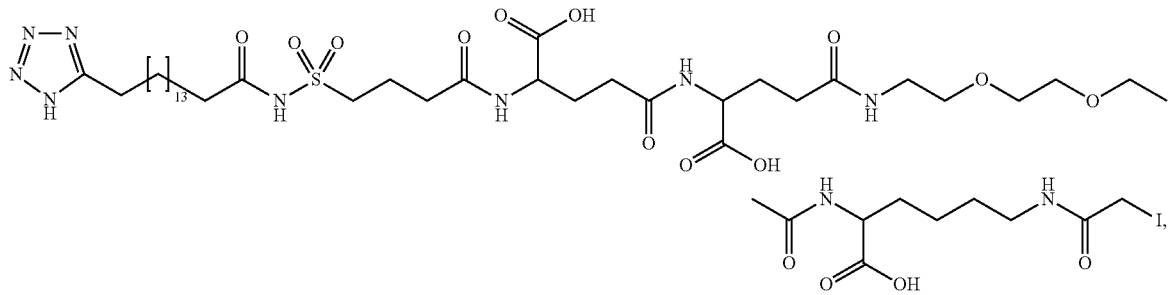

TOF-MS: mass 1174.14 (M+1)

Example 12

In a similar way as described in Example 1 above the following compound was prepared using Fmoc-Lys(Mtt)-OH, chloroacetic acid and Wang Resin.

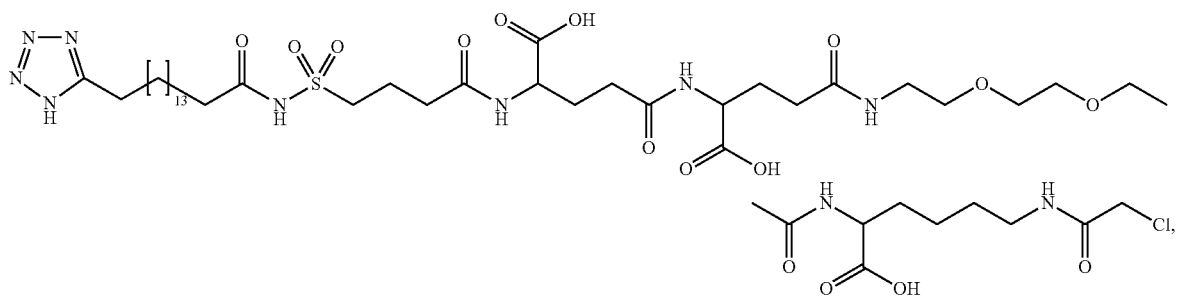

TOF-MS: mass 1061.89 (M+1)

Example 13

(19-carboxynonadecanoyl)-Thx-γGlu-Glu-N-{3-[2-(2-{3-[3-malimidopropionylamino]propoxy}ethoxy)ethoxy]propyl}amide (II)

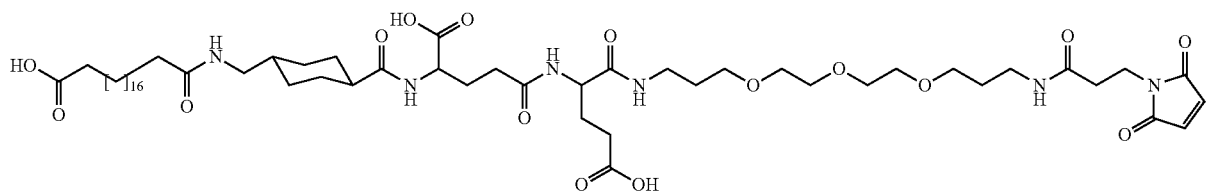

(II)

2-Chlorotrityl resin (2.0 g, 2.6 mmol) was svelled in DCM for 0.5 hr. A solution of 4,7,10-trioxa-1,13-diamine in DCM (30 mL) was added. Resin was stirred at rt for 1 hr. The resin was washed once with DCM, then added a solution of DIPEA:MeOH:DCM (15 mL:15 mL:20 mL). The resin was shaken for 0.5 hr, then washed trice with DCM. Fmoc-Glu(OtBu)—OH, Fmoc-Glu-OtBu and FmocThexOH were then coupled sequentially by standard peptide chemistry as follows: A 0.5 M solution each of Fmoc-AA-OH/DIC/HOBt in NMP (11.7 mL)—was mixed and after 2 min. added to the resin. The resin was shaken for 45 min. at rt. and then washed with 5×NMP and 5×DCM. A solution of Ac₂O/DIPEA/NMP (1:1:5) was added and the resin was stirred at rt for 10 min. The resin was washed (5×NMP and 5×DCM). The resin was then treated with 30% piperidin in NMP for 2×10 min. and finally washed with 5×NMP and 5×DCM. The peptide was then added a 0.25 M solution of eicosanediacid (6 eq) containing 0.125 M HOAt (3 eq), 0.125 M DIC (3 eq) and 0.125 M lutidine (3 eq). The resin was shaken at rt for 2 hrs following by washing with 5×NMP and 8×DCM.

Product was cleaved from the resin using 10% TFA-DCM for 20 min. The resin was filtrated off and treated one more time with 10% TFA-DCM for an additional 20 min. The combined filtrates were collected, and evaporated to dryness.

The dry product from above was dissolved in DMF (6 mL), and added TSTU-activated 3 maleimidopropionic acid (premade by reacting TSTU with was 3 maleimidopropionic acid in DMF (2 mL) for 45 min.) and DIPEA (200 µL). The mixture was stirred at rt. for 1 hr. The reaction mixture was evaporated to dryness and the residue dissolved in 95% TFA-MilliQ water and stirred at rt. for 20 min. The mixture was evaporated to dryness. To the residue was added a minimum of water to precipitate solid. The precipitate was filtered off and recrystallized from MeCN. The crystals were collected and washed extensively with $Et_2O$ affording compound (II) as a white solid.

TOF-MS: mass 1094.39 (M+1).

Example 14

In a similar way as described in Example 1 above and depicted in scheme 2 below the following compound was prepared using Boc-Gly-PAM resin as starting material and mono-tert-butyl-eicosanoic acid, 4-Boc-aminobenzoic acid, Fmoc-Thx-OH, Fmoc-OEG-OH, Fmoc-Glu(O-t-Bu)-OH, Fmoc-Glu(OH)-t-Bu protected amino acids. After mild deprotection, peptide product was cleaved from the resin using 2,2-dimethoxyethylamine followed by deacetalisation using TFA which afford albumin binder (IV).

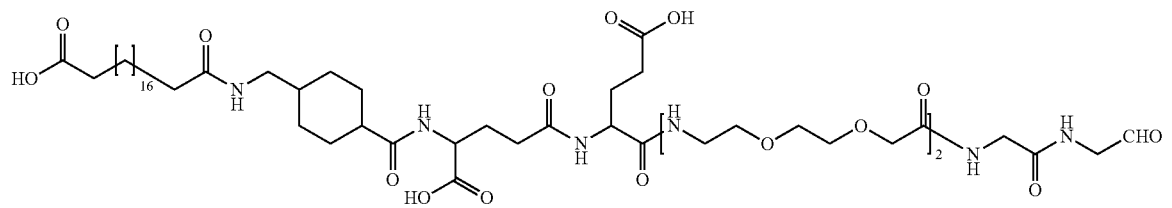

(IV)

TOF-MS: mass 1128.38 (M+1)

Scheme 2:

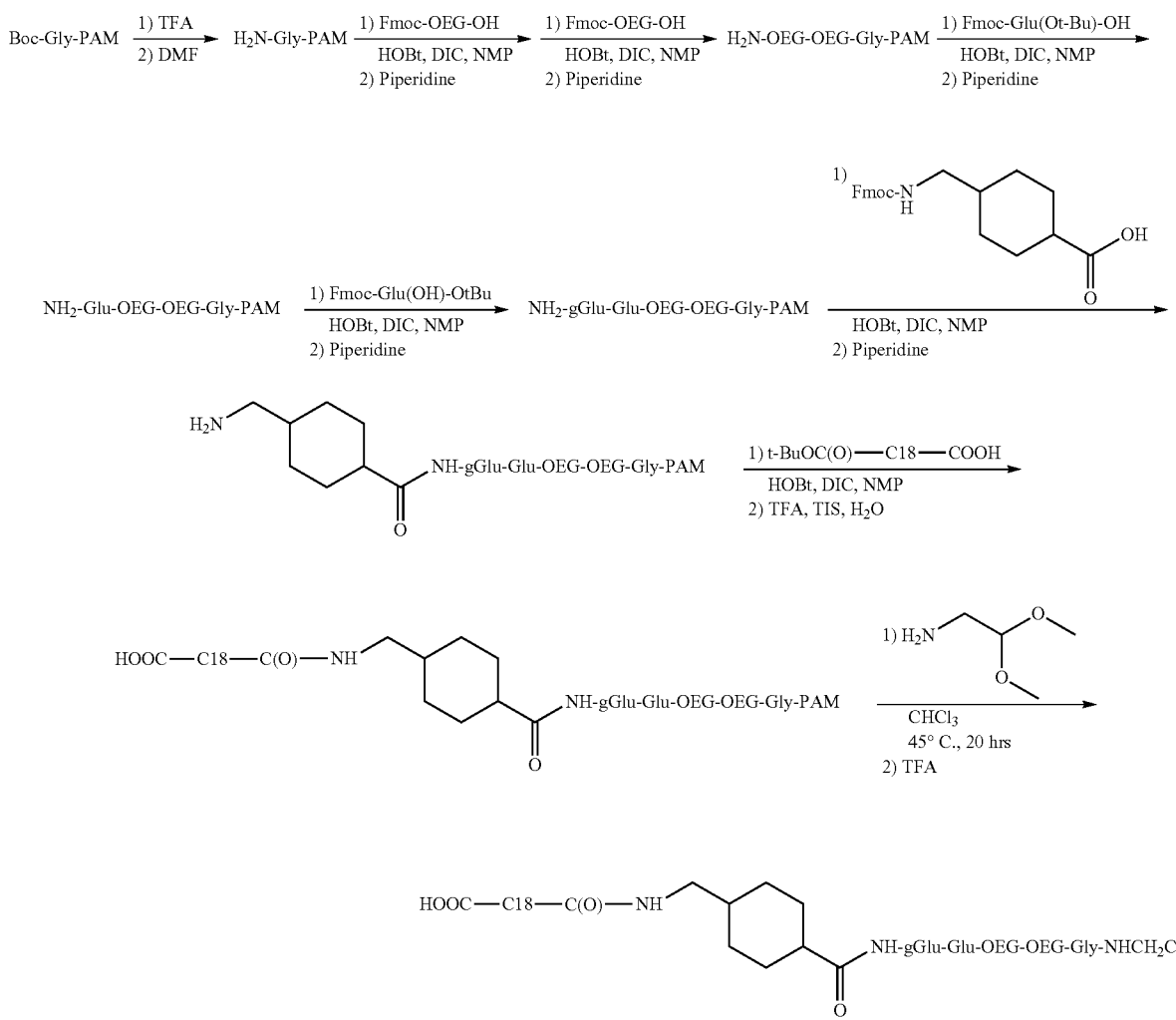

Example 15

In a similar way as described in Example 14 above the following compound was prepared using Boc-Gly-PAM resin as starting material and mono-tert-butyl-eicosanoic acid, 4-Boc-aminobenzoic acid, Fmoc-Thx-OH, Fmoc-OEG-OH, Fmoc-Glu(O-t-Bu)-OH, Fmoc-Glu(OH)-t-Bu protected amino acids. After mild deprotection, peptide product was cleaved from the resin using 2,2-dimethoxy-ethylamine followed by deacetalisation using TFA which afford albumin binder (V).

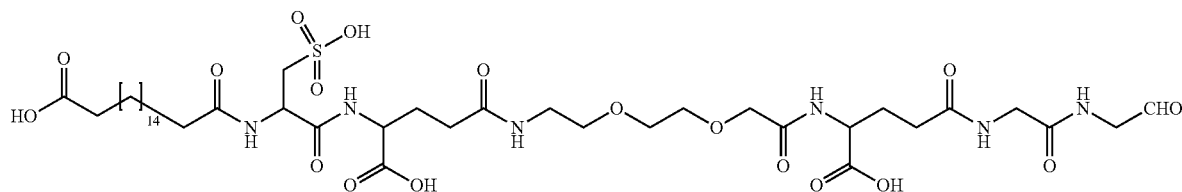

(V)

TOF-MS: Rt=15.2 min, mass=967.11 (M+1)

Example 16

In a similar way as described in Example 14 above compound (VI) was prepared using Fmoc-Lys(Mtt)-Wang resin as starting material and mono-tert-butyl-octadecane-dioic acid, Boc-Ser(t-Bu)-OH, Fmoc-OEG-OH, Fmoc-Glu(O-t-Bu)-OH, and oxidised Fmoc-Cys-OH protected amino acids. The peptide product was cleaved from the resin using 2.5% TIS, 2.5% H$_2$O in THF for 3 hrs and purified by prep-HPLC:

Column: 2 cm C18
Eluent A: 0.1% TFA i Milli-Q water
Eluent B: 0.1% TFA i MeCN
Start % B: 40%
End % B: 75%
Gradient: 5 min. with 10% MeCN, 5-10 min. up to start % B over 51 min., 5 min. with end % B+10% MeCN approx. 1 hr
Fractions were analysed by LC-MS-TOF.
Desired fractions were collected, pooled and lyophilised affording compound (VI)

TOF-MS: Rt=6.3 min, mass=955.1 (M+1)

Oxidation of (VI):

MTP-Solution:

3-Methyl-thio-1-propanol (290 mg) dissolved in 4 mL 25 mM HEPES, pH=7.00

Periodate-Solution:

96 mg NaIO$_4$ dissolved in 2 mL Milli-Q water

To a solution of compound (VI) in Milli-Q water (1 mL) was added MTP-solution (3.6 mL)+periodate-solution (560 µL) and the pH was adjusted to 9.5 with one drop of 1N NaOH. The reaction flask was covered with tin-foil and stirred for 1 hr at RT. An additional portion of periodate-solution (560 µL) was added and the reaction mixture was left for 4.5 hours at ambient temperature. The resulting mixture was run through two NAP columns, to get rid of the NaIO$_4$. The columns were prewashed with 25 mM HEPES (5×2.5 mL) pH=7.0. Sample (2.5 mL) applicated on each column and eluated with 3.5 mL 25 mM HEPES, pH=7.00. 2×3.5 mL were pooled in total—10.5 mL containing keto-aldehyde (VII) which were used directly for conjugation with an GH analogue.

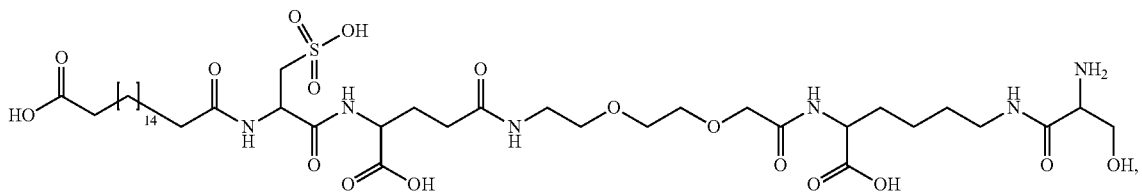

(VI)

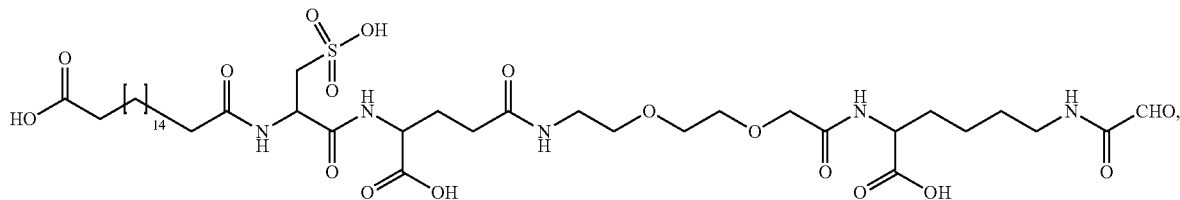

TOF-MS: mass=924.08 (M+1)

Example 17

4-(1H-Tetrazol-16-yl-hexadecanoylsulfamoyl)bu-tanoyl-OEG-γGlu-γGlu-OEG-N$^\varepsilon$(4-aminobenzoyl)Lys-NH$_2$ (VIII)

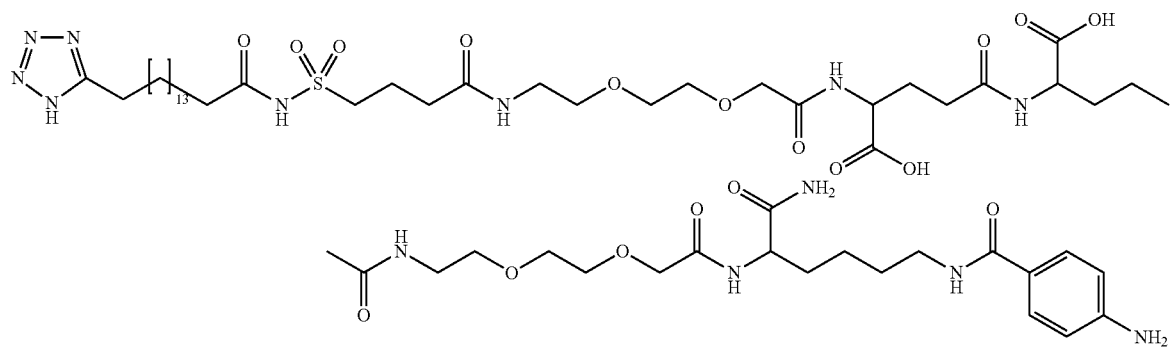

The compound (VIII) was synthesised on solid support according to scheme 3. Fmoc protected Rink-Amide-Resin (2.2 g, 0.6 mMol/g) was weighed into a flask. The resin was swelled with NMP (3×30 mL) for 2 hrs. The resin was shaken with 25% piperidine in NMP (30 mL) for 10 min. The resin was drained and treated with 25% piperidine in NMP (30 mL) for 1 hr followed by draining and wash with NMP (6×30 mL). Fmoc-Lys(Mtt)-OH and HOBt were weighed into a flask, dissolved in bromo phenol blue in NMP (30 mL, 0.5 mM). This solution was added to the drained resin above followed by addition of DIC. The reaction was shaken at ambient temperature for 21 hrs. The resin was drained and washed with NMP (6×30 mL) followed by washing with DCM (3×30 mL). The resin was treated with hexafluorisopropanol (20 mL) for 10 min. Shaken for 10 min. The resin was drained and washed with DCM (3×30 mL). The resin was treated with hexafluorisopropanol (20 mL) for 10 min again and shaken for 10 min. The resin was drained and washed with DCM (3×30 mL) followed by drained and washed with NMP (3×30 mL). 4-(Boc-amino)benzoic acid and HOBt were weighed into a flask, dissolved in bromo phenol blue in NMP (30 mL, 0.5 mM). This solution was added to the drained resin above followed by addition of DIC. The reaction was shaken at ambient temperature. The resin was drained and washed with NMP (6×30 mL). The resin was shaken with 25% piperidine in NMP (10 mL) for 10 min. The resin was drained and treated with 25% piperidine in NMP (10 mL) for 1 hr followed by draining and wash with NMP (6×15 mL). Fmoc-OEG-OH and HOBt were weighed into a flask, dissolved in brom phenol blue in NMP (15 mL, 0.5 mM). This solution was added to the drained resin followed by addition of DIC. The reaction was shaken at ambient temperature for 23 hrs. The resin was drained and washed with NMP (6×15 mL). The resin was shaken with 25% piperidine in NMP (10 mL) for 10 min. The resin was drained and treated with 25% piperidine in NMP (10 mL) for 1 hr followed by draining and wash with NMP (6×15 mL). Fmoc-Glu-O-t-Bu and HOBt were weighed into a flask, dissolved in bromo phenol blue in NMP (15 mL, 0.5 mM). This solution was added to the drained resin followed by addition of DIC. The reaction was shaken at ambient temperature for 18 hrs. The resin was drained and washed with NMP (6×15 mL). The resin was shaken with 25% piperidine in NMP (10 mL) for 10 min. The resin was drained and treated with 25% piperidine in NMP (10 mL) for 1 hour followed by draining and wash with NMP (6×15 mL). Fmoc-Glu-O-t-Bu and HOBt were weighed into a flask, dissolved in 15 ml 0.5 mM bromo phenol blue in NMP. This solution was added to the drained resin followed by addition of DIC. The reaction was shaken at ambient temperature for 18 hrs. The resin was drained and washed with NMP (6×15 mL). The resin was shaken with 25% piperidine in NMP (10 mL) for 10 min. The resin was drained and treated with 25% piperidine in NMP (10 mL) for 1 hr followed by draining and washing with NMP (6×15 mL). Fmoc-OEG-OH and HOBt were weighed into a flask, dissolved in bromo phenol blue in NMP (15 mL, 0.5 mM). This solution was added to the drained resin followed by addition of DIC. The reaction was shaken at ambient temperature. The resin was drained and washed with NMP (6×15 mL). The resin was shaken with 25% piperidine in NMP (10 mL) for 10 min. The resin was drained and treated with 25% piperidine in NMP (10 mL) for 1 hr followed by draining and washing with NMP (6×15 mL).

4-(16-1H-Tetrazol-5-yl-hexadecanoylsulfamoyl)butyric acid and HOBt were weighed into a flask, dissolved in bromo phenol blue in NMP (15 mL, 0.5 mM). This solution was added to the drained resin followed by the addition of DIC. The reaction was shaken at ambient temperature for 21 hrs. The resin was drained and washed with NMP (6×15 mL) followed by draining and wash with DCM (6×15 mL). The resin was cleaved with a mixture of 95% TFA in water (10 mL)+DCM (0.25 mL) and TIS (0.25 mL). The resin was shaken for 2 hours at ambient temperature and filtered into ice cold Et$_2$O (75 mL). The resulting precipitate was isolated by centrifugation followed by washing with Et$_2$O (3×) and dried in vacuum for 48 hours affording crude 300 mg of compound (VIII).

Crude compound (VIII) was purified on prep-HPLC (GILSON), 30->80% MeCN. Pooled fractions were evaporated to dryness and the residue dissolved in H$_2$O/MeCN 1:1 and freeze-dried over night affording 170 mg of the compound (VIII).

TOF-MS: Rt=4.7 min, mass 1268.71 (M+1)

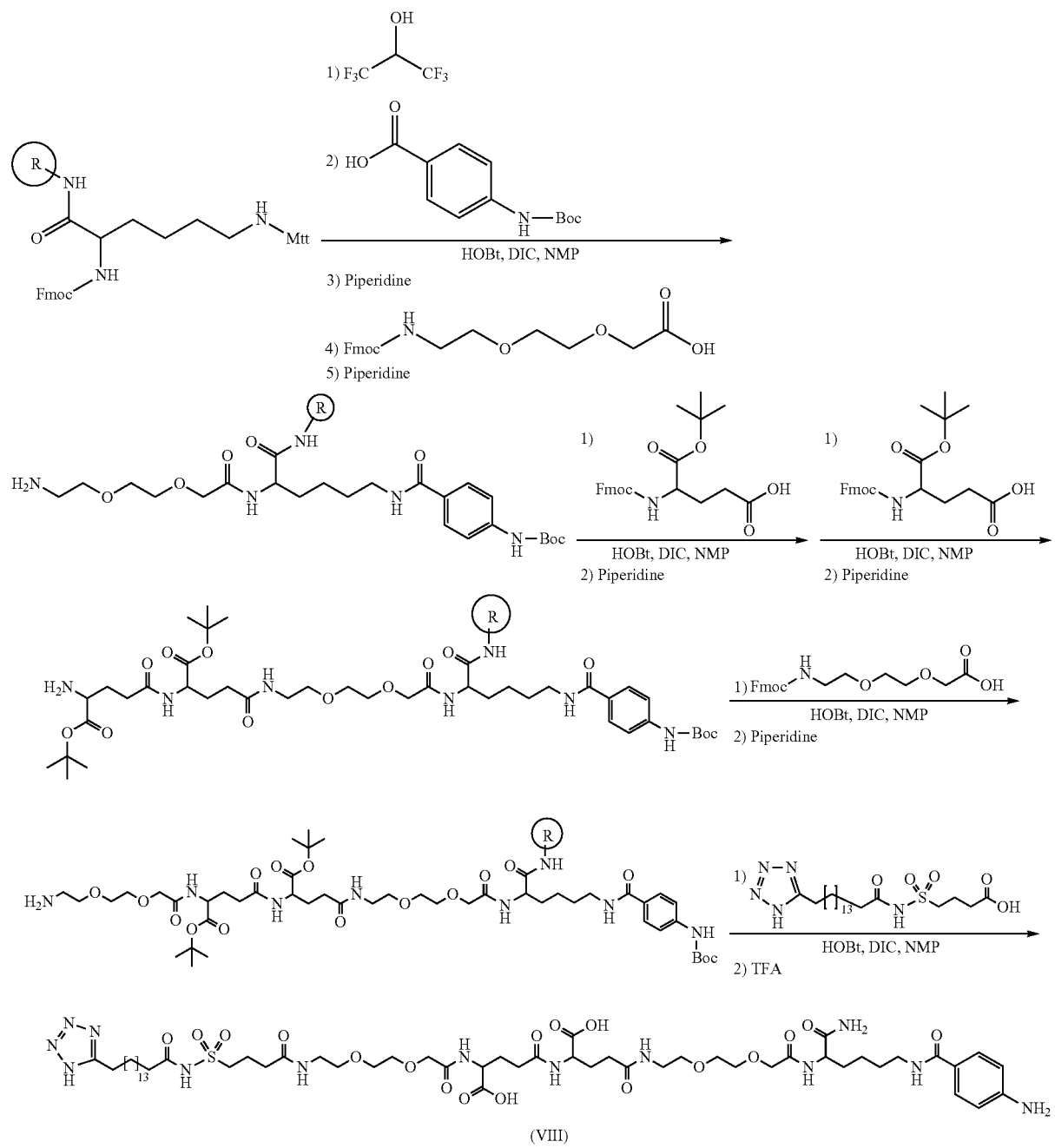

Scheme 3.

Example 18

In a similar way as described in Example 17 above the following compound was prepared using Fmoc-Lys(Mtt)-OH and Wang Resin.

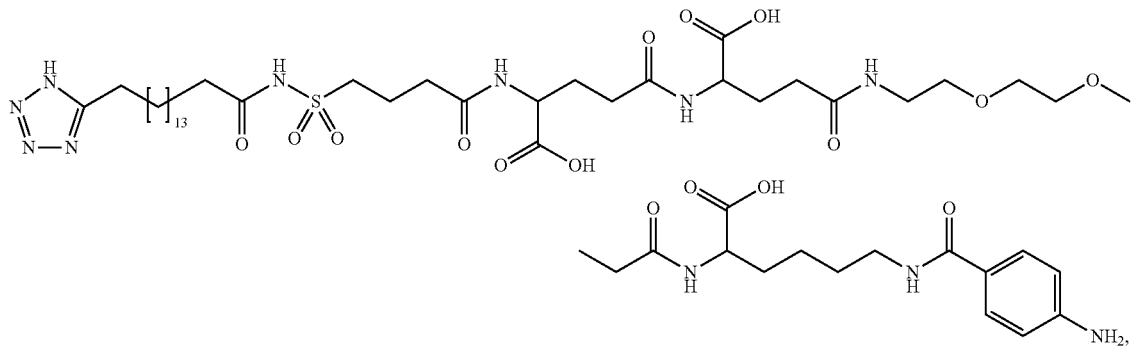

TOF-MS: mass 1124.33 (M+1)

Example 19

In a similar way as described in Example 17 above the following compound was prepared using FMOC-Lys(Mtt)-OH and Rink amid resin.

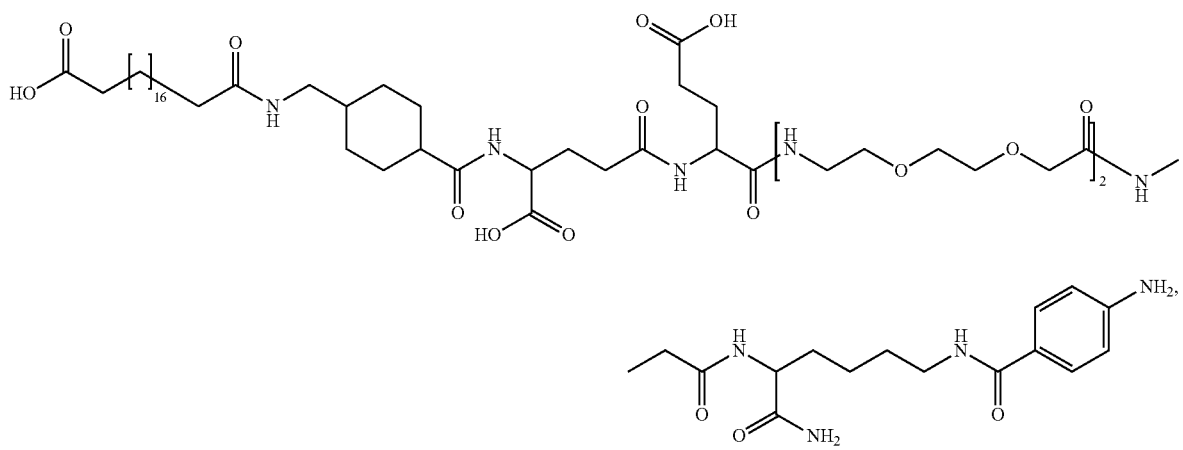

TOF-MS: mass 1333.64 (M+1)

Example 20

In a similar way as described in Example 17 above the following compound was prepared using FMOC-Lys(Mtt)-OH and Rink amid resin.

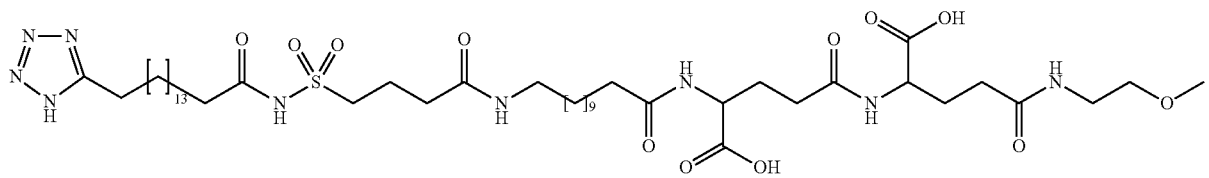

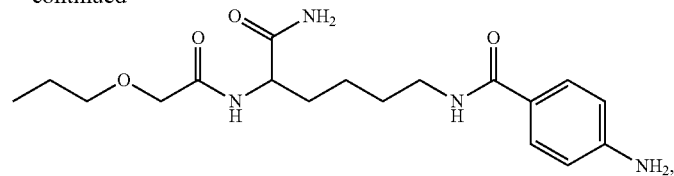
TOF-MS: mass 1320.67 (M+1)
Example 21
In a similar way as described in Example 17 above the following compound was prepared using FMOC-Lys(Mtt)-OH and Rink amid resin.
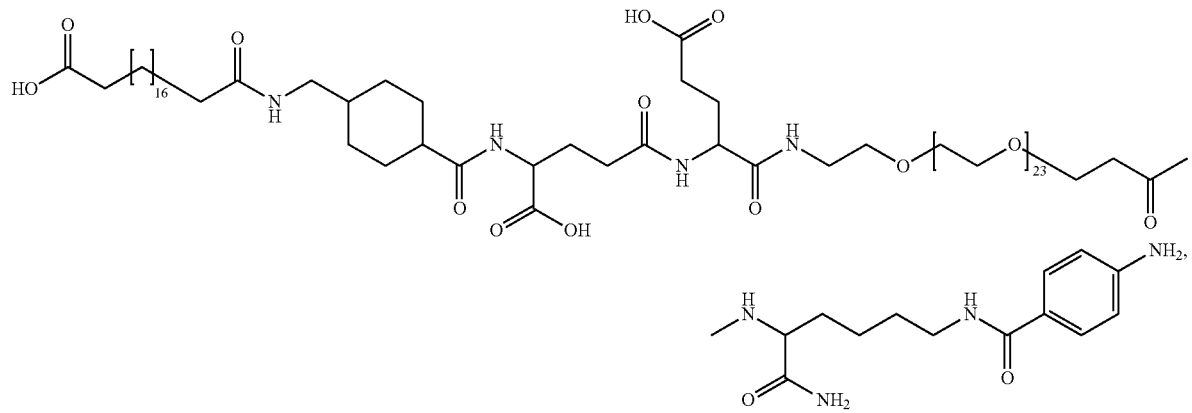
TOF-MS: mass 2114.64 (M+1)
Example 22
In a similar way as described in Example 17 above the following compound was prepared using FMOC-Lys(Mtt)-OH and Rink amid resin.
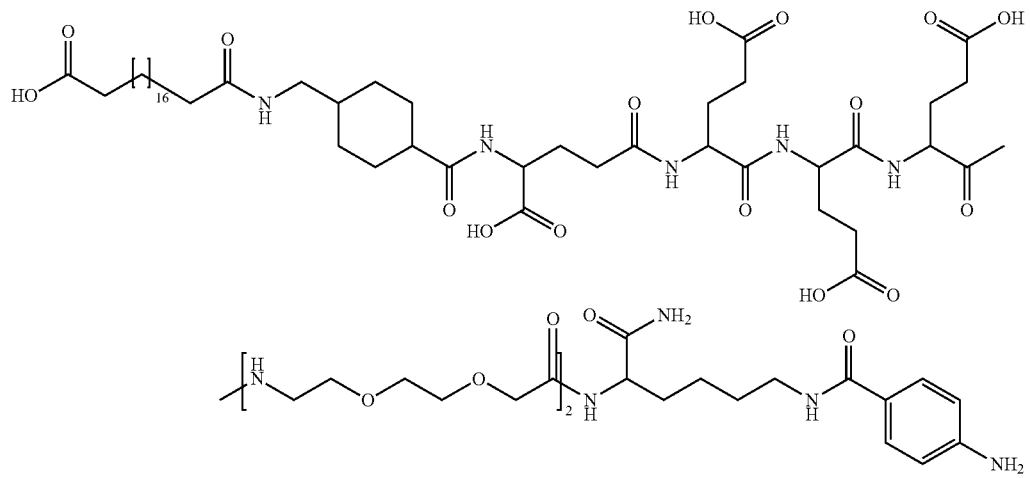
TOF-MS: mass 1534.82 (M+1)

Example 23

In a similar way as described in Example 17 above the following compound was prepared using FMOC-Lys(Mtt)-OH and Rink amid resin.

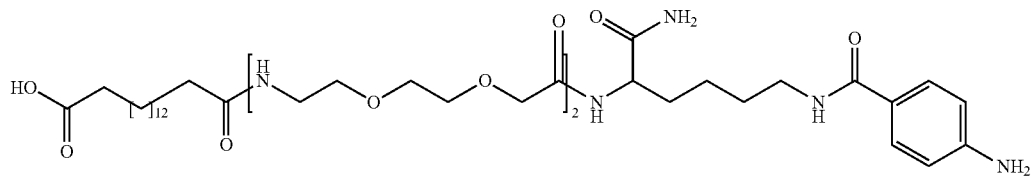

TOF-MS: mass 823.05 (M+1)

Example 24

In a similar way as described in Example 17 above the following compound was prepared using FMOC-Lys(Mtt)-OH and Wang Resin.

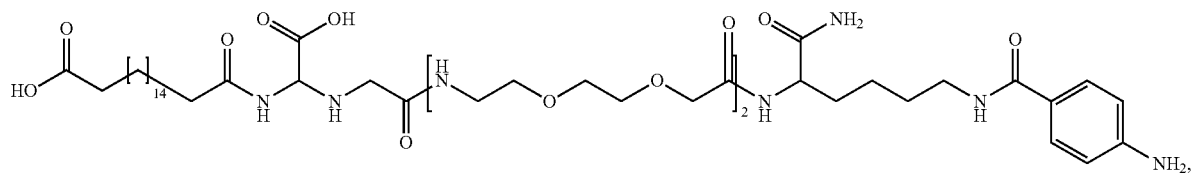

TOF-MS: mass 980.22 (M+1)

Example 25

In a similar way as described in Example 17 above the following compound was prepared using FMOC-Lys(Mtt)-OH and Rink amid resin.

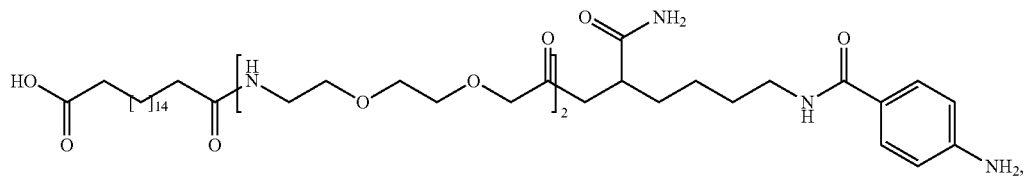

TOF-MS: mass 851.10 (M+1)

Example 26

In a similar way as described in Example 17 above the following compound was prepared using FMOC-Lys(Mtt)-OH and Rink amid resin.

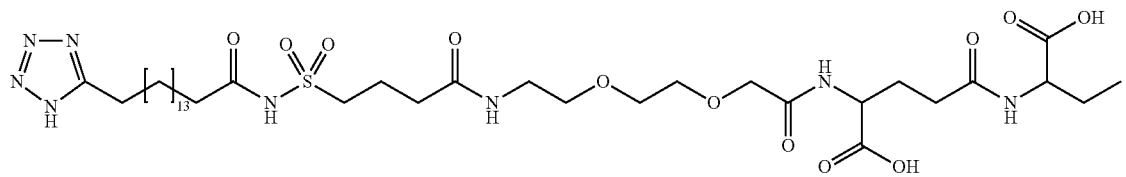

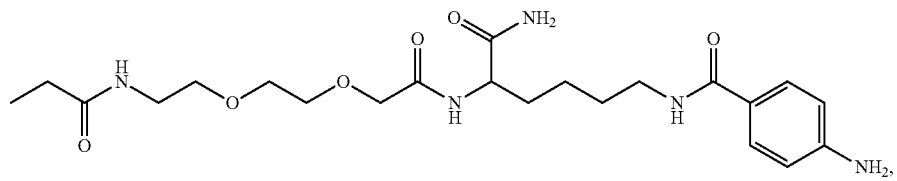
TOF-MS: mass 1258.51 (M+1)
Example 27
In a similar way as described in Example 17 above the following compound was prepared using FMOC-Lys(Mtt)-OH and Wang Resin.
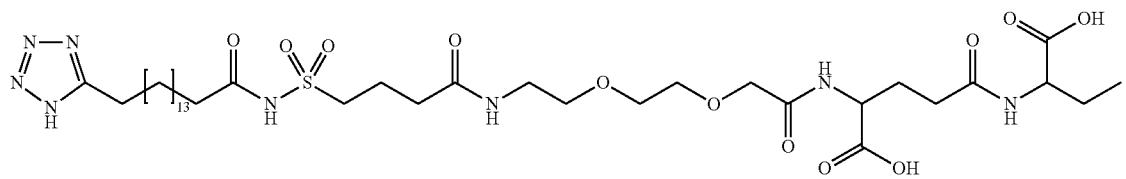
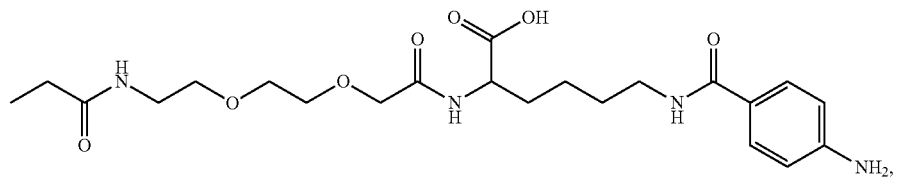
TOF-MS: mass 1269.49 (M+1)
Example 28
In a similar way as described in Example 17 above the following compound was prepared using FMOC-Lys(Mtt)-OH and Rink amid resin.
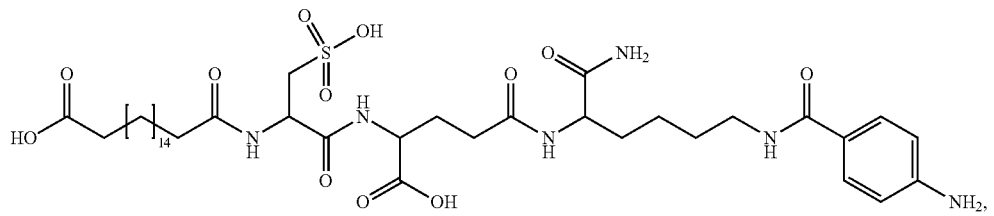
TOF-MS: mass 841.04 (M+1)

Example 29

In a similar way as described in Example 17 above the following compound was prepared using FMOC-Lys(Mtt)-OH and Rink amid resin.

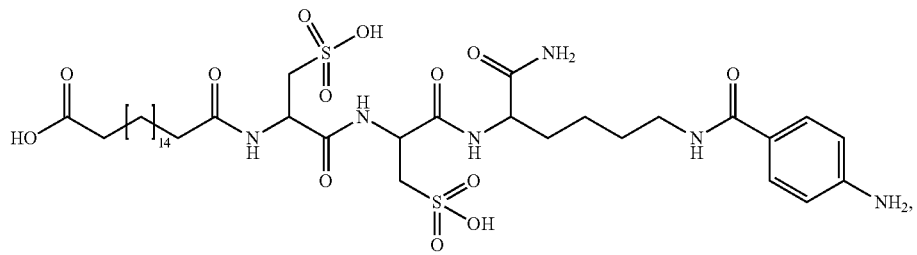

TOF-MS: mass 863.07 (M+1)

Example 30

In a similar way as described in Example 17 above the following compound was prepared using FMOC-Lys(Mtt)-OH and Rink amid resin.

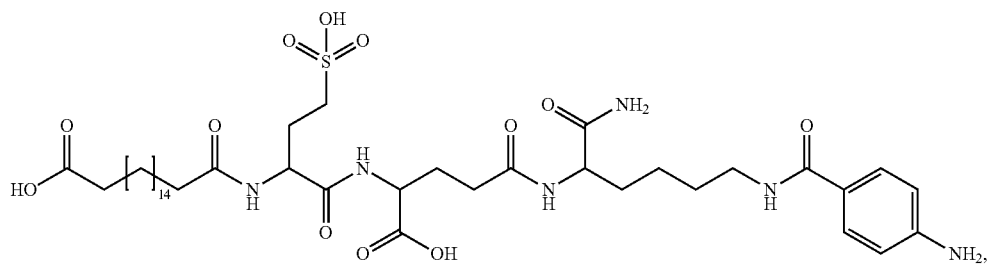

TOF-MS: mass 855.07 (M+1)

Example 31

In a similar way as described in Example 17 above the following compound was prepared using FMOC-Lys(Mtt)-OH and Rink amid resin.

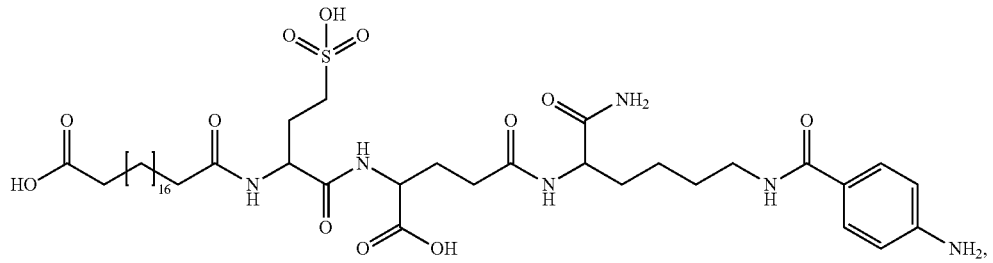

TOF-MS: mass 883.12 (M+1)

Example 32

In a similar way as described in Example 17 above the following compound was prepared using FMOC-Lys(Mtt)-OH and Rink amid resin.

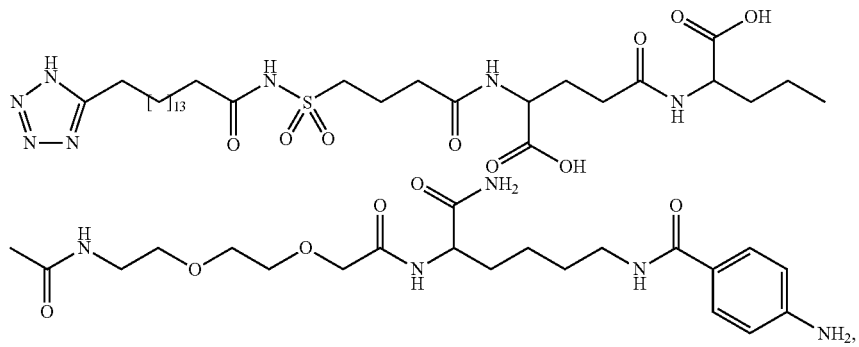

TOF-MS: mass 1123.35 (M+1)

Example 33

In a similar way as described in Example 17 above the following compound was prepared using FMOC-Lys(Mtt)-OH and Rink amid resin.

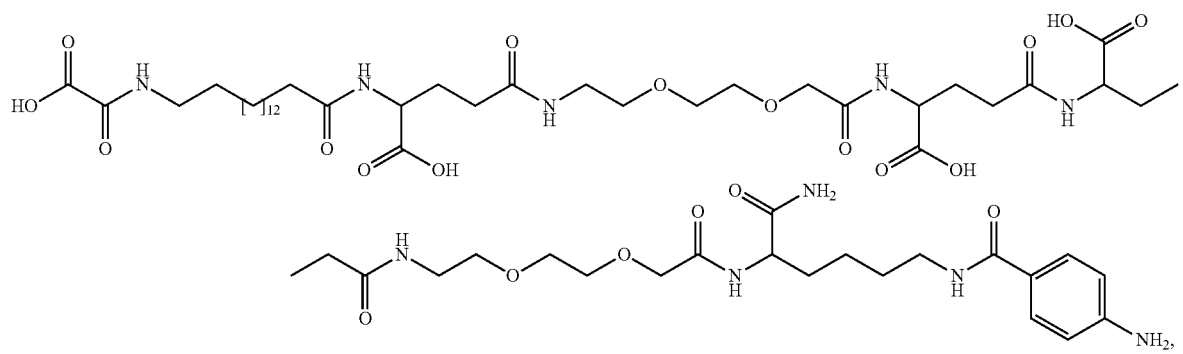

TOF-MS: Rt=4.7 min, mass 1267.45 (M+1)

Example 34

In a similar way as described in Example 17 above the following compound was prepared using FMOC-Lys(Mtt)-OH and Rink amid resin.

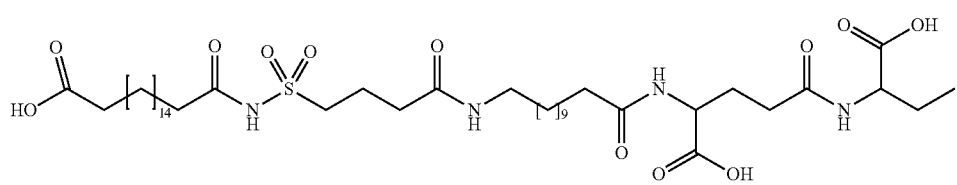

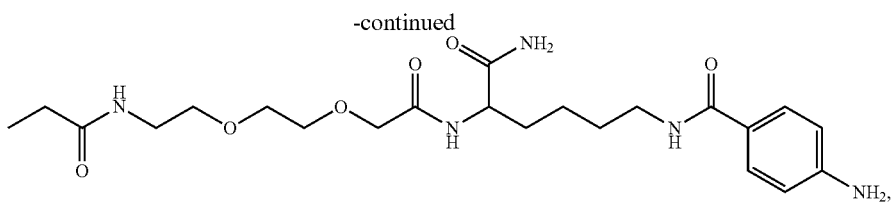
TOF-MS: mass 1310.67 (M+1)
Example 35
In a similar way as described in Example 17 above the following compound was prepared using FMOC-Lys(Mtt)-OH and Rink amid resin.
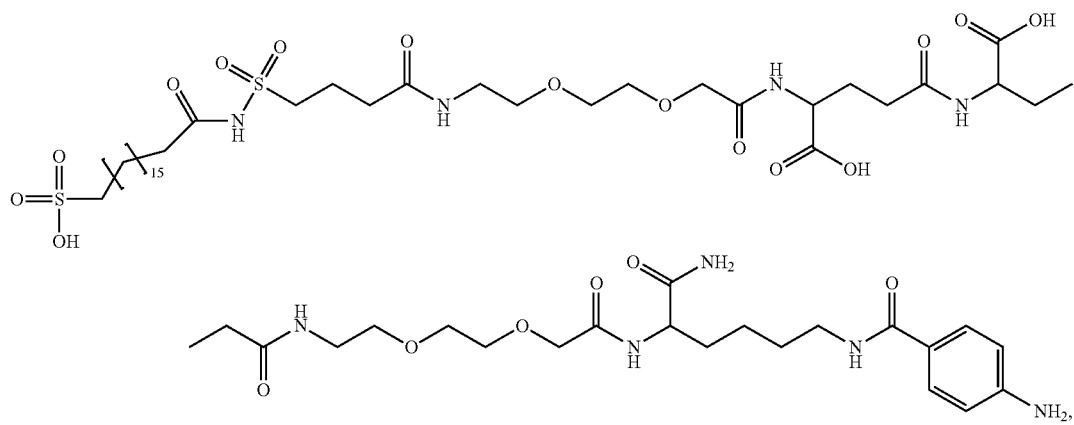
TOF-MS: mass 1308.58 (M+1)
Example 36
In a similar way as described in Example 17 above the following compound was prepared using FMOC-Glu(ODmab)-OH and 2-chlorotrityl chloride resin.
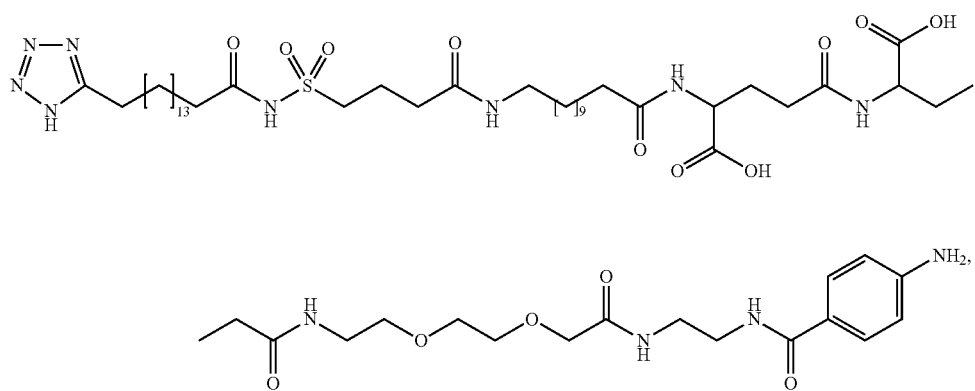
TOF-MS: mass 1235.56 (M+1)

Example 37

In a similar way as described in Example 17 above the following compound was prepared using FMOC-Glu(ODmab)-OH and 2-chlorotrityl chloride resin.

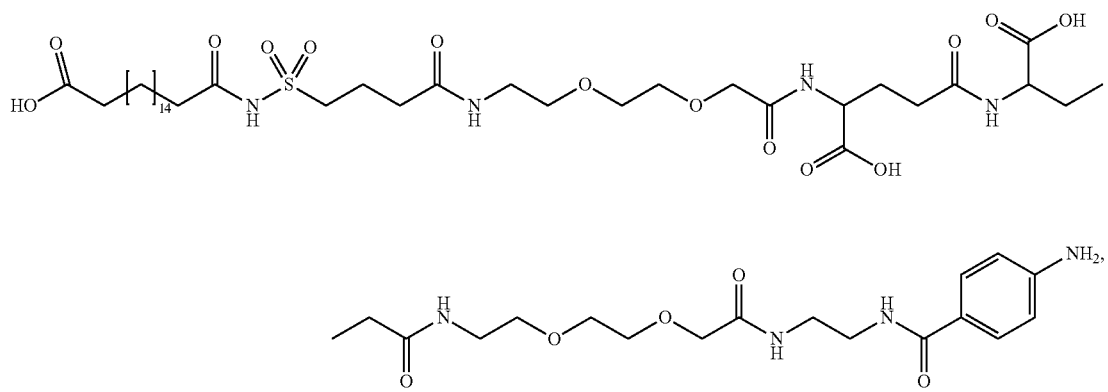

TOF-MS: mass 1173.40 (M+1)

Example 38

In a similar way as described in Example 17 above the following compound was prepared using FMOC-Lys(Mtt)-OH and Rink amid resin.

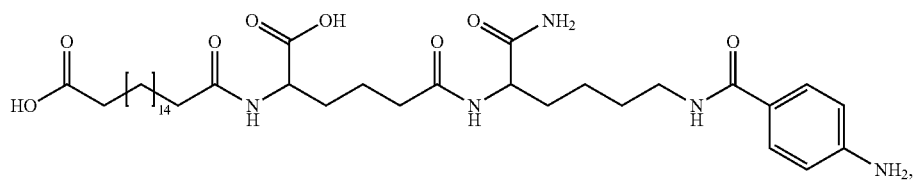

TOF-MS: mass 703.93 (M+1)

Example 39

In a similar way as described in Example 17 above the following compound was prepared using FMOC-Lys(Mtt)-OH and Rink amid resin.

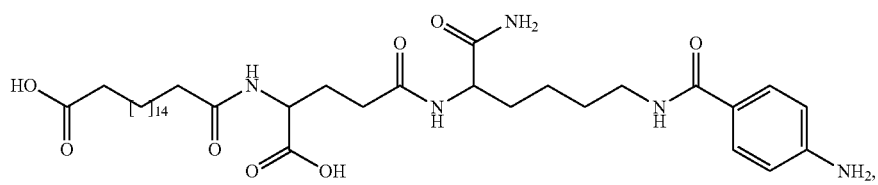

TOF-MS: mass 689.90 (M+1)

Example 40

In a similar way as described in Example 17 above the following compound was prepared using FMOC-Glu (ODmab)-OH and 2-chlorotrityl chloride resin.

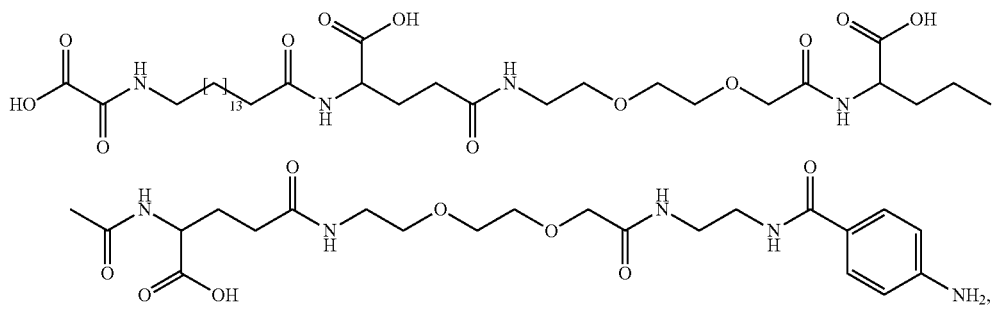

TOF-MS: mass 1182.34 (M+1)

Example 41

17-[(S)-3-(2-{2-[(2-{2-[(5-Aminopentylcarbamoyl)methoxy]ethoxy}ethylcarbamoyl)methoxy]ethoxy}ethylcarbamoyl)-1-carboxy-propylcarbamoyl]-heptadecanoic acid

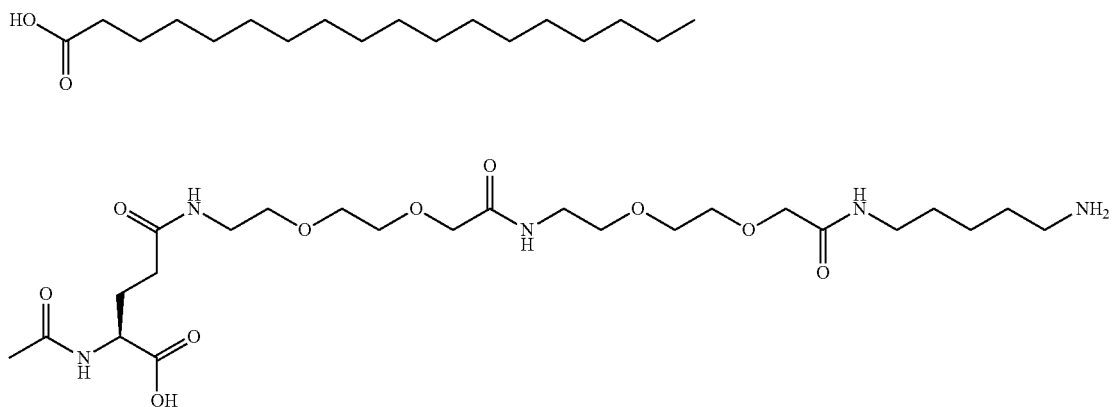

N-tert-butoxycarbonyl cadaverine (24.3 mg; 0.12 mmol) was added to a solution of 17-((S)-1-Carboxy-3-{2-[2-({2-[2-(2,5-dioxo-pyrrolidin-1-yloxycarbonylmethoxy)ethoxy]ethylcarbamoyl}methoxy)ethoxy]ethylcarbamoyl}propylcarbamoyl)-heptadecanoic acid (100 mg; 0.12 mmol) and DIPEA (46.68 mg; 0.36 mmol) in THF (2.0 ml). Reaction mixture was stirred over night at room temperature, and then concentrated in vacuo. The residue was dissolved in a mixture of water (5 ml) and THF (2 ml), and purified by preparative HPLC (RP18 column). Fractions containing the Boc-protected coupling product was pooled and taken to dryness. The residual was dissolved in 50% TFA-DCM (4 ml) and stirred for 1 h at room temperature, then concentrated in vacuo to provide 54 mg (55%) of the title material as its trifluoroacetic acid salt.

TOF-MS: mass 815.5 (M+1)

Preparation of GH Albumin Binder Compounds

Example 42

The use of a transglutaminase to attach a handle to GH has previously been described in WO2005/070468 and may be used in accordance with the present invention for attachment of an albumine binder. The TGase used is microbial transglutaminase from *Streptoverticilium mobaraense* according to U.S. Pat. No. 5,156,956. A general method is described in the section Chemistry I above.

1. Coupling of transaminated and oxidised GH compound (I) with an albumine binder (II)

The following solution was prepared:

Buffer A: Triethanolamine (119 mg, 0.8 mmol) was dissolved in water (40 mL) and pH adjusted to 8.5.

(A) Transamination of hGH (III) with 1,3-diamino-2-propanol

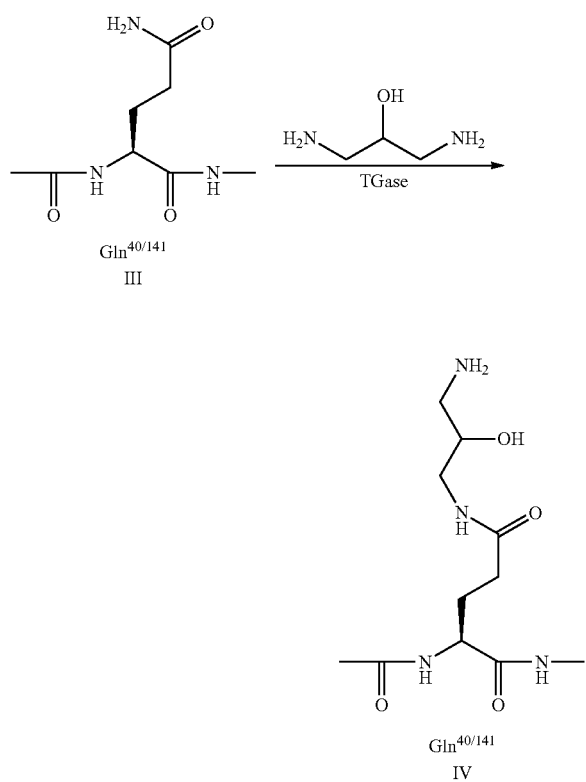 [SMILES: CNC(=O)[C@H](CCC(N)=O)NC(C)=O ; NCC(O)CN ; CNC(=O)[C@H](CCC(=O)NCC(O)CN)NC(C)=O]

In the next step, transaminated GH (III) is added periodate. The oxidation is typically done at low temperature, such as 4-10° C. over 30 min. optionally in the dark. Periodate may oxidize metheonine residues in GH to their corresponding metheonine sulfoxide residues. To minimize this oxidation risk, small molecule organic thioethers may be added during periodate oxidation. A suitable organic thioether is 3-methylthiopropan-1-ol but the skilled person will be able to suggest others.

Oxidation of Transaminated GH Compound (IV):

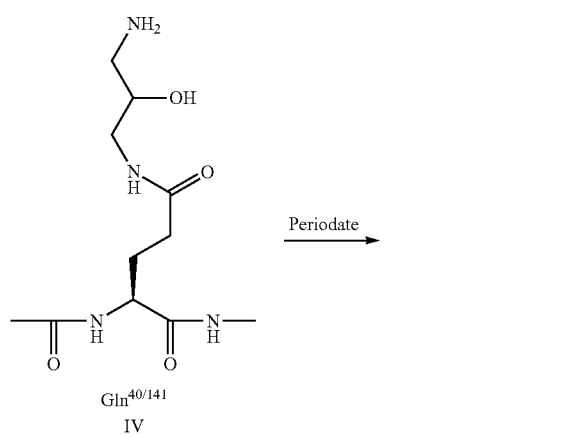

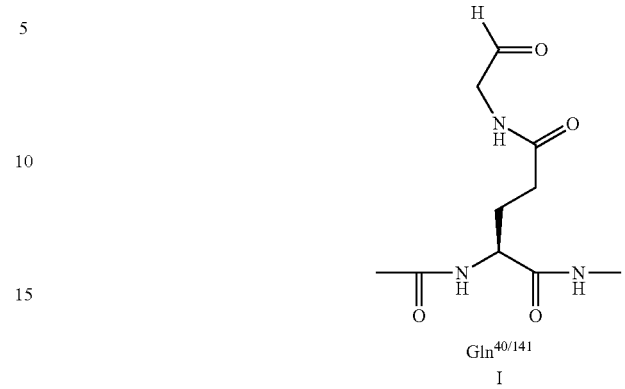

Buffer change may be performed in order to obtain an acid solution required for efficient sodium cyano borohydride reduction. Typically, an excess of A-W—B1-NH2 amine is used, and sodium cyanoborohydride may be added in smaller portions over time.

The following solutions were prepared:

Buffer A: Triethanolamine (119 mg, 0.8 mmol) was dissolved in water (40 mL) and pH adjusted to 8.5.

Buffer B: 3-methylthiopropanol (725 mg, 7.1 mmol) was dissolved in Buffer A (10 mL).

Buffer C: HEPES (5.96 g) was dissolved in water (1.0 L) and pH adjusted to 7.0

Periodate: $NaIO_4$ (48.1 mg, 0.225 mmol) was dissolved in water (1.0 mL).

To a solution of (IV) (10 mg, 0.5 µmol) was added Buffer B (0.2 mL) followed by the periodate solution (0.03 mL). After 20 min. of cold incubation the mixture is dialyzed 4 times with buffer C. The residue is concentrated to 1 mL.

(C) Reductive amination of (I) with albumin binder (II)

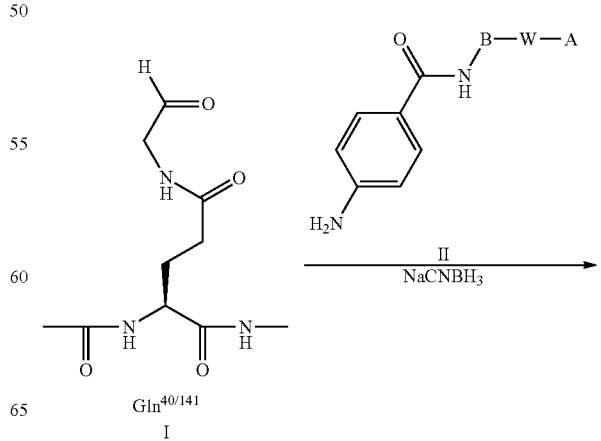

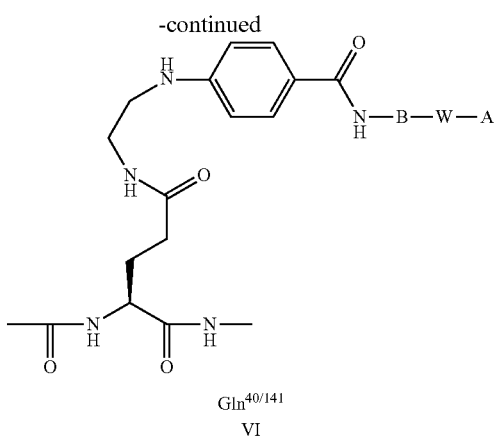

Gln⁴⁰/¹⁴¹
VI

Albumin binder (II) as described in Example 17 through 40 may be used.

The final solution from (B) (1 mL, 10 mg, 0.45 μmol (I)) was mixed with an albumine binder (II) solution (2 mL, 10 mg, 0.3 μmol) in 25 mM HEPES buffer pH 7.0 and the resulting mixture was slowly rotated at room temperature for 1 hr. After 1 hr NaCNBH₃ (100 μL of a solution of NaCNBH₃ (20 mg) in water (0.5 mL)) was added portionwise. The mixture is kept at room temperature in the dark for 18-24 hrs.

The later reaction may be performed as follows:

A solution of oxidized transaminated GH is added a solution of albumin binder linker in a mixture of AcOH (1.5 mL) and 50 mM MES (0.5 mL) at pH 6.00. The resulting reaction mixture is gently shaken at RT for 30 min. at which time a NaCNBH₃ solution (15 μL, (22 mg NaCNBH₃ dissolved in 500 μL Milli-Q water+AcOH (15 μL))) is added. The sample is covered with tin foil and stirrer over night at RT.

The conjugate can be isolated by anion exchange chromatography as follows: Acetic acid is removed by buffer changed with pure water (3×) using Amicon Ultra15 devices (Ultracel 10K tubes) by centrifugation at 4000 rpm/min. for 3×8 min. The mixture is then buffer changed to 20 mM TEA, pH: 8.50 using Amicon Filter devises and diluted to a final volume of 50 mL with 20 mM TEA, before loading it on a HiLoad Q Sepharose, 26/10 column. The column is initially washed with 20 mM TEA, pH 8.50 (buffer A) and then eluted with 20 mM TEA, 500 mM NaCl, pH 8.50 (buffer B) using a 0-100% (B) gradient over 20 CV, with a flow rate of 2 mL/min. The pooled fractions were buffer changed 5 times to 10 mM ammoniumbicarbonate buffer in pure water using Amicon Ultra15 devices (Ultracel 10K tubes) by centrifugation at 4000 rpm/min. for 3×8 min Using the albumin binder from Example 18 will result in the following compound

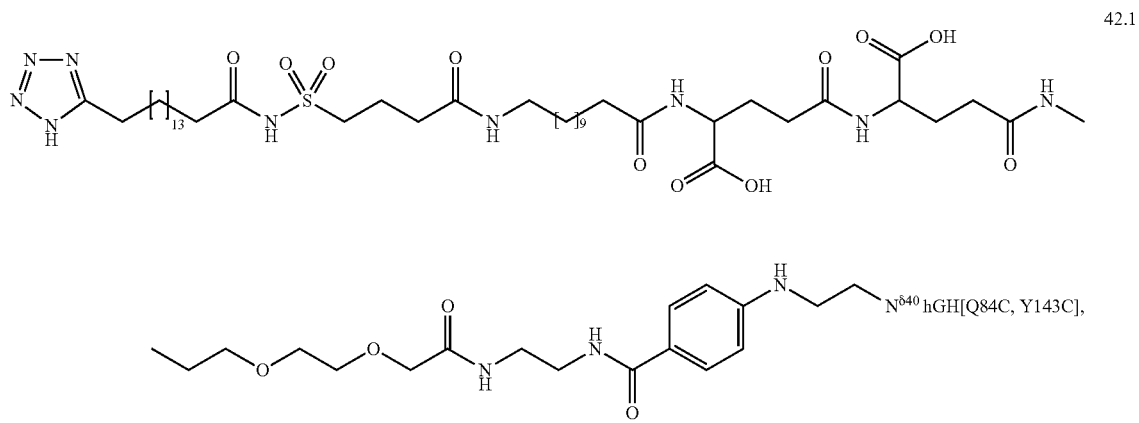

42.1

TOF-MS: mass 23301.63

The following compound was prepared using the albumin binder from Example 41

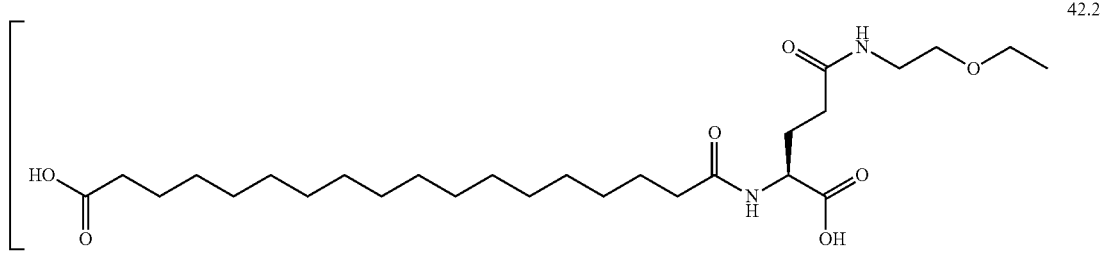

42.2

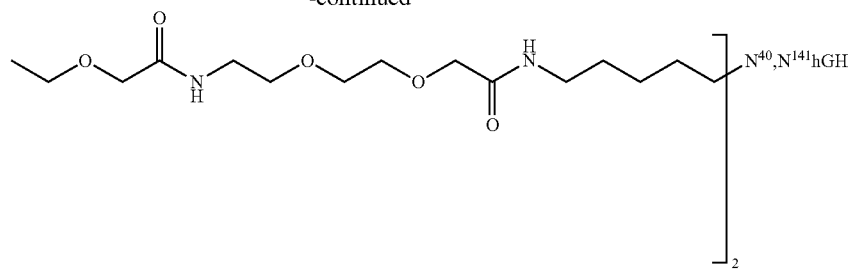

TOF-MS: mass 23727.6245

To a solution of hGH (1 mg, 45 nmol) and 17-[(S)-3-(2-{2-[(2-{2-[(5-aminopentylcarbamoyl)methoxy]ethoxy}ethylcarbamoyl)methoxy]ethoxy}ethylcarbamoyl)-1-carboxy-propylcarbamoyl]heptadecanoic acid (2.10 mg; 2250 nmol) in 20 mM triethanolamin (1000 ul; pH 8.5) was added TGase (0.12 nmol; *Streptoverticillium mobaraense*). The reaction mixture was incubated at 25° C. for 146 hrs, where upon double derivatized hGH analogue of the above formula was obtained.

Example 43

1. Coupling of a GH Compound (I) N-Terminally with an Albumine Binder (IV)

(A) Reductive alkylation of (I) with an albumin binder aldehyde (IV)

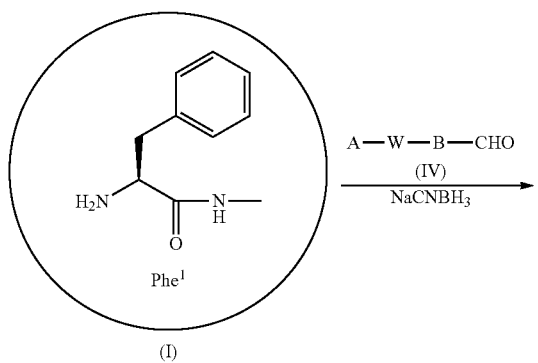

(I)

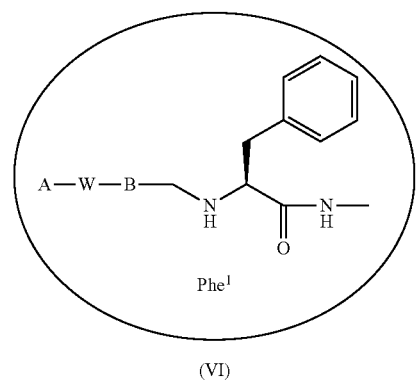

(VI)

The derivatization process as shown above utilise an albumin binding linker A-W—B wherein B has a terminal aldehyde functionality. Conjugation of hGH with A-W—B—CHO occurs via reductive alkylation (hGH→VI). Reductive alkylation is exemplified herein and is well-recognized in the art and results in hGH compounds modified at the N-terminal position.

Albumin binder (IV) was obtained as described in Example 14.

Synthesis of: 2-($C_{20}$diacid-Trx-yGlu-Glu-OEG-OEG-Gly-Glycin amid)-ethyl-$Na^{\alpha 1}$-hGH [Q84C, Y143C]

43.0

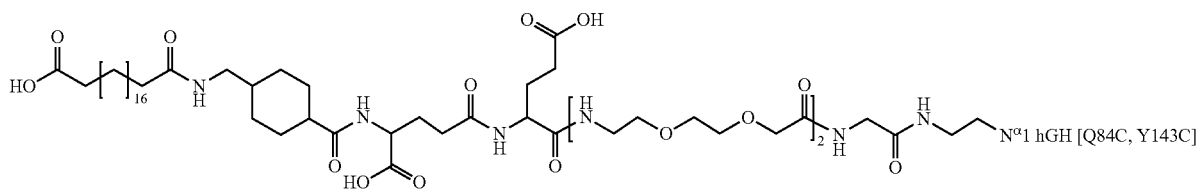

hGH[Q84C, Y143C] (23 mg) was dissolved in Hepes buffer (2.3 mL 0.25 mM pH 7.0). $C_{20}$diacid-Trx-yGlu-Glu-OEG-OEG-Gly-Gly-dimethylacetal (2 mg, see example 14 above) was treated with TFA (50 µL) for 6 min. and evaporated to dryness in vacuum. The residue was stripped with EtOH (200 µL) and evaporated to dryness in vacuum. The residue was dissolved in DMF (100 µL) and added to the hGH solution. A precipitate was formed and redissolved by addition of DMF (1 mL). After 1 hr a solution of NaCNBH$_3$ (20 mg, in 0.5 mL MeCN (230 µL)) was added portionwise and left for 20 hrs. The reaction was quenched by addition of AcOH (2 mL) and diluted with water to a total volume of 20 mL and purified on prep. HPLC on a C18 column with a gradient of 0.1% TFA in MeCN from 40-80% against 0.1% TFA in water. The latest eluting peak was collected, diluted from 70% MeCN to 10% with water and lyophilized affording 4.51 mg of 2-($C_{20}$diacid-Trx-γGlu-Glu-OEG-OEG-Gly-Glycin amid)-ethyl-$N^{α1}$-hGH [Q84C, Y143C].

TOF-MS: Rt=15.25 min, mass=23150

In a similar way as described above the following compound was prepared using albumin binder from Example 16.

43.1

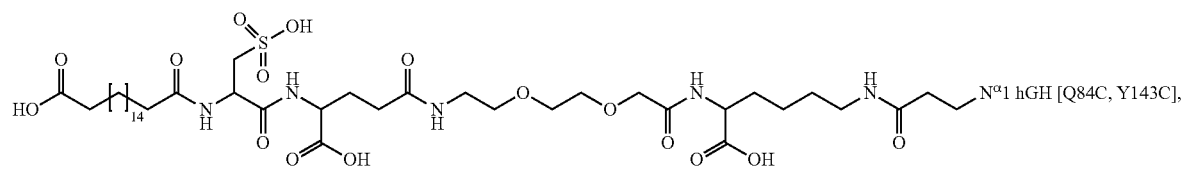

TOF-MS: Rt=15.2 min, mass=23033

In a similar way as described above the following compound was prepared using albumin binder from Example 15.

43.2

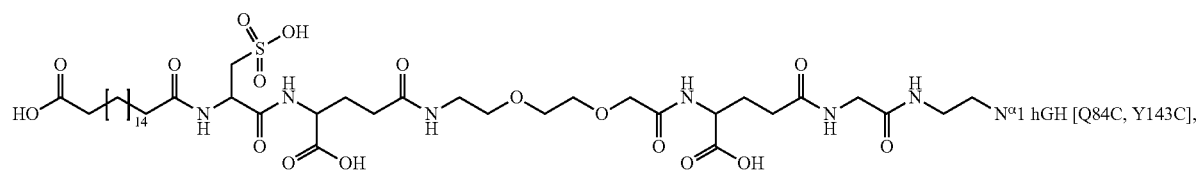

TOF-MS: Rt=15 min, mass=22989.1

Example 44

1. Coupling of a GH compound (VII) having an internal free single cys with an albumine binder (VIII)
   1) Liberation of free Cys GH (VII) via reduction of disulfide (VI) with a suitable selective reducing agent:
   2) Alkylation of free Cys GH (VII) with a halogen activated albumin binder (VIII) affording Cys conjugated GH compound (IX)

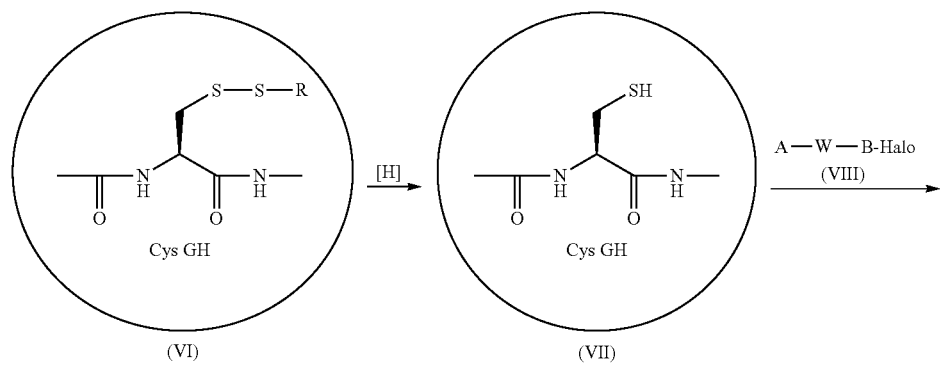

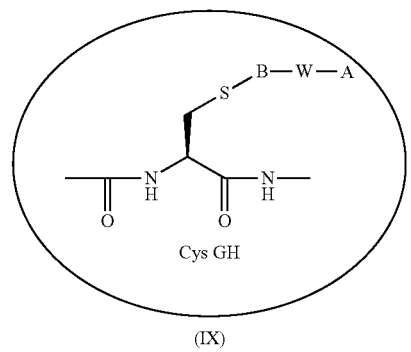

(IX)

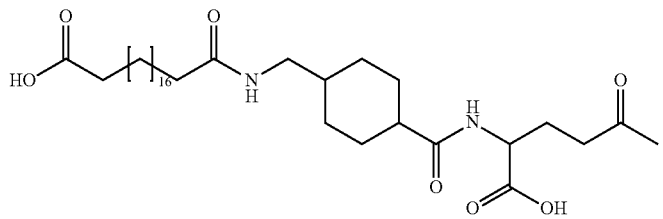

44.1

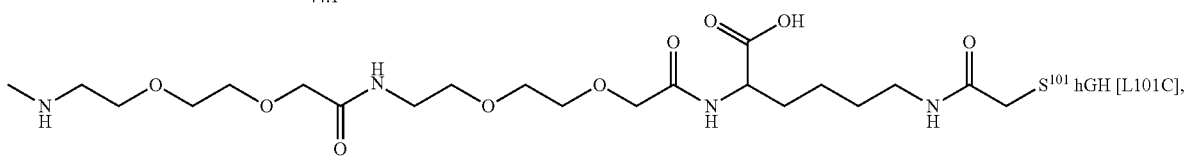

2-(C$_{20}$diacid-Trx-yGlu-OEG-OEG-6Lys)-carbonylmethylene-S$^{101}$-hGH[L101C]

Preparation of hGH[L101C] (VII):

hGH[L101C] as obtained above had part of its free cystein blocked with glutathione and cystamine. Deblocking was performed enzymatically using glutaredoxin II (Grx2) in an equilibrium buffer containing GSH and GSSG. Deblocked hGH[L101C] was separated from low molecular weight GSH/GSSG by buffer exchanged on a Sephadex G25 column.

Conjugation of Albumin Binder (VIII) with hGH[L101C] (VII):

Albumin binder from example 5 (78 mg, 5 eq) was dissolved in 170 mL HEPES/EDTA buffer with 5% hydroxypropyl-R-cyclodextrin and added MTP (2.1 mL, 1%) and 0.5 M NaCl (6.34 g). To this mixture was added concentrated hGH[L101C] (1 eq, 46 mL) and the mixture was left over night at RT. The solution became cloudy over night. As HPLC indicated unreacted starting material another 5 eq. albumin binder from example 5 dissolved in a minimum of NMP was added. The resulting mixture was stirred at RT for an additional 16 hrs.

Purification:
Buffers Used:
Buffer A.
20 mM Triethanolamine (TEA)+10% Ethylen glycol
5.96 g triethanolamine
200 mL ethylen glycol
MQ water added to 2 L.
pH adjusted to 8.5 with 1N HCl
Buffer B:
20 mM Triethanolamine (TEA)+1.0 M NaCl+10% Ethylen glycol
5.96 g triethanolamine
116.88 g NaCl
200 mL ethylen glycol
MQ water added to 2 L.
pH adjusted to 8.5 with 1N HCl The reaction buffer was changed to TEA-buffer A with ethylen glycol on a Sephadex column over 3 runs:
Column: 50/30 Sephadex G25 fine
Buffer A:
Flow: 10 mL/min
Temp: RT (fractions collected at 12° C.)
Fractions: 30 mL per fraction Desired fractions were collected, pooled and then purified on a Q Sepharose column:
Column: 26/10 Q Sepharose HP
Buffer A:
Buffer B:
Gradient 1: 0-10% Buffer B over 1 CV
Gradient 2: 10-40% buffer B over 20 CV
Gradient 3: 40-100% Buffer B over 1 CV
Flow: 8 mL/min
Temp: RT (fractions collected at RT)
Fractions: 5 mL per fraction Desired fractions were collected, pooled and buffer exchanged to 10 mM ammoniumbicarbonate pH 8.0 on a Sephadex G25 column:
Column: 50/30 Sephadex G25 fine
Buffer A: 10 mM Ammoniumbicarbonate pH 8.0
Flow: 10 mL/min
Temp: RT (fractions collected at 12° C.)
Fractions: 30 mL per fraction
Five fractions were pooled and freeze-dried.
The pool was analysed by MS and large amounts of dimer (MS 44491.7) was seen.
The freezedried vials were dissolved in buffer A and purified again on a new Q Sepharose column:
Column: 26/10 Q Sepharose HP
Buffer A:
Buffer B:
Gradient 1: 0-10% Buffer B over 1 CV
Gradient 2: 10-40% buffer B over 20 CV
Gradient 3: 40-100% Buffer B over 1 CV
Flow: 8 mL/min
Temp: RT (fractions collected at RT)

Fractions: 5 mL per fraction
Fractions were pooled and desalted/buffer exchanged to 10 mM ammoniumbicarbonate by ultrafiltration. The pool was concentrated to 25 mL and quantified by RP-HPLC and MS-TOF:
TOF-MS: Rt=16.15 min, mass=23315.96
The following compounds were prepared using the same method.

44.2

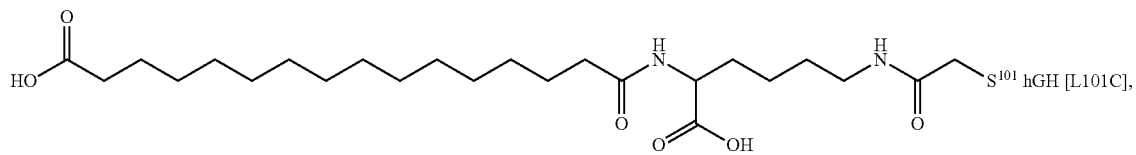

TOF-MS: Rt=15.24 min, mass=22676.8

44.3

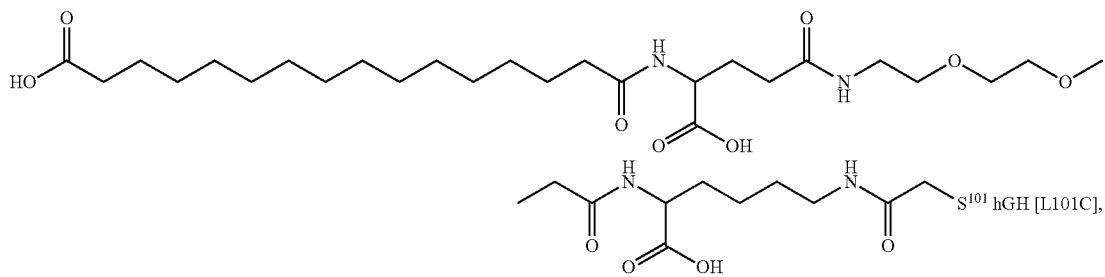

TOF-MS: Rt=10.5 min, mass=22975.1

44.4

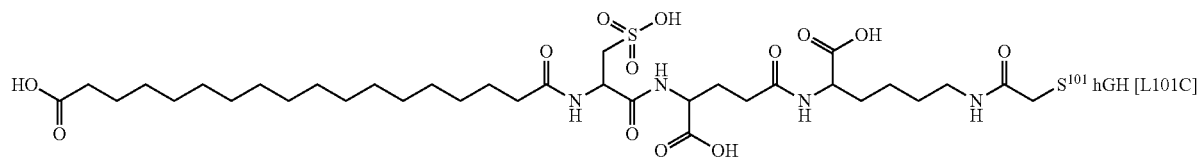

TOF-MS: Rt=15.5 min, mass=23009

44.5

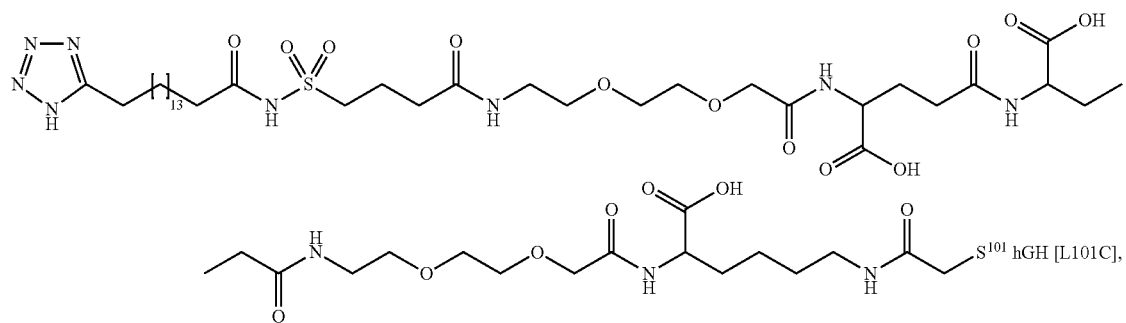

TOF-MS: Rt=14.0 min, mass=23305.5

247 248
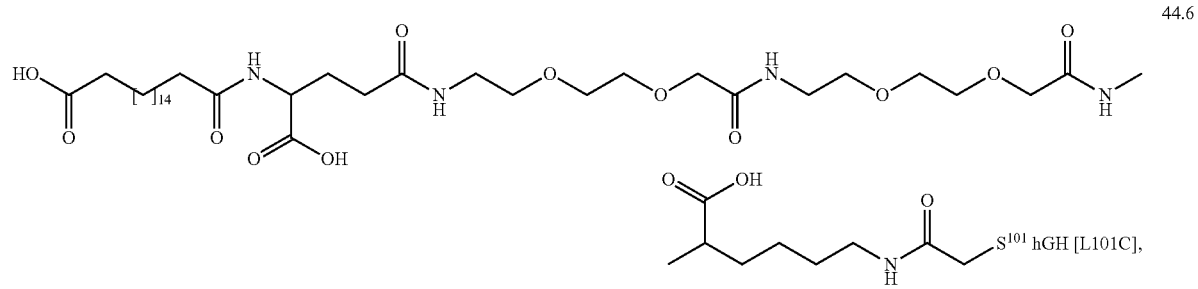
44.6
TOF-MS: Rt=15.27 min, mass=23148
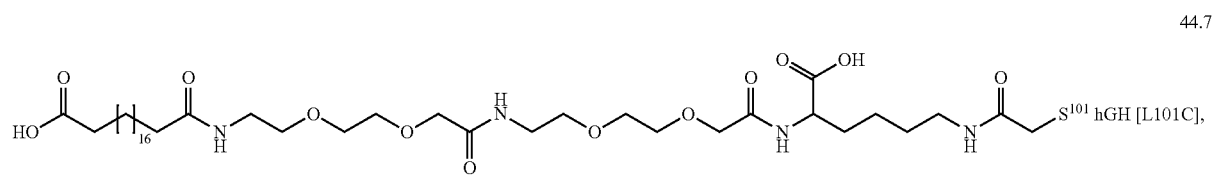
44.7
TOF-MS: Rt=16.40 min, mass=23048
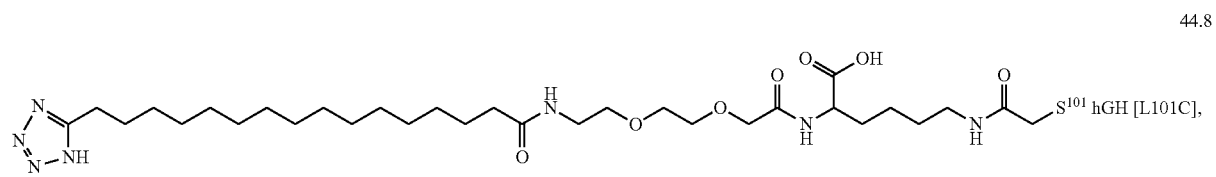
44.8
TOF-MS: Rt=15.3 min, mass=22884.4
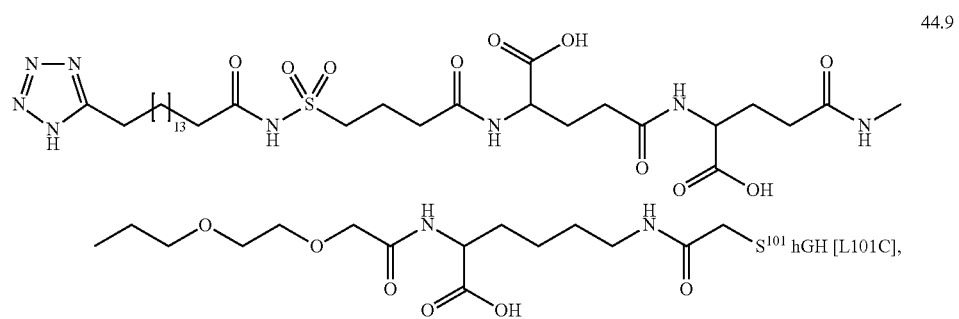
44.9
TOF-MS: Rt=14.6 min, mass=23291.4
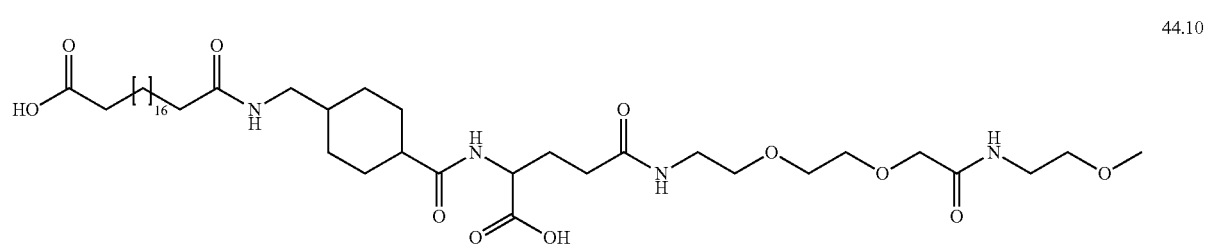
44.10

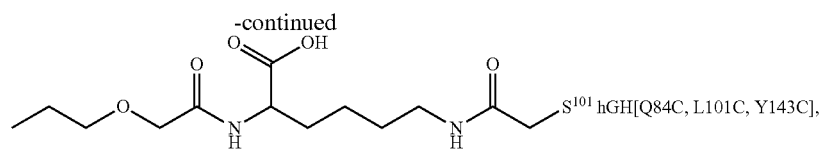
TOF-MS: Rt=15.05 min, mass=23097.76
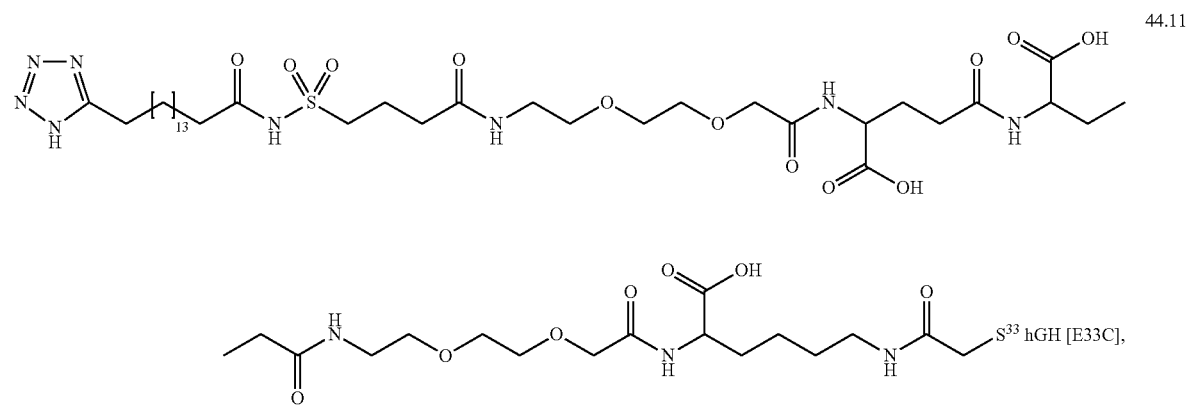
TOF-MS: Rt=14.2 min, mass=23420.83
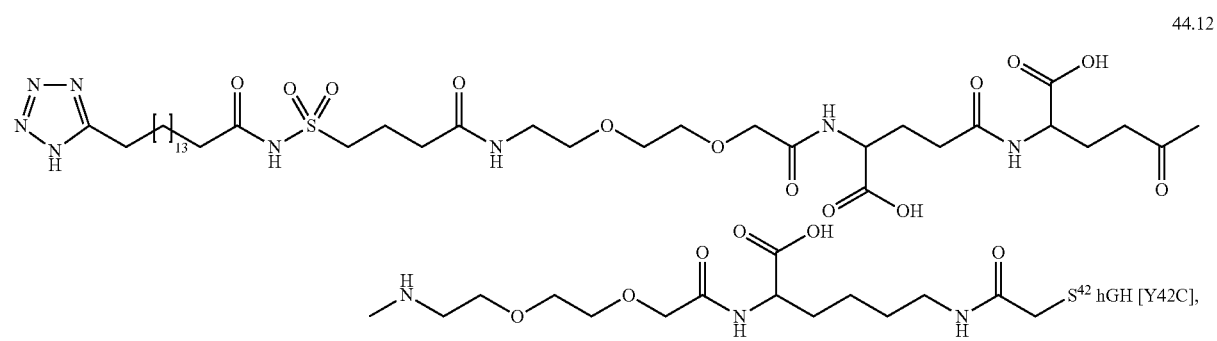
TOF-MS: Rt=15.7 min, mass=23289.6
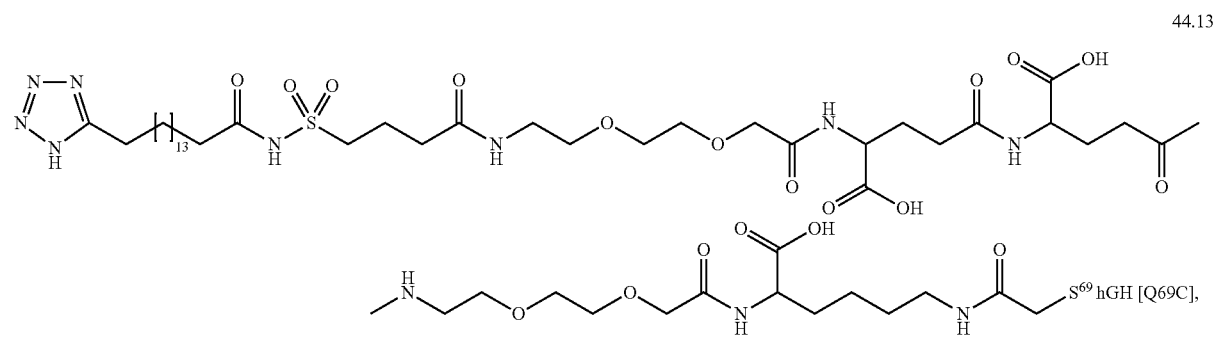
TOF-MS: Rt=17.0 min, mass=23324.55

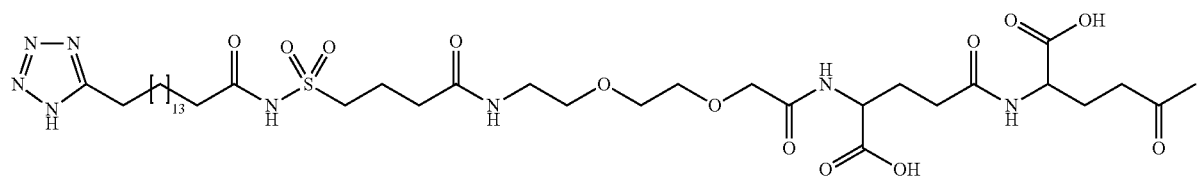
44.15
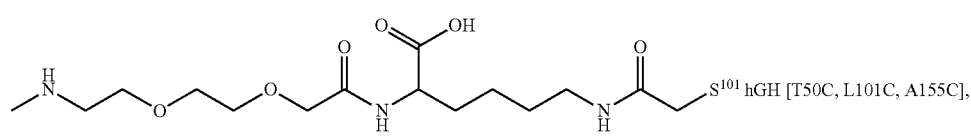
TOF-MS: Rt=12.85 min, mass=23337.5
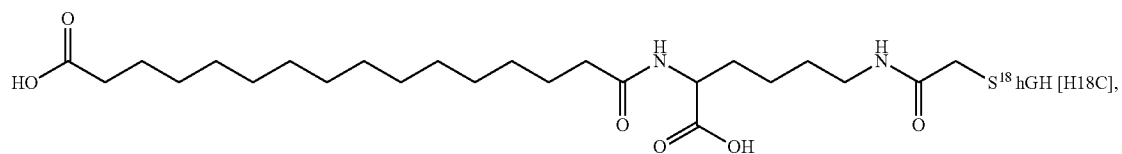
44.16
TOF-MS: Rt=15.24 min, mass=22676.8
Example 45
1. Coupling of a GH compound (VII) having an internal free single cys with an albumine binder (X)
   1) Alkylation of free Cys GH (VII) with a malimide substituted albumin binder (X) affording Cys conjugated GH compound (XI)
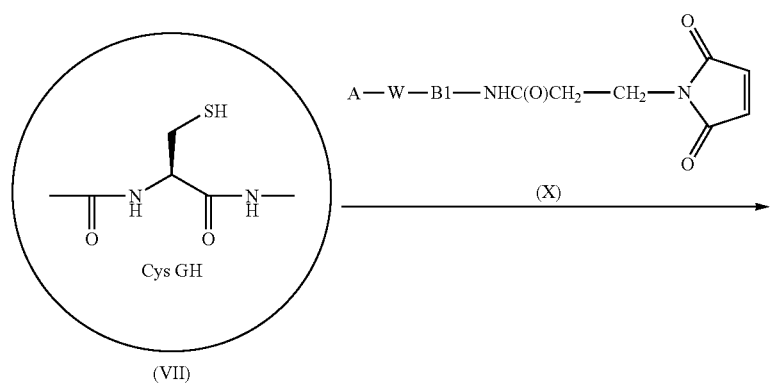

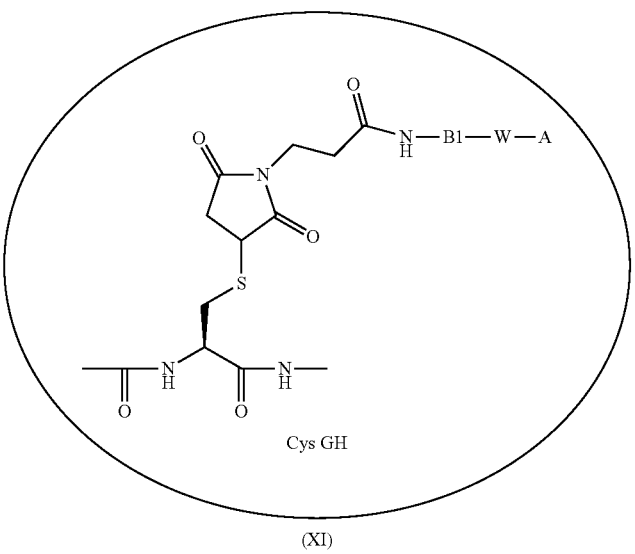

(XI)

Deprotected Cys GH compound (VII) as obtained above in Example 44 can be reacted with a malimide substituted albumin binder linker (X) affording GH conjugate A-W—B1-NHC(O)CH$_2$CH$_2$-pyrrolidin-2,5-dione-3-hGH (XI) wherein B1 is defined as described in Chemistry IV above.

Conjugation of Maleimide Functionalised Albumin Binder (X) to hGH L101C

Step (a) Deblocking of Cysteine Residue

Glutathione/cysteamine blocked Cys hGH (VI) was enzymatically deblocked using glutaredoxin II (Grx2) in an equilibrium buffer containing GSH and GSSG. Deblocked Cys hGH (VII) was separated from low molecular GSH/GSSG by buffer exchanged on a Sephadex G25 column.

Step (b) Coupling to Maleimide Functionalized Albumin Binder (X)

Maleimide functionalized albumin binder (X) was dissolved in buffer containing 5% hydroxypropyl-β-cyclodextrin. The solution was then added to de-blocked Cys hGH (VII) and allowed to reacted over night at room temperature.

After conjugation the conjugated protein was purified on a Q Sepharose HiLoad column in 20 mM triethanolamine buffer containing 10% ethylene glycol at pH 8.5 using a gradient of sodium chloride. The collected fractions were pooled and transferred to 10 mM ammonium bicarbonate using a G25 column and lyophilized.

45.1

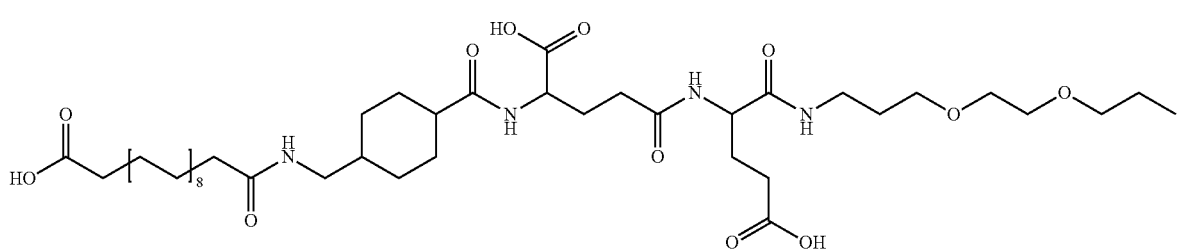

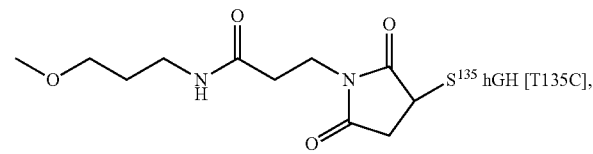

TOF-MS: Rt=16.0 min, mass=23352

255 256
45.2
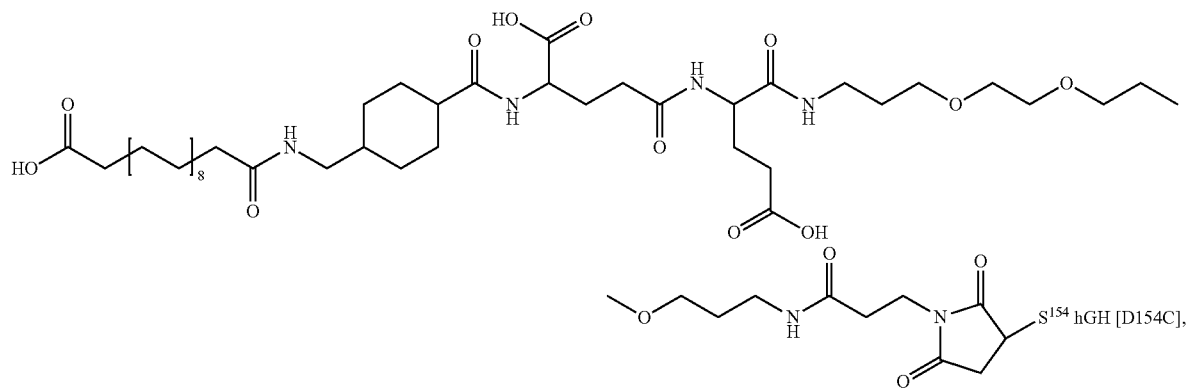
TOF-MS: Rt=15.98 min, mass=23338
45.3
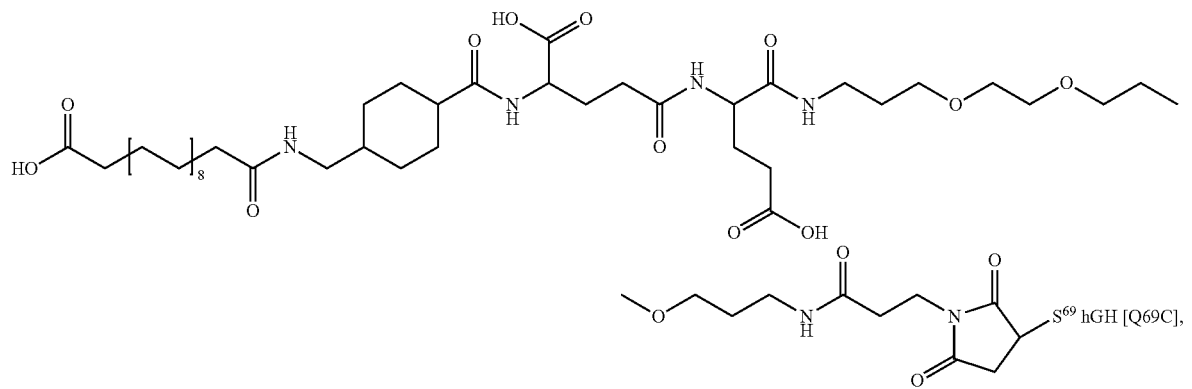
TOF-MS: Rt=16.62 min, mass=23324.6
45.4
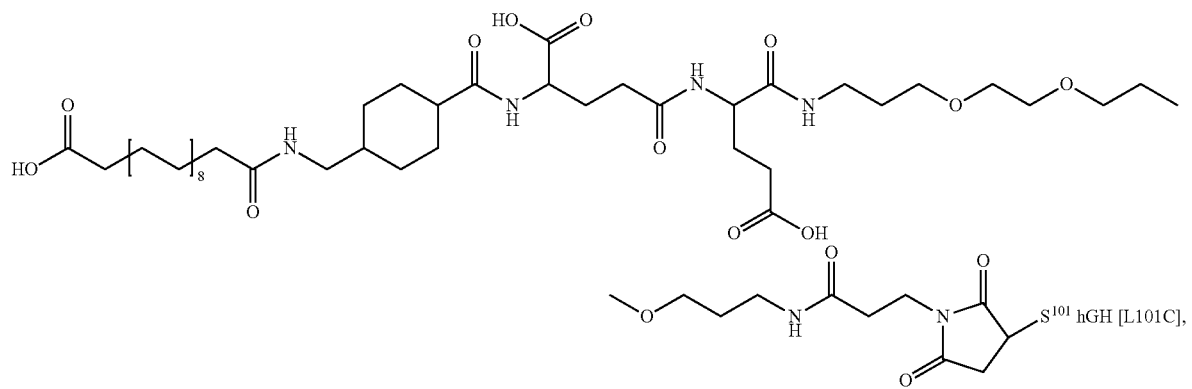
TOF-MS: Rt=16.20 min, mass=23339.7

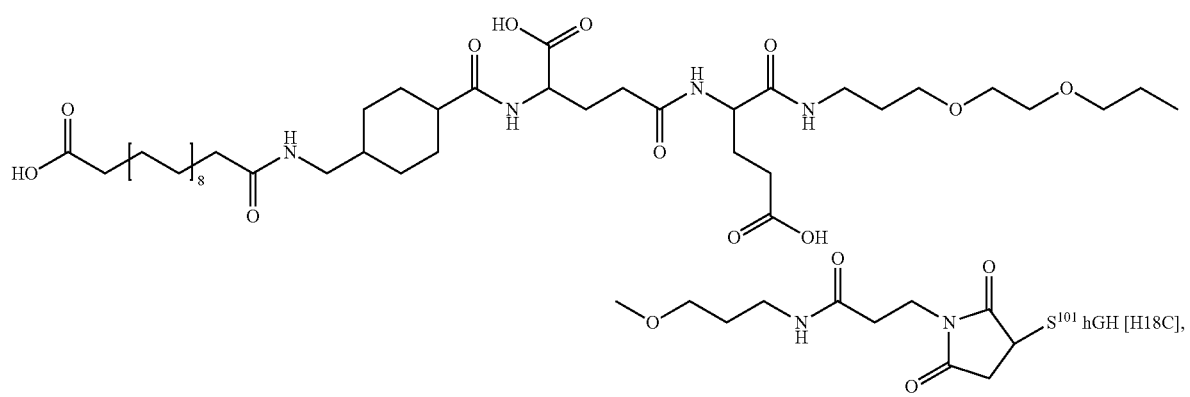
45.5
TOF-MS: Rt=15.72 min, mass=23316.35
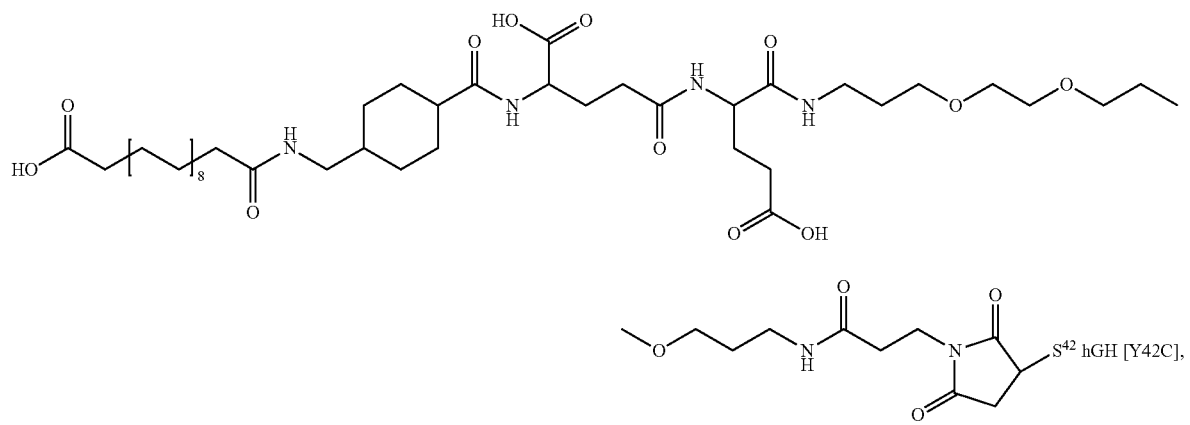
45.6
TOF-MS: Rt=17.2 min, mass=23365.9
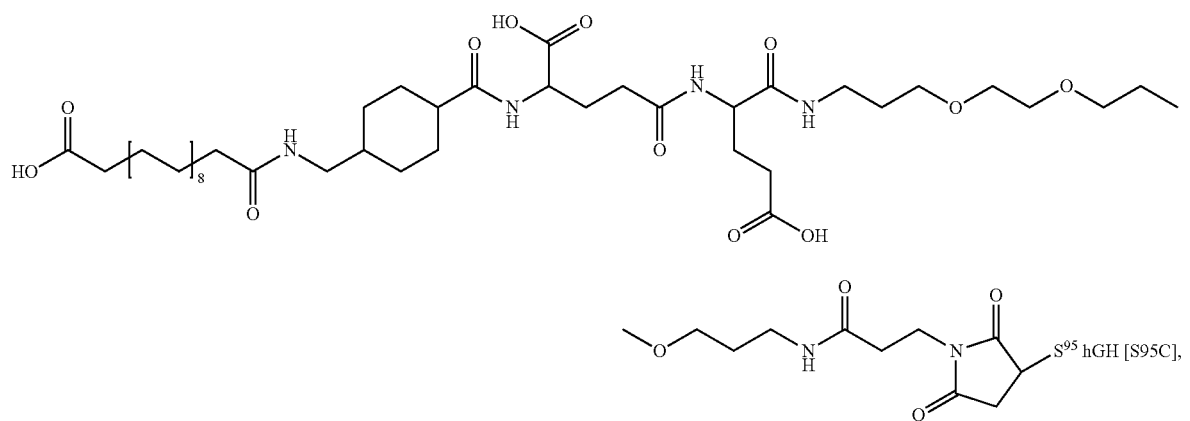
45.7
TOF-MS: Rt=17.2 min, mass=23366

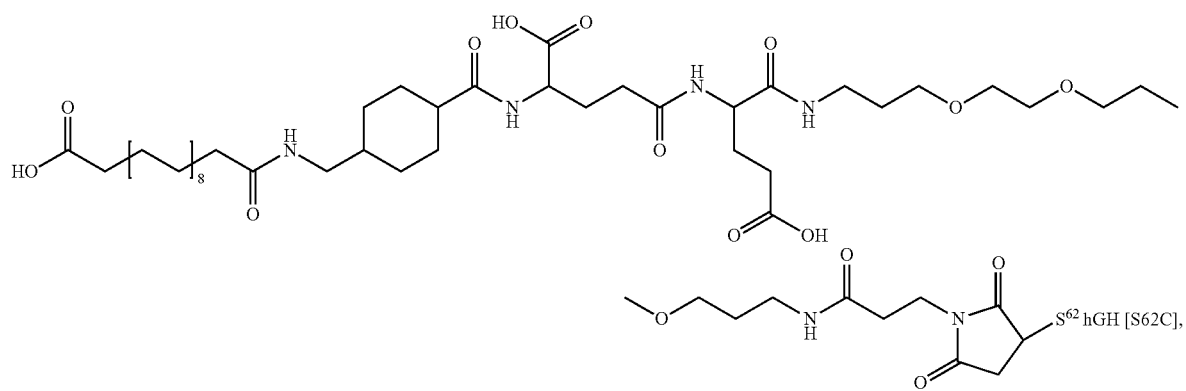
TOF-MS: Rt=16.5 min, mass=23366
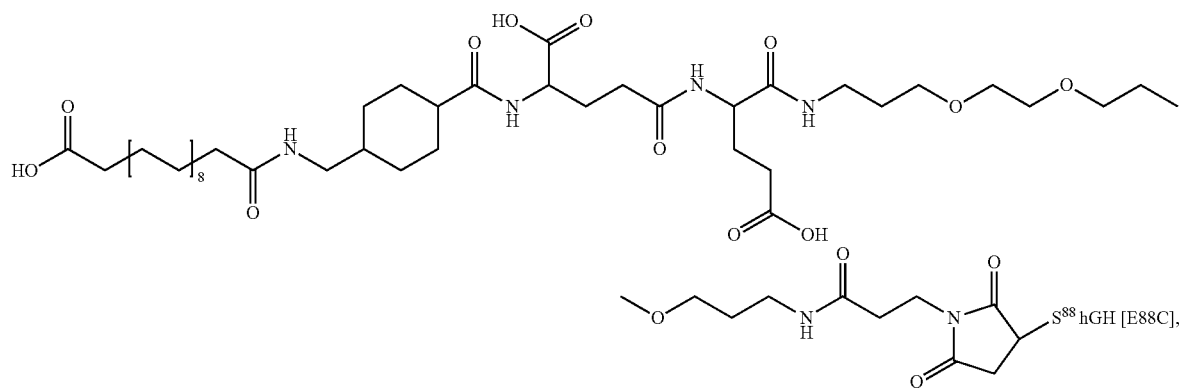
TOF-MS: Rt=16.8 min, mass=23323.8
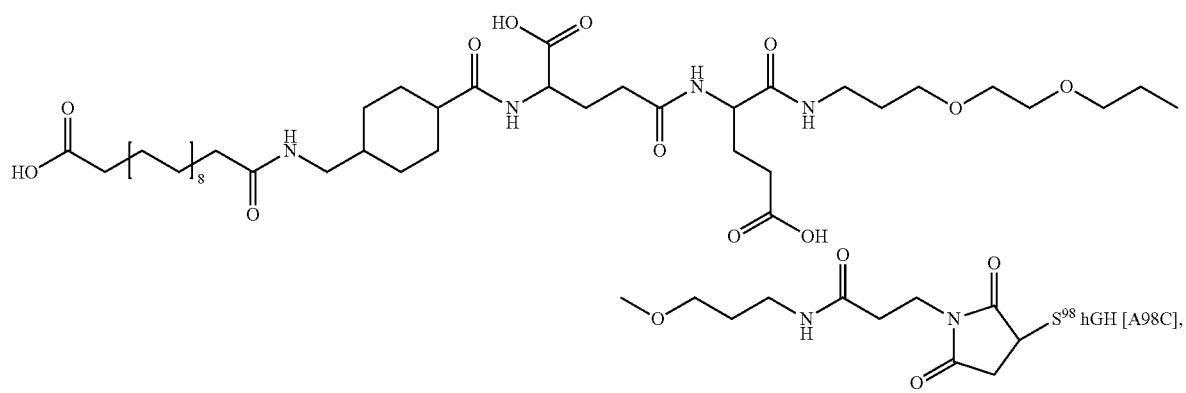
TOF-MS: Rt=17.1 min, mass=23382

45.11
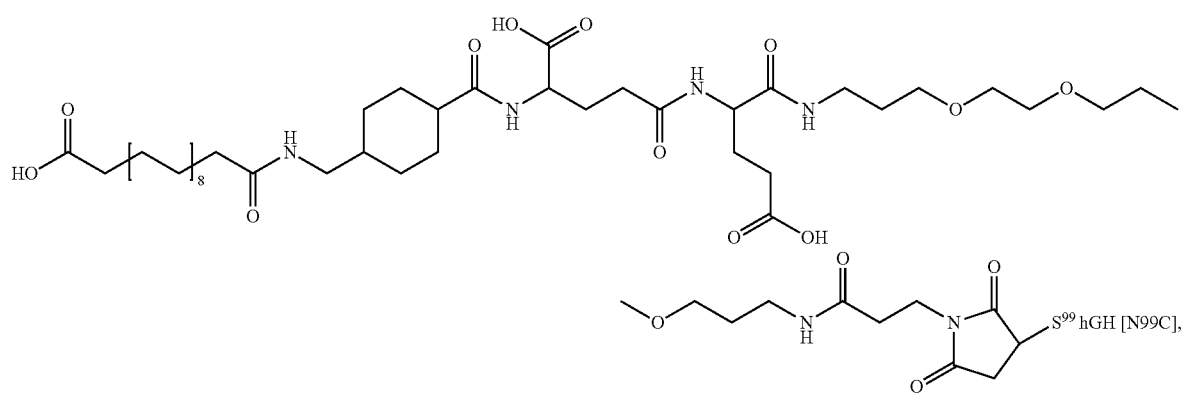
TOF-MS: Rt=17.2 min, mass=23338.8
45.12
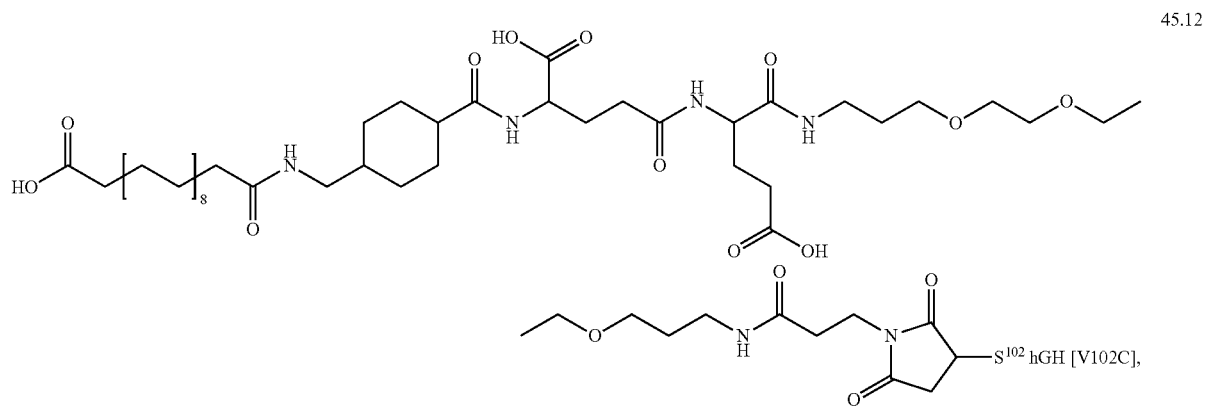
TOF-MS: Rt=17 min, mass=23353.9
45.13
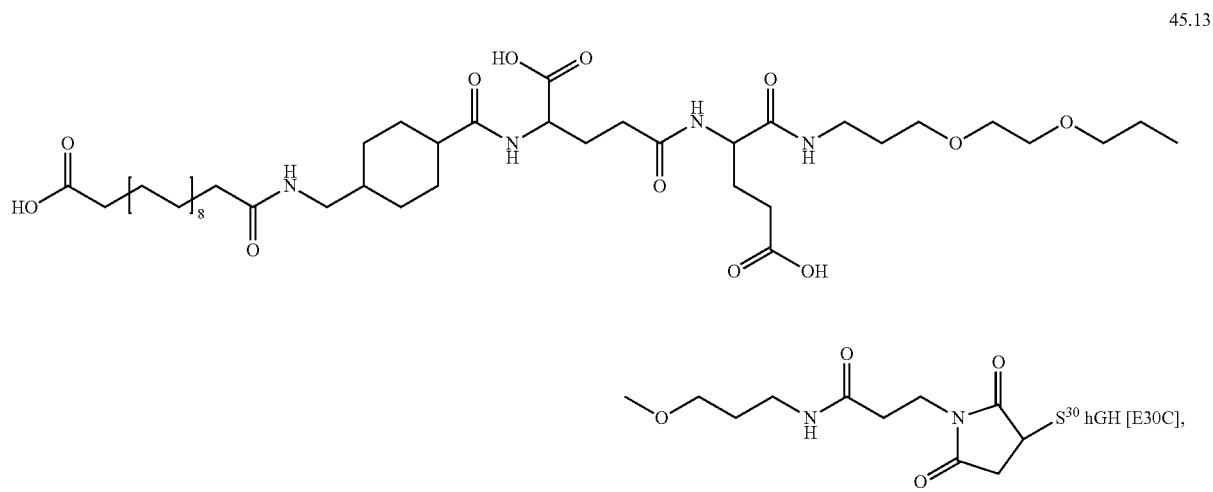
TOF-MS: Rt=15.65 min, mass=23323.7

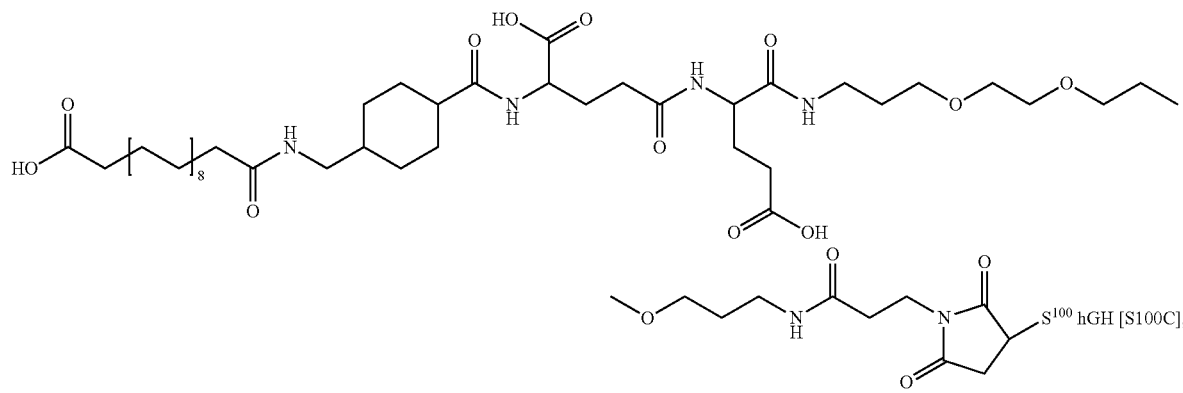

TOF-MS: Rt=16.5 min, mass=23365.8

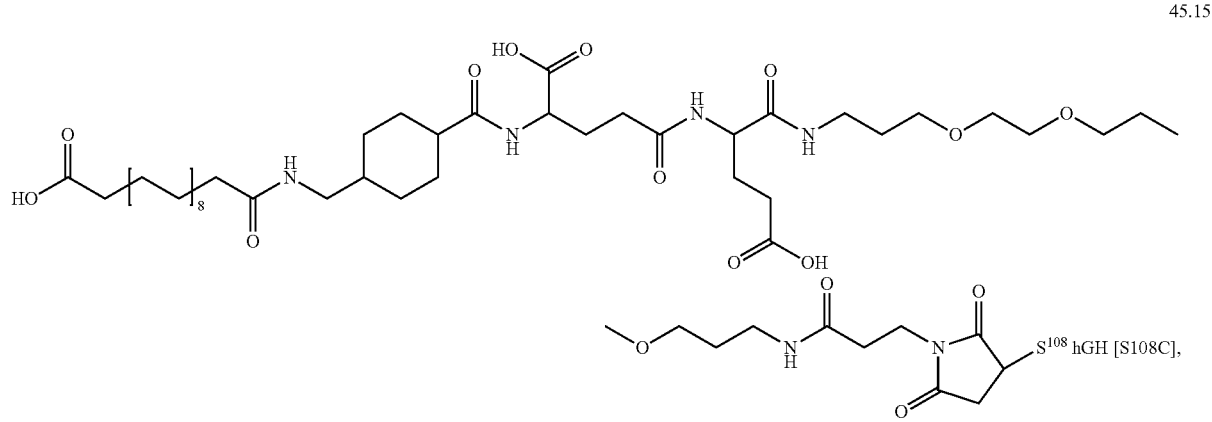

TOF-MS: Rt=17.2 min, mass=23365.9

Example 46

Assay (I) BAF-3 GHR Assay to Determine Growth Hormone Activity

The BAF-3 cells (a murine pro-B lymphoid cell line derived from the bone marrow) was originally IL-3 dependent for growth and survival. IL-3 activates JAK-2 and STAT which are the same mediators GH is activating upon stimulation. After transfection of the human growth hormone receptor the cell line was turn into a growth hormone-dependent cell line. This clone can be used to evaluate the effect of different growth hormone samples on the survival of the BAF-3 GHR.

The BAF-3 GHR cells are grown in starvation medium (culture medium without growth hormone) for 24 hrs at 37° C., 5% $CO_2$.

The cells are washed and re-suspended in starvation medium and seeded in plates. 10 µL of growth hormone compound or human growth hormone in different concentrations or control is added to the cells, and the plates are incubated for 68 hrs at 37° C., 5% $CO_2$.

AlamarBlue® is added to each well and the cells are then incubated for another 4 hrs. The AlamarBlue® is a redox indicator, and is reduced by reactions innate to cellular metabolism and, therefore, provides an indirect measure of viable cell number.

Finally, the metabolic activity of the cells is measure in a fluorescence plate reader. The absorbance in the samples is expressed in % of cells not stimulated with growth hormone compound or control and from the concentration-response curves the activity (amount of a compound that stimulates the cells with 50%) can be calculated.

In vitro potency of compound 45.4 in the BAF-3 hGH receptor assay is shown in table 1 below.

Protease stability of compound 45.5 was determined as described in the general method by incubating the compound for 4 hours with chymotrypsin or elastase. The percent of intact GH compound was measured and the results are included in table 1.

TABLE 1

| Data relating to compound 45.4 | | | | | |
|---|---|---|---|---|---|
| Compound | EC50 (nM) | Ratio ($EC_{50}$ cmp/ $EC_{50}$ hGH) | n | Chymotrypsin (% intact GH compound) | Elastase (% intact GH compound) |
| hGH | 0.026 ± 0.012 | 1 | 6 | 40 | 25 |
| 45.4 | 0.09 ± 0.043 | 3.5 | 6 | 75 | 65 |

Example 47

Pharmacokinetics

The pharmacokinetic of the compounds of the examples is investigated in male Sprague Dawley rats after intravenous (i.v.) and subcutaneous (s.c.) single dose administration.

Test compounds are diluted to a final concentration of 1 mg/mL in a dilution buffer consisting of: Glycine 20 mg/mL, mannitol 2 mg/mL, $NaHCO_3$ 2.5 mg/mL, pH adjusted to 8.2.

The test compounds are studied in male Sprague Dawley rats weighing 250 g. The test compounds are administered as a single injection either i.v. in the tail vein or s.c. in the neck with a 25 G needle at a dose of 60 nmol/kg body weight.

For each test compound blood sampling is conducted according to the following schedule presented in table 2.

TABLE 2

Blood sampling schedule for each test compound.

| Animal no. | RoA | Predose | 0.08 | 0.25 | 0.5 | 1 | 2 | 4 | 6 | 8 | 18 | 24 | 48 | 72 |
|---|---|---|---|---|---|---|---|---|---|---|---|---|---|---|
| 1 | s.c. | | | | | | | X | X | X | | X | X | X |
| 2 | | | | | | | | X | X | X | | X | X | X |
| 3 | | | | X | X | X | X | | | | | | | |
| 4 | | | | X | X | X | X | | | | | | | |
| 5 | | | X | | | | | | | | X | | | |
| 6 | | | X | | | | | | | | X | | | |
| 7 | i.v. | | | X | X | | | X | X | | X | X | X | |
| 8 | | | | X | X | | | X | X | | X | X | X | |
| 9 | | X | X | | | | | | | | X | | | |
| 10 | | X | X | | | | | | | | X | | | |

At each sampling time 0.25 ml blood is drawn from the tail vein using a 25 G needle. The blood is sampled into a EDTA coated test tube and stored on ice until centrifugation at 1200×G for 10 min at 4° C. Plasma is transferred to a Micronic tube and stored at −20° C. until analysis.

Test compound concentrations are determined by a sandwich ELISA using a guinea pig anti-hGH polyclonal antibody as catcher, and biotinylated hGH binding-protein (soluble part of human GH receptor) as detector. The limit of detection of the assay was 0.2 nM.

A non-compartmental pharmacokinetic analysis is performed on mean concentration-time profiles of each test compound using WinNonlin Professional (Pharsight Inc., Mountain View, Calif., USA). The pharmacokinetic parameter estimates of terminal half-life ($t_{1/2}$) and mean residence time (MRT) are calculated.

TABLE 3

Half-life ($t_{1/2}$) and mean residence time (MRT) of GH compounds from the examples in Spraque Dawley rats after single dose i.v. and s.c. administration.

| Compound (Example #) | RoA | $T_{1/2}$ (h) | MRT (h) |
|---|---|---|---|
| 43.0 | i.v. | 7.2 | 9.8 |
| 43.2 | i.v. | 4.4 | 7.4 |
| 44.1 | i.v. | 5.6 | 7.2 |
| 44.3 | i.v. | 1.3 | 0.9 |
| 44.4 | i.v. | 2.5 | 2.7 |
| 44.5 | i.v. | 4.1 | 6.8 |
| 44.6 | i.v. | 3.2 | 4.0 |
| 44.7 | i.v. | 3.8 | 6.0 |
| 44.9 | i.v. | 4.2 | 6.5 |
| 44.10 | i.v | 4.1 | 7.1 |
| 45.4 | i.v. | 8.6 | 9.8 |
| 45.4 | s.c. | 19.8 | 31.2 |
| 45.12 | i.v. | 5.8 | 6.8 |

The bioavailability of example 45.4 was estimated to 48.3%. The time to maximum plasma concentration (t max) after subcutaneous administration was 8.0 hrs. Cmax was 1670 and 151 nM after i.v. and s.c. administration, respectively. The extrapolated plasma concentration at time zero after i.v. administration concentration was 1710 nM.

Example 48

The in vitro potency and half lives of a series of compounds were determined as described above. The conjugates of the compounds are identical but attached via an alternative cysteine introduced by mutation as described in the table 4.

TABLE 4

In vitro potency and half lives ($t_{1/2}$).

| Compound | In vitro potency | $T_{1/2}$ (i.v. Rat) (hour) | MRT (hour) | Attachement site (variant) |
|---|---|---|---|---|
| hGH | 1.0 (def) | 0.23 | — | |
| 45.1 | | 2.6 | 3.8 | T135C |
| 45.2 | | 2.8 | 8.7 | D154C |
| 45.3 | | 2.1 | 3.1 | Q69C |
| 45.4 | 2.9 | 6.3/8.6 | 7.8/9.8 | L101C |
| 45.5 | | 4.1 | 4.5 | L18C |
| 45.6 | | 4.1 | 5.5 | Y42C |
| 45.7 | | 0.72 | 6.5 | S95C |
| 45.8 | | 0.59 | 2.0 | S62C |
| 45.9 | | 1.8 | 4.1 | E88C |
| 45.10 | 2.6 | 3.4 | 4.3 | A98C |
| 45.11 | 3.1 | 5.8 | 6.8 | N99C |
| 45.12 | 2.5 | 1.9 | 3.0 | V102C |
| 45.13 | 16.5 | 1.9 | 2.6 | E30C |
| 45.14 | 4.4 | 1.5 | 2.0 | S100C |

Example 49

In Vivo Dose-Response Study in Hypophysectomised Sprague Dawley Rats

The in vivo dose-response relationship is studied in hypophysectomised male Sprague Dawley rats. The hypophysectomised rat is a well known and recognised animal model of growth hormone deficiency, where no production of growth hormone occurs after the surgical removal of the pituitary gland. This also leads to low circulating levels of insulin-like growth factor-1 (IGF-1) another important clinical feature of growth hormone deficiency in humans.

The hypophysectomy is performed on 4 week old male rats weighing 90-100 g. The animals entering the study 3-4 weeks after the surgery weighing 100-110 g. Animals with a body weight gain of more than 10% during the 3-4 weeks after surgery are not allowed to enter the study.

Dose response studies are performed using five dose levels of compound 45.4 from 1-150 nmol/rat.

Baseline levels of plasma IGF-1 in hypophysectomised Sprague Dawley rats were approximately 80-100 ng/mL in all dosing groups. After a single dose IGF-1 levels rapidly increased to 800-1000 ng/mL on Day 1 almost independently of dose. The plasma IGF-1 levels declined again during the following days in a dose-dependent manner with the fastest decline seen with the lowest dose and the slowest decline with the highest dose. At the highest dose the IGF-1 plasma level was maintained at 800-900 ng/mL for 3 days before it started to decline more rapidly. IGF-1 plasma concentration levels were elevated compared to the vehicle control group for all dosing groups until Day 3. For dosing groups 10 nmol, 50 nmol and 150 nmol it was elevated during the entire study (7 days).

Example 50

Disappearance

It is hypothesized that absorption rate is related to the ability of a molecule to pass the tight junctions of the subcutaneous capillaries, a property related to molecular size. A PEG-hGH with a 40 kDa PEG has an apparent molecular weight (mw) of 150-250 kDa. A hGH molecule with covalent bound albumin has mw=87 kDa, whereas a hGH molecule with a non-covalent bound albumin will be dissociated from albumin part of the time and thus have mw=22 kDa. The time spend in the dissociated state will depend on the affinity of the albumin binding moiety. Thus the absorption rate of such compounds should be faster than for PEG-hGH and the rate should increase with the use of albumin binding moieties having lower affinity for albumin.

The test solutions were diluted in standard buffer consisting of: Glycine 20 mg/mL, mannitol 2 mg/mL, NaHCO$_3$ 2.4 mg/mL, pH adjusted to 8.2.

Iodination with $^{125}$I was performed by Chemistry & Isotope Lab. Novo Nordisk A/S. The final radioactive formulation had a specific radioactive activity of 3 μCi/mL and was supplied in 3 mL Penfills.

The solutions were stored at 2-8° C. until used.

Disappearance rate for selected compounds were measured in five female pigs of crossbred LYD. The pigs are weighted, fasted and issued a special "pig coat" in order to carry the gamma counter and transmitter and placed in single pens before the start of the study.

All pigs are fasted for 18 hrs prior the study.

The animals were dosed (60 nmol) subcutaneously on the left and the right side of the neck respectively with a Novopen3® and a NovoFine® 28 G needle with fixed black needle stopper. Injection depth was 5 mm.

The disappearance of the radioactive depots were measured by portable equipment for about 24-48 hrs.

For each individual animal, the results were presented as AUC (0-45 hrs) as shown in table 5.

The in vitro potency, half lives and further characteristics of a series of compounds were determined as described above and shown in the table 5.

TABLE 5

Compound charateristics.

| Compound | In vitro potency | T$_{1/2}$ (i.v. Rat) (hour) | Disapperance AUC (0-45 hour) | Duration of IGF-1 increase (hour) |
|---|---|---|---|---|
| hGH | 1.0 (def) | 0.23 | 519 | — |
| 44.9 | 8.2 | 4.2 | 2259 | >48 |
| 44.8 | 1.8 | 2.6 | 1490 | >24 |
| 44.1 | 4.7 | 5.6 | 1750 | >48 |
| 44.3 | 1.5 | 1.3 | 2152 | <24 |
| 44.6 | 4.7 | 3.2 | 1558 | <24 |
| 44.7 | 4.5 | 3.8 | 2039 | <24 |
| 44.5 | 5.8 | 4.1 | 1599 | >48 |
| 44.4 | 3.9 | 2.5 | 1588 | >48 |

Example 51

In Vivo Study in Pigs

To further confirm the functionality of hGH albumin conjugates according to the invention three compounds were selected for additional pharmacokinetic studies in pigs. Compounds equal to compounds 44.1, 44.4 and 44.5 were prepared conjugating the albumin binder to the hGH variant after removal of the MAEA purification tag.

The test compounds were diluted to the final concentration of 100 nmol/mL in standard buffer (20 mg/mL Glycine, 2 mg/mL Mannitol, 2.4 mg/mL NaHCO$_3$, pH adjusted to 8.2). Twenty four male Gottingen minipigs 5 months of age and weighing 9-12 kg were used in the study. Each test compound was dosed to eight animals with four minipigs receiving intravenous bolus administration and four animals receiving subcutaneous administration. The intravenous injections were given through a 24 G Venflon in the ear. The dose was given as a bolus over maximum 5 seconds followed by 2 mL of 0.9% NaCl. The subcutaneous injections were given on the right side of the neck, approximately 5-7 cm from the ear and 7-9 cm from the middle of the neck. Each animal received a single dose of test compound of 10 nmol/kg. Blood samples were collected from each animal at the following time points: Predose, 0.08, 0.25, 0.5, 1, 2, 4, 6, 8, 18, 24, 48, 72, 96, 120, 168, 240, and 336 hours post injection. Plasma was isolated from each blood sample and stored at −20° C. before analysed for test compound. Plasma concentration-time data were analysed by a non-compartmental pharmacokinetic method.

TABLE 6

Pharmacokinetic parameter estimates after single dose subcutaneous administration of 10 nmol/kg.

| Compound | ABW-Halo as in | AUC/dose (h * kg/l) | $T_{1/2}$ (h) | MRT (h) | MAT (h) | F (%) |
|---|---|---|---|---|---|---|
| 51.1 | 44.1 | 139 (37.5) | 11 (1.2) | 30.6 (4.1) | 10.0 | 38.6 |
| 51.2 | 44.5 | 101 (22.5) | 12 (2.7) | 25.2 (3.9) | 11.6 | 60.8 |
| 51.3 | 44.4 | 144 (34.7) | 12.6 (3.5) | 33.1 (1.7) | 12.1 | 35.6 |

Mean ± SD in ( )

Table 6 is showing key pharmacokinetic parameters for the three test compounds. The AUC/Dose is an estimate for the dose corrected exposure of the test compounds. $T_{1/2}$ is the terminal half-life of the test compounds after the absorption phase has been completed. MRT is the mean residence time of the test compounds corresponding to the time the average test compound molecule is in the body. MAT is the corresponding mean absorption time and is an estimate of the average time the molecule is in the absorption phase. F is the absolute bioavailability of the test compounds relative to intravenous administration.

The invention claimed is:

1. A growth hormone conjugate which comprises a growth hormone compound (GH) comprising a single Cys mutation selected from the group consisting of E88C, Q91C, S95C, A98C, N99C, S100C, L101C, V102C, Y103C, D107C, S108C, D112C, Q122C, and G126C, numbered according to SEQ ID NO: 1,
wherein an albumin binding residue via a hydrophilic spacer is linked to the sulphur residue of said single Cys of said GH, and wherein said albumin binding residue comprises a linear lipophilic moiety containing 12-40 carbon atoms, or a pharmaceutically acceptable salt thereof.

2. The growth hormone conjugate of claim 1 wherein the growth hormone conjugate has the formula (I):

A-W—B-GH     (I)

wherein
GH represents the growth hormone compound;
B represents a hydrophilic spacer linked to the sulphur residue of said single Cys of said GH;
W is a chemical group linking A and B; and
A represent an albumin binding residue comprising a linear lipophilic moiety containing 12-40 carbon atoms;
and pharmaceutically acceptable salts thereof.

3. The growth hormone conjugate of claim 1, wherein the GH further comprising an additional disulfide bridge between at least one of the amino acid pairs in the positions selected from the group consisting of R16C/L117C, A17C/E174C, H21C/M170C, D26C/V102C, D26C/Y103C, N47C/T50C, Q49C/G161C, F54C/Y143C, F54C/S144C, F54C/F146C, S55C/Y143C, S57C/Y143C, I58C/Q141C, I58C/Y143C, I58C/S144C, P59C/Q137C, P61C/E66C, P61C/T67C, S71C/S132C, L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C, F92C/T148C, R94C/D107C, V102C/A105C, L156C/F146C, L156C/T148C and V185C/S188C in SEQ ID NO: 1.

4. The growth hormone conjugate of claim 2, wherein A is selected from the group consisting of:

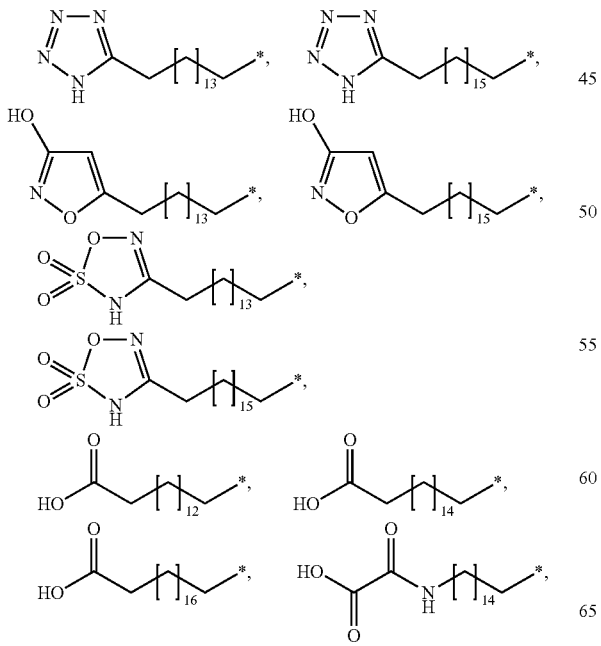

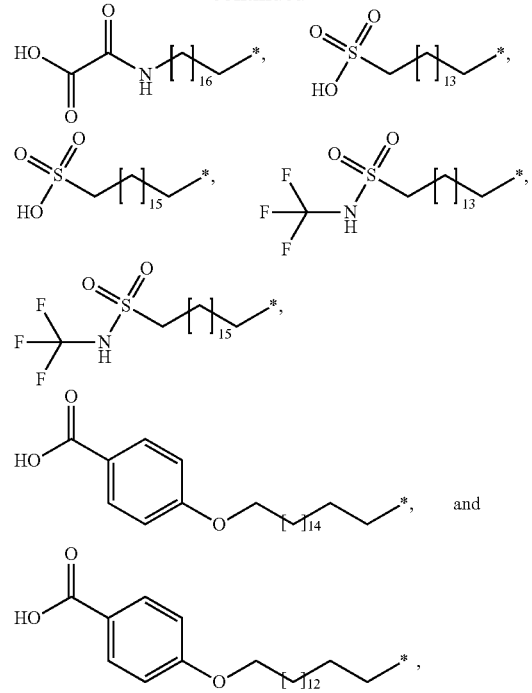

wherein * denotes the attachment to B through W.

5. The growth hormone conjugate of claim 2, wherein W has the formula

—W₇—Y—, wherein
Y is —(CH₂)₁₇—C₃₋₁₀-cycloalkyl-W₈— or a valence bond;
I7 is 0-6;
W₇ is selected from —C(O)NH—, —NHC(O)—, —C(O)NHCH₂—, —CH₂NHC(O)—, —C(O)NHS(O)₂—, —S(O)₂NHC(O)—, —OC(O)NH—, —NHC(O)O—, —C(O)CH₂—, —CH₂C(O)—, —C(O)CH=CH—, —CH=CHC(O)—, —(CH₂)ₛ₃—, —C(O)—, —C(O)O—, —OC(O)—, or a valence bond;
wherein s3 is 0 or 1;
W₈ is selected from —C(O)NH—, —NHC(O)—, —C(O)NHCH₂—, —CH₂NHC(O)—, —C(O)NHS(O)₂—, —S(O)₂NHC(O)—, —OC(O)NH—, —NHC(O)O—, —C(O)CH₂—, —CH₂C(O)—, —C(O)CH=CH—, —CH=CHC(O)—, —(CH₂)ₛ₄—, —C(O)—, —C(O)O—, —OC(O)—, or a valence bond;
wherein s4 is 0 or 1.

6. The growth hormone conjugate of claim 2, wherein B has the formula

—X₁—X₂—X₃—X₄— wherein
X₁ is —W₁—[(CHR¹)ᵢ₁—W₂]ₘ₁—{[(CH₂)ₙ₁E1]ₘ₂—[(CHR²)ᵢ₂—W₃]ₘ₃}ₙ₂—;
X₂ is —[(CHR³)ᵢ₃—W₄]ₘ₄—{[(CH₂)ₙ₃E2]ₘ₅—[(CHR⁴)ᵢ₄—W₅]ₘ₆}ₙ₄—;
X₃ is —[(CHR⁵)ᵢ₅—W₆]ₘ₇—;
X₄ is F-D1-(CH₂)ᵢ₆-D2-;
I1, I2, I3, I4, I5 and I6 independently are selected from 0-16, such as from 0-6 m1, m3, m4, m6 and m7 independently are selected from 0-10, such as from 0-6 m2 and m5 independently are selected from 0-25, such as from 0-10 n1, n2, n3 and n4 independently are selected from 0-16, such as from 0-10

F is aryl, hetaryl, pyrrolidine-2,5-dione or a valence bond, wherein the aryl and hetaryl groups are optionally substituted with halogen, —CN, —OH, —C(O)OH, —C(O)NH$_2$, —S(O)$_2$OH or C$_{1-6}$-alkyl;

R$^1$, R$^2$, R$^3$, R$^4$ and R$^5$ independently are selected from hydrogen, —C(O)OH, —C(O)NH$_2$, —S(O)OH, —S(O)$_2$OH, —NH—C(=NH)—NH$_2$, C$_{1-6}$-alkyl, aryl or hetaryl, wherein the alkyl, aryl and hetaryl groups optionally are substituted with halogen, —C(O)OH, —C(O)NH$_2$, —S(O)OH, —S(O)$_2$OH, —CN or —OH;

D1, D2, E1 and E2 independently are selected from —O—, —N(R$^6$)—, —N(C(O)R$^7$)— or a valence bond, wherein R$^6$ and R$^7$ independently represent hydrogen or C$_{1-6}$-alkyl;

W$_1$ to W$_5$ independently are selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s2}$—, —C(O)—, —C(O)O—, —OC(O)—, or a valence bond, wherein s2 is 0 or 1;

W$_6$ is selected from —C(O)NH—, —NHC(O)—, —C(O)NHCH$_2$—, —CH$_2$NHC(O)—, —C(O)NHS(O)$_2$—, —S(O)$_2$NHC(O)—, —OC(O)NH—, —NHC(O)O—, —C(O)CH$_2$—, —CH$_2$C(O)—, —C(O)CH=CH—, —CH=CHC(O)—, —(CH$_2$)$_{s1}$—, —C(O)—, —C(O)O—, —OC(O)—, —NHC(O)C$_{1-6}$-alkyl, —C(O)NHC$_{1-6}$-alkyl, or a valence bond, wherein s1 is 0 or 1 and the C$_{1-6}$-alkyl group is optionally substituted with oxo, pyrrolidine-2,5-dione, —NHC(O)CH*CH$_2$COOH or —NHC(O)CH$_2$CH*COOH, wherein (*) indicates the attachment point from the carbon atom of CH to X$_4$.

7. The growth hormone conjugate of claim 6, wherein D1 and D2 are independently selected from —O— or —N(R$^6$)— or a valence bond.

8. The growth hormone conjugate of claim 6, wherein E1 and E2 are independently selected from —O— or —N(R$^6$)— or a valence bond.

9. The growth hormone conjugate of claim 5, wherein W$_7$ and W$_8$ independently are selected from the group consisting of —C(O)NH—, —NHC(O)—, —CH$_2$NHC(O)—, —C(O)NHS(O)$_2$—, —S(O)$_2$NHC(O)—, —NHC(O)C$_{1-6}$-alkyl or —C(O)NHC$_{1-6}$-alkyl or a valence bond, wherein the alkyl group is optionally substituted with oxo, pyrrolidine-2,5-dione, —NHC(O)CH*CH$_2$COOH or —NHC(O)CH$_2$CH*COOH, wherein (*) indicates the attachment point from the carbon atom of CH to B.

10. The growth hormone conjugate of claim 6, wherein R$^1$, R$^2$, R$^3$, R$^4$ and R$^5$ independently are selected from hydrogen, —C(O)OH, —C(O)NH$_2$, —S(O)$_2$OH or C$_{1-6}$-alkyl; wherein the alkyl group optionally is substituted with —C(O)OH, —C(O)NH$_2$ or —S(O)$_2$OH.

11. The growth hormone conjugate of claim 6, wherein X$_4$ is a valence bond and W$_6$ is selected from either pyrrolidine-2,5-dione, —NHC(O)CH*CH$_2$COOH or —NHC(O)CH$_2$CH*COOH, wherein (*) indicates the attachment point from the carbon atom of CH to GH.

12. The growth hormone conjugate of claim 2 wherein B is selected from the group consisting of:

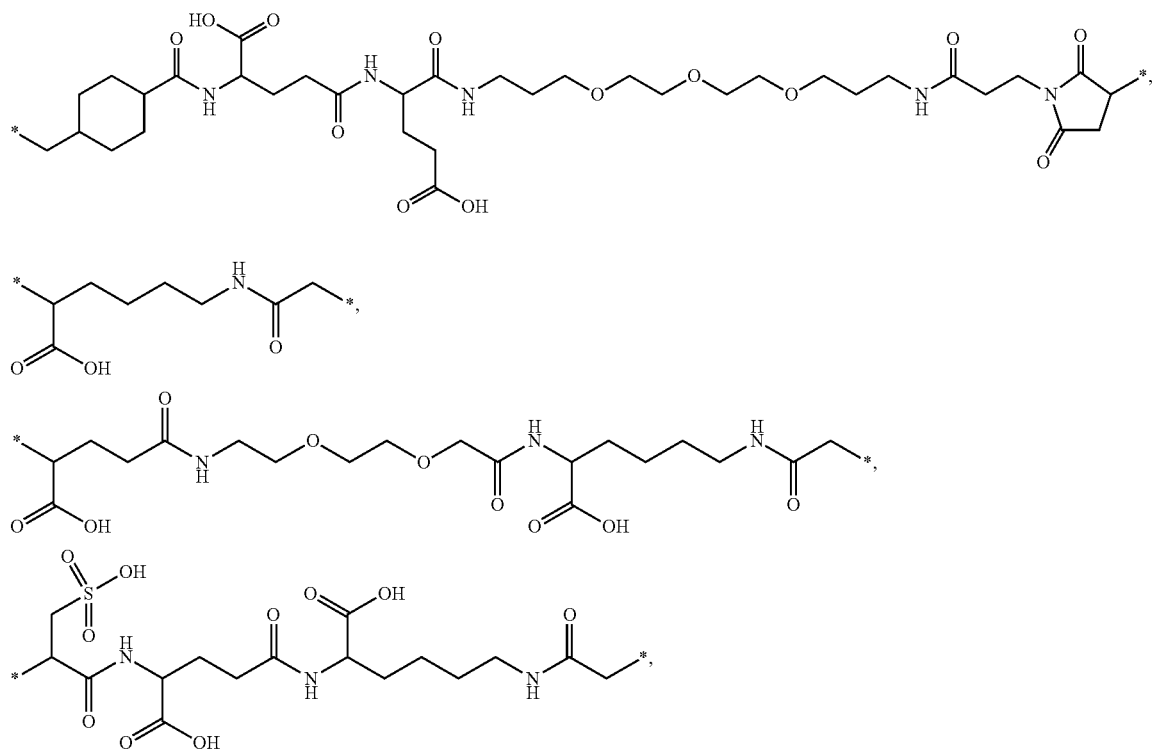

-continued
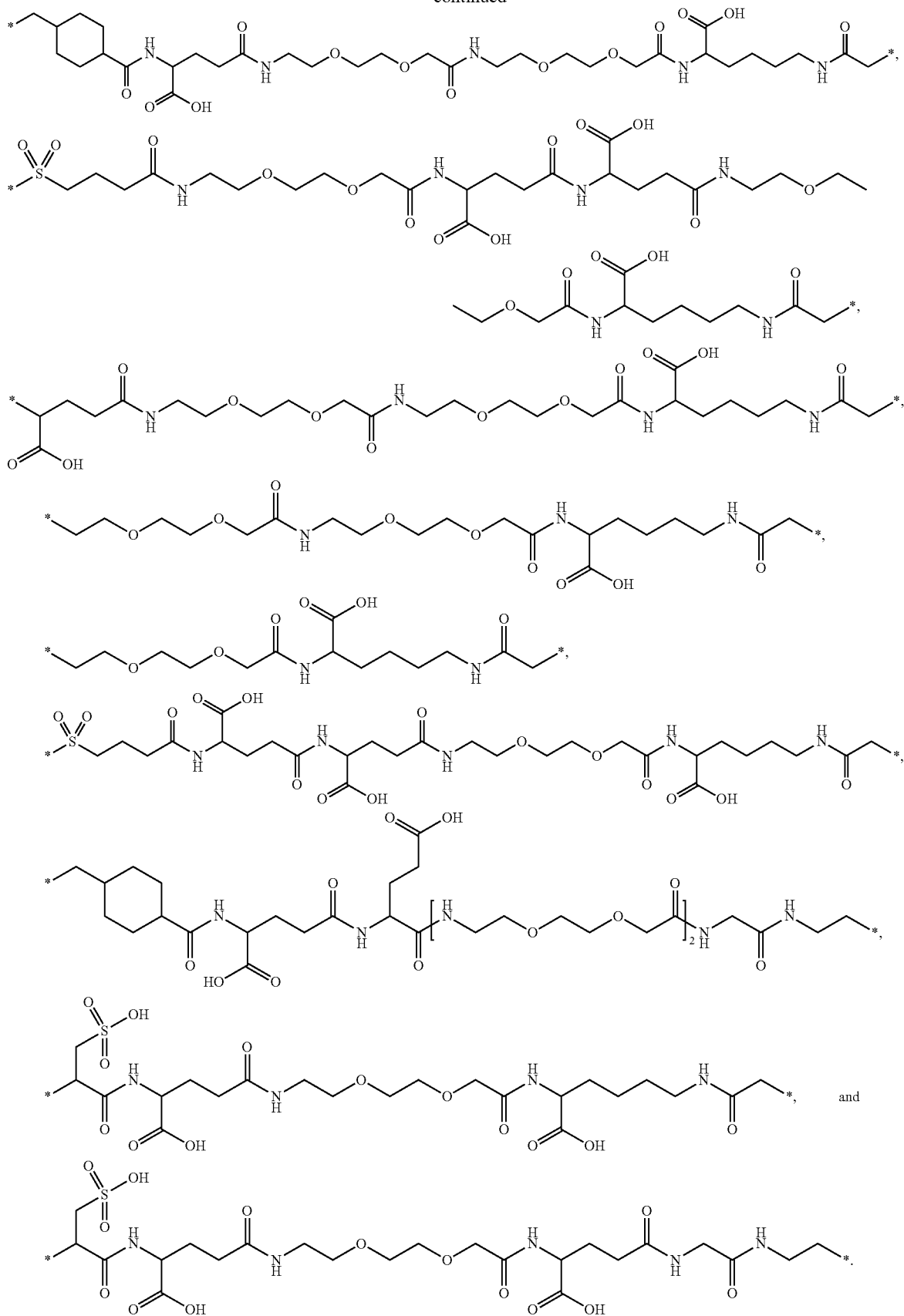

13. A growth hormone conjugate selected from the group consisting of:
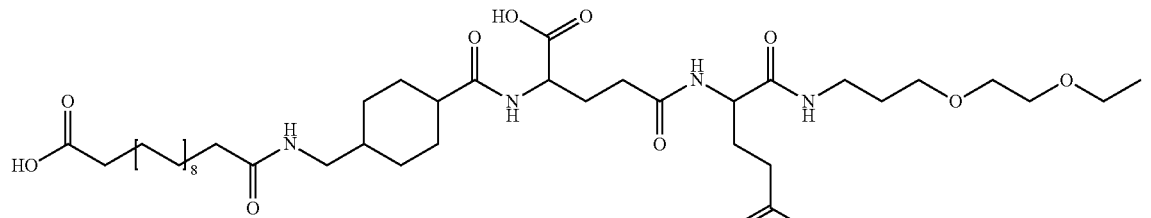
S$^{101}$ hGH [L101C],
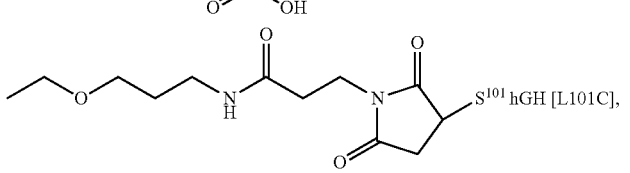
S$^{18}$ hGH [H18C],
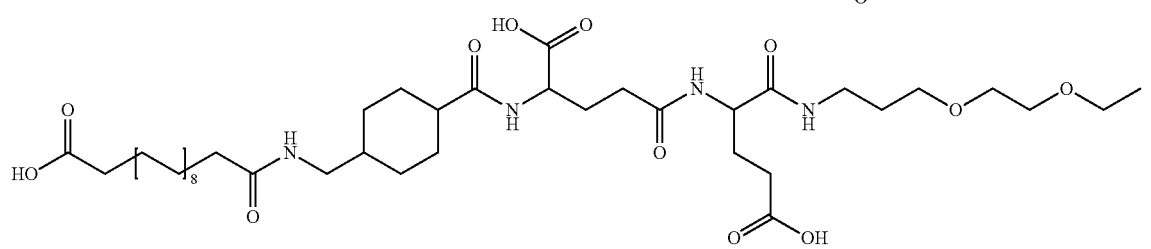
S$^{95}$ hGH [S95C],
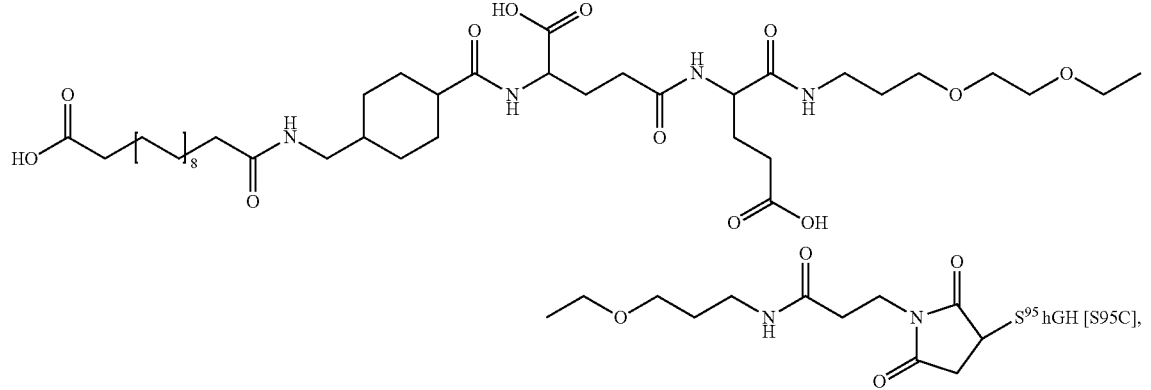
S$^{88}$ hGH [E88C],

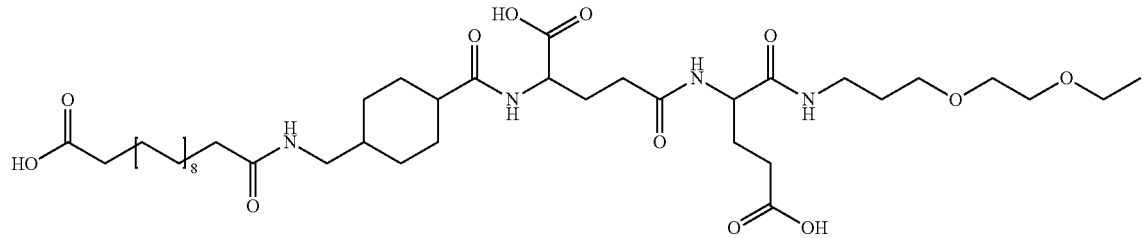
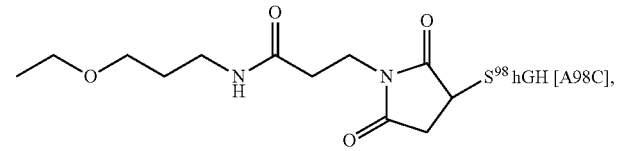
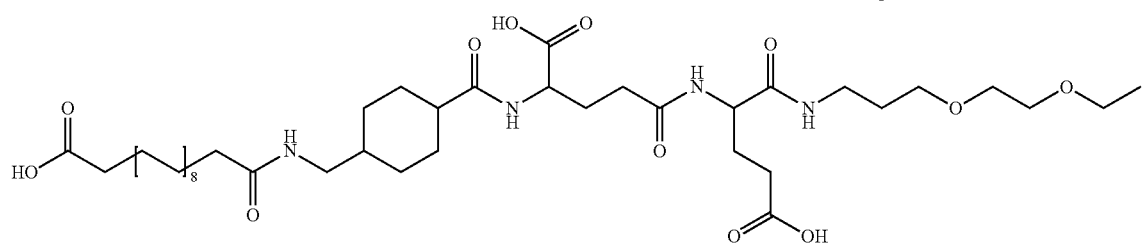
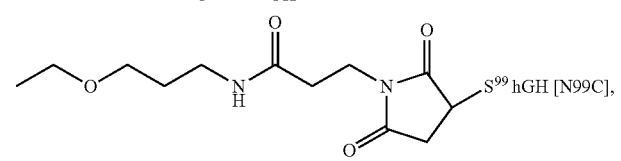
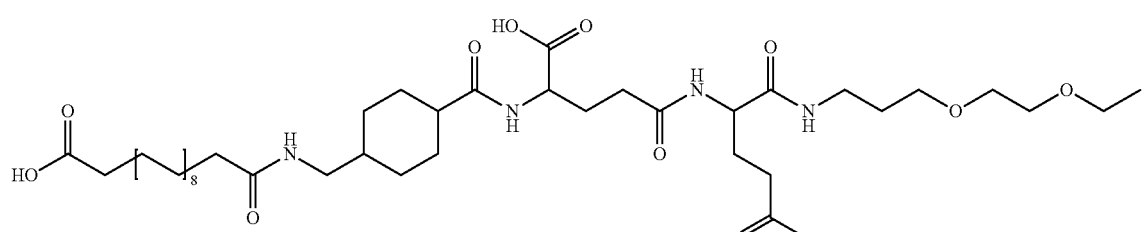
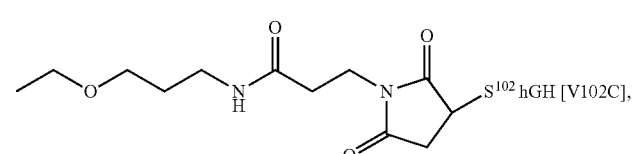
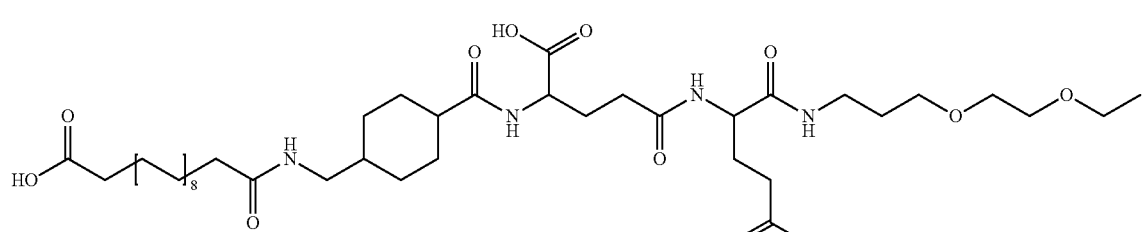
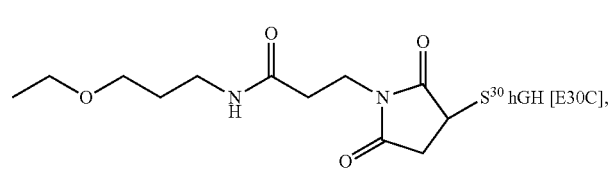

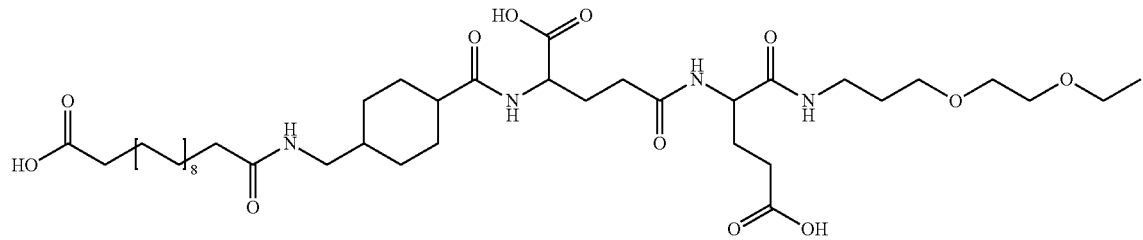
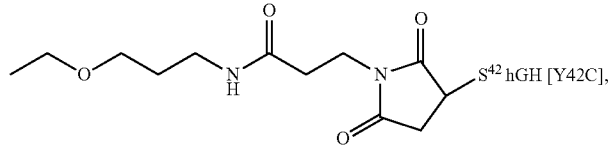
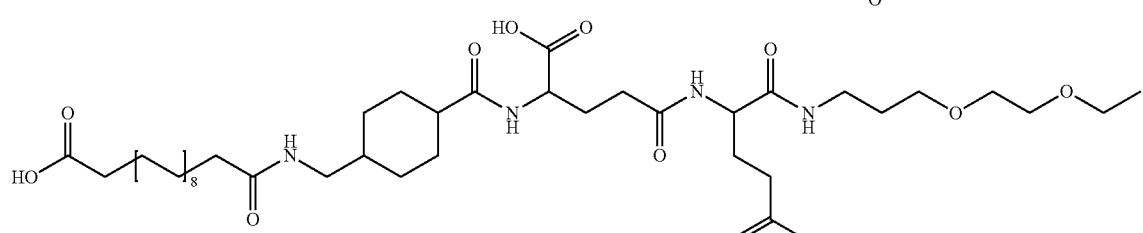
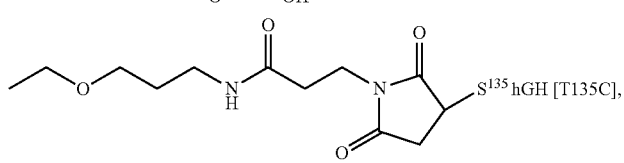
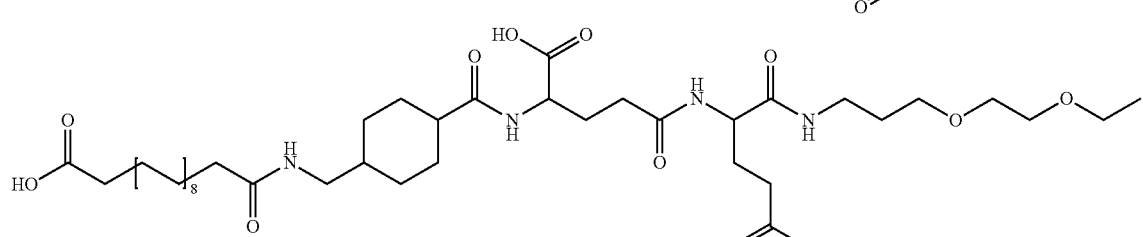
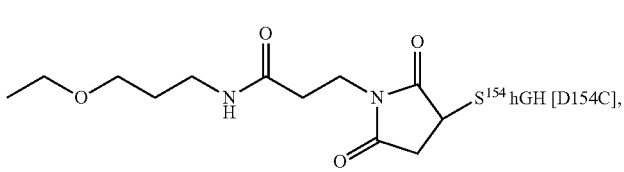
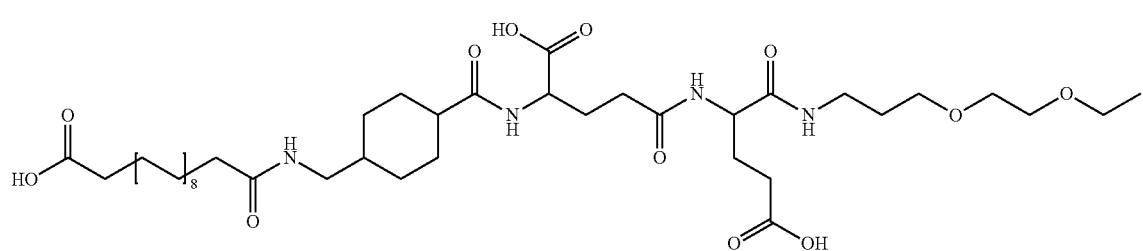
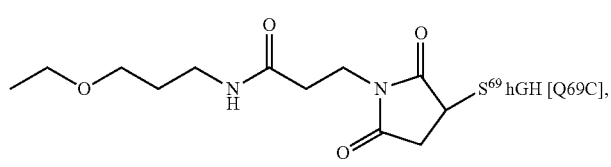

-continued
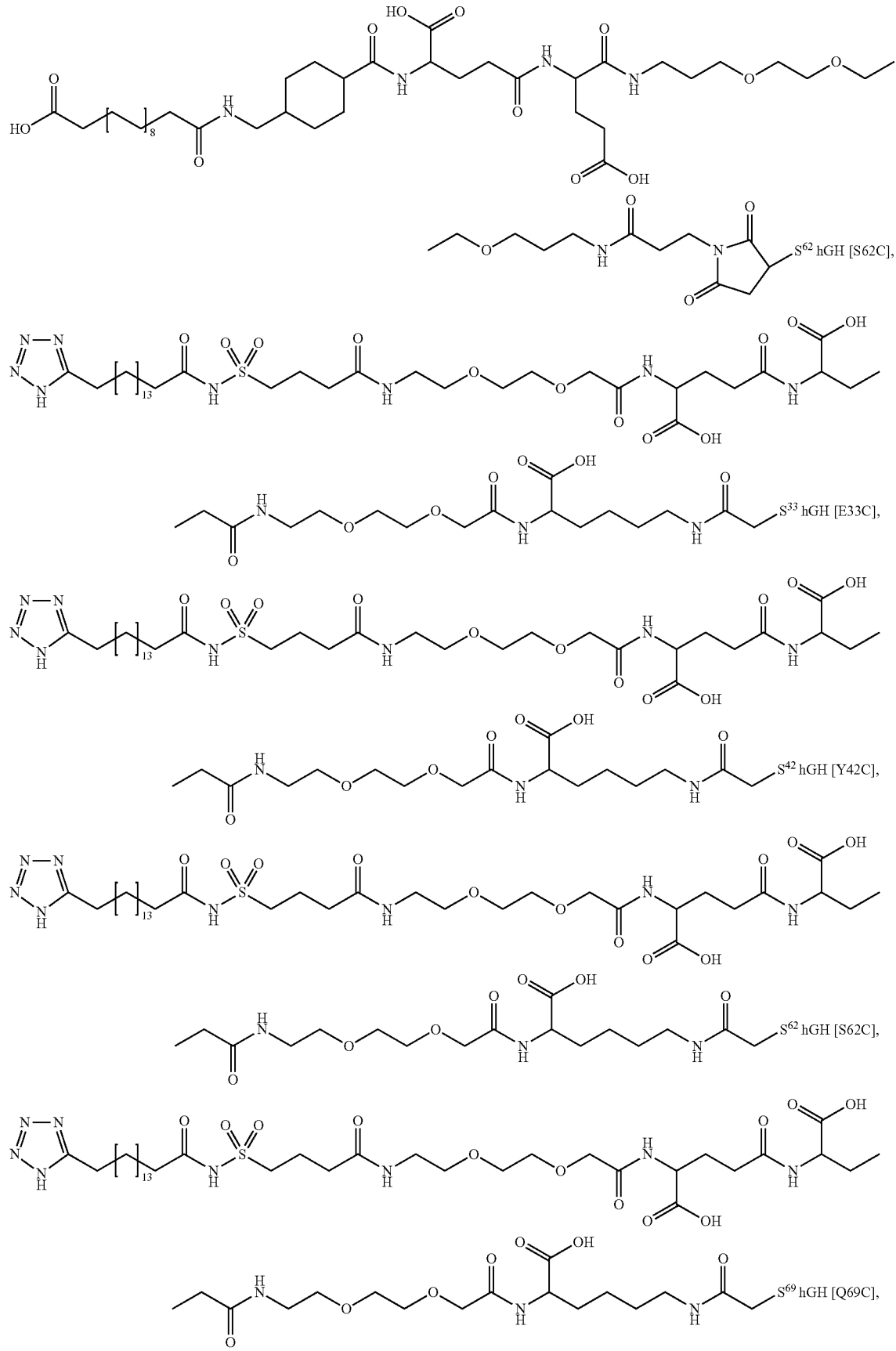

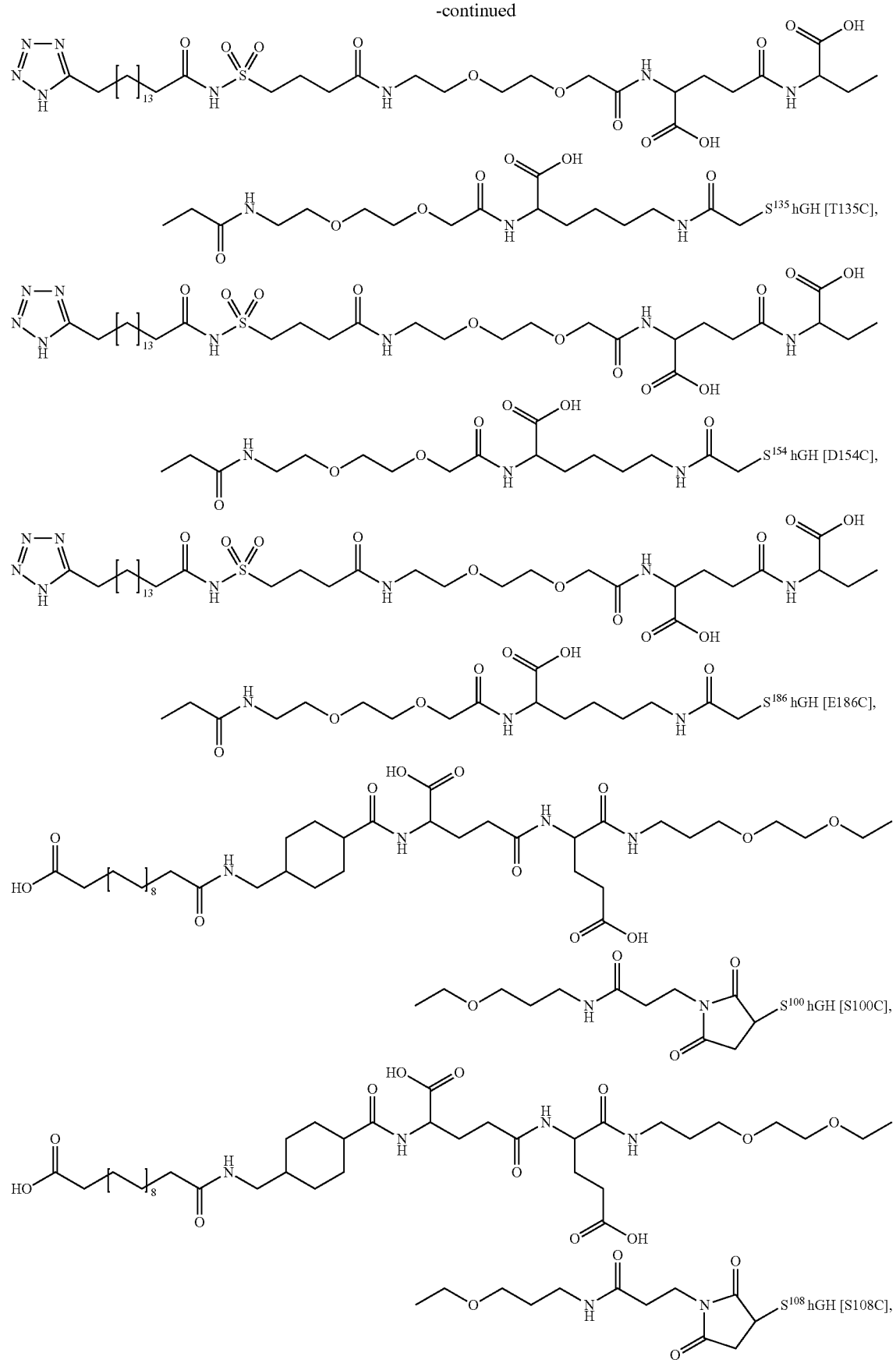

-continued
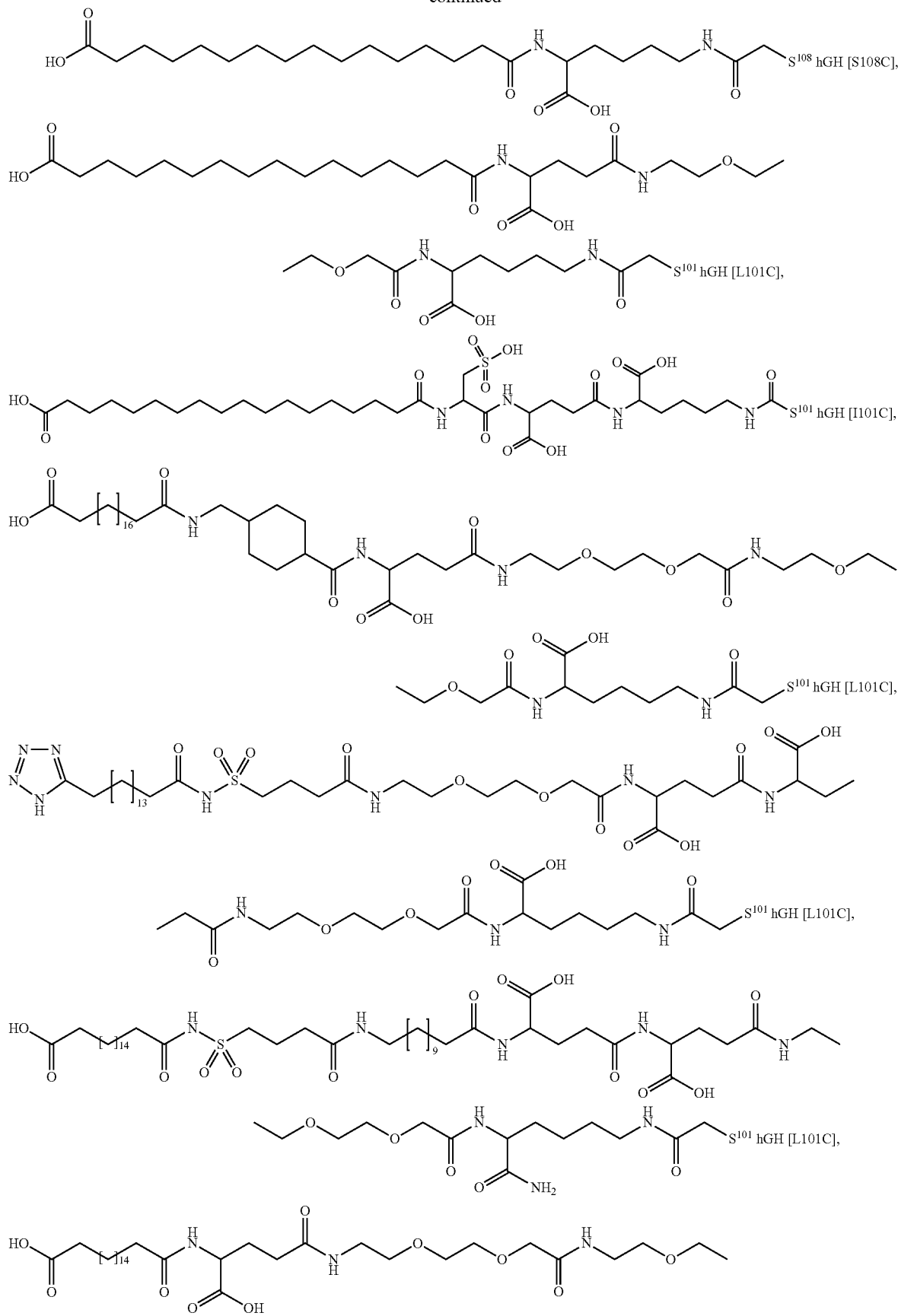

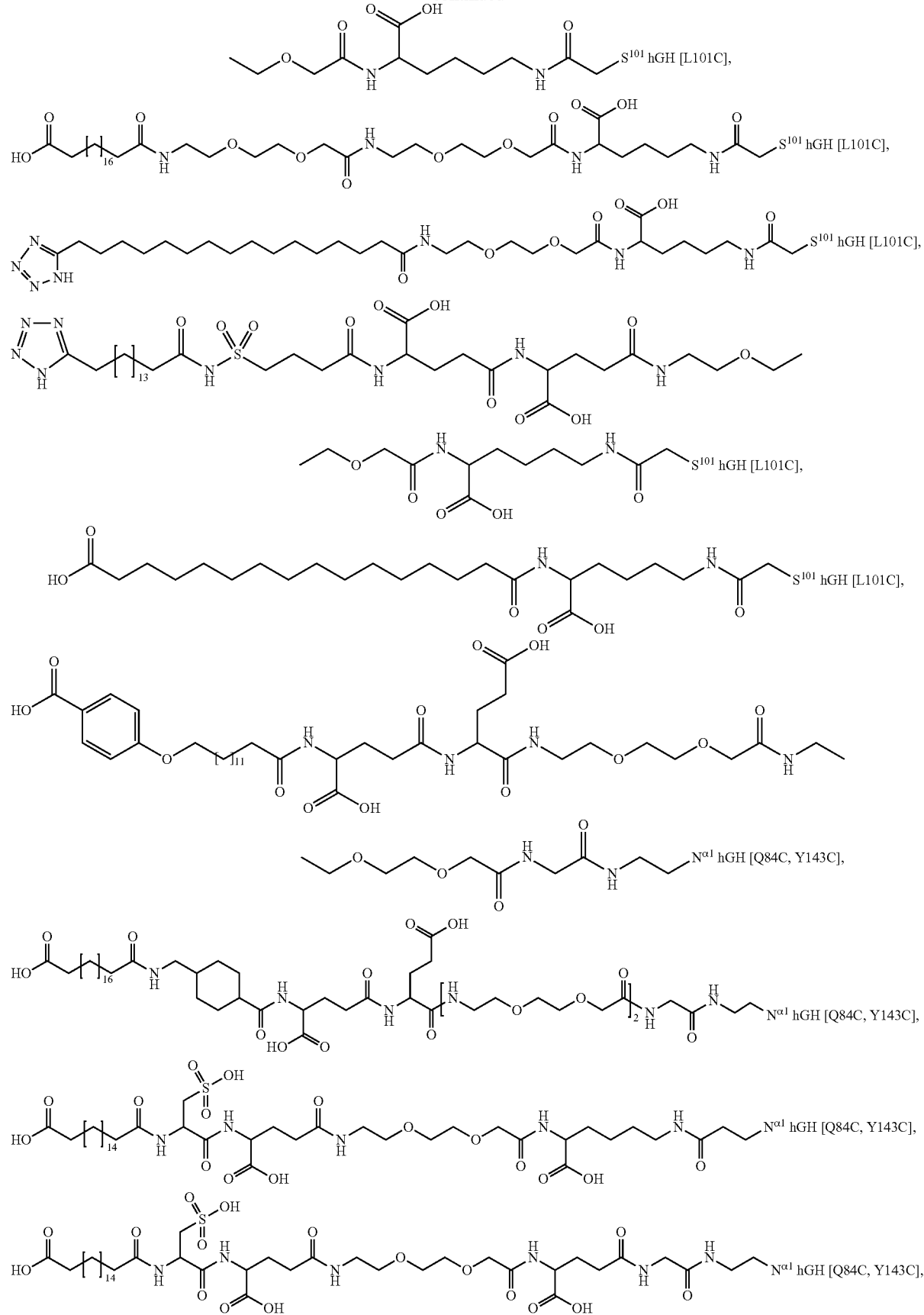

-continued
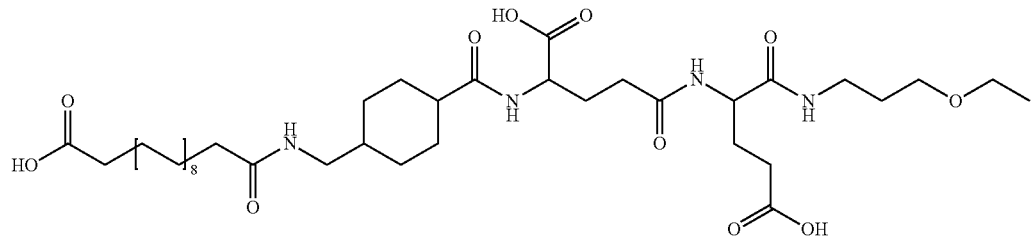
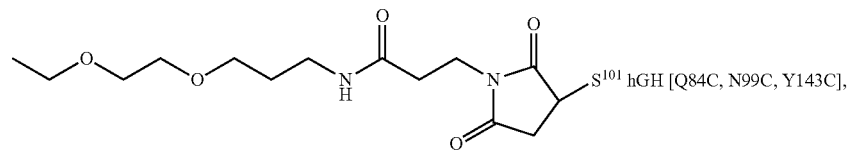
S[101] hGH [Q84C, N99C, Y143C],
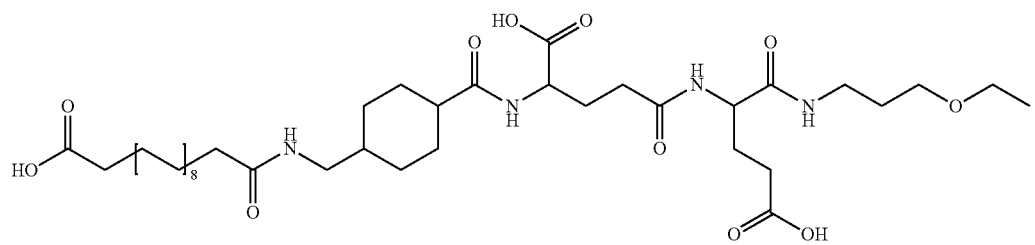
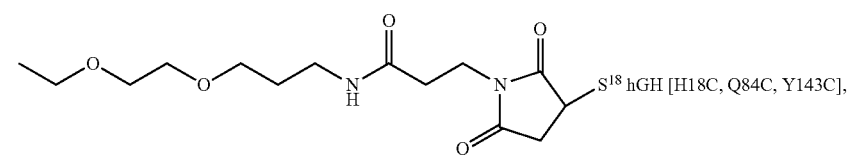
S[18] hGH [H18C, Q84C, Y143C],
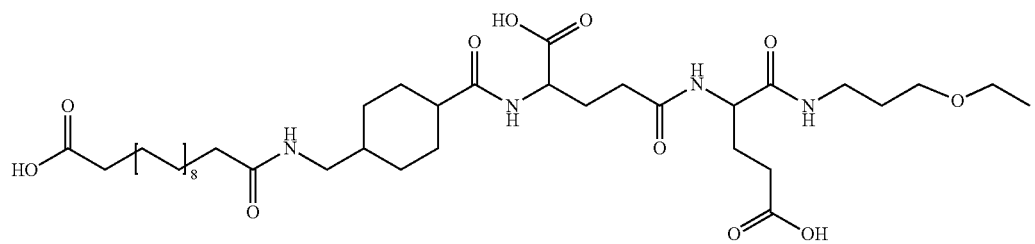
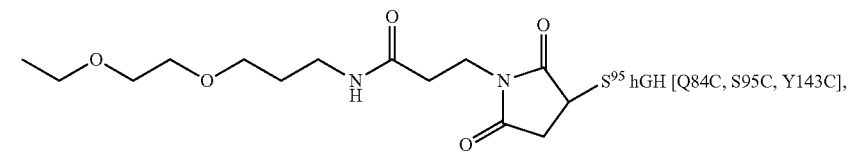
S[95] hGH [Q84C, S95C, Y143C],
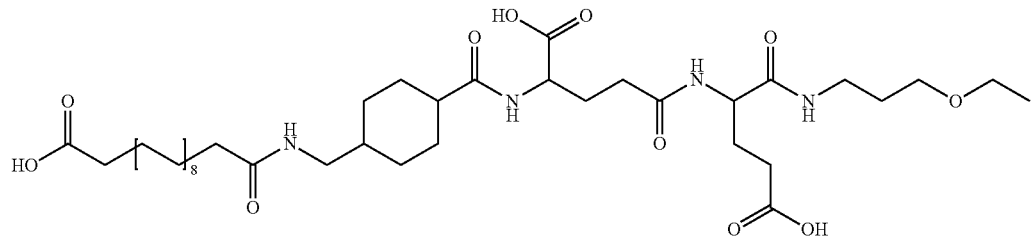
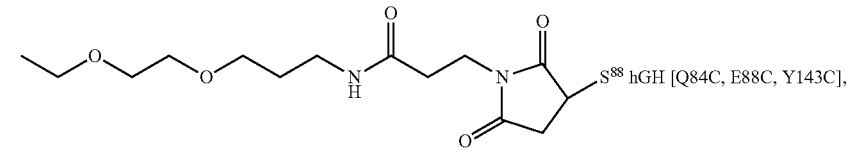
S[88] hGH [Q84C, E88C, Y143C], -continued
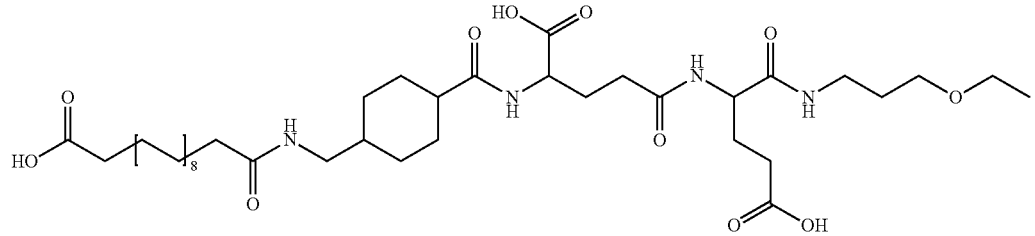
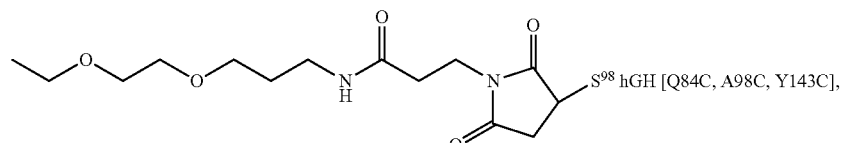 S⁹⁸ hGH [Q84C, A98C, Y143C],
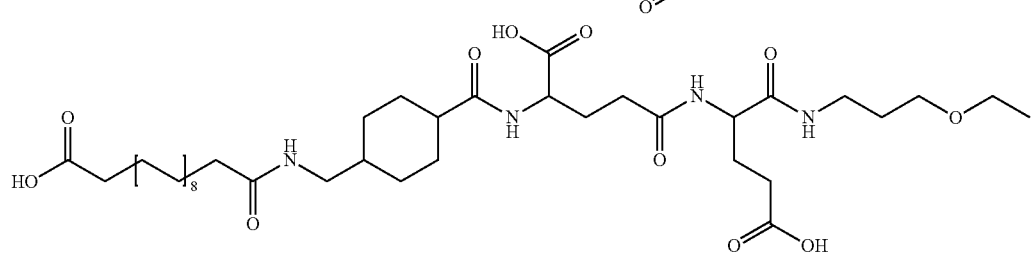
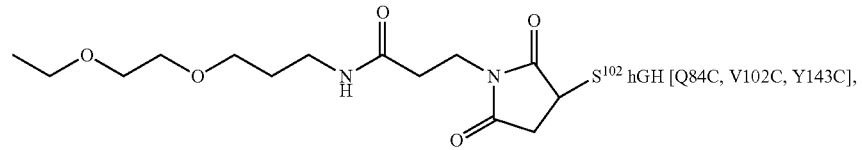 S¹⁰² hGH [Q84C, V102C, Y143C],
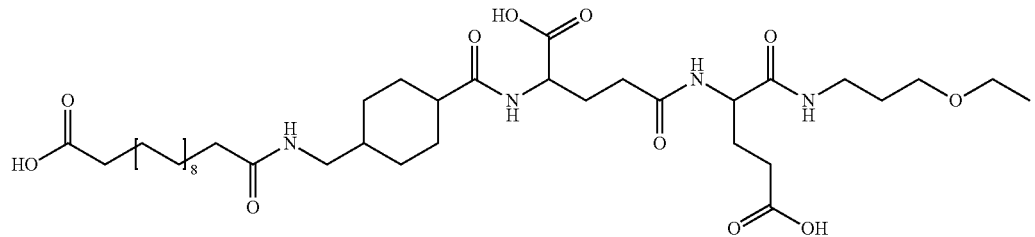
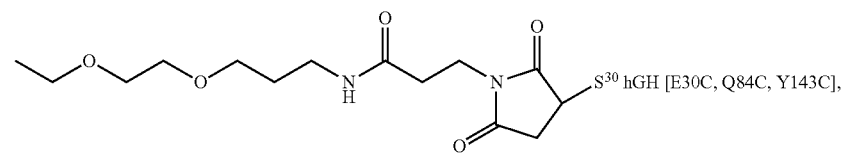 S³⁰ hGH [E30C, Q84C, Y143C],
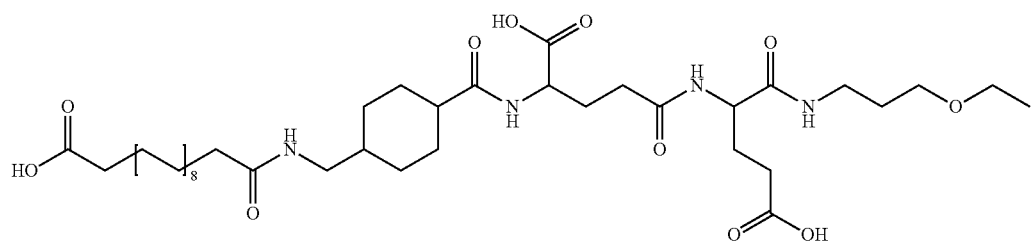
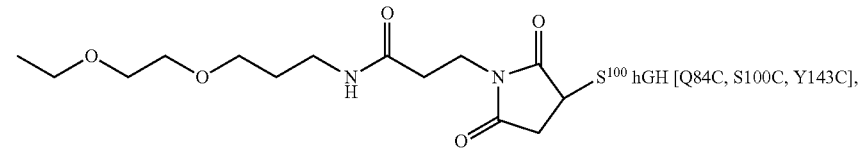 S¹⁰⁰ hGH [Q84C, S100C, Y143C],

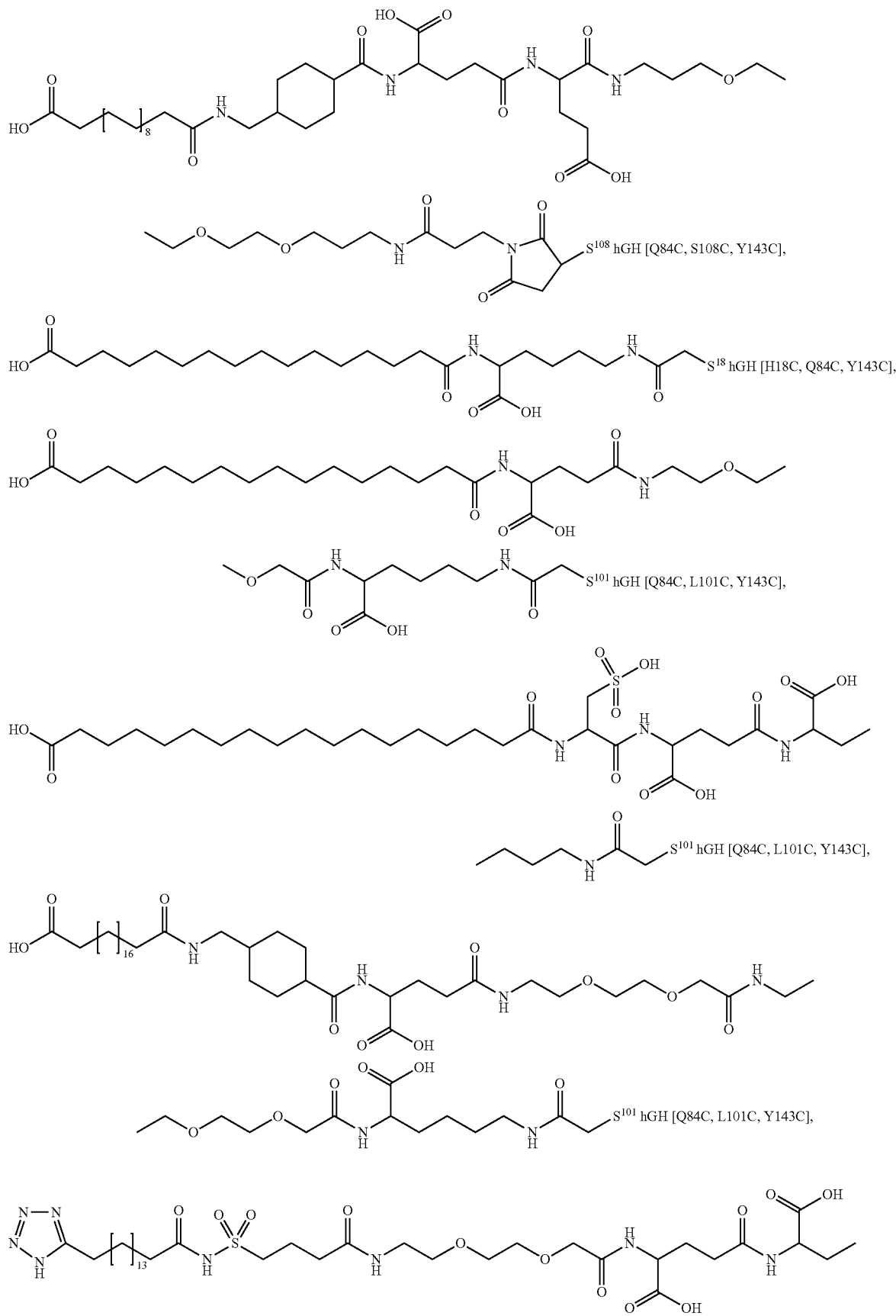

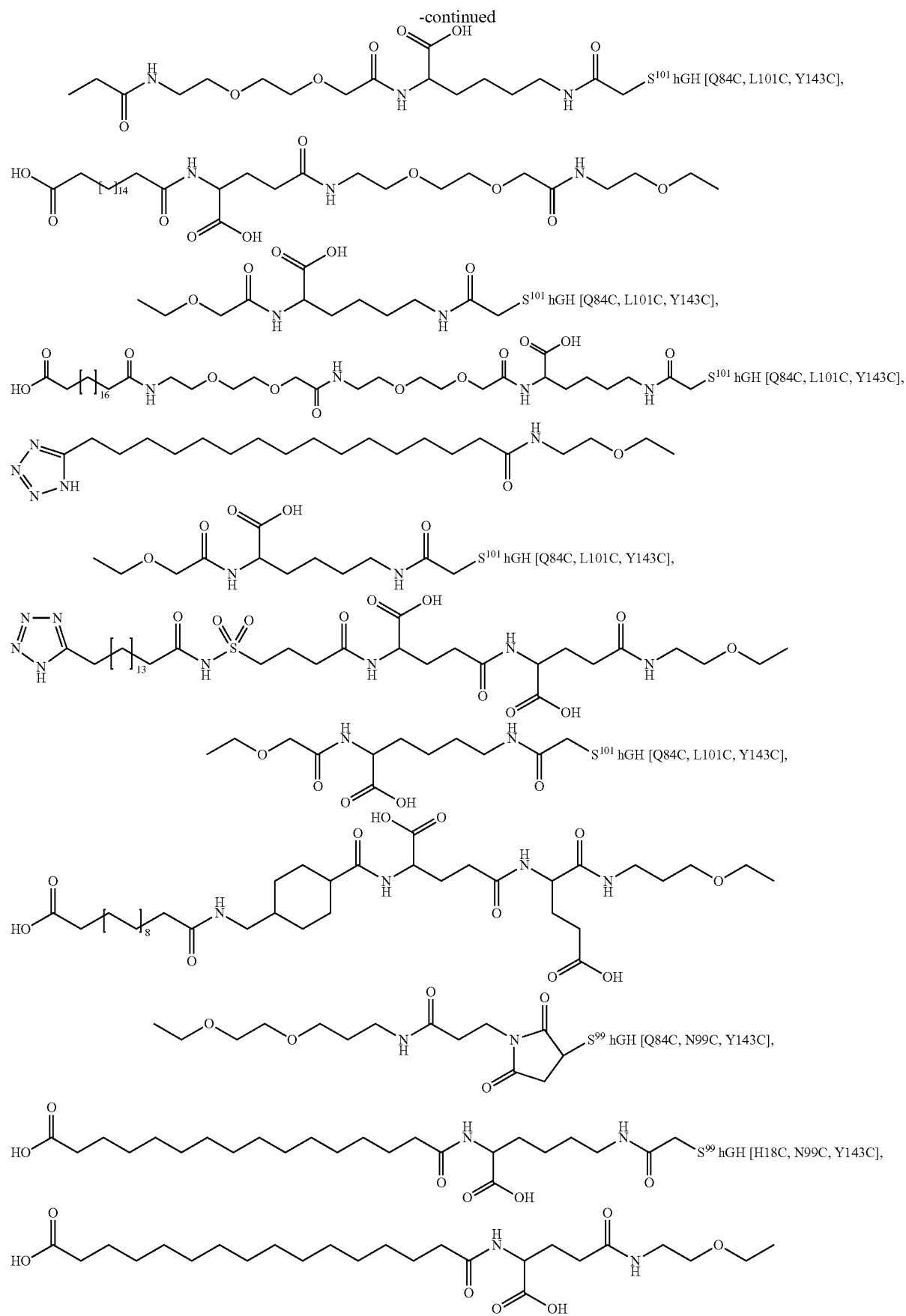

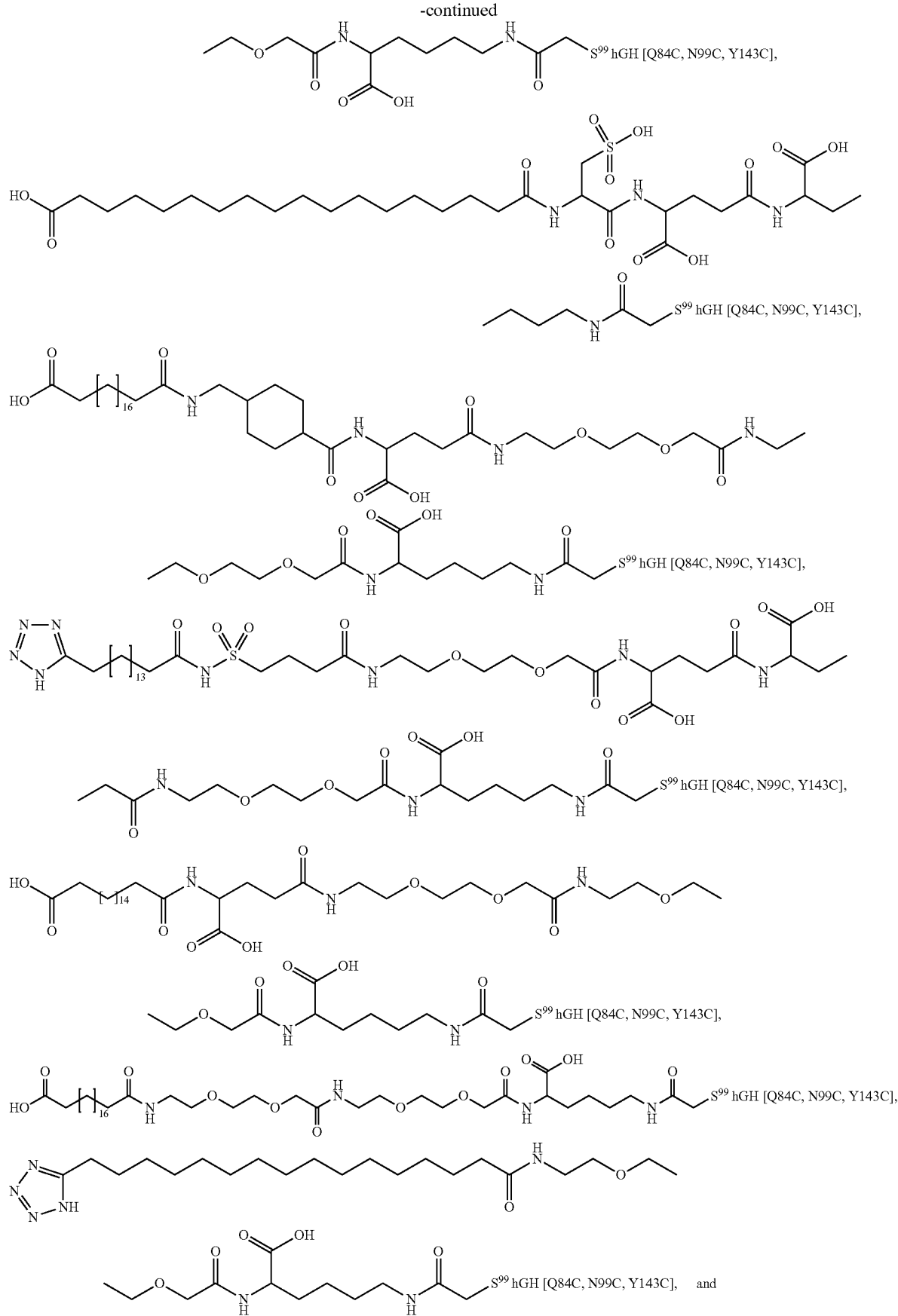

-continued
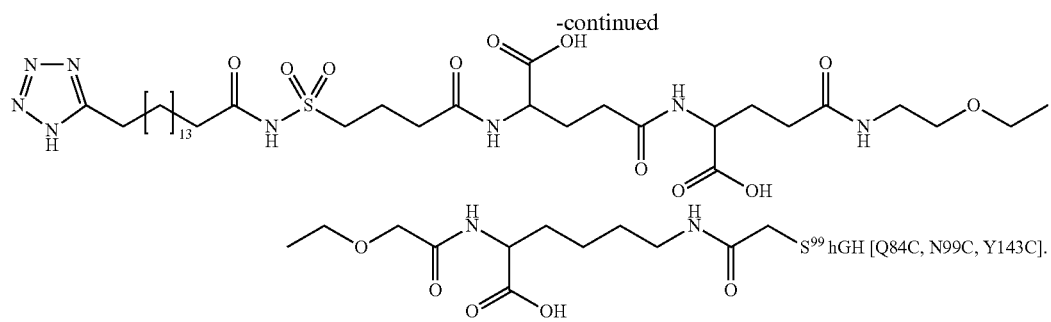
14. The growth hormone conjugate of claim 1 wherein said single Cys mutation is L101C numbered according to SEQ ID NO: 1.
* * * * *

SEQUENCE LISTING

<160> NUMBER OF SEQ ID NOS: 1

<210> SEQ ID NO 1
<211> LENGTH: 191
<212> TYPE: PRT
<213> ORGANISM: Homo sapiens

<400> SEQUENCE: 1

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
        50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
            115                 120                 125

Glu Asp Gly Ser Pro Arg Thr Gly Gln Ile Phe Lys Gln Thr Tyr Ser
        130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```